(12) United States Patent
Unger et al.

(10) Patent No.: US 6,231,834 B1
(45) Date of Patent: May 15, 2001

(54) METHODS FOR ULTRASOUND IMAGING INVOLVING THE USE OF A CONTRAST AGENT AND MULTIPLE IMAGES AND PROCESSING OF SAME

(75) Inventors: Evan C. Unger; Thomas A. Fritz, both of Tucson; Edward W. Gertz, Paradise Valley, all of AZ (US)

(73) Assignee: ImaRx Pharmaceutical Corp., Tucson, AZ (US)

( * ) Notice: Subject to any disclaimer, the term of this patent is extended or adjusted under 35 U.S.C. 154(b) by 0 days.

(21) Appl. No.: 08/982,829

(22) Filed: Dec. 2, 1997

Related U.S. Application Data

(63) Continuation-in-part of application No. 08/932,273, filed on Sep. 17, 1997, which is a continuation-in-part of application No. 08/666,129, filed on Jun. 19, 1996, now Pat. No. 6,033,645, and a continuation-in-part of application No. 08/660,032, filed on Jun. 6, 1996, now abandoned, which is a continuation-in-part of application No. 08/640,464, filed on May 1, 1996, now abandoned, which is a continuation-in-part of application No. 08/497,684, filed on Jun. 7, 1995, now abandoned.

(51) Int. Cl.[7] ........................................................ A61B 8/13
(52) U.S. Cl. ........................ 424/9.51; 424/9.52; 600/431
(58) Field of Search ................................ 424/9.52, 9.51; 600/431

(56) References Cited

U.S. PATENT DOCUMENTS

| | | |
|---|---|---|
| 3,015,128 | 1/1962 | Sommerville et al. ................ 18/2.6 |
| 3,291,843 | 12/1966 | Fritz et al. ............................ 260/614 |
| 3,293,114 | 12/1966 | Kenaga et al. ....................... 162/168 |
| 3,401,475 | 9/1968 | Morehouse et al. ................... 40/306 |
| 3,479,811 | 11/1969 | Walters ................................. 57/153 |
| 3,488,714 | 1/1970 | Walters et al. ....................... 161/161 |
| 3,532,500 | 10/1970 | Priest et al. ............................. 96/91 |
| 3,557,294 | 1/1971 | Dear et al. ............................ 424/342 |
| 3,594,326 | 7/1971 | Himmel et al. ...................... 252/316 |
| 3,615,972 | 10/1971 | Morehouse et al. ................... 156/79 |
| 3,650,831 | 3/1972 | Jungermann et al. ................. 134/27 |
| 3,732,172 | 5/1973 | Herbig et al. ........................ 252/316 |
| 3,873,564 | 3/1975 | Schneider et al. ................ 270/309.6 |
| 3,945,956 | 3/1976 | Garner ............................... 270/2.5 B |
| 3,960,583 | 6/1976 | Netting et al. ....................... 106/122 |
| 3,968,203 | 7/1976 | Spitzer et al. ........................ 424/47 |
| 4,027,007 | 5/1977 | Messina ................................. 424/46 |
| 4,089,801 | 5/1978 | Schneider ............................ 252/316 |
| 4,108,806 | 8/1978 | Cohrs et al. .......................... 521/54 |
| 4,138,383 | 2/1979 | Rembaum et al. ............. 270/29.7 H |
| 4,162,282 | 7/1979 | Fulwyler et al. ....................... 274/9 |
| 4,179,546 | 12/1979 | Garner et al. ......................... 521/56 |
| 4,192,859 | 3/1980 | Mackaness et al. .................... 424/5 |
| 4,224,179 | 9/1980 | Schneider ............................ 252/316 |
| 4,229,360 | 10/1980 | Schneider et al. ................... 270/403 |
| 4,265,251 | 5/1981 | Tickner ............................... 128/660 |
| 4,276,885 | 7/1981 | Tickner et al. ...................... 128/660 |
| 4,310,505 | 1/1982 | Baldeschwieler et al. .............. 424/1 |
| 4,310,506 | 1/1982 | Baldeschwieler et al. .............. 424/1 |
| 4,315,514 | 2/1982 | Drewes et al. ...................... 128/653 |
| 4,331,654 | 5/1982 | Morris .................................. 424/38 |
| 4,342,826 | 8/1982 | Cole ....................................... 435/7 |
| 4,344,929 | 8/1982 | Bonsen et al. ......................... 424/15 |
| 4,420,442 | 12/1983 | Sands ................................... 274/13 |
| 4,421,562 | 12/1983 | Sands et al. ......................... 106/75 |
| 4,427,330 | 1/1984 | Sears ................................... 270/403 |
| 4,427,649 | 1/1984 | Dingle et al. ......................... 424/38 |
| 4,428,924 | 1/1984 | Millington ............................. 424/4 |
| 4,442,843 | 4/1984 | Rasor et al. ......................... 128/660 |
| 4,466,442 | 8/1984 | Hilmann et al. .................... 128/653 |
| 4,530,360 | 7/1985 | Duarte ............................. 128/419 F |
| 4,533,254 | 8/1985 | Cook et al. .......................... 366/176 |
| 4,534,899 | 8/1985 | Sears ................................... 270/403 |
| 4,540,629 | 9/1985 | Sands et al. ......................... 428/402 |
| 4,544,545 | 10/1985 | Ryan et al. .......................... 424/1.1 |
| 4,549,892 | 10/1985 | Baker et al. .......................... 65/21.4 |
| 4,569,836 | 2/1986 | Gordon ............................... 424/1.1 |
| 4,572,203 | 2/1986 | Feinstein ............................. 128/661 |
| 4,586,512 | 5/1986 | Do-huu et al. ...................... 128/660 |
| 4,603,044 | 7/1986 | Geho et al. ............................ 424/9 |
| 4,615,879 | 10/1986 | Runge et al. .......................... 424/9 |

(List continued on next page.)

FOREIGN PATENT DOCUMENTS

| | | |
|---|---|---|
| 641363 | 3/1990 | (AU) . |
| 30351/89 | 3/1993 | (AU) . |
| 25 21 003 | 8/1976 | (DE) . |

(List continued on next page.)

OTHER PUBLICATIONS

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1974).

(List continued on next page.)

*Primary Examiner*—Gary E. Hollinden
(74) *Attorney, Agent, or Firm*—Woodcock Washburn Kurtz Mackiewicz & Norris LLP

(57) ABSTRACT

Improved methods for providing an image of an internal region of a patient. Embodiments of the invention involve the administration to the patient of a contrast agent which comprises, in an aqueous carrier, a lipid, protein, polymer or surfactant, and a gas. The patient is scanned using ultrasound imaging to obtain a visible image of the region. In embodiments of the invention, the scanning step may comprise applying a first quantity of ultrasound energy to the patient to provide a first image, followed by the application substantially immediately thereafter of a second quantity of ultrasound energy to provide a second image. The first and second images are then processed. The methods are particularly useful for obtaining on-line images of the cardiovascular region which may be employed, for example, to diagnose the presence of diseased tissue in the cardiovascular region of a patient.

115 Claims, 2 Drawing Sheets

(1 of 2 Drawing Sheet(s) Filed in Color)

U.S. PATENT DOCUMENTS

| | | | |
|---|---|---|---|
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,663,161 | 5/1987 | Mannimo et al. | 424/89 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,693,999 | 9/1987 | Axelsson et al. | 514/174 |
| 4,718,433 | 1/1988 | Feinstein | 128/660 |
| 4,728,575 | 3/1988 | Gamble et al. | 428/402.2 |
| 4,728,578 | 3/1988 | Higgins et al. | 428/462 |
| 4,731,239 | 3/1988 | Gordon | 424/9 |
| 4,737,323 | 4/1988 | Martin et al. | 274/4.3 |
| 4,774,958 | 10/1988 | Feinstein | 128/660.01 |
| 4,775,522 | 10/1988 | Clark, Jr. | 424/9 |
| 4,776,991 | 10/1988 | Farmer et al. | 274/4.3 |
| 4,781,871 | 11/1988 | West, III et al. | 274/4.3 |
| 4,789,501 | 12/1988 | Day et al. | 252/645 |
| 4,790,891 | 12/1988 | Halliday et al. | 149/2 |
| 4,822,534 | 4/1989 | Lencki et al. | 274/4.3 |
| 4,830,858 | 5/1989 | Payne et al. | 424/450 |
| 4,834,964 | 5/1989 | Rosen | 424/9 |
| 4,844,882 | 7/1989 | Widder et al. | 424/9 |
| 4,863,717 | 9/1989 | Keana | 424/9 |
| 4,865,836 | 9/1989 | Long, Jr. | 424/5 |
| 4,877,561 | 10/1989 | Iga et al. | 274/4.3 |
| 4,893,624 | 1/1990 | Lele | 128/399 |
| 4,895,719 | 1/1990 | Radhakrishnan | 424/45 |
| 4,898,734 | 2/1990 | Mathiowitz et al. | 424/427 |
| 4,900,540 | 2/1990 | Ryan et al. | 424/9 |
| 4,918,065 | 4/1990 | Stindl et al. | 514/179 |
| 4,919,895 | 4/1990 | Heldebrandt et al. | 422/129 |
| 4,921,706 | 5/1990 | Roberts et al. | 424/450 |
| 4,927,623 | 5/1990 | Long, Jr. | 424/5 |
| 4,933,121 | 6/1990 | Law et al. | 264/4.3 |
| 4,938,947 | 7/1990 | Nicolau et al. | 424/1.1 |
| 4,957,656 | 9/1990 | Cerny et al. | 252/311 |
| 4,981,692 | 1/1991 | Popescu et al. | 424/422 |
| 4,984,573 | 1/1991 | Leunbach | 128/653 |
| 4,985,550 | 1/1991 | Charpiot et al. | 536/18.4 |
| 4,987,154 | 1/1991 | Long, Jr. | 514/772 |
| 4,993,415 | 2/1991 | Long | 128/653 A |
| 4,996,041 | 2/1991 | Arai et al. | 424/9 |
| 5,000,960 | 3/1991 | Wallach | 424/450 |
| 5,004,611 | 4/1991 | Leigh | 424/450 |
| 5,008,050 | 4/1991 | Cullis et al. | 274/4.3 |
| 5,008,109 | 4/1991 | Tin | 424/422 |
| 5,013,556 | 5/1991 | Woodle et al. | 424/450 |
| 5,019,370 | 5/1991 | Jay et al. | 424/4 |
| 5,045,304 | 9/1991 | Schneider et al. | 424/9 |
| 5,049,388 | 9/1991 | Knight et al. | 424/450 |
| 5,078,994 | 1/1992 | Nair et al. | 424/501 |
| 5,088,499 | 2/1992 | Unger | 128/662.2 |
| 5,107,842 | 4/1992 | Levene et al. | 128/662.02 |
| 5,114,703 | 5/1992 | Wolf et al. | 424/5 |
| 5,123,414 | 6/1992 | Unger | 128/654 |
| 5,135,000 | 8/1992 | Akselrod et al. | 128/662.02 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |
| 5,149,319 | 9/1992 | Unger | 604/22 |
| 5,171,755 | 12/1992 | Kaufman | 514/759 |
| 5,186,922 | 2/1993 | Shell et al. | 128/654 |
| 5,190,766 | 3/1993 | Ishihara | 424/489 |
| 5,190,982 | 3/1993 | Erbel et al. | 521/56 |
| 5,192,549 | 3/1993 | Barenolz et al. | 424/450 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9 |
| 5,196,348 | 3/1993 | Schweighardt et al. | 436/173 |
| 5,198,225 | 3/1993 | Meybeck et al. | 424/450 |
| 5,205,287 | 4/1993 | Erbel et al. | 128/632 |
| 5,205,290 | 4/1993 | Unger | 128/653.4 |
| 5,209,720 | 5/1993 | Unger | 604/22 |
| 5,213,804 | 5/1993 | Martin et al. | 424/450 |
| 5,215,680 | 6/1993 | D'Arrigo | 252/307 |
| 5,219,538 | 6/1993 | Henderson et al. | 428/402.2 |
| 5,228,446 | 7/1993 | Unger et al. | 128/662.02 |
| 5,230,882 | 7/1993 | Unger | 424/9 |
| 5,247,935 | 9/1993 | Cline et al. | 128/653.2 |
| 5,271,928 | 12/1993 | Schneider et al. | 424/9 |
| 5,281,408 | 1/1994 | Unger | 424/4 |
| 5,305,757 | 4/1994 | Unger et al. | 128/662.02 |
| 5,310,540 | 5/1994 | Giddey et al. | 424/9 |
| 5,312,617 | 5/1994 | Unger et al. | 424/9 |
| 5,315,997 | 5/1994 | Widder et al. | 128/653.3 |
| 5,315,998 | 5/1994 | Tachibana et al. | 128/660.01 |
| 5,316,771 | 5/1994 | Barenholz et al. | 424/450 |
| 5,334,381 | 8/1994 | Unger | 424/9 |
| 5,339,814 | 8/1994 | Lasker | 128/653.4 |
| 5,344,930 | 9/1994 | Riess et al. | 544/84 |
| 5,350,571 | 9/1994 | Kaufman et al. | 424/9 |
| 5,352,435 | 10/1994 | Unger | 424/9 |
| 5,354,549 | 10/1994 | Klaveness et al. | 424/3 |
| 5,358,702 | 10/1994 | Unger | 424/9 |
| 5,362,477 | 11/1994 | Moore et al. | 424/9 |
| 5,362,478 | 11/1994 | Desai et al. | 424/9 |
| 5,380,519 | 1/1995 | Schneider et al. | 424/9 |
| 5,393,524 | 2/1995 | Quay | 424/9 |
| 5,409,688 | 4/1995 | Quay | 424/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.51 |
| 5,456,900 | 10/1995 | Unger | 424/9.4 |
| 5,460,800 | 10/1995 | Walters | 424/9.6 |
| 5,466,467 | 11/1995 | Singh | 424/450 |
| 5,469,854 | 11/1995 | Unger et al. | 128/662.02 |
| 5,470,582 | 11/1995 | Supersaxo et al. | 424/489 |
| 5,485,839 | 1/1996 | Aida et al. | 128/653.1 |
| 5,487,390 | 1/1996 | Cohen et al. | 128/662.02 |
| 5,496,535 | 3/1996 | Kirkland | 424/9.37 |
| 5,498,421 | 3/1996 | Grinstaff et al. | 424/450 |
| 5,498,601 | 3/1996 | Sato et al. | 514/17 |
| 5,501,863 | 3/1996 | Rössling et al. | 424/489 |
| 5,502,094 | 3/1996 | Moore et al. | 524/145 |
| 5,505,932 | 4/1996 | Grinstaff et al. | 424/9.3 |
| 5,508,021 | 4/1996 | Grinstaff et al. | 424/9.322 |
| 5,527,521 | 6/1996 | Unger | 424/93 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| 5,542,935 | 8/1996 | Unger et al. | 604/190 |
| 5,545,396 | 8/1996 | Albert et al. | 424/93 |
| 5,547,656 | 8/1996 | Unger | 424/9.4 |
| 5,552,133 | 9/1996 | Lambert et al. | 424/9.52 |
| 5,552,155 | 9/1996 | Bailey et al. | 424/450 |
| 5,556,372 | 9/1996 | Talish et al. | 601/2 |
| 5,556,610 | 9/1996 | Yan et al. | 424/9.52 |
| 5,558,092 | 9/1996 | Unger et al. | 128/660.03 |
| 5,558,094 | 9/1996 | Quay | 128/662.02 |
| 5,558,853 | 9/1996 | Quay | 424/9.5 |
| 5,558,854 | 9/1996 | Quay | 424/9.52 |
| 5,558,855 | 9/1996 | Quay | 424/9.5 |
| 5,558,856 | 9/1996 | Klaveness et al. | 424/9.37 |
| 5,560,364 | 10/1996 | Porter | 128/662.02 |

| | | | | | | |
|---|---|---|---|---|---|---|
| 5,562,608 | 10/1996 | Sekins et al. | 604/20 | 0 614 656 A1 | 9/1994 | (EP). |
| 5,562,893 | 10/1996 | Lohrmann | 424/9.52 | 0 422 938 B1 | 2/1995 | (EP). |
| 5,565,215 | 10/1996 | Gref et al. | 424/501 | 0 727 225 A2 | 8/1996 | (EP). |
| 5,567,413 | 10/1996 | Klaveness et al. | 424/9.51 | 2 700 952 | 8/1994 | (FR). |
| 5,567,414 | 10/1996 | Schneider et al. | 424/9.52 | 1044680 | 10/1966 | (GB). |
| 5,567,765 | 10/1996 | Moore et al. | 524/801 | 2193095 | 2/1988 | (GB). |
| 5,569,448 | 10/1996 | Wong et al. | 424/9.45 | 62-286534 | 12/1987 | (JP). |
| 5,569,449 | 10/1996 | Klaveness et al. | 424/9.51 | 63-60943 | 3/1988 | (JP). |
| 5,571,797 | 11/1996 | Ohno et al. | 514/44 | WO 80/02365 | 11/1980 | (WO). |
| 5,573,751 | 11/1996 | Quay | 424/9.52 | WO 82/01642 | 5/1982 | (WO). |
| 5,578,292 | 11/1996 | Schneider et al. | 424/9.51 | WO 85/01161 | 3/1985 | (WO). |
| 5,580,575 | 12/1996 | Unger et al. | 424/450 | WO 86/00238 | 1/1986 | (WO). |
| 5,585,112 | 12/1996 | Unger et al. | 424/450 | WO 86/01103 | 2/1986 | (WO). |
| 5,593,680 | 1/1997 | Bara et al. | 424/401 | WO 89/05040 | 6/1989 | (WO). |
| 5,595,723 | 1/1997 | Quay | 424/9.5 | WO 90/01952 | 3/1990 | (WO). |
| 5,605,673 | 2/1997 | Schutt et al. | 424/9.51 | WO 90/04384 | 5/1990 | (WO). |
| 5,606,973 | 3/1997 | Lambert et al. | 128/662.02 | WO 90/04943 | 5/1990 | (WO). |
| 5,612,057 | 3/1997 | Lanza et al. | 424/450 | WO 91/00086 | 1/1991 | (WO). |
| 5,612,318 | 3/1997 | Weichselbaum et al. | 514/44 | WO 91/03267 | 3/1991 | (WO). |
| 5,614,169 | 3/1997 | Klaveness et al. | 424/9.52 | WO 91/12823 | 9/1991 | (WO). |
| 5,620,689 | 4/1997 | Allen et al. | 424/178.1 | WO 91/15244 | 10/1991 | (WO). |
| 5,626,833 | 5/1997 | Schutt et al. | 424/9.52 | WO 92/10166 | 6/1992 | (WO). |
| 5,639,443 | 6/1997 | Schutt et al. | 424/9.52 | WO 92/11873 | 7/1992 | (WO). |
| 5,643,553 | 7/1997 | Schneider et al. | 424/9.52 | WO 92/15284 | 9/1992 | (WO). |
| 5,648,095 | 7/1997 | Illum et al. | 424/489 | WO 92/17212 | 10/1992 | (WO). |
| 5,672,585 | 9/1997 | Pierschbacher et al. | 514/11 | WO 92/17213 | 10/1992 | (WO). |
| 5,676,928 | 10/1997 | Klaveness et al. | 424/9.32 | WO 92/17436 | 10/1992 | (WO). |
| 5,679,459 | 10/1997 | Riess et al. | 428/402.2 | WO 92/17514 | 10/1992 | (WO). |
| 5,686,060 | 11/1997 | Schneider et al. | 424/9.52 | WO 92/21382 | 10/1992 | (WO). |
| 5,686,102 | 11/1997 | Gross et al. | 424/450 | WO 92/22249 | 12/1992 | (WO). |
| 5,701,899 | 12/1997 | Porter | 428/662.02 | WO 92/22298 | 12/1992 | (WO). |
| 5,707,352 | 1/1998 | Sekins et al. | 604/56 | 93/00933 | 1/1993 | (WO). |
| 5,707,606 | 1/1998 | Quay | 424/9.52 | WO 93/05819 | 1/1993 | (WO). |
| 5,707,607 | 1/1998 | Quay | 424/9.52 | WO 93/06869 | 4/1993 | (WO). |
| 5,711,933 | 1/1998 | Bichon et al. | 424/9.52 | WO 93/13809 | 7/1993 | (WO). |
| 5,716,597 | 2/1998 | Lohrmann et al. | 424/9.5 | WO 93/17718 | 9/1993 | (WO). |
| 5,732,707 | 3/1998 | Widder et al. | 128/661.08 | WO 93/20802 | 10/1993 | (WO). |
| 5,733,527 | 3/1998 | Schutt | 424/9.52 | WO 94/00110 | 1/1994 | (WO). |
| 5,736,121 | 4/1998 | Unger | 424/9.4 | WO 9/06477 | 3/1994 | (WO). |
| 5,740,807 | 4/1998 | Porter | 128/662.02 | WO 94/07539 | 4/1994 | (WO). |
| 5,804,162 | 9/1998 | Kabalnov et al. | 424/9.51 | WO 94/09829 | 5/1994 | (WO). |
| 5,840,023 | 11/1998 | Oraevsky et al. | 600/407 | WO 84/02909 | 8/1994 | (WO). |
| 5,855,865 | 1/1999 | Lambert et al. | 424/9.52 | WO 94/16739 | 8/1994 | (WO). |
| 5,858,399 | 1/1999 | Lanza et al. | 424/450 | WO 94/21301 | 9/1994 | (WO). |
| 5,874,062 | 2/1999 | Unger | 424/9.4 | WO 94/21302 | 9/1994 | (WO). |
| 5,897,851 | 4/1999 | Quay et al. | 424/9.52 | WO 94/28780 | 12/1994 | (WO). |
| 5,976,501 | 11/1999 | Jablonski | 424/9.52 | WO 94/28873 | 12/1994 | (WO). |
| B1 4,229,360 | 11/1991 | Schneider et al. | 270/403 | WO 95/00126 | 1/1995 | (WO). |
| | | | | WO 95/03835 | 2/1995 | (WO). |

FOREIGN PATENT DOCUMENTS

| | | |
|---|---|---|
| 0 052 575 | 5/1982 | (EP). |
| 0 107 559 | 5/1984 | (EP). |
| 0 077 752 B1 | 3/1986 | (EP). |
| 0 243 947 | 4/1987 | (EP). |
| 0 231 091 | 8/1987 | (EP). |
| 0 272 091 | 6/1988 | (EP). |
| 0 320 433 A2 | 12/1988 | (EP). |
| 0 324 938 | 7/1989 | (EP). |
| 0 338 971 | 10/1989 | (EP). |
| 357163 A1 | 3/1990 | (EP). |
| 0 361 894 | 4/1990 | (EP). |
| 0 368 486 A2 | 5/1990 | (EP). |
| 0 382 451 A2 | 8/1990 | (EP). |
| 0 216 730 | 1/1991 | (EP). |
| 0 467 031 A2 | 5/1991 | (EP). |
| 441468 A2 | 8/1991 | (EP). |
| 0 357 164 B1 | 10/1991 | (EP). |
| 0 458 745 A1 | 11/1991 | (EP). |
| 0 314 764 B1 | 9/1992 | (EP). |
| 0 554 213 A1 | 8/1993 | (EP). |
| 0 586 875 | 3/1994 | (EP). |

| | | |
|---|---|---|
| WO 95/06518 | 3/1995 | (WO). |
| WO 95/07072 | 3/1995 | (WO). |
| WO 95/23615 | 9/1995 | (WO). |
| WO 95/24184 | 9/1995 | (WO). |
| WO 95/29705 | 11/1995 | (WO). |
| WO 95/32005 | 11/1995 | (WO). |
| WO 96/04018 | 2/1996 | (WO). |
| WO 96/09793 | 4/1996 | (WO). |
| WO 96/36286 | 11/1996 | (WO). |
| WO 96/40281 | 12/1996 | (WO). |
| WO 98/00172 | 1/1998 | (WO). |

OTHER PUBLICATIONS

Thanassi, "Aminomalonic Acid: Spontaneous Decarboxylation and Reaction with 5–Deoxypyridoxal", *Biochemistry*, vol. 9, No. 3, pp. 525–532 (1970).

Stelmashok et al., Koordinatsionnaya Khimiya, vol. 3, No. 4, pp. 524–527 (1977) (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812: 55–65 (1985).

Mayer et al., "Vesicles of Variable Size Produced by a Rapid Extrusion Procedure", *Biochimica et Biophysica Acta*, vol. 858, pp. 161–168 (1986).

Cheng, et al., "The Production and Evaluation of Contrast–Carrying Liposomes Made with an Automatic High Pressure System", *Investigative Radiology*, vol. 22, pp. 47–55 (1987).

Jain, et al., *Introduction to Biological Membranes*, Ch. 9, pp. 192–231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesicles From Long–chain Saturated Phosphatidylcholines by Extrusion Techniques", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocardiography, I: In Vitro Development and Quantitative Analysis of Echo Contrast Agents", *JACC*, vol. 3, No. 1, pp. 14–20 (1984).

Ten Cate et al., "Two–Dimensional Contrast Echocardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp. 77–80 (1989).

Mann et al., "Formation of Iron Oxides in Unilamellar Vesicles", *Journal of Colloid and Interface Science*, vol. 122, No.2, pp. 326–335 (1988).

Anderson et al., "Manganese (III) Complexes in Oxidative Decarboxylation of Acids", *J. Am. Chem. Soc.*, vol. 92, No.8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman D., "Physiochemical Properties of Phospholipids and Lipid Water Systems", *Liposome Technology*, Gregoriadis, G., ed., vol. 1, pp. 1–18 (CRC Press, Boca Raton, FL, 1984).

Violante et al., "Particulate Suspensions as Ultrasonic Contrast Agents for Liver and Spleen", *Inv. Rad.*, vol. 23, pp. S294–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, Experience, Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimenthylammonium Methacrylate", *J. Am. Chem. Soc.*, vol. 108, pp. 2321–2327 (1986).

Regen, "Polymerized Vesicles", *J. Am. Chem. Soc.*, vol. 102, pp. 6638–6640 (1989).

Rose, A. and Rose, E., "The Condensed Chemical Dictionary", Reinhold Publishing, New York, pp. 728 and 743 (1966).

A. G. Belykh, *Farmakol Toksikol. (MOSC)*, vol. 44(3), pp. 322–326 (1981) (abstract).

J. Vion–Dury et al., *J. Pharmacol. Exper. Ther.*, vol. 250(3), pp. 1113–1118 (1989) (abstract).

M.R. Zalutsky et al., *Invest. Radiol.*, vol. 22(2), pp. 141–147 (1987).

Crowe et al., *Archives of Biochemistry and Biophysics*, vol. 242, pp. 240–247 (1985).

Crowe et al., *Archives of Biochemistry and Biophysics*, vol. 220, pp. 477–484 (1983).

Dorland's Illustrated Medical Dictionary, p. 946, 27th ed. (W.B. Saunders Company, Philadelphia 1988).

Liposome Technology, Gregoriadis, G., ed., vol. I, pp. 30–35, 51–65 and 79–107 (CRC Press Inc., Boca Raton, FL, (1984).

Madden et al., *Chemistry and Physics of Lipids*, vol. 53, pp. 37–46 (1990).

Sinkula et al., *J. Pharm. Sci.*, vol. 64, pp. 181–210 (1975).

Shiina et al., "Hyperthermiably Low–frequency Synthesized Ultrasound", *IEEE Engineering*, pp. 879–880, vol. 2 (1988) (abstract).

McAvoy et al., *IEEE Engineering, Ultrasonics Symposium Proceedings*, vol. 2, pp. 677–1248 (1989) (abstract).

Chapman et al., "Biomembrane Phase Transitions", *J. Biol. Chem.*, 1974, 249:2512–2521.

Hug et al., "Liposomes for the Transformation of Eukaryotic Cells", *Biochimica et Biophysica Acta*, 1991, 1097:1–17.

Marsh, *CRC Handbook of Lipid Bilayers* (CRC Press, Boca Raton, FL 1990) pp. 139–141.

Szoka et al., "Procedure for Preparation of Liposomes With Large Internal Aqueous Space . . .", *Proc. Natl. Acad. Sci.* 1978, 75:4194–4198.

Acoustic Imaging AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.*, 1965, 13:238–252.

Carson et al., *Ultrasound in Med. & Biol. 3*, 1978, 341–350.

Kost et al., *Polymers in Medicine II: Biomedical and Pharmaceutical Applications*, "Ultrasonic Modulated Drug Delivery Systems", Chiellini et al., ed., (Plenum Press, New York and London), pp. 387–396 (1985).

deGier et al., "Relations Between Liposomes and Biomembranes", *Annals of The New York Academy of Sciences*, 1978, 308:85–99.

Felgner et al., "Lipofection: A highly efficient, lipid–mediated DNA–transfection procedure", *Proc. Natl. Acad. Sci.*, 1987, 84:7413–7417.

Gabizon et al., "Liposome formulations with prolonged circulation time in blood and enhanced uptake by tumors", *Proc. Natl. Acad. Sci.*, 1988, 85:6949–6953.

Garelli, et al., *Biochimica et Biophysica Acta*, vol. 1127:41–48 (1992).

Kawai et al., "New Procedure for DNA Transfection with Polycation and Dimethyl Sulfoxide", *Molecular and Cellular Biology*, 1984, 4:1172–1174.

Kuo et al., "Metallocene Antitumor Agents. Solution and Solid–State Molybdenocene Coordination . . . ", *J. Am. Chem. Soc.*, 1991, 113:9027–9045.

MacDonald, *Mammalian Cell Biotechnology: A Practical Approach*, M. Butler, ed., 1991 (Oxford University Press, New York), p. 57–70.

Mathiowitz et al., "Photochemical Rupture of Microcapsules: A Model System", *Journal of Applied Polymer Science*, 1981, 27:809–822.

May et al., "Cationic Liposomes Enable Bovine Herpesvirus Type 2 DNA to Infect Cells", Acta virol., 1991, 35:107.

Poznansky et al., "Biological Approaches to the Controlled Delivery of Drugs: A Critical Review", *Pharmacol*, Rev., 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature*, 1992, 359:67–70.

Thompson, Larry, "At Age 2, Gene Therapy Enters a Growth Phase", *Science 1992*, 258:744–746.

Trubetskoy et al. "Cationic liposomes enhance targeted delivery and expression of exogenous DNA . . . ", Biochimica et Biophysica Acta 1992, 131:311–313.

Umemura et al., "Studies on Sonodynamic Cancer Therapy", *IEEE*, 1992, O–7803–0785, pp. 354–355.

Williams, "Human Gene Therapy: Searching for Better Vectors", *ASM News* [American Society for Microbiology] 1992, 58:67–69.

Woodle et al., "Versatility in lipid compositions showing prolonged circulation . . . ", *Biochimica et Biophysica Acta 1992*, 1105:193–200.

Zhou et al., "Targeted delivery of DNA by liposomes and polymers", *J. of Controlled Release 1992*, 19:269–274.

Mathiowitz et al., "Polyanhydride Microspheres as Drug Carriers", *Journal of Applied Polymer Science*, vol. 35, pp. 755–774 (1988).

Sankaram et al., "Cholesterol–Induced Fluid–Phase Immiscibility in Membranes", *Proc. Natl. Acad. Sci.*, vol. 88, pp. 8686–8690 (1991).

Scientific Apparatus Catalog 92/93 (VWR Scientific, 1991). "Syringes", pp. 1511–1513; "Filtration, Syringe Filters", pp. 766–768; "Filtration, Membranes", pp. 750–753; "Filtration, Filter Holders", p. 744.

Gramiak et al., Radiology, "Detection of Intracardiac Blood Flow by Pulsed Echo–Ranging", pp. 15–418 (1971).

Feigenbaum et al., Circulation, "Identification of Ultrasound Echoes from the Left Ventricle by Use of Intracardiac Injections of Indocyanine Green", vol. XL1, pp. 615–631 (1970).

Santaella, et al., *FEBS 13463*, "Extended In Vivo Blood Circulation Time of Fluorinated Liposomes", vol. 336, No. 3, pp. 481–484 (1993).

Brown and Langer, *Annual Review Medicine*, 1988, 39:221 29, Annual Review, Inc., "Transdermal Delivery of Drugs", pp. 221–229.

Moseley, et al., *Microbubbles: A Novel MR Susceptibility Contrast Agent*, abstract, 1991 Napa, California Meeting of the Society for Magnetic Resonance in Medicine.

Ter–Pogossian Tomography, Kee, et al., n, "Physical Principles and Instrumentation", Computed Body eds., Raven Press, New York, Chapter 1, pp. 1–7 (1988).

Aronberg, "Techniques", *Computed Body Tomography*, Kee, et al., eds., Raven Press, New York, Chapter 2, pp. 9–36 (1988).

Miller, *Ultrasonics* (Sep. 1981), "Ultrasonic detection of resonant cavitation bubbles in a flow tube by their second–harmonic emissions," pp. 217–224.

Dittrich, "Cardiac Muscle Ischemia and Infarction", *The Second Annual International Symposium on Contrast Agents in Diagnostic Ultrasound*, Atlantic City, NJ (May 7, 1996) (abstract).

Pantely, "Intravenous Contrast Echocardiography–Tissue Imaging & Quantification of Coronary Blood Flow", *The Second Annual International Symposium on Contrast Agents in Diagnostic Ultrasound*, Atlantic City, NJ (May 7, 1996) (abstract).

Schutt et al., "Osmotically Stabilized Microbubble Sonographic Contrast Agents", *Acad. Radiol.*, vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta*, 1192, pp. 61–70 (1994).

Frézard, et al., "Fluorinated Phospholipid–Based Vesicles as Potential Drug Carriers: Encapsulation/Sustaining of Drugs and Stability in Human Serum", *Art, Cells, Blood Subs.*, and *Immob. Biotech.*, 22(4), pp. 1403–1408 (1994).

Chang et al., "Semipermeable Aqueous Microcapsules", *Canadian J. of Phys. and Pharm.*, 1966, 44, 115–128.

Chang, "Semipermeable Microcapsules", *Science*, 1964, 146, 524–525.

Deasy, *Microencapsulation and Related Drug Processes*, 1983, vol. 20, Chs. 9 and 10, 195–240 (Marcel Dekker, Inc., NY).

Yeung et al., "Preparation of Microencapsulated Liposomes", *J. Microencapsulation*, 1988, 5, 331–337.

Mattrey et al., *Gas Emulsions as Ultrasound Contrast Agents; Preliminary Results in Rabbits and Dogs*, Investigative Radiology, vol. 29, Jun. Supp. 2, pp. S139–S141, 1994.

Meltzer et al., *Transmission of Ultrasonic Contrast Through the Lungs, Ultrasound in Med. & Biol.*, vol. 7, No. 4, 377–384, 1981.

PR Newswire, Apr. 1, 1986.

Swanson et al., Chapter 22, "Enhancement Agents for Ultrasound: Fundamentals", *Pharmaceuticals in Medical Imaging*, pp. 682–687 (1990).

Ophir et al., "Contrast Agents in Diagnostic Ultrasound", *Ultrasound in Med. & Biol.*, vol. 15, No. 4, pp. 319–333 (1989).

Jacobs, "Intraocular gas measurement using A–scan ultrasound", *Current Eye Research*, vol. 5, No. 8, pp. 575–578 (1986).

Lincoff et al., "Intravitreal Expansion of Perfluorocarbon Bubbles", *Arch. Ophthalmol.*, vol. 98, p. 1646, Sep. 1980.

Lincoff et al., "Intravitreal Longevity of Three Perfluorocarbon Gases", *Arch. Ophthalmol.*, vol. 98, pp. 1610–1611, Sep. 1980.

Lincoff et al., "The Perfluorocarbon Gases in the Treatment of Retinal Detachment", *Ophthalmology*, vol. 90, No. 5, pp. 546–551, May 1983.

Gardner et al., "A Survey of Intraocular Gas Use in North America", *Arch. Ophthalmol.*, vol. 106, pp. 1188–1189, Sep. 1988.

Unger et al., "Liposomal MR Contrast Agents", *J. Liposome Research*, 4(2), pp. 811–834 (1994).

Feinstein, Steven B., "Myocardial Perfusion Imaging: Contrast Echocardiography Today and Tomorrow," *Journal of the American College of Cardiology*, 8(1) :251–253 (1986).

Keller et al., "The Behavior of Sonicated Albumin Microbubbles Within the Microcirulation: A Basis for Their Use During Myocardial Contrast Echocardiography", *Circulation Res.*, 65(2) :458–465 (1989).

Lincoff et al., "Perfluoro–n–butane: A Gas for Maximum Duration Retinal Tamponade," *Arch Ophthalmology*, 101:460–462 (1983).

*Remington's Pharmaceutical Sciences*, John Hoover, managing ed., Mack Publishing Company, Easton, PA, pp. 295–298; 736; 1242–1244 (1975).

*Handbook of Pharmaceutical Excipients*, American Pharmaceutical Association, Washington, D.C. and The Pharmaceutical Society of Great Britain, London, England, pp. 181–183 (1986).

Barnhart et al., "Characteristics of Albunex™: Air–Filled Microspheres for Echocardiography Contrast Enhancement," *Investigative Radiology*, 25:S162–164 (1990).

Levene et al., "Characterization of Albunex™," *J. Acoust. Soc. Am.*, 87(Suppl.1) :569–70 (1990).

Miller et al., "Physiochemical Approaches to the Mode of Action of General Anesthetics," *J. Amer. Soc. Anesthesiologists*, 36(4) :339–351 (1972).

"Properties and Applications of the 'Freon' Fluorocarbons" in DuPont Freon Technical Bulletin B–2 (E.I. DuPont de Nemours and Company, Wilmington, DE), pp. 1–10 (1987).

"Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley and Sons, New York, 1:164–169 (1985).

"Concise Encyclopedia of Polymer Science and Engineering," *J. Kroschwitz*, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials*, 11:713–717 (1990).

Villanueva et al., "Characterization of Spatial Patters of Flow Within the Reperfused Myocardium by Myocardial Contrast Echocardiography", *Circulation*, vol. 88, No. 6, pp. 2596–2606 (Dec. 1993).

Desir et al., "Assessment of regional myocardial perfusion with myocardial contrast echocardiography in a canine model of varying degrees of coronary stenosis", *American Heart Journal*, vol. 127, No. 1, pp. 56–63 (Jan. 1994).

Sekins et al., "Lung Cancer Hyperthermia via Ultrasound and PFC Liquids", *Published in Proceedings of 5th International Symposium on Hyperthermic Oncology, Kyoto, Japan*, (3 pages) (Aug. 29–Sep. 3, 1998).

Pietersen, "A New Warning System for Fires of Electrical Origin", *CERN European Organization for Nuclear Research, Health and Safety Division*, pp. 1–5 (Mar. 1977).

Allcock, H.R., "Covalent Linkage of Proteins to Surface–Modified Poly(organophosphazenes) : Immobilization of Glucose–6–Phosphate Dehydrogenase and Trypsin", *Macromolecules*, 1986, 19, 1502–1508.

Allcock, H.R., "Schiff Base Coupling of Cyclic and High–Polymeric Phosphazenes to Aldehydes and Amines: Chemotherapeutic Models", *Macromolecules*, 1981, 14, 1616–1622.

Bloemberger, N., "Proton Relaxation Times in Paramagnetic Solutions", *J. Chem. Phys.*, 1957, 27(2), 572–573 and 595–596.

Canfield et al., "Incorporation of $\beta$–Carotene into Mixed Micelles", *Methods in Enzymology*, 1990, 189, 418–422.

Chemical Rubber Company Handbook of Chemistry and Physics, Robert C. Weast and David R. Lide (eds.), CRC Press, Inc., Boca Raton, FL, 1989–1990.

*Concise Encyclopedia of Biochemistry*, Second Edition, Walter de Gruyter & Co., New York, 1988, 282–283.

De Jager, R. et al., "Current Status of Cancer Immunodetection with Radiolabeled Human Monoclonal Antibodies", *Seminars in Nuclear Med.*, 1993, 23(2), 165–179.

Elgorab et al., "Solubilization of $\beta$–Carotene and Retinol into Aqueous Solutions of Mixed Micelles", *Biochem. Biophys. Acta.*, 1973, 306, 58–66.

Gioanni, J. et al., "Characterization of a New Surface Epitope Specific for Human Epithelial Cells Defined by a Monoclonal Antibody and Application to Tumor Diagnosis", *Cancer Res.*, 1987, 47, 4417–4424.

Goldberger, A.L., "Electrocardiography", *Harrison's Principles of Internal Medicine*, Thirteenth Ed., McGraw–Hill, Inc., 1994, Ch. 189, 954–966.

Kawabata, K. et al., "Effect of second–harmonic superimposition on efficient induction of sonochemical effect", *Ultrasonics Sonochemistry*, 1966, 3, 1–5.

Kean, D.M. and Smith, M.A., *Magnetic Resonance Imaging: Principles and Applications*, William and Wilkins, Baltimore, 1986.

Kohler,G. et al., "Continuous cultures of fused celles secreting antibody of predefined specificity", *Nature*, 1975, 256, 495–497.

Kornmesser et al., "Gastrointestinal Contrast Enhancement in MRI: First Clinical Experience with Gadolinium–DTPA", *Magnetic Resonance Imaging*, 1988, 6(1), 124.

Lundblad, R.L., "The Chemical Cross–Linking of Peptide Chains", *Techniques in Protein Modification*, CRC Press, Chapter 15, 249–267.

Matheson Company, Inc., *Matheson Gas Data Book*, 1966.

The Merck Index, An Encyclopedia of Chemicals, Drugs, and Biologicals, 10th Ed., Martha Windholz et al. (eds.), Merck & Co., Inc., 1983, 489–490.

Merimsky, O. et al., "Antigens and Antibodies in Malignant Melanoma", *Tumor Biol.*, 1994, 15, 188–202.

Mousa, S.A. et al., "Intravenous Antiplatelet Efficacy and Safety of the Platelet GPIIb/IIIa Antagonist, DMP 728 in Anesthetized Dogs", *Thrombosis Res.*, 1994, 76(2), 109–119.

Nicol, L. et al., "Immunoscintigraphie Des Mélanomes Malins", *Pathologie Biologie*, 1990, 38(8), 866–869 (Summary of article in English).

Shahinian, S. et al., "A novel strategy affords high–yield coupling of antibody Fab' fragments to liposomes", *Biochimica et Biophysica Acta*, 1995, 1239, 157–167.

Shinoda, K., et al., "The Formation of Micelles", *Colloidal Surfactant*, Academic Press, New York, 1963, Chapter 1, 1–88.

Siegall, "Targeted Toxins as Anticancer Agents", *Cancer*, 1994, 74(3), 1006–1012.

Skorton, D.J. et al., "Ultrasonic Characterization of Cardiovascular Tissue", *Cardiac Imaging: A Companion to Braunwald's Heart Disease*, Marcus et al. (eds.), W.B. Saunders Co., Harcourt Brace Jovanovich, Inc., Philadelphia, Pennsylvania, 1991, 536–556.

Solomon, I., "Relaxation Processes in a System of Two Spins", *Phys. Rev.*, 1955, 99(2), 559–565.

Sutherland et al., "Color Doppler Myocardial Imaging: A New Technique for the Assessment of Myocardial Function", *J. Am. Soc of Echocardiogr*, 1994, 7(5), 441–458.

Tagliaferri, P. et al., "Pharmacological modulation of peptide growth factor receptor expression on tumor cells as a basis for cancer therapy", *Anti–Cancer Drugs*, 1994, 5, 379–393.

Thorpe, P.E. et al., "Antibody–directed targeting of the vasculature of solid tumors", *Breast Cancer Res. and Treatment*, 1995, 36, 237–251.

Tsuji, Y. et al., "Identification of Two Different Surface Epitopes of Human Ovarian Epithelial Carcinomas by Monoclonal Antibodies", *Cancer Res.*, 1985, 45, 2358–2362.

Ulendorf, "Physics of Ultrasound Contrast Imaging: Scattering in the Linear Range", *IEEE Transactions on Ultrasonics, Ferroelectrics, and Frequency Control*, 1994, 41(1), 70–79.

van Boeckel, C.A.A. et al., "Synthesis of Phosphatidyl–α–Glucosyl Glycerol Containing a Dioleoyl Phosphatidyl Moiety. Application of the Tetraisopropyldisiloxane–1, 3–Diyl (Tips) Protecting Group in Sugar Chemistry. Part III", *Tetrahedron*, 1985, 41, 4545.

Van Dongen et al., "Progress in radioimmunotherapy of head and neck cancer", *Oncology Reports*, 1994, 1, 259–264.

Wu, T.Z., "Immunology of the human papilloma virus in relation to cancer", *Curr. Opin. In Immunol.*, 1994, 6, 746–754.

Xueyong, Z. et al., "Use of MG Series Monoclonal Antibodies in the Diagnosis and Experimental Targeting Therapy of Gastric Cancer", *Chin Med. Sci. J.*, 1991, 6(1), 56–59.

Reexamination of U.S. Patent No. 5,527,521, Reexam Control No. 90/004, 719.

Reexamination of U.S. Patent No. 5,547,656, Reexam Control No. 90/004,720.

Nomura et al., "US Contrast Enhancement of Hepatic Tumor with Helium Gas Microbubbles: A Preliminary Report", *Jpn. J. Med. Ultrasonics*, 1991, 18(5), (Japanese with English language abstract).

Lindner et al., "Myocardial Perfusion Characteristics and Hemodynamic Profile of MRX–115, a Venous Echocardiographic Contrast Agent, During Acute Myocardial Infarction", *J. Am. Soc. Echocardiography*, 1998, 11(1), 36–46.

Regen et al., "Polymerized Phosphatidylcholine Vesicles. Synthesis and Characterization", *J. Am. Chem. Soc.*, 1982, 104(3), 191–195.

Wei et al., "Quantification of Myocardial Blood Flow with Ultrasound–Induced Destruction of Microbubbles Administered as a Constant Venous Infusion", *Circulation*, 1998, 97, 473–483.

Hynynen et al., "The Usefulness of a Contrast Agent and Gradient Recalled Acquistion in a Steady–State Imaging Sequence for Magnetic Resonance Imaging–Guided Noninvasive Ultrasound Surgery", *Investigative Radiology*, 1994, 29(10), 897–903.

Lejbkowicz et al., "The response of normal and malignant cells to ultrasound in vitro", Database *BIOSIS*, No. 1993:95122245 (abstract only).

Jackson et al., "Effect of ultrasound therapy on the repair of Achilles tendon injuries in rats", *Med. Sci. Sports Exercise*, 1991, 23(2), 171–176.

Maxwell, "Therapeutic Ultrasound: Its Effects on the Cellular and Molecular Mechanisms of Inflammation and Repair", *Physiotherapy*, 1992, 78(6), 421–426.

Tuncay et al., "Expression of Genes Associated with Tissue Remodeling Upon Ultrasound Perturbation in the Gingival Fibroblast", *J. Dental Res.*, 1996, 75, 143, (abstract only).

Wang et al., "Low Intensity Ultrasound Treatment Increase Strength in a Rat Femoral Fracture Model", *J. Orthopaedic Res.*, 1994, 12(1), 40–47.

Yang et al., "Exposure to Low–Intensity Ultrasound Increases Aggrecan Gene Expression in a Rat Femur Fracture Model", *J. Orthopaedic Res.*, 1996, 14(5), 802–809.

Young et al., "Effect of therapeutic ultrasound on the healing of full–thickness excised skin lesions", *Ultrasonics*, 1990, 28(3), 175–180.

Young et al., "The Effect of Therapeutic Ultrasound on Angiogenesis", *Ultrasound Med. Biol.*, 1990, 16(3), 261–269.

Chortkoff, B.S. et al., "Pharmacokinetics Do Not Explain the Absence of an Anesthetic Effect of Perfluoropropane or Perfluoropentane," *Anesth. Analg.*, 1994, 79, 234–237.

Sharma, S.K. et al., "Emulsification Methods For Perfluorochemicals," *Drug Develop. Indust. Pharm.*, 1988, 14(15–17), 2371–2376.

Tilcock, C. et al., "PEG–coated Lipid Vesicles with Encapsulated Technetium–99m as Blood Pool Agents for Nuclear Medicine," *Nucl. Med. Biol.*, 1994, 21(2), 165–170.

Tilcock, C. et al., "$^{99m}$Tc–labeling of Lipid Vesicles Containing the Lipophilic Chelator PE–DTTA: Effect of Tin–to–chelate Ratio, Chelate Content and Surface Polymer on Labeling Efficiency and Biodistribution Behavior," *Nucl. Med. Biol.*, 1994, 21(1), 89–96.

Zarif, L.et al., "Synergistic Stabilization of Perfluorocarbon– Pluronic F–68 Emulsion by Perfluoroalkylated Polyhydroxylated Surfactants," *JAOCS*, 1989, 66(10), 1515–1523.

Ding, X.C., "Scavenging effect of EDTA–fluorocarbon microspheres on 210 lead,"*Chung Kuto Yao Li Hsueh Pao*, 1989, 10(5), 473–475 (abstract only).

MCE End Systole      $^{99m}$Tc Sestamibi

C      D

METHODS FOR ULTRASOUND IMAGING INVOLVING THE USE OF A CONTRAST AGENT AND MULTIPLE IMAGES AND PROCESSING OF SAME

CROSS-REFERENCE TO RELATED APPLICATIONS

This application is a continuation-in-part of U.S. application Ser. No. 08/932,273, filed Sep. 17, 1997, now allowed, which in turn is a continuation-in-part of application Ser. No. 08/666,129, filed on Jun. 19, 1996 now U.S. Pat. No. 6,033,645, issued, Mar. 7, 2000 and U.S. application Ser. No. 08/660,032, filed Jun. 6, 1996, now abandoned, the latter of which is a continuation-in-part of U.S. application Ser. No. 08/640,464, filed May 1, 1996, now abandoned, which is a continuation-in-part of U.S. application Ser. No.08/497,684, filed Jun. 7, 1995, now abandoned. The disclosures of each of the foregoing applications are hereby incorporated herein by reference, in their entireties.

FIELD OF THE INVENTION

The present invention relates to improved methods for diagnostic imaging. More particularly, the present invention relates to improved methods for ultrasound imaging which involve the administration to a patient of a contrast agent and the use of multiple images and processing of same.

BACKGROUND OF THE INVENTION

A variety of imaging techniques have been used to diagnose diseases. Included among these imaging techniques is X-ray imaging. In X-rays, the images produced reflect the different densities of structures and tissue in the body of the patient. To improve the diagnostic usefulness of this imaging technique, contrast agents may be employed to increase the density of tissues of interest relative to surrounding tissues. Examples of such contrast agents include, for example, barium and iodinated compounds, which may be used for X-ray studies of the gastrointestinal region, including the esophagus, stomach, intestines and rectum. Contrast agents may also be used for computed tomography (CT) and computer assisted tomography (CAT) studies to improve visualization of tissue of interest, for example, the gastrointestinal tract.

Magnetic resonance imaging (MRI) is another imaging technique which, unlike X-rays, does not involve ionizing radiation. MRI may be used for producing cross-sectional images of the body in a variety of scanning planes such as, for example, axial, coronal, sagittal or orthogonal. MRI employs a magnetic field, radio frequency energy and magnetic field gradients to make images of the body. The contrast or signal intensity differences between tissues mainly reflect the T1 (longitudinal) and T2 (transverse) relaxation values and the proton density, which generally corresponds to the free water content, of the tissues. To change the signal intensity in a region of a patient by the use of a contrast medium, several possible approaches are available. For example, a contrast medium may be designed to change either the T1, the T2 or the proton density.

Generally speaking, MRI requires the use of contrast agents. If MRI is performed without employing a contrast agent, differentiation of the tissue of interest from the surrounding tissues in the resulting image may be difficult. In the past, attention has focused primarily on paramagnetic contrast agents for MRI. Paramagnetic contrast agents involve materials which contain unpaired electrons. The unpaired electrons act as small magnets within the main magnetic field to increase the rate of longitudinal (T1) and transverse (T2) relaxation. Paramagnetic contrast agents typically comprise metal ions, for example, transition metal ions, which provide a source of unpaired electrons. However, these metal ions are also generally highly toxic. In an effort to decrease toxicity, the metal ions are typically chelated with ligands.

Metal oxides, most notably iron oxides, have also been employed as MRI contrast agents. While small particles of iron oxide, for example, particles having a diameter of less than about 20 nm, may have desirable paramagnetic relaxation properties, their predominant effect is through bulk susceptibility. Nitroxides are another class of MRI contrast agent which are also paramagnetic. These have relatively low relaxivity and are generally less effective than paramagnetic ions.

The existing MRI contrast agents suffer from a number of limitations. For example, increased image noise may be associated with certain contrast agents, including contrast agents involving chelated metals. This noise generally arises out of intrinsic peristaltic motions and motions from respiration or cardiovascular action. In addition, the signal intensity for contrast agents generally depends upon the concentration of the agent as well as the pulse sequence employed. Absorption of contrast agents can complicate interpretation of the images, particularly in the distal portion of the small intestine, unless sufficiently high concentrations of the paramagnetic species are used. See, e.g., Kornmesser et al., *Magnetic Resonance Imaging*, 6:124 (1988).

Other contrast agents may be less sensitive to variations in pulse sequence and may provide more consistent contrast. However, high concentrations of particulates, such as ferrites, can cause magnetic susceptibility artifacts which are particularly evident, for example, in the colon where the absorption of intestinal fluid occurs and the superparamagnetic material may be concentrated.

Toxicity is another problem which is generally associated with currently available contrast agents, including contrast agents for MRI. For example, ferrites often cause symptoms of nausea after oral administration, as well as flatulence and a transient rise in serum iron. The gadolinium ion, which is complexed in Gd-DTPA, is highly toxic in free form. The various environments of the gastrointestinal tract, including increased acidity (lower pH) in the stomach and increased alkalinity (higher pH) in the intestines, may increase the likelihood of decoupling and separation of the free ion from the complex.

Ultrasound is another valuable diagnostic imaging technique for studying various areas of the body, including, for example, the vasculature, such as tissue microvasculature. Ultrasound provides certain advantages over other diagnostic techniques. For example, diagnostic techniques involving nuclear medicine and X-rays generally involves exposure of the patient to ionizing electron radiation. Such radiation can cause damage to subcellular material, including deoxyribonucleic acid (DNA), ribonucleic acid (RNA) and proteins. Ultrasound does not involve such potentially damaging radiation. In addition, ultrasound is relatively inexpensive relative to other diagnostic techniques, including CT and MRI, which require elaborate and expensive equipment.

Ultrasound involves the exposure of a patient to sound waves. Generally, the sound waves dissipate due to absorption by body tissue, penetrate through the tissue or reflect off of the tissue. The reflection of sound waves off of tissue, generally referred to as backscatter or reflectivity, forms the basis for developing an ultrasound image. In this connection, sound waves reflect differentially from different body tissues. This differential reflection is due to various factors, including the constituents and the density of the particular tissue being observed. Ultrasound involves the detection of the differentially reflected waves, generally with a transducer that can detect sound waves having a frequency of one megahertz (MHZ) to ten MHZ. The detected waves can be integrated into an image which is quantitated and the quantitated waves converted into an image of the tissue being studied.

As with the diagnostic techniques discussed above, ultrasound also generally involves the use of contrast agents. Exemplary contrast agents include, for example, suspensions of solid particles, emulsified liquid droplets, and gas-filled bubbles. See, e.g., Hilmann et al., U.S. Pat. No. 4,466,442, and published International Patent Applications WO 92/17212 and WO 92/21382. Widder et al., published application EP-A-0 324 938, discloses stabilized microbubble-type ultrasonic imaging agents produced from heat-denaturable biocompatible protein, for example, albumin, hemoglobin, and collagen.

The use of echocardiography for the diagnosis of cardiovascular diseases has generally been limited to indirect methods which involve the detection and quantitation of abnormalities in wall motion of the heart. Echocardiography has also been used in connection with methods for detecting pathologies of the heart to identify cardiac masses, emboli, thrombi, vegetative lesions (endocarditis), myxomas, and other lesions. See, e.g., M. L. Marcus et al., *Cardiac Imaging: A Companion to Braunwald's Heart Disease*, W. B. Saunders Co., Harcourt Brace Jovanovich, Inc., Philadelphia, Pa., pp. 536–556 (1991). Emboli or thrombi may be associated with certain cardiovascular diseases, particularly arrhythmic disorders. As used throughout the present disclosure, the term "arrhythmic disorder" refers to cardiovascular disorders which are characterized by the presence of an arrhythmia, i.e., a variation from the normal rhythm of the heart beat. Examples of arrhythmic disorders include, for example, sinus arrhythmia, premature beat, heart block, atrial fibrillation, atrial flutter, pulsus alternans and paroxysmal tachycardia. Of these, atrial fibrillation (AF) is particularly problematic, and is characterized by a chaotic, rapid ECG pattern of rates of greater than about 350 beats per minute. AF may occur in paroxysmal and persistent forms, and may occur in the presence or absence of other underlying cardiovascular diseases, such as rheumatic heart disease, coronary artery disease, hypertension or hyperthyroidism. AF is more common in males, and tends to increase in incidence with increasing age. Hemodynamic consequences of AF are manifest as weakness, fainting, shortness of breath and general chest discomfort. AF is often a predisposition for systemic emboli and/or thrombi, which can lead, for example, to stroke due to thrombus formation in the fibrillating atrium. To prevent emboli and/or thrombi in patients suffering from AF, anticoagulants, such as warfarin (coumadin) are frequently prescribed. However, a serious drawback of this type of therapy is that the use of anticoagulants is associated with an increased risk of hemorrhaging, especially when anticoagulants are used over an extended period of time. Accordingly, anticoagulants are preferably only administered to patients who are in real need of such treatment, i.e., patients experiencing emboli and/or thrombi.

The quality of images produced from ultrasound has improved significantly. Nevertheless, further improvement is needed, particularly with respect to images involving vasculature in tissues that are perfused with a vascular blood supply. Accordingly, there is a need for improved ultrasound techniques, including improved contrast agents which are capable of providing medically useful images of the vasculature and vascular-related organs, as well as improved techniques which enable the detection of emboli and/or thombi, for example, prior to the administration of an anticoagulant.

The reflection of sound from a liquid-gas interface is extremely efficient. Accordingly, bubbles, including gas-filled bubbles, are useful as contrast agents. The term "bubbles", as used herein, refers to vesicles which are generally characterized by the presence of one or more membranes or walls surrounding an internal void that is filled with a gas or precursor thereto. Exemplary bubbles include, for example, liposomes, micelles and the like. As discussed more fully hereinafter, the effectiveness of bubbles as contrast agents depends upon various factors, including, for example, the size and/or elasticity of the bubble.

With respect to the effect of bubble size, the following discussion is provided. As known to the skilled artisan, the signal which is reflected off of a bubble is a function of the radius ($r^6$) of the bubble (Rayleigh Scatterer). Thus, in the frequency range of diagnostic ultrasound, a bubble having a diameter of 4 micrometer ($\mu$m) possesses about 64 times the scattering ability of a bubble having a diameter of 2 $\mu$m. Thus, generally speaking, the larger the bubble, the greater the reflected signal.

However, bubble size is limited by the diameter of capillaries through which the bubbles must pass. Generally, contrast agents which comprise bubbles having a diameter of greater than 10 $\mu$m can be dangerous since microvessels may be occluded. Accordingly, it is desired that greater than about 99% of the bubbles in a contrast agent have a diameter of less than 10 $\mu$m. Mean bubble diameter is important also, and should be greater than 1 $\mu$m, with greater than 2 $\mu$m being preferred. The volume weighted mean diameter of the bubbles should be about 7 to 10 micrometer.

The elasticity of bubbles is also important. This is because highly elastic bubbles can deform, as necessary, to "squeeze" through capillaries and/or to permit the flow of blood around the bubbles. This decreases the likelihood of occlusion. The effectiveness of a contrast agent which comprises bubbles is also dependent on the bubble concentration. Generally, the higher the bubble concentration, the greater the reflectivity of the contrast agent.

Another important characteristic which is related to the effectiveness of bubbles as contrast agents is bubble stability. As used herein, particularly with reference to gas-filled bubbles, "bubble stability" refers to the ability of bubbles to retain gas entrapped therein after exposure to a pressure greater than atmospheric pressure. To be effective as contrast agents, bubbles generally need to retain greater than 50% of entrapped gas after exposure to pressure of 300 millimeters (mm) of mercury (Hg) for about one minute. Particularly effective bubbles retain 75% of the entrapped gas after being exposed for one minute to a pressure of 300 mm Hg, with an entrapped gas content of 90% providing especially effective contrast agents. It is also highly desirable that, after release of the pressure, the bubbles return to their original size. This is referred to generally as "bubble resilience."

Bubbles which lack desirable stability provide poor contrast agents. If, for example, bubbles release the gas entrapped therein in vivo, reflectivity is diminished. Similarly, the size of bubbles which possess poor resilience will be decreased in vivo, also resulting in diminished reflectivity.

The stability of bubbles disclosed in the prior art is generally inadequate for use as contrast agents. For example, the prior art discloses bubbles, including gas-filled liposomes, which comprise lipid-containing walls or membranes. See, e.g., Ryan et al., U.S. Pat. Nos. 4,900,540 and 4,544,545; Tickner et al., U.S. Pat. No. 4,276,885; Klaveness et al., WO 93/13809 and Schneider et al., EPO 0 554 213 and WO 91/15244. Lanza et al., WO 93/20802 discloses acoustically reflective oligolamellar liposomes, which are multilamellar liposomes with increased aqueous space between bilayers or have liposomes nested within bilayers in a nonconcentric fashion, and thus contain internally separated bilayers. Their use as ultrasonic contrast agents to enhance ultrasonic imaging, and in monitoring a drug delivered in a liposome administered to a patient, is also described. D'Arrigo, U.S. Pat. Nos. 4,684,479 and 5,215,680 disclose gas-in-liquid emulsions and lipid-coated microbubbles, respectively.

Many of the bubbles disclosed in the prior art have undesirably poor stability. Thus, the prior art bubbles are more likely to rupture in vivo resulting, for example, in the untimely release of any therapeutic and/or diagnostic agent contained therein. Various studies have been conducted in an attempt to improve bubble stability. Such studies have included, for example, the preparation of bubbles in which the membranes or walls thereof comprise proteins, such as albumin, or materials which are apparently strengthened via crosslinking. See, e.g., Klaveness et al., WO 92/17212, in which there are disclosed bubbles which comprise proteins crosslinked with biodegradable crosslinking agents. A presentation was made by Moseley et al., at a 1991 Napa, Calif. meeting of the Society for Magnetic Resonance in Medicine, which is summarized in an abstract entitled "Microbubbles: A Novel MR Susceptibility Contrast Agent." The microbubbles described by Moseley et al. comprise air coated with a shell of human albumin. Alternatively, bubble membranes can comprise compounds which are not proteins but which are crosslinked with biocompatible compounds. See, e.g., Klaveness et al., WO 92/17436, WO 93/17718 and WO 92/21382.

Prior art techniques for stabilizing bubbles, including the use of proteins in the outer membrane or crosslinking of the membrane components, suffer from various drawbacks. For example, the crosslinking described above generally involves the use of new materials, including crosslinked proteins or other compounds, for which the metabolic fate is unknown. In addition, crosslinking requires additional chemical process steps, including isolation and purification of the crosslinked compounds. Moreover, the use in bubble membranes of proteins, such as albumin, and crosslinking of the bubble membrane components, can impart rigidity to the walls of the bubbles. This results in bubbles having reduced elasticity and, therefore, a decreased ability to deform and pass through capillaries. Thus, there is a greater likelihood of occlusion of vessels with prior art contrast agents that involve proteins and/or crosslinking.

Accordingly, new and/or better contrast agents and methods for providing same are needed. The present invention is directed to this, as well as other, important ends.

SUMMARY OF THE INVENTION

The present invention is directed, in part, to improved methods for diagnostic imaging. Specifically, in one embodiment, there is provided a method for providing an image of an internal region of a patient comprising (a) administering to the patient a contrast agent which comprises, in an aqueous carrier, a lipid, protein or polymer, and a gas, and (b) scanning the patient using ultrasound imaging to obtain a visible image of the region, wherein said scanning step comprises:

(i) applying a first quantity of ultrasound energy to the patient to provide a first image;

(ii) applying substantially immediately thereafter a second quantity of ultrasound energy to the patient to provide a second image; and (iii) processing said first and second images.

Another embodiment of the invention relates to a method for diagnosing the presence of diseased tissue in a patient comprising (a) administering to the patient a contrast agent which comprises, in an aqueous carrier, a lipid, protein or polymer, and a gas, and (b) scanning the patient using ultrasound imaging to obtain a a visible image of any diseased tissue in the patient, wherein said scanning step comprises:

(i) applying a first quantity of ultrasound energy to the patient to provide a first image;

(ii) applying substantially immediately thereafter a second quantity of ultrasound energy to the patient to provide a second image; and (iii) processing said first and second images.

These and other aspects of the invention will become more apparent from the following detailed description.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
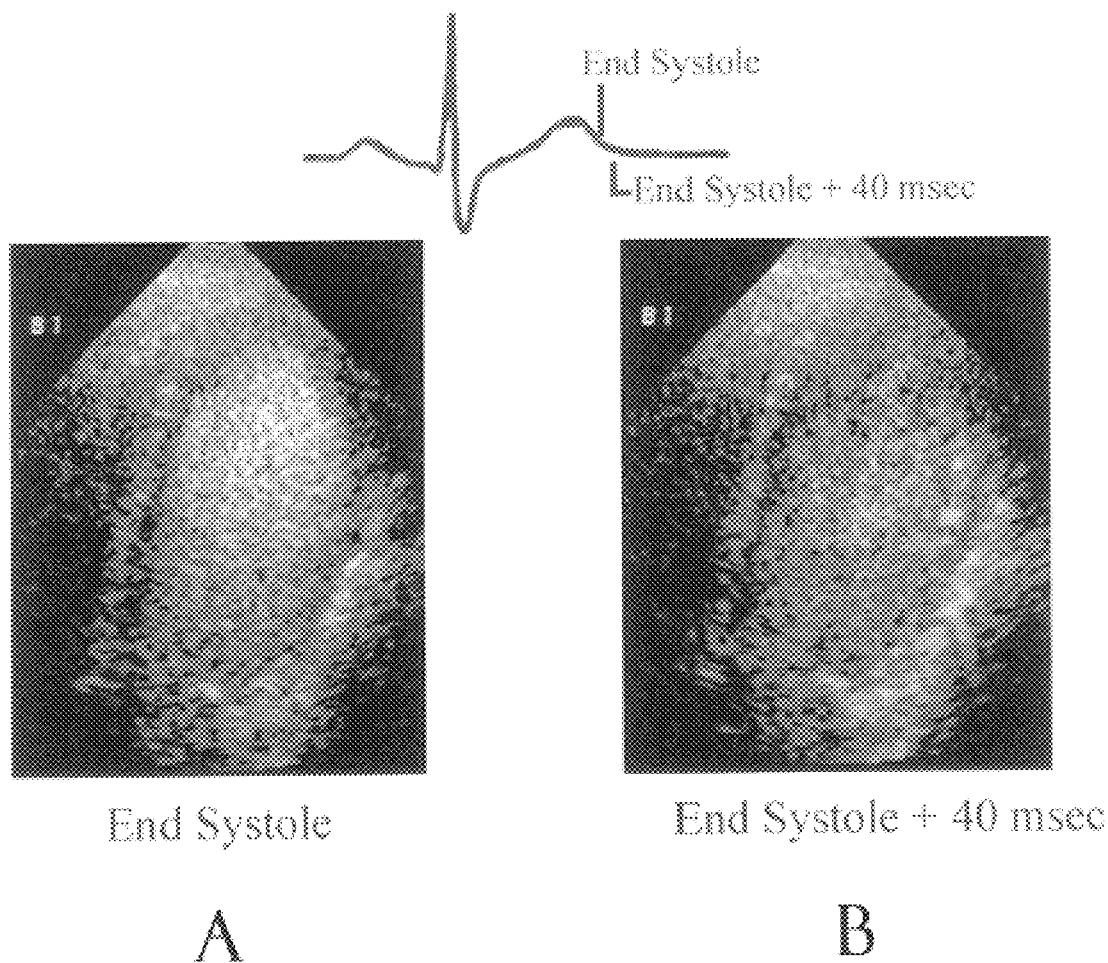
FIG. 1 includes photographs (photographs A and B) which are typical of ultrasound images of the cardiovascular region that may be obtained employing methods of the present invention. Photograph A corresponds to an ultrasound image obtained at about end systole on an ECG. Photograph B corresponds to an ultrasound image obtained at about 40 milliseconds after end systole on the ECG. Representative locations in an ECG waveform at which ultrasound images exemplified in photographs A and B may be obtained, according to an embodiment of the present invention, are also included in FIG. 1.

As employed above and throughout the disclosure, the following terms, unless otherwise indicated, shall be understood to have the following meanings.

"Lipid" refers to a synthetic or naturally-occurring compound which is generally amphipathic and biocompatible. The lipids typically comprise a hydrophilic component and a hydrophobic component. Exemplary lipids include, for example, fatty acids, neutral fats, phosphatides, glycolipids, aliphatic alcohols, waxes, terpenes, steroids and surfactants.

"Lipid composition" refers to a composition which comprises a lipid compound, typically in an aqueous medium. Exemplary lipid compositions include suspensions, emulsions and vesicle compositions.

"Lipid formulation" refers to a lipid composition which also comprises a bioactive agent.

"Vesicle" refers to a spherical entity which is generally characterized by the presence of one or more walls or membranes which form one or more internal voids. Vesicles may be formulated, for example, from lipids, including the various lipids described herein, proteinaceous materials, or polymeric materials, including natural, synthetic and semi-synthetic polymers. Preferred vesicles are those which comprise walls or membranes formulated from lipids. In these preferred vesicles, the lipids may be in the form of a monolayer or bilayer, and the mono- or bilayer lipids may be used to form one or more mono- or bilayers. In the case of more than one mono- or bilayer, the mono- or bilayers may be concentric. Lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). Similarly, the vesicles prepared from proteins or polymers may comprise one or more concentric walls or membranes. The walls or membranes of vesicles prepared from proteins or polymers may be substantially solid (uniform), or they may be porous or semi-porous. The vesicles described herein include such entities commonly referred to as, for example, liposomes, micelles, bubbles, microbubbles, microspheres, lipid-, polymer- and/or protein-coated bubbles, microbubbles and/or microspheres, microballoons, aerogels, clatlirate bound vesicles, and the like. The internal void of the vesicles may be filled with a liquid (including, for example, an aqueous liquid), a gas, a gaseous precursor, and/or a solid or solute material, including, for example, a targeting ligand and/or a bioactive agent, as desired.

"Liposome" refers to a generally spherical cluster or aggregate of amphipathic compounds, including lipid compounds, typically in the form of one or more concentric layers, for example, bilayers. They may also be referred to herein as lipid vesicles. The liposomes may be formulated, for example, from ionic lipids and/or non-ionic lipids. Liposomes which are formulated from non-ionic lipids may also be referred to as "niosomes."

"Micelle" refers to colloidal entities formulated from lipids. In certain preferred embodiments, the micelles comprise a monolayer or hexagonal H2 phase configuration. In other preferred embodiments, the micelles may comprise a bilayer configuration.

"Aerogel" refers to generally spherical entities which are characterized by a plurality of small internal voids. The aerogels may be formulated from synthetic materials (for example, a foam prepared from baking resorcinol and formaldehyde), as well as natural materials, such as polysaccharides or proteins.

"Clathrate" refers to a solid, semi-porous or porous particle which may be associated with vesicles. In preferred form, the clathrates may form a cage-like structure containing cavities which comprise the vesicles. One or more vesicles may be bound to the clathrate. A stabilizing material may, if desired, be associated with the clathrate to promote the association of the vesicle with the clathrate. Suitable materials from which clathrates may be formulated include, for example, porous apatites, such as calcium hydroxyapatite, and precipitates of polymers and metal ions, such as alginic acid precipitated with calcium salts.

The vesicles of the present invention preferably contain a gas or gaseous precursor. "Gas filled vesicle" refers to vesicles in which there is encapsulated a gas. "Gaseous precursor filled vesicle" refers to vesicles in which there is encapsulated a gaseous precursor. The vesicles may be minimally, partially or substantially completely filled with the gas and/or gaseous precursor. In certain preferred embodiments, the vesicles may be substantially or completely filled with the gas and/or gaseous precursor. The term "substantially", as used in reference to the gas and/or gaseous precursor filled vesicles, means that greater than about 50% of the internal void volume of the vesicle consists of a gas. Preferably, greater than about 60% of the internal void of the substantially filled vesicles consists of a gas, with greater than about 70% being more preferred. Even more preferably, greater than about 80% of the internal void of the substantially filled vesicles consists of a gas, with greater than about 90% being still more preferred. In particularly preferred embodiments, greater than about 95% of the internal void of the vesicles consists of a gas, with about 100% being especially preferred. Although not considered a preferred embodiment of the present invention, the vesicles may also contain, if desired, no or substantially no gas or gaseous precursor.

"Vesicle composition" refers to a composition, typically in an aqueous medium, which comprises vesicles.

"Vesicle formulation" refers to a vesicle composition which also comprises a bioactive agent. Suitable vesicles or vesicle species for use in vesicle formulations include, for example, gas filled vesicles and gaseous precursor filled vesicles.

"Emulsion" refers to a mixture of two or more generally immiscible liquids, and is generally in the form of a colloid which, upon drying, forms a porous solid matrix. The solid matrix is porous, i.e., the matrix forms a lattice with microvoids or microcavities, as a result, for example, of a spray drying blowing agent used in the drying process. The mixture may comprise, for example, lipids, which may be homogeneously or heterogeneously dispersed throughout the emulsion. Alternatively, the lipids may be aggregated in the form of, for example, clusters or layers, including mono- or bilayers.

"Suspension" or "dispersion" refers to a mixture, preferably finely divided, of two or more phases (solid, liquid or gas), such as, for example, liquid in liquid, solid in liquid, gas in liquid, and the like, which can preferably remain stable for extended periods of time.

"Hexagonal H II phase structure" refers to a generally tubular aggregation of lipids in liquid media, for example, aqueous media, in which the hydrophilic portion(s) of the lipids generally face inwardly in association with a liquid environment inside the tube. The hydrophobic portion(s) of the lipids generally radiate outwardly and the complex assumes the shape of a hexagonal tube. A plurality of tubes is generally packed together in the hexagonal phase structure.

"Patient" refers to animals, including mammals, preferably humans.

The phrases "internal region of a patient" and "region of interest" refer to the entire patient or to a particular area or portion of the patient. Internal regions of a patient and regions of interest may include, for example, areas being imaged with diagnostic imaging and/or areas being treated with a bioactive agent. Exemplary of such areas include, for example, the heart region, including myocardial tissue, as well as other bodily tissues, including the vasculature and circulatory system and cancerous tissue, as well as. The phrase "vasculature," as used herein, denotes the blood vessels in the body or in an organ or part of the body.

"Arrhythmic disorder" refers to cardiovascular disorders which are characterized by the presence of an arrhythmia, i.e., a variation from the normal rhythm of the heart beat. Examples of arrhythmic disorders include, for example, sinus arrhythmia, premature beat, heart block, atrial fibrillation, atrial flutter, pulsus alternans and paroxysmal tachycardia.

"Bioactive agent" refers to a substance which may be used in connection with an application that is therapeutic or diagnostic in nature, such as in methods for diagnosing the presence or absence of a disease in a patient and/or in methods for the treatment of disease in a patient. As used herein, "bioactive agent" refers also to substances which are capable of exerting a biological effect in vitro and/or in vivo. The bioactive agents may be neutral or positively or negatively charged. Examples of suitable bioactive agents include diagnostic agents, pharmaceuticals, drugs, synthetic organic molecules, proteins, peptides, vitamins, steroids and genetic material, including nucleosides, nucleotides and polynucleotides.

"Diagnostic agent" refers to any agent which may be used in connection with methods for imaging an internal region of a patient and/or diagnosing the presence or absence of a disease in a patient. Exemplary diagnostic agents include, for example, contrast agents for use in connection with ultrasound, magnetic resonance imaging or computed tomography of a patient including, for example, the lipid and/or vesicle compositions described herein.

"Polymer", as used herein, refers to molecules formed from the chemical union of two or more repeating units. Accordingly, included within the term "polymer" may be, for example, dimers, trimers and oligomers. The polymer may be synthetic, naturally-occurring or semisynthetic. In preferred form, the term "polymer" refers to molecules which comprise 10 or more repeating units. The polymers which may be employed in the present compositions may possess surface active properties, i.e., they may be polymeric surfactants.

"Thickening agent" refers to any of a variety of generally hydrophilic materials which, when incorporated in the lipid and/or vesicle compositions described herein, may act as viscosity modifying agents, emulsifying and/or solubilizing agents, suspending agents, and tonicity raising agents. It is contemplated that the thickening agents may be capable of aiding in maintaining the stability of the compositions due to such properties.

"Dispersing agent" refers to a surface-active agent which, when added to a suspending medium of colloidal particles, including, for example, certain of the lipid and/or vesicle compositions described herein, may promote uniform separation of particles. In certain preferred embodiments, the dispersing agent may comprise a polymeric siloxane compound.

"Genetic material" refers generally to nucleotides and polynucleotides, including deoxyribonucleic acid (DNA) and ribonucleic acid (RNA). The genetic material may be made by synthetic chemical methodology known to one of ordinary skill in the art, or by the use of recombinant technology, or by a combination of the two. The DNA and RNA may optionally comprise unnatural nucleotides and may be single or double stranded. "Genetic material" refers also to sense and anti-sense DNA and RNA, that is, a nucleotide sequence which is complementary to a specific sequence of nucleotides in DNA and/or RNA.

"Pharmaceutical" or "drug" refers to any therapeutic or prophylactic agent which may be used in the treatment (including the prevention, diagnosis, alleviation, or cure) of a malady, affliction, disease or injury in a patient. Therapeutically useful peptides, polypeptides and polynucleotides may be included within the meaning of the term pharmaceutical or drug.

"Diagnostic artifact" refers generally to imperfections, defects and/or flaws in a diagnostic image including, for example, ultrasound, computed tomography and magnetic resonance images, which may hamper and/or prevent visualization of a region of interest. Diagnostic artifacts may be associated with excess and/or insufficient concentrations of contrast agent. In the case of excess concentrations, diagnostic artifacts may be manifested as undesired darkening and/or shadowing. It is contemplated that the excess concentration of contrast agent may form, for example, an obstruction or barrier, which may prevent penetration, for example, of sound waves in the case of ultrasound, through the contrast agent and into tissues and/or structures in the patient which are proximate the contrast agent and/or the region being imaged. In the case of insufficient concentrations, diagnostic artifacts may be manifested as undesired lightening and/or brightening.

"Ultrasound artifact" and "computed tomography artifact" refer respectively to diagnostic artifacts associated with ultrasound and computed tomography.

"Substantial elimination" refers to the prevention or substantial prevention of the occurrence of diagnostic artifacts in a diagnostic image. The term "substantial prevention" means that at least about 50% of the artifacts may be eliminated by the methods of the present invention as compared to at least one prior art diagnostic method. Preferably, at least about 60% of the artifacts may be eliminated by the methods of the present invention as compared to at least one prior art diagnostic method, with the elimination of at least about 70% of the artifacts being more preferred. Even more preferably, at least about 80% of the artifacts may be eliminated by the methods of the present invention as compared to at least one prior art diagnostic method, with the elimination of at least about 90% of the artifacts being still more preferred. Yet more preferably, at least about 95% of the artifacts may be eliminated by the methods of the present invention as compared to at least one prior art diagnostic method, with the elimination of at least about 100% being still more preferred.

The terms "administered" and "administration" refer generally to the administration to a patient of a biocompatible material, including, for example, lipid and/or vesicle compositions and flush agents. Accordingly, "administered" and "administration" refer, for example, to the injection into a blood vessel of lipid and/or vesicle compositions and/or flush agents. The terms "administered" and "administration" can also refer to the delivery of lipid and/or vesicle compositions and/or flush agents to a region of interest.

"Flushing" refers to the administration to a patient of a flush agent after the administration of a lipid and/or vesicle composition. The term "flush agent" refers to biocompatible materials which may be capable, upon administration, of facilitating the movement of a lipid and/or vesicle composition through the circulatory system. An exemplary flush agent is saline solution. In embodiments which involve the administration of a lipid and/or vesicle composition intravenously (IV), the flush is preferably also administered IV, typically at or near the location that the lipid and/or vesicle composition is administered.

"Constant infusion" refers to the administration to a patient of a lipid and/or vesicle composition at a rate which may be maintained constant or substantially constant during administration. The term "substantially constant" means that, during administration of the lipid and/or vesicle compositions, there may be less than about 25% variation in the rate of administration in accordance with methods of the present invention. Preferably, there may be less than about 20% variation in the rate of administration of the lipid and/or vesicle compositions in accordance with methods of the present invention, with less than about 15% variation being more preferred. Even more preferably, there may be less than about 10% variation in the rate of administration of the lipid and/or vesicle compositions in accordance with methods of the present invention, with less than about 5% variation being still more preferred. In particularly preferred embodiments, the lipid and/or vesicle compositions may be administered with no (i.e., 0%) variation in the rate of administration.

"Surfactant" refers to a surface active agent including, for example, agents that may modify the nature of surfaces such as, for example, by reducing the surface tension of an aqueous solution. Exemplary surfactants include those which may be used as wetting agents, detergents, emulsifiers, dispersing agents, penetrating agents and antifoaming agents. Classes of surfactants may include, for example, cationic surfactants (such as, e.g., modified onium salts), anionic surfactants (such as, e.g., alkylarylsulfonates), nonionic surfactants (such as, e.g., polyethylene oxides) and ampholytic surfactants. Other surfactants which may be employed in the present compositions are fluorinated surfactants, including fluorinated surfactants which are commercially available as ZONYL® surfactants (the DuPont Company, Wilmington, Del.).

"Stabilizing material" refers to a substance which is biocompatible and which is capable of promoting the formation of vesicles in a lipid composition. As used herein, "stabilizing material" refers also to a substance which is biocompatible and which is capable of improving the stability of a vesicle. In certain preferred embodiments, the stabilizing material comprises a polymer. "Polymer", as used herein, refers to molecules formed from the chemical union of two or more repeating units. Accordingly, included within the term "polymer" are, for example, dimers, trimers and oligomers. In certain other preferred embodiments, the stabilizing material comprises a non-polymeric material, including, for example, monomeric molecules. Encompassed also in the definition of "stabilizing material" are certain of the present bioactive agents. The stabilizing material may be neutral or positively or negatively charged. Preferred among the neutral stabilizing materials are polar materials. In the case of preferred embodiments involving lipids, the stabilizing materials may be associated covalently and/or non-covalently with the lipid compounds.

"Vesicle stability" refers to the ability of gas-filled vesicles to retain the gas entrapped therein after being exposed, for about one minute, to a pressure of about 300 mm Hg. Vesicle stability is measured in percent (%), this being the fraction of the amount of gas which is originally entrapped in the vesicle and which is retained after release of the pressure. Vesicle stability includes reference also to "vesicle resilience" which refers to the ability of a vesicle to return to its original size after release of the pressure.

"Covalent association" refers to an intermolecular association or bond which involves the sharing of electrons in the bonding orbitals of two atoms.

"Non-covalent association" refers to intermolecular interaction among two or more separate molecules which does not involve a covalent bond. Intermolecular interaction is dependent upon a variety of factors, including, for example, the polarity of the involved molecules, the charge (positive or negative), if any, of the involved molecules, and the like. Non-covalent associations are preferably selected from the group consisting of ionic interaction, dipole-dipole interaction and van der Waal's forces and combinations thereof.

"Ionic interaction" or "electrostatic interaction" refers to intermolecular interaction among two or more molecules, each of which is positively or negatively charged. Thus, for example, "ionic interaction" or "electrostatic interaction" refers to the attraction between a first, positively charged molecule and a second, negatively charged molecule. Exemplary ionic or electrostatic interactions include, for example, the attraction between a negatively charged stabilizing material, for example, genetic material, and a positively charged lipid, for example, a cationic lipid, such as lauryltrimethylammonium bromide.

"Dipole-dipole interaction" refers generally to the attraction which can occur among two or more polar molecules. Thus, "dipole-dipole interaction" refers to the attraction of the uncharged, partial positive end of a first polar molecule, commonly designated as $\delta^+$, to the uncharged, partial negative end of a second polar molecule, commonly designated as $\delta^-$. Dipole-dipole interactions are exemplified, for example, by the attraction between the electropositive head group, for example, the choline head group, of phosphatidylcholine and an electronegative atom, for example, a heteroatom, such as oxygen, nitrogen or sulphur, which is present in a stabilizing material, such as a polysaccharide. "Dipole-dipole interaction" refers also to intermolecular hydrogen bonding in which a hydrogen atom serves as a bridge between electronegative atoms on separate molecules and in which a hydrogen atom is held to a first molecule by a covalent bond and to a second molecule by electrostatic forces.

"Van der Waal's forces" refers to the attractive forces between non-polar molecules that are accounted for by quantum mechanics. Van der Waal's forces are generally associated with momentary dipole moments which are induced by neighboring molecules and which involve changes in electron distribution.

"Hydrogen bond" refers to an attractive force, or bridge, which may occur between a hydrogen atom which is bonded covalently to an electronegative atom, for example, oxygen, sulfur, nitrogen, and the like, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding).

"Hydrophilic interaction" refers to molecules or portions of molecules which may substantially bind with, absorb and/or dissolve in water. This may result in swelling and/or the formation of reversible gels.

"Hydrophobic interaction" refers to molecules or portions of molecules which do not substantially bind with, absorb and/or dissolve in water.

"Biocompatible" refers to materials which are generally not injurious to biological functions and which will not result in any degree of unacceptable toxicity, including allergenic responses and disease states.

"In combination with" refers, in certain embodiments, to the incorporation of a targeting ligand in a composition of the present invention, including lipid compositions and vesicle compositions. "In combination with" may refer also to the incorporation of a bioactive agent in a composition of the present invention, including lipid compositions and vesicle compositions. The bioactive agent and/or targeting ligand can be combined with the present compositions in any of a variety of ways. For example, in the case of lipid compositions, the bioactive agent and/or targeting ligand may be associated covalently and/or non-covalently with the lipid compounds or optional stabilizing materials. In the case of vesicle compositions, the bioactive agent and/or targeting ligand may be entrapped within the internal void of the vesicle. The bioactive agent and/or targeting ligand may also be integrated within the layer(s) or wall(s) of the vesicle, for example, by being interspersed among lipids which are contained within the vesicle layer(s) or wall(s). In addition, it is contemplated that the bioactive agent and/or targeting ligand may be located on the surface of a vesicle. In any case, the bioactive agent and/or targeting ligand may interact chemically with the walls of the vesicles, including, for example, the inner and/or outer surfaces of the vesicle and may remain substantially adhered thereto. Such interaction may take the form of, for example, covalent association or non-covalent association. In certain embodiments, the interaction may result in the stabilization of the vesicle.

"Targeting ligand" refers to any material or substance which may promote targeting of tissues, cells and/or receptors in vivo with the compositions of the present invention. The terms "target(s)", "targeted" and "targeting", as used herein, refer to the ability of targeting ligands and compositions containing them to bind with or be directed towards tissues, cells and/or receptors. The targeting ligand may be synthetic, semi-synthetic, or naturally-occurring. Materials or substances which may serve as targeting ligands include, for example, proteins, including antibodies, glycoproteins and lectins, peptides, polypeptides, saccharides, including mono- and polysaccharides, vitamins, steroids, steroid analogs, hormones, cofactors, bioactive agents, and genetic material, including nucleosides, nucleotides and polynucleotides. Preferred targeting ligands include those which promote targeting of tissues, cells and/or receptors which may be associated with coagula.

A "precursor" to a targeting ligand refers to any material or substance which may be converted to a targeting ligand. Such conversion may involve, for example, anchoring a precursor to a targeting ligand. Exemplary targeting precursor moieties include maleimide groups, disulfide groups, such as ortho-pyridyl disulfide, vinylsulfone groups, azide groups, and α-iodo acetyl groups.

"Peptide" refers to a nitrogenous compound which may contain from about 2 to about 100 amino acid residues. In certain embodiments, the peptides may possess surface-active properties, i.e., they may be surfactants.

"Protein" refers to a nitrogenous compound which may contain more than about 100 amino acid residues. In certain embodiments, the proteins may possess surface-active properties, i.e., they may be surfactants.

"Coat" or "coating" refers to the interaction of the stabilizing material with the lipid and/or vesicles and may involve covalent and/or non-covalent association.

"Tissue" refers generally to specialized cells which may perform a particular function. It should be understood that the term "tissue," as used herein, may refer to an individual cell or a plurality or aggregate of cells, for example, membranes or organs. Exemplary tissues include, for example, myocardial tissue (also referred to as heart tissue or myocardium), including myocardial cells and cardiomyocites, membranous tissues, including endothelium and epithelium, laminae, connective tissue, including interstitial tissue, and tumors.

"Receptor" refers to a molecular structure within a cell or on the surface of the cell which is generally characterized by the selective binding of a specific substance. Exemplary receptors include, for example, cell-surface receptors for peptide hormones, neurotransmitters, antigens, complement fragments, and immunoglobulins and cytoplasmic receptors for steroid hormones. An exemplary receptor is the glycoprotein GPIIbIIIa which is a platelet integrin and which is frequently associated with coagula.

"Coagulum" refers to a solid or semisolid mass of tissue or other foreign material which may cause an obstruction in the vascular system. Exemplary coagula within the context of the present invention include thrombi and emboli. "Thrombus" or "thrombi" refer to coagula which may, for example, comprise aggregations of blood factors, primarily platelets and fibrin with entrapment of cellular elements, that may cause a vascular obstruction at their point of formation. Thrombi are generally formed in the left portion of the heart, frequently the left atrium. "Embolism" or "emboli" generally refer to coagula which may, for example, cause blockage of an artery and which may be brought to its site of lodgment by the blood current. Exemplary emboli include clots, such as blood clots and lymph clots, as well as thrombi which have broken loose from their point of attachment and/or formation.

"Endothelial cells" or "endothelium" refers to an aggregate of cells and/or tissue which may be normal and/or diseased and which may comprise a single layer of flattened transparent endothelial cells that may be joined edge to edge or in an overlapping fashion to form a membrane. Endothelial cells may be found on the free surfaces of the serous membranes, as part of the lining membrane of the heart, blood vessels, and lymphatics, on the surface of the brain and spinal cord, and in the anterior chamber of the eye. Endothelium originates from the embryonic mesoblast and includes heart tissue, including infarcted heart tissue, cardiovasculature, the peripheral vasculature, such as arteries, veins, and capillaries (the location of which is noted as peripheral to the heart), coagula, including blood clots, and the region surrounding atherosclerotic plaque.

"Epithelial cells" or "epithelium" refers to an aggregate of cells and/or tissue which may be normal and/or diseased and which may comprise one or more layers of cells that may be united together by an interstitial cementitious substance supported on a basement-membrane. Epithelium may be classified into various classes, including, for example, a single layer of cells (simple epithelium); more than a single layer of cells (stratified epithelium); and about three or four layers of cells that are fitted together substantially without the appearance of stratification. The different forms of simple epithelium are usually referred to as squamous, pavement, columnar, glandular, spheroidal and/or ciliated. Epithelium originates from the embryonic epiblast or hypoblast. Epithelium includes heart tissue, including infarcted heart tissue, cardiovasculature, the peripheral vasculature, such as arteries, veins, and capillaries, coagula, including blood clots, and the region surrounding atherosclerotic plaque.

"Myocardial" refers generally to heart tissue, including cardiomyocyte, myocardial, endocardial and epicardial cells. The term "myocardial" includes reference to infarcted heart tissue, the cardiovasculature, the peripheral vasculature, such as arteries, veins, and capillaries (the location of which is noted as peripheral to the heart), coagula, including blood clots, and the region surrounding atherosclerotic plaque.

"Tumor cells" or "tumor" refers to an aggregate of abnormal cells and/or tissue which may be associated with diseased states that are characterized by uncontrolled cell proliferation. The disease states may involve a variety of cell types, including, for example, endothelial, epithelial and myocardial cells. Included among the disease states are neoplasms, cancer, leukemia and restenosis injuries.

"Alkyl" refers to linear, branched or cyclic hydrocarbon groups. Preferably, the alkyl is a linear or branched hydrocarbon group, more preferably a linear hydrocarbon group. Exemplary linear and branched alkyl groups include, for example, methyl, ethyl, n-propyl, i-propyl, n-butyl, t-butyl, n-pentyl, hexyl, heptyl, octyl, nonyl, and decyl groups. Exemplary cyclic hydrocarbon groups (that is, cycloalkyl groups) include, for example, cyclopentyl, cyclohexyl and cycloheptyl groups.

"Alkenyl" refers to an alkyl group containing at least one carbon-carbon double bond. Exemplary alkenyl groups include, for example, vinyl, allyl, butenyl, pentenyl, decenyl and dodecenyl groups.

"Alkoxy" refers to an alkyl-O— group where alkyl is as previously described. Exemplary alkoxy groups include, for example, methoxy, ethoxy, propoxy, butoxy and heptoxy.

"Electrocardiogram" refers to a graphic tracing of variations in electrical potential caused by the excitation of the heart muscle which may be detected at the body surface. "Electrocardiogram" may be abbreviated as "ECG" or "EKG". The signals may be detected by means of metal electrodes attached to the extremities and chest wall, and may then be amplified by a sensitive voltmeter such as the electrocardiograph. The ECG waveforms are generally labeled alphabetically beginning with the P wave, which represents atrial depolarization. Approximately 0.16 seconds after the onset of the P wave, the QRS waves generally appear as a result of depolarization of the ventricular muscle, which initiates contraction of the ventricles. Finally, the T wave results from repolarization of the ventricles, which represents the onset of ventricular relaxation. The duration of the "T" wave cycle time is that time in a heart cycle when it is most vulnerable to fibrillation, a condition where the cardiac muscle fiber contracts asynchronously. Electrocardiography is further described in *Harrison's Principles of Internal Medicine,* Thirteenth Ed., McGraw-Hill, Inc., Chapter 189, pp. 954–966 (1994), the disclosures of which are hereby incorporated herein by reference, in their entirety.

"Cardiac cycle" refers to a complete cardiac movement or heart beat. Thus, the cardiac cycle may mean the period from the beginning of one heart beat to the beginning of the next, i.e., the systolic and diastolic movement, with the interval between them.

"Substantially immediately", as used herein in connection with the methods of the present invention, means that a second quantity of ultrasound energy may be applied after application of a first quantity of ultrasound energy such that processing of images obtained from the first and second applications of ultrasound energy provides highly enhanced images of the region of interest. In preferred form, the second quantity of ultrasound energy may be applied no more than about 100 milliseconds after the application of the first quantity of ultrasound energy. More preferably, the second quantity of ultrasound energy may be applied at a time which ranges from about 5 to less than about 100 milliseconds after application of the first quantity of ultrasound, and all combinations and subcombinations of ranges therein. Even more preferably, the second quantity of ultrasound is applied from about 10 to about 80 milliseconds after application of the first quantity of ultrasound, with from about 20 to about 60 milliseconds being still more preferred. Yet more preferably, the second quantity of ultrasound is applied from about 30 to about 40 milliseconds after application of the first quantity of ultrasound energy, with about 40 milliseconds being even more preferred.

The present invention is directed, in part, to methods for diagnostic imaging involving lipid and/or vesicle compositions. Embodiments are provided which comprise methods for diagnostic imaging involving a lipid composition comprising a lipid, and a gas or gaseous precursor. Embodiments are also provided herein which comprise methods for diagnostic imaging involving vesicle compositions comprising, in an aqueous carrier, vesicles comprising lipids, proteins or polymers, and a gas or gaseous precursor.

In connection with lipid compositions, and especially lipid compositions in the form of vesicle compositions, it may be advantageous to prepare the lipid compositions at a temperature below the gel to liquid crystalline phase transition temperature of the involved lipids. This phase transition temperature is the temperature at which a lipid bilayer will convert from a gel state to a liquid crystalline state. See, for example, Chapman et al., *J. Biol. Chem.* 1974 249, 2512–2521. It is generally believed that vesicles which are prepared from lipids that possess higher gel state to liquid crystalline state phase transition temperatures tend to have enhanced impermeability at any given temperature. See Derek Marsh, *CRC Handbook of Lipid Bilayers* (CRC Press, Boca Raton, Fla. 1990), at p. 139 for main chain melting transitions of saturated diacyl-sn-glycero-3-phosphocholines. The gel state to liquid crystalline state phase transition temperatures of various lipids will be readily apparent to those skilled in the art and are described, for example, in Gregoriadis, ed., *Liposome Technology,* Vol. I, 1–18 (CRC Press, 1984). The following table lists some of the representative lipids and their phase transition temperatures.

TABLE 1

Saturated Diacyl-sn-Glycero-3-Phosphocholines:
Main Chain Melting Transition Temperatures

| Number of Carbons in Acyl Chains | Main Phase Transition Temperature (° C.) |
| --- | --- |
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

See, for example, Derek Marsh, *CRC Handbook of Lipid Bilayers,* p. 139 (CRC Press, Boca Raton, Fla. 1990).

It may be possible to enhance the stability of vesicles by incorporating in the present lipid and/or vesicle compositions at least a minor amount, for example, about 1 to about 10 mole percent, based on the total amount of lipid employed, of a negatively charged lipid. Suitable negatively charged lipids include, for example, phosphatidylserine, phosphatidic acid, and fatty acids. Without intending to be bound by any theory or theories of operation, it is contemplated that such negatively charged lipids provide added stability by counteracting the tendency of vesicles to rupture by fusing together. Thus, the negatively charged lipids may act to establish a uniform negatively charged layer on the outer surface of the vesicle, which will be repulsed by a similarly charged outer layer on other vesicles which are proximate thereto. In this way, the vesicles may be less prone to come into touching proximity with each other, which may lead to a rupture of the membrane or skin of the respective vesicles and consolidation of the contacting vesicles into a single, larger vesicle. A continuation of this process of consolidation will, of course, lead to significant degradation of the vesicles.

The lipid materials used, especially in connection with vesicle compositions, are also preferably flexible. This means, in the context of the present invention, that the vesicles can alter their shape, for example, to pass through an opening having a diameter that is smaller than the diameter of the vesicle.

A wide variety of lipids are believed to be suitable for incorporation in the lipid compositions. With particular reference to vesicle compositions, for example, micelles and/or liposomes, any of the materials or combinations thereof which are known to those skilled in the art as suitable for their preparation may be used. The lipids used may be of either natural, synthetic or semi-synthetic origin. As noted above, suitable lipids generally include, for example, fatty acids, neutral fats, phosphatides, glycolipids, aliphatic alcohols and waxes, terpenes and steroids.

Exemplary lipids which may be used to prepare the present lipid compositions included, for example, fatty acids, lysolipids, phosphocholines, such as those associated with platelet activation factors (PAF) (Avanti Polar Lipids, Alabaster, Ala.), including 1-alkyl-2-acetoyl-sn-glycero 3-phosphocholines, and 1-alkyl-2-hydroxy-sn-glycero 3-phosphocholines, which target blood clots; phosphatidylcholine with both saturated and unsaturated lipids, including dioleoylphosphatidylcholine; dimyristoylphosphatidylcholine; dipentadecanoylphosphatidylcholine; dilauroylphosphatidylcholine; dipalmitoylphosphatidylcholine (DPPC); distearoylphosphatidylcholine (DSPC); and diarachidonylphosphatidylcholine (DAPC); phosphatidylethanolamines, such as dioleoylphosphatidylethanolamine, dipahnitoylphosphatidylethanolamine (DPPE) and distearoylphosphatidylefhanolamine (DSPE); phosphatidylserine; phosphatidylglycerols, including distearoylphosphatidylglycerol (DSPG); phosphatidylinositol; sphingolipids such as sphingomyelin; glycolipids such as ganglioside GM1 and GM2; glucolipids; sulfatides; glycosphingolipids; phosphatidic acids, such as dipahmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG), also referred to herein as "pegylated lipids", with preferred lipids bearing polymers including DPPE-PEG (DPPE-PEG), which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyethylene fatty acid esters, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers, and polyoxyethylene fatty acid stearates; sterol aliphatic acid esters including cholesterol sulfate, cholesterol butyrate, cholesterol iso-butyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palritate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipahmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl)carbonyl)methylamino) octadecanoic acid; N-[12-(((7'-diethylaminocoumarin-3-yl) carbonyl)methylamino)octadecanoyl]-2-aminopalmitic acid; cholesteryl)4'-trimethylammonio)butanoate; N-succinyldioleoylphosphatidylethanol-amine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine, and/or combinations thereof.

If desired, a cationic lipid may be used, such as, for example, N-[1-(2,3-dioleoyloxy)propyl]-N,N,N-trimethylammonium chloride (DOTMA), 1,2-dioleoyloxy-3-(trimethylammonio)propane (DOTAP); and 1,2-dioleoyl-3-(4'-trimethylammonio)butanoyl-sn-glycerol (DOTB). If a cationic lipid is employed in the lipid compositions, the molar ratio of cationic lipid to non-cationic lipid may be, for example, from about 1:1000 to about 1:100. Preferably, the molar ratio of cationic lipid to non-cationic lipid may be from about 1:2 to about 1:10, with a ratio of from about 1:1 to about 1:2.5 being preferred. Even more preferably, the molar ratio of cationic lipid to non-cationic lipid may be about 1:1.

In the case of lipid compositions which contain both cationic and non-cationic lipids, a wide variety of lipids may be employed as the non-cationic lipid. Preferably, this non-cationic lipid comprises one or more of DPPC, DPPE and dioleoylphosphatidylethanolamine. In lieu of the cationic lipids listed above, lipids bearing cationic polymers, such as polylysine or polyarginine, as well as alkyl phosphonates, alkyl phosphinates, and alkyl phosphites, may also be used in the lipid compositions In certain preferred embodiments of the present invention, the lipid compositions may comprise one or more cationic lipids having the following formula:

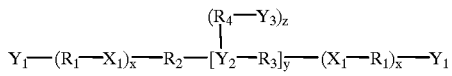
(I)

wherein:
each of x, y and z is independently an integer from 0 to about 100;
each $X_1$ is independently —O—, —S—, —NR$_5$—, —C(=X$_2$)—, —C(=X$_2$)—N(R$_5$)—, —N(R$_5$)—C(=X$_2$)—, —C(=X$_2$)—O—, —O—C(=X$_2$)— or —X$_2$—(R$_5$X$_2$)P(=X$_2$)—X$_2$—;
each $X_2$ is independently O or S;
each $Y_1$ is independently a phosphate residue, N(R$_6$)$_a$—, S(R$_6$)$_a$—, P(R$_6$)$_a$— or —CO$_2$R$_6$, wherein a is an integer from 1 to 3;
each $Y_2$ is independently —N(R$_6$)$_b$—, —S(R$_6$)$_b$— or —P(R$_6$)$_b$—, wherein b is an integer from 0 to 2;
each $Y_3$ is independently a phosphate residue, N(R$_6$)$_a$—, S(R$_6$)$_a$—, P(R$_6$)$_a$— or —CO$_2$R$_6$, wherein a is an integer from 1 to 3;
each of $R_1$, $R_2$, $R_3$ and $R_4$ is independently alkylene of 1 to about 20 carbons;
each $R_5$ is independently hydrogen or alkyl of 1 to about 10 carbons; and
each $R_6$ is independently —[R$_7$—X$_3$]$_c$—R$_8$ or —R$_9$—[X$_4$—R$_{10}$]$_d$—Q wherein:
each of c and d is independently an integer from 0 to about 100;
each Q is independently a phosphate residue, —N(R$_{11}$)$_q$, —S(R$_{11}$)$_q$, —P(R$_{11}$)$_q$ or —CO$_2$R$_6$, wherein q is an integer from 1 to 3;
each of $X_3$ and $X_4$ is independently —O—, —S—, —NR$_5$—, —C(=X$_2$)—, —C(=X$_2$)—N(R$_5$)—, —N(R$_5$)—C(=X$_2$)—, —C(=X$_2$)—O—, —O—C(=X$_2$)— or —X$_2$—(R$_5$X$_2$)P(=X$_2$)—X$_2$—;
each $R_7$ is independently alkylene of 1 to about 20 carbons;
each $R_8$ is independently hydrogen or alkyl of 1 to about 60 carbons;
each of $R_9$ and $R_{10}$ is independently alkylene of 1 to about 20 carbons; and
each $R_{11}$ is independently —[R$_7$—X$_3$]$_c$—R$_8$ or —R$_9$—[X$_4$—R$_{10}$]$_d$—W, wherein:
each W is independently a phosphate residue, —N(R$_{12}$)$_w$, —S(R$_{12}$)$_w$, —P(R$_{12}$)$_w$ or —CO$_2$R$_6$, wherein w is an integer from 1 to 3; and
$R_{12}$ is —[R$_7$—X$_3$]$_c$—R$_8$, with the proviso that the compound of formula (I) comprises at least one, and preferably at least two, quaternary salts.

Another cationic lipid compound which may be incorporated in the compositions of the present invention is a compound of the formula:

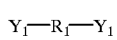
(II)

wherein:
each $Y_1$ is independently a phosphate residue, N(R$_2$)$_a$—, S(R$_2$)$_a$—, P(R$_2$)$_a$ or —CO$_2$R$_2$, wherein a is an integer from 1 to 3;
$R_1$ is alkylene of 1 to about 60 carbons containing 0 to about 30 —O—, —S—, —NR$_3$— or —X$_2$—(R$_3$X$_2$)P(=X$_2$)—X$_2$— heteroatoms or heteroatom groups;
$R_2$ is a residue of the formula —R$_4$—[(X$_1$—R$_5$)$_x$—Y$_2$]$_y$—R$_6$, wherein:
each of x and y is independently an integer from 0 to about 100;
each $X_1$ is independently a direct bond, —O—, —S—, —NR$_3$—, —C(=X$_2$)—, —C(=X$_2$)—N(R$_3$)—, —N(R$_3$)—C(=X$_2$)—, —C(=X$_2$)—O—, —O—C(=X$_2$)— or —X$_2$—(R$_3$X$_2$)P(=X$_2$)—X$_2$—;
each $X_2$ is independently O or S;
each $Y_2$ is independently —S(R$_2$)$_b$—, —N(R$_2$)$_b$— or —P(R$_2$)$_b$—, wherein b is an integer from 0 to 2;
each $R_3$ is independently hydrogen or alkyl of 1 to about 10 carbons;
each of $R_4$ and $R_5$ is independently a direct bond or alkylene of 1 to about 30 carbons containing 0 to about 15 —O—, —S—, —NR$_3$— or —X$_2$—(R$_3$X$_2$)P(=X$_2$)—X$_2$— heteroatoms or heteroatom groups; and
each $R_6$ is independently hydrogen or alkyl of 1 to about 60 carbons containing 0 to about 30 —O—, —S—, —NR$_3$— or —X$_2$—(R$_3$X$_2$)P(=X$_2$)—X$_2$— heteroatoms or heteroatom groups; with the proviso that the compound of formula (II) comprises at least one, and preferably at least two, quaternary salts.

In yet another embodiment, the present lipid compositions may comprise a cationic lipid compound of the formula:

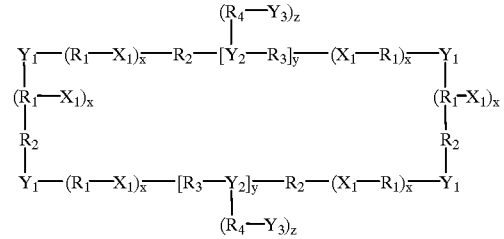
III wherein:
each of x, y and z is independently an integer from 0 to about 100;
each $X_1$ is independently —O—, —S—, —NR$_5$—, —C(=X$_2$)—, —C(=X$_2$)—N(R$_5$)—, —N(R$_5$)—C(=X$_2$)—, —C(=X$_2$)—O—, —O—C(=X$_2$)— or —X$_2$—(R$_5$X$_2$)P(=X$_2$)—X$_2$—;
each $X_2$ is independently O or S;
each $Y_1$ is independently —O—, —N(R$_6$)$_a$—, —S(R$_6$)$_a$— or —P(R$_6$)$_a$—, wherein a is an integer from 0 to 2;
each $Y_2$ is independently —N(R$_6$)$_a$—, —S(R$_6$)$_a$— or —P(R$_6$)$_a$—, wherein a is an integer from 0 to 2;
each $Y_3$ is independently a phosphate residue, N(R$_6$)$_b$—, S(R$_6$)$_b$—, P(R$_6$)$_b$— or —CO$_2$R$_6$, wherein b is an integer from 1 to 3;

each of $R_1$, $R_2$, $R_3$ and $R_4$ is independently alkylene of 1 to about 20 carbons;

each $R_5$ is independently hydrogen or alkyl of 1 to about 10 carbons; and each $R_6$ is independently —[$R_7$—$X_3$]$_c$—$R_8$ or —$R_9$—[$X_4$—$R_{10}$]$_d$—Q, wherein:

each of c and d is independently an integer from 0 to about 100;

each Q is independently a phosphate residue, —N($R_{11}$)$_q$, —S($R_{11}$)$_q$, —P($R_{11}$)$_q$ or —$CO_2R_{11}$, wherein q is an integer from 1 to 3;

each of $X_3$ and $X_4$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—;

each $R_7$ is independently alkylene of 1 to about 20 carbons;

each $R_8$ is independently hydrogen or alkyl of 1 to about 60 carbons;

each of $R_9$ and $R_{10}$ is independently alkylene of 1 to about 20 carbons; and each $R_{11}$ is independently —[$R_7$—$X_3$]$_c$—$R_8$ or —$R_9$—[$X_4$—$R_{10}$]$_d$—W, wherein:

each W is independently a phosphate residue, —N($R_{12}$)$_w$, —S($R_{12}$)$_w$, —P($R_{12}$)$_w$ or —$CO_2R_{12}$, wherein w is an integer from 1 to 3; and $R_{12}$ is —[$R_7$—$X_3$]$_c$—$R_8$; with the proviso that the compound of formula (III) comprises at least one, and preferably at least two, quaternary salts. The cationic lipid compounds which are described generically above are set forth in copending U.S. application Ser. No. 08/391,938, the disclosures of which are hereby incorporated by reference herein, in their entirety.

In certain preferred embodiments, the lipid compositions comprise phospholipids, particularly one or more of DPPC, DPPE, DPPA, DSPC, DSPE, DSPG, and DAPC (20 carbons).

In addition, saturated and unsaturated fatty acids may be employed in the present lipid compositions may include molecules that preferably contain from about 12 carbons to about 22 carbons, in linear or branched form. Hydrocarbon groups consisting of isoprenoid units and/or prenyl groups can be used as well. Examples of saturated fatty acids that are suitable include, for example, lauric, myristic, palmitic, and stearic acids. Suitable unsaturated fatty acids that may be used include, for example, lauroleic, physeteric, myristoleic, palmitoleic, petroselinic, and oleic acids. Examples of branched fatty acids that may be used include, for example, isolauric, isomyristic, isopalmitic, and isostearic acids.

In addition to lipid compositions and/or vesicle compositions formulated from lipids, embodiments of the present invention may also involve vesicles formulated from proteins or derivatives thereof Vesicles which are formulated from proteins that may be used to prepare the targeted vesicles of the present invention are described, for example, in Feinstein, U.S. Pat. Nos. 4,572,203, 4,718,433 and 4,774,958, and Cerny et al., U.S. Pat. No. 4,957,656. Other protein-based vesicles, in addition to those described in the aforementioned patents, would be apparent to one of ordinary skill in the art, once armed with the present disclosure.

In addition to lipid compositions and/or vesicle compositions formulated from lipids and/or proteins, embodiments of the present invention may also involve vesicles formulated from polymers which may be of natural, semi-synthetic (modified natural) or synthetic origin. As used herein, the term polymer denotes a compound comprised of two or more repeating monomeric units, and preferably 10 or more repeating monomeric units. The phrase semi-synthetic polymer (or modified natural polymer), as employed herein, denotes a natural polymer that has been chemically modified in some fashion. Exemplary natural polymers suitable for use in the present invention include naturally occurring polysaccharides. Such polysaccharides include, for example, arabinans, fructans, fucans, galactans, galacturonans, glucans, mannans, xylans (such as, for example, inulin), levan, fucoidan, carrageenan, galatocarolose, pectic acid, pectins, At including amylose, pullulan, glycogen, amylopectin, cellulose, dextran, dextrin, dextrose, polydextrose, pustulan, chitin, agarose, keratan, chondroitan, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, mannose, gulose, idose, galactose, talose, erytbrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin. Exemplary semi-synthetic polymers include carboxymethylcellulose, hydroxymethylcellulose, hydroxypropylmethylcellulose, methylcellulose, and methoxycellulose. Exemplary synthetic polymers suitable for use in the present invention include polyethylenes (such as, for example, polyethylene glycol, polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbons, fluorinated carbons (such as, for example, polytetrafluoroethylene), and polymethylmethacrylate, and derivatives thereof. Preferred are biocompatible synthetic polymers or copolymers prepared from monomers, such as acrylic acid, methacrylic acid, ethyleneimine, crotonic acid, acrylamide, ethyl acrylate, methyl methacrylate, 2-hydroxyethyl methacrylate (HEMA), lactic acid, glycolic acid, ε-caprolactone, acrolein, cyanoacrylate, bisphenol A, epichlorhydrin, hydroxyalkylacrylates, siloxane, dimethylsiloxane, ethylene oxide, ethylene glycol, hydroxyalkylmethacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethylmethacrylate, vinyl pyridine, aminoethyl methacrylates, 2-methacryloyloxy-trimethylammonium chloride, and polyvinylidene, as well polyfunctional crosslinking monomers such as N,N'-methylenebisacrylamide, ethylene glycol dimethacrylates, 2,2'-(p-phenylenedioxy)-diethyl dimethacrylate, divinylbenzene, triallylamine and methylenebis-(4-phenyl-isocyanate), including combinations thereof. Preferable polymers include polyacrylic acid, polyethyleneimine, polymethacrylic acid, polymethylmethacrylate, polysiloxane, polydimethylsiloxane, polylactic acid, poly(ε-caprolactone), epoxy resin, poly(ethylene oxide), poly(ethylene glycol), and polyamide (nylon) polymers. Preferable copolymers include the following: polyvinylidene-polyacrylonitrile, polyvinylidene-polyacrylonitrile-polymethylmethacrylate, polystyrene-polyacrylonitrile and poly d-l, lactide co-glycolide polymers. A preferred copolymer is polyvinylidene-polyacrylonitrile. Other suitable biocompatible monomers and polymers will be readily apparent to those skilled in the art, once armed with the present disclosure.

As noted above, the present lipid compositions also preferably comprise a gas, such as an inert gas. The gas provides the lipid compositions with enhanced reflectivity, particularly in connection with vesicle compositions in which the gas is entrapped within the vesicles. This may increase their effectiveness as contrast agents.

Preferred gases are gases which are inert and which are biocompatible, that is, gases which are not injurious to biological function. Preferred gases include those selected from the group consisting of air, noble gases, such as helium, rubidium hyperpolarized xenon, hyperpolarized argon, hyperpolarized helium, neon, argon and xenon, carbon dioxide, nitrogen, fluorine, oxygen, sulfur-based gases, such as sulfur hexafluoride and sulfur tetrafluoride, fluorinated gases, including, for example, partially fluorinated gases or completely fluorinated gases. Exemplary fluorinated gases include the fluorocarbon gases, such as the perfluorocarbon gases, and mixtures thereof. Paramagnetic gases, such as $^{17}O_2$ may also be used in the lipid compositions.

In preferred embodiments, the gas comprises a fluorinated gas. Such fluorinated gases include materials which contain one, or more than one, fluorine atom. Preferred are gases which contain more than one fluorine atom, with perfluorocarbons (that is, fully fluorinated fluorocarbons) being more preferred. Preferably, the perfluorocarbon gas is selected from the group consisting of perfluoromethane, perfluoroethane, perfluoropropane, perfluorobutane, perfluoropentane, perfluorocyclobutane and mixtures thereof. More preferably, the perfluorocarbon gas is perfluoropropane or perfluorobutane, with perfluoropropane being particularly preferred. Another preferable gas is sulfur hexafluoride. Yet another preferable gas is heptafluoropropane, including 1,1,1,2,3,3,3-heptafluoropropane and its isomer, 1,1,2,2,3,3,3-heptafluoropropane. It is contemplated that mixtures of different types of gases, such as mixtures of a perfluorocarbon gas and another type of gas, such as air, can also be used in the compositions of the present invention. Other gases, including the gases exemplified above, would be readily apparent to one skilled in the art based on the present disclosure.

In certain preferred embodiments, a gas, for example, air or a perfluorocarbon gas, is combined with a liquid perfluorocarbon, such as perfluoropentane, perfluorohexane, perfluoroheptane, perfluorooctylbromide (PFOB), perfluorodecalin, perfluorododecalin, perfluorooctyliodide, perfluorotripropylamine and perfluorotributylamine.

It may also be desirable to incorporate in the lipid compositions a precursor to a gaseous substance. Such precursors include materials that are capable of being converted to a gas in vivo. Preferably, the gaseous precursor is biocompatible, and the gas produced in vivo is biocompatible also.

Among the gaseous precursors which are suitable for use in compositions described herein are agents which are sensitive to pH. These agents include materials that are capable of evolving gas, for example, upon being exposed to a pH that is neutral or acidic. Examples of such pH sensitive agents include salts of an acid which is selected from the group consisting of inorganic acids, organic acids and mixtures thereof. Carbonic acid ($H_2CO_3$) is an example of a suitable inorganic acid, and aminomalonic acid is an example of a suitable organic acid. Other acids, including inorganic and organic acids, would be readily apparent to one skilled in the art based on the present disclosure.

Gaseous precursors which are derived form salts are preferably selected from the group consisting of alkali metal salts, ammonium salts and mixtures thereof. More preferably, the salt is selected from the group consisting of carbonate, bicarbonate, sesquecarbonate, aminomalonate and mixtures thereof.

Examples of suitable gaseous precursor materials which are derived from salts include, for example, lithium carbonate, sodium carbonate, potassium carbonate, lithium bicarbonate, sodium bicarbonate, potassium bicarbonate, magnesium carbonate, calcium carbonate, magnesium bicarbonate, ammonium carbonate, ammonium bicarbonate, ammonium sesquecarbonate, sodium sesquecarbonate, sodium aminomalonate and ammonium aminomalonate. Aminomalonate is well known in the art, and its preparation is described, for example, in Thanassi, *Biochemistry*, Vol. 9, no. 3, pp. 525–532 (1970); Fitzpatrick et al., *Inorganic Chemistry*, Vol. 13, no. 3 pp. 568–574 (1974); and Stelmashok et al., *Koordinatsionnaya Khimiya*, Vol. 3, no. 4, pp. 524–527 (1977). The disclosures of these publications are hereby incorporated herein by reference.

In addition to, or instead of, being sensitive to changes in pH, the gaseous precursor materials may also comprise compounds which are sensitive to changes in temperature. Exemplary of suitable gaseous precursors which are sensitive to changes in temperature are the perfluorocarbons. As the artisan will appreciate, a particular perfluorocarbon may exist in the liquid state when the lipid compositions are first made, and are thus used as a gaseous precursor. Alternatively, the perfluorocarbon may exist in the gaseous state when the lipid compositions are made, and are thus used directly as a gas. Whether the perfluorocarbon is used as a liquid or a gas generally depends on its liquid/gas phase transition temperature, or boiling point. For example, a preferred perfluorocarbon, perfluoropentane, has a liquid/gas phase transition temperature (boiling point) of 29.5° C. This means that perfluoropentane is generally a liquid at room temperature (about 25° C.), but is converted to a gas within the human body, the normal temperature of which is about 37° C., which is above the transition temperature of perfluoropentane. Thus, under normal circumstances, perfluoropentane is a gaseous precursor. As a further example, there are the homologs of perfluoropentane, namely perfluorobutane and perfluorohexane. The liquid/gas transition of perfluorobutane is 4° C. and that of perfluorohexane is 57° C. Thus, perfluorobutane can be useful as a gaseous precursor, although more likely as a gas, whereas perfluorohexane can be useful as a gaseous precursor because of its relatively high boiling point. As known to one of ordinary skill in the art, the effective boiling point of a substance may be related to the pressure to which that substance is exposed. This relationship is exemplified by the ideal gas law: PV=nRT, where P is pressure, V is volume, n is moles of substance, R is the gas constant, and T is temperature. The ideal gas law indicates that as pressure increases, the effective boiling point increases also. Conversely, as pressure decreases, the effective boiling point decreases.

A wide variety of materials can be used as gaseous precursors in the present compositions. It is only required that the material be capable of undergoing a phase transition to the gas phase upon passing through the appropriate temperature. Suitable gaseous precursors include, for example, hexafluoroacetone, isopropyl acetylene, allene, tetrafluoroallene, boron trifluoride, 1,2-butadiene, 2,3-butadiene, 1,3-butadiene, 1,2,3-trichloro-2-fluoro-1,3-butadiene, 2-methyl-1,3-butadiene, hexafluoro-1,3-butadiene, butadiyne, 1-fluorobutane, 2-methylbutane, perfluorobutane, 1-butene, 2-butene, 2-methyl-1-butene, 3-methyl-1-butene, perfluoro-1-butene, perfluoro-2-butene, 4-phenyl-3-butene-2-one, 2-methyl-1-butene-3-yne, butyl nitrate, 1-butyne, 2-butyne, 2-chloro-1,1,1,4,4,4-hexafluorobutyne, 3-methyl-1-butyne, perfluoro-2-butyne, 2-bromobutyraldehyde, carbonyl sulfide, crotononitrile, cyclobutane, methylcyclobutane, octafluorocyclobutane, perfluorocyclobutene, 3-chlorocyclopentene, perfluorocyclopentane, octafluorocyclopentene, cyclopropane, perfluorocyclopropane, 1,2-dimethylcyclopropane, 1,1-dimethylcyclopropane, 1,2-dimethylcyclopropane, ethylcyclopropane, methylcyclopropane, diacetylene, 3-ethyl-3-methyl diaziridine, 1,1,1-trifluorodiazoethane, dimethyl amine, hexafluorodimethylamine, dimethylethylamine, bis (dimethylphosphine)amine, perfluorohexane, perfluoroheptane, perfluorooctane, 2,3-dimethyl-2-norbornane, perfluorodimethylamine, dimethyloxonium chloride, 1,3-dioxolane-2-one, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro-1,1-difluoroethane, 1,1-dichloro-2-fluoroethane, 1-chloro-1,1,2,2-tetrafluoroethane, 2-chloro-1,1-difluoroethane, chloroethane, chloropentafluoroethane, dichlorotrifluoroethane, fluoroethane, perfluoroethane, nitropentafluoroethane, nitrosopentafluoroethane, perfluoroethylamine, ethyl vinyl ether, 1,1-dichloroethane, 1,1-dichloro-1,2-difluoroethane, 1,2-difluoroethane, methane, trifluoromethanesulfonylchloride, trifluoromethanesulfonylfluoride, bromodifluoronitrosomethane, bromofluoromethane, bromochlorofluoromethane, bromotrifluoromethane, chlorodifluoronitromethane, chlorodinitromethane, chlorofluoromethane, chlorotrifluoromethane, chlorodifluoromethane, dibromodifluoromethane, dichlorodifluoromethane, dichlorofluoromethane, difluoromethane, difluoroiodomethane, disilanomethane, fluoromethane, iodomethane, iodotrifluoromethane, nitrotrifluoromethane, nitrosotrifluoromethane, tetrafluoromethane, trichlorofluoromethane, trifluoromethane, 2-methylbutane, methyl ether, methyl isopropyl ether, methyllactate, methylnitrite, methylsulfide, methyl vinyl ether, neopentane, nitrous oxide, 1,2,3-nonadecanetricarboxylic acid 2-hydroxytrimethyl ester, 1-nonene-3-yne, 1,4pentadiene, n-pentane, perfluoropentane, 4-amino-4-methylpentan-2-one, 1-pentene, 2-pentene (cis and trans), 3-bromopent-1-ene, perfluoropent-1-ene, tetrachlorophthalic acid, 2,3,6-trimethylpiperidine, propane, 1,1,1,2,2,3-hexafluoropropane, 1,2-epoxypropane, 2,2-difluoropropane, 2-aminopropane, 2-chloropropane, heptafluoro-1-nitropropane, heptafluoro-1-nitrosopropane, perfluoropropane, propene, hexafluoropropane, 1,1,1,2,3,3-hexafluoro-2,3-dichloropropane, 1-chloropropane, chloropropane-(trans), 2-chloropropane, 3-fluoropropane, propyne, 3,3,3-trifluoropropyne, 3-fluorostyrene, sulfur (di)-decafluoride $(S_2F_{10})$, 2,4-diaminotoluene, trifluoroacetonitrile, trifluoromethyl peroxide, trifluoromethyl sulfide, tungsten hexafluoride, vinyl acetylene and vinyl ether.

Perfluorocarbons are both preferred gases and preferred gaseous precursors for use in connection with the compositions employed in the methods of the present invention. Included among such perfluorocarbons are saturated perfluorocarbons, unsaturated perfluorocarbons, and cyclic perfluorocarbons. The saturated perfluorocarbons, which are usually preferred, have the formula $C_nF_{2n+2}$, where n is from 1 to about 12, preferably about 2 to about 10, more preferably about 3 to about 8, and even more preferably about 3 to about 6. Suitable perfluorocarbons include, for example, perfluoromethane, perfluoroethane, perfluoropropane, perfluorobutane, perfluorocyclobutane, perfluoropentane, perfluorohexane, perfluoroheptane, perfluorooctane and perfluorononane. Preferably, the perfluorocarbon is selected from the group consisting of perfluoropropane, perfluorobutane, perfluorocyclobutane, perfluoropentane, perfluorohexane and perfluorooctane, with perfluoropropane being particularly preferred. Cyclic perfluorocarbons, which have the formula $C_nF_{2n}$, where n is from 3 to 8, preferably 3 to 6, may also be preferred, and include, for example, hexafluorocyclopropane, octafluorocyclobutane, and decafluorocyclopentane.

In addition to the perfluorocarbons, it may be desirable to utilize stable fluorocarbons which are not completely fluorinated. Such fluorocarbons include heptafluoropropane, for example, 1,1,1,2,3,3,3-heptafluoropropane and its isomer, 1,1,2,2,3,3,3-heptafluoropropane.

The gaseous precursor materials may be also photoactivated materials, such as diazonium ion and aminomalonate. As discussed more fully hereinafter, certain lipid and/or vesicle compositions, and particularly vesicle compositions, may be formulated so that gas is formed at the target tissue or by the action of sound on the lipid composition. Examples of gaseous precursors are described, for example, in U.S. Pat. Nos. 5,088,499 and 5,149,319, the disclosures of which are hereby incorporated herein by reference, in their entirety. Other gaseous precursors, in addition to those exemplified above, will be apparent to one skilled in the art based on the present disclosure.

The gaseous substances and/or gaseous precursors are preferably incorporated in the lipid and/or vesicle compositions irrespective of the physical nature of the composition. Thus, it is contemplated that the gaseous substances and/or precursors thereto may be incorporated, for example, in lipid compositions in which the lipids are aggregated randomly, as well as in vesicle compositions, including vesicle compositions which are formulated from lipids, such as micelles and liposomes. Incorporation of the gaseous substances and/or precursors thereto in the lipid and/or vesicle compositions may be achieved by using any of a number of methods. For example, in the case of vesicles based on lipids, the formation of gas filled vesicles can be achieved by shaking or otherwise agitating an aqueous mixture which comprises a gas or gaseous precursor and one or more lipids. This promotes the formation of stabilized vesicles within which the gas or gas precursor is encapsulated.

In addition, a gas may be bubbled directly into an aqueous mixture of lipid and/or vesicle-forming compounds. Alternatively, a gas instillation method can be used as disclosed, for example, in U.S. Pat. Nos. 5,352,435 and 5,228,446, the disclosures of which are hereby incorporated herein by reference, in their entirety. Suitable methods for incorporating the gas or gas precursor in cationic lipid compositions are disclosed also in U.S. Pat. No. 4,865,836, the disclosures of which are hereby incorporated herein by reference. Other methods would be apparent to one skilled in the art based on the present disclosure. Preferably, the gas may be instilled in the lipid and/or vesicle compositions after or during the addition of the stabilizing material and/or during formation of vesicles.

In preferred embodiments, the gaseous substances and/or gaseous precursor materials are incorporated in vesicle compositions, with micelles and liposomes being preferred. As discussed in detail below, vesicles in which a gas or gaseous precursor or both are encapsulated are advantageous in that they provide improved reflectivity in vivo.

As discussed more fully hereinafter, it is preferred that the lipid compositions, and especially the vesicle compositions, be formulated from lipids and optional stabilizing compounds to promote the formation of stable vesicles. In addition, it is also preferred that the lipid and/or vesicle compositions comprise a highly stable gas as well. The phrase "highly stable gas" refers to a gas which has limited solubility and diffusability in aqueous media. Exemplary highly stable gases include perfluorocarbons since they are generally less diffusible and relatively insoluble in aqueous media. Accordingly, their use may promote the formation of highly stable vesicles.

In certain embodiments, it may be desirable to use a fluorinated compound, especially a perfluorocarbon compound, which may be in the liquid state at the temperature of use of the lipid and/or vesicle compositions, including, for example, the in vivo temperature of the human body, to assist or enhance the stability of the lipid and/or vesicle compositions, and especially, the gas filled vesicles. Suitable fluorinated compounds include, for example, fluorinated surfactants, such as fluorinated surfactants which are commercially available as ZONYL® surfactants (the DuPont Company, Wilmington, Del.), as well as liquid perfluorocarbons, such as for example, perfluorooctylbromide (PFOB), perfluorodecalin, perfluorododecalin, perfluorooctyliodide, perfluorotripropylamine, and perfluorotributylamine. In general, perfluorocarbons comprising about six or more carbon atoms will be liquids at normal human body temperature. Among these perfluorocarbons, perfluorooctylbromide and perfluorohexane, which are liquids at room temperature, are preferred. The gas which is present may be, for example, nitrogen or perfluoropropane, or may be derived from a gaseous precursor, which may also be a perfluorocarbon, for example, perfluoropentane. In the latter case, the lipid and/or vesicle compositions may be prepared from a mixture of perfluorocarbons, which for the examples given, would be perfluoropropane (gas) or perfluoropentane (gaseous precursor) and perfluorooctylbromide (liquid). Although not intending to be bound by any theory or theories of operation, it is believed that, in the case of vesicle compositions, the liquid fluorinated compound may be situated at the interface between the gas and the membrane or wall surface of the vesicle. There may be thus formed a further stabilizing layer of liquid fluorinated compound on the internal surface of the stabilizing compound, for example, a biocompatible lipid used to form the vesicle, and this perfluorocarbon layer may also prevent the gas from diffusing through the vesicle membrane. A gaseous precursor, within the context of the present invention, is a liquid at the temperature of manufacture and/or storage, but becomes a gas at least at or during the time of use.

Thus, it has been discovered that a liquid fluorinated compound, such as a perfluorocarbon, when combined with a gas or gaseous precursor ordinarily used to make the lipid and/or vesicle compositions described herein, may confer an added degree of stability not otherwise obtainable with the gas or gaseous precursor alone. Thus, it is within the scope of the present invention to utilize a gas or gaseous precursor, such as a perfluorocarbon gaseous precursor, for example, perfluoropentane, together with a perfluorocarbon which remains liquid after administration to a patient, that is, whose liquid to gas phase transition temperature is above the body temperature of the patient, for example, perfluorooctylbromide. Perfluorinated surfactants, such as ZONYL® fluorinated surfactants, may be used to stabilize the lipid and/or vesicle compositions, and to act, for example, as a coating for vesicles. Preferred perfluorinated surfactants are the partially fluorinated phosphocholine surfactants. In these preferred fluorinated surfactants, the dual alkyl compounds may be fluorinated at the terminal alkyl chains and the proximal carbons may be hydrogenated. These fluorinated phosphocholine surfactants may be used for making the targeted lipid and/or vesicle compositions of the present invention.

In connection with embodiments involving vesicle compositions, the size of the vesicles can be adjusted for the particular intended end use including, for example, diagnostic and/or therapeutic use. The size of the vesicles may preferably range from about 30 nanometers (nm) to about 100 micrometers ($\mu$m) in diameter, and all combinations and subcombinations of ranges therein. More preferably, the vesicles have diameters of from about 100 nm to about 10 $\mu$m, with diameters of from about 200 nm to about 7 $\mu$m being even more preferred. In connection with particular uses, for example, intravascular use, including magnetic resonance imaging of the vasculature, it may be preferred that the vesicles be no larger that about 30 $\mu$m in diameter, with smaller vesicles being preferred, for example, vesicles of no larger than about 12 $\mu$m in diameter. In certain preferred embodiments, the diameter of the vesicles may be about 7 $\mu$m or less, with vesicles having a mean diameter of about 5 $\mu$m or less being more preferred, and vesicles having a mean diameter of about 3 $\mu$m or less being even more preferred. It is contemplated that these smaller vesicles may perfuse small vascular channels, such as the microvasculature, while at the same time providing enough space or room within the vascular channel to permit red blood cells to slide past the vesicles.

The size of the gas filled vesicles can be adjusted, if desired, by a variety of procedures including, for example, shaking, microemulsification, vortexing, extrusion, filtration, sonication, homogenization, repeated freezing and thawing cycles, extrusion under pressure through pores of defined size, and similar methods.

As noted above, compositions employed herein may also include, with respect to their preparation, formation and use, gaseous precursors that can be activated to change from a liquid or solid state into a gas by temperature, pH, light, and energy (such as ultrasound). The gaseous precursors may be made into gas by storing the precursors at reduced pressure. For example, a vial stored under reduced pressure may create a headspace of perfluoropentane or perfluorohexane gas, useful for creating a preformed gas prior to injection. Preferably, the gaseous precursors may be activated by temperature. Set forth below is a table listing a series of gaseous precursors which undergo phase transitions from liquid to gaseous states at relatively close to normal body temperature (37° C.) or below, and the size of the emulsified droplets that would be required to form a vesicle of a maximum size of 10 $\mu$m.

TABLE 2

Physical Characteristics of Gaseous Precursors and
Diameter of Emulsified Droplet to Form a 10 μm Vesicle*

| Compound | Molecular Weight | Boiling Point (° C.) | Density | Diameter (μm) of emulsified droplet to make 10 micron vesicle |
|---|---|---|---|---|
| perfluoro pentane | 288.04 | 28.5 | 1.7326 | 2.9 |
| 1-fluorobutane | 76.11 | 32.5 | 0.67789 | 1.2 |
| 2-methyl butane (isopentane) | 72.15 | 27.8 | 0.6201 | 2.6 |
| 2-methyl 1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |
| octafluoro cyclobutane | 200.04 | −5.8 | 1.48 | 2.8 |
| decafluoro butane | 238.04 | −2 | 1.517 | 3.0 |
| hexafluoro ethane | 138.01 | −78.1 | 1.607 | 2.7 |

*Source: Chemical Rubber Company Handbook of Chemistry and Physics, Robert C. Weast and David R. Lide, eds., CRC Press, Inc. Boca Raton, Florida (1989–1990).

The perfluorocarbons, as already indicated, are preferred for use as the gas or gaseous precursors, as well as additional stabilizing components.

As noted above, it is preferred to optimize the utility of the lipid and/or vesicle compositions, especially vesicle compositions formulated from lipids, by using gases of limited solubility. The phrase "limited solubility" refers to the ability of the gas to diffuse out of the vesicles by virtue of its solubility in the surrounding aqueous medium. A greater solubility in the aqueous medium imposes a gradient with the gas in the vesicle such that the gas may have a tendency to diffuse out of the vesicle. A lesser solubility in the aqueous milieu, may, on the other hand, decrease or eliminate the gradient between the vesicle and the interface such that diffusion of the gas out of the vesicle may be impeded. Preferably, the gas entrapped in the vesicle has a solubility less than that of oxygen, that is, about 1 part gas in about 32 parts water. See *Matheson Gas Data Book*, 1966, Matheson Company Inc. More preferably, the gas entrapped in the vesicle possesses a solubility in water less than that of air; and even more preferably, the gas entrapped in the vesicle possesses a solubility in water less than that of nitrogen.

It may be desirable, in certain embodiments, to formulate vesicles from substantially impermeable polymeric materials. In these embodiments, it is generally unnecessary to employ a gas which is highly insoluble also. For example, stable vesicle compositions which comprise substantially impermeable polymeric materials may be formulated with gases having higher solubilities, for example, air or nitrogen.

In addition to, or instead of, the lipid, proteinaceous and/or polymeric compounds discussed above, the compositions described herein may comprise one or more stabilizing materials. Exemplary of such stabilizing materials are, for example, biocompatible polymers. The stabilizing materials may be employed to desirably assist in the formation of vesicles and/or to assure substantial encapsulation of the gases or gaseous precursors. Even for relatively insoluble, non-diffusible gases, such as perfluoropropane or sulfur hexafluoride, improved vesicle compositions may be obtained when one or more stabilizing materials are utilized in the formation of the gas and gaseous precursor filled vesicles. These compounds may help improve the stability and the integrity of the vesicles with regard to their size, shape and/or other attributes.

The terms "stable" or "stabilized", as used herein, means that the vesicles may be substantially resistant to degradation, including, for example, loss of vesicle structure or encapsulated gas or gaseous precursor, for a useful period of time. Typically, the vesicles employed in the present invention have a desirable shelf life, often retaining at least about 90% by volume of its original structure for a period of at least about two to three weeks under normal ambient conditions. In preferred form, the vesicles are desirably stable for a period of time of at least about 1 month, more preferably at least about 2 months, even more preferably at least about 6 months, still more preferably about eighteen months, and yet more preferably up to about 3 years. The vesicles described herein, including gas and gaseous precursor filled vesicles, may also be stable even under adverse conditions, such as temperatures and pressures which are above or below those experienced under normal ambient conditions.

The stability of the vesicles described herein may be attributable, at least in part, to the materials from which the vesicles are made, including, for example, the lipids, polymers and/or proteins described above, and it is often not necessary to employ additional stabilizing materials, although it is optional and may be preferred to do so. Such additional stabilizing materials and their characteristics are described more fully hereinafter.

The materials from which the vesicles are constructed are preferably biocompatible lipid, protein or polymer materials, and of these, the biocompatible lipids are preferred. In addition, because of the ease of formulation, including the capability of preparing vesicles immediately prior to administration, these vesicles may be conveniently made on site.

The biocompatible polymers useful as stabilizing materials for preparing the gas and gaseous precursor filled vesicles may be of natural, semi-synthetic (modified natural) or synthetic origin. As used herein, the term polymer denotes a compound comprised of two or more repeating monomeric units, and preferably 10 or more repeating monomeric units. The phrase semi-synthetic polymer (or modified natural polymer), as employed herein, denotes a natural polymer that has been chemically modified in some fashion. Exemplary natural polymers suitable for use in the present invention include naturally occurring polysaccharides. Such polysaccharides include, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, polydextrose, pustulan, chitin, agarose, keratan, chondroitan, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threorine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin. Exemplary semi-synthetic polymers include carboxymethylcellulose, hydroxymethylcellulose, hydroxypropylmethylcellulose, methylcellulose, and methoxycellulose. Exemplary synthetic polymers suitable for use in the present invention include polyethylenes (such as, for example, polyethylene glycol, polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbons, fluorinated carbons (such as, for example, polytetrafluoroethylene), and polymethylmethacrylate, and derivatives thereof. Methods for the preparation of vesicles which employ polymers as stabilizing compounds will be readily apparent to those skilled in the art, once armed with the present disclosure, when the present disclosure is coupled with information known in the art, such as that described and referred to in Unger, U.S. Pat. No 5,205,290, the disclosures of which are hereby incorporated herein by reference, in their entirety.

Particularly preferred embodiments of the present invention may involve vesicles which comprise three components: (1) a neutral lipid, for example, a nonionic or zwitterionic lipid, (2) a negatively charged lipid, and (3) a lipid bearing a stabilizing material, for example, a hydrophilic polymer. Preferably, the amount of the negatively charged lipid will be greater than about 1 mole percent of the total lipid present, and the amount of lipid bearing a hydrophilic polymer will be greater than about 1 mole percent of the total lipid present. Exemplary and preferred negatively charged lipids include phosphatidic acids. The lipid bearing a hydrophilic polymer will desirably be a lipid covalently linked to the polymer, and the polymer will preferably have a weight average molecular weight of from about 400 to about 100,000. Suitable hydrophilic polymers are preferably selected from the group consisting of polyethylene glycol (PEG), polypropylene glycol, polyvinylalcohol, and polyvinylpyrrolidone and copolymers thereof, with PEG polymers being preferred. Preferably, the PEG polymer has a molecular weight of from about 1000 to about 7500, with molecular weights of from about 2000 to about 5000 being more preferred. The PEG or other polymer may be bound to the lipid, for example, DPPE, through a covalent bond, such as an amide, carbamate or amine linkage. In addition, the PEG or other polymer may be linked to a targeting ligand, or other phospholipids, with a covalent bond including, for example, amide, ester, ether, thioester, thioamide or disulfide bonds. Where the hydrophilic polymer is PEG, a lipid bearing such a polymer will be said to be "pegylated." In preferred form, the lipid bearing a hydrophilic polymer may be DPPE-PEG, including, for example, DPPE-PEG5000, which refers to DPPE having a polyethylene glycol polymer of a mean weight average molecular weight of about 5000 attached thereto (DPPE-PEG5000). Another suitable pegylated lipid is distearoylphosphatidylethanol-amine-polyethylene glycol 5000 (DSPE-PEG5000).

In certain preferred embodiments of the present invention, the lipid compositions may include about 77.5 mole % DPPC, 12.5 mole % of DPPA, and 10 mole % of DPPE-PEG5000. Also preferred are compositions which comprise about 80 to about 90 mole % DPPC, about 5 to about 15 mole % DPPA and about 5 to about 15 mole % DPPE-PEG5000. Especially preferred are compositions which comprise DPPC, DPPA and DPPE-PEG5000 in a mole % ratio of 82:10:8, respectively. DPPC is substantially neutral, since the phosphatidyl portion is negatively charged and the choline portion is positively charged. Consequently, DPPA, which is negatively charged, may be added to enhance stabilization in accordance with the mechanism described above. DPPE-PEG provides a pegylated material bound to the lipid membrane or skin of the vesicle by the DPPE moiety, with the PEG moiety free to surround the vesicle membrane or skin, and thereby form a physical barrier to various enzymatic and other endogenous agents in the body whose function is to degrade such foreign materials. The DPPE-PEG may provide more vesicles of a smaller size which are safe and stable to pressure when combined with other lipids, such as DPPC and DPPA, in the given ratios. It is also theorized that the pegylated material, because of its structural similarity to water, may be able to defeat the action of the macrophages of the human immune system, which would otherwise tend to surround and remove the foreign object. The result is an increase in the time during which the stabilized vesicles may function as diagnostic imaging contrast media.

The vesicle compositions may be prepared from other materials, in addition to the materials described above, provided that the vesicles so prepared meet the stability and other criteria set forth herein. These materials may be basic and fundamental, and form the primary basis for creating or establishing tie stabilized gas and gaseous precursor filled vesicles. On the other hand, they may be auxiliary, and act as subsidiary or supplementary agents which can enhance the functioning of the basic stabilizing material or materials, or contribute some desired property in addition to that afforded by the basic stabilizing material.

However, it is not always possible to determine whether a given material is a basic or an auxiliary agent, since the functioning of the material in question is determined empirically, for example, by the results produced with respect to producing stabilized vesicles. As examples of how these basic and auxiliary materials may function, it has been observed that the simple combination of a biocompatible lipid and water or saline when shaken will often give a cloudy solution subsequent to autoclaving for sterilization. Such a cloudy solution may function as a contrast agent, but is aesthetically objectionable and may imply instability in the form of undissolved or undispersed lipid particles. Cloudy solutions may be also undesirable where the undissolved particulate matter has a diameter of greater than about 7 $\mu$m, and especially greater than about 10 $\mu$m. Manufacturing steps, such as sterile filtration, may also be problematic with solutions which contain undissolved particulate matter. Thus, propylene glycol may be added to remove this cloudiness by facilitating dispersion or dissolution of the lipid particles. The propylene glycol may also function as a wetting agent which can improve vesicle formation and stabilization by increasing the surface tension on the vesicle membrane or skin. It is possible that the propylene glycol can also function as an additional layer that may coat the membrane or skin of the vesicle, thus providing additional stabilization. As examples of such further basic or auxiliary stabilizing materials, there are conventional surfactants which may be used; see D'Arrigo U.S. Pat. Nos. 4,684,479 and 5,215,680.

Additional auxiliary and basic stabilizing materials include such agents as peanut oil, canola oil, olive oil, safflower oil, corn oil, or any other oil commonly known to be ingestible which is suitable for use as a stabilizing compound in accordance with the teachings herein. Various auxiliary and basic stabilizing materials are disclosed, for example, in U.S. application Ser. No. 08/444,574, filed May 19, 1995, the disclosures of which are incorporated herein by reference, in their entirety.

In addition, compounds used to make mixed micelle systems may be suitable for use as basic or auxiliary stabilizing materials, and these include, for example, lauryltrimethylammonium bromide (dodecyl-), cetyltrimethylammonium bromide (hexadecyl-), myristyltrimethylammonium bromide (tetradecyl-), alkyldimethylbenzylammonium chloride (where alkyl is $C_{12}$, $C_{14}$ or $C_{16}$,), benzyldimethyldodecylammonium bromide/chloride, benzyldimethyl hexadecylammonium bromide/chloride, benzyldimethyl tetradecylammonium bromide/chloride, cetyldimethylethylammonium bromide/chloride, or cetylpyridinium bromide/chloride.

It has also been found that the gas and gaseous precursor filled vesicles used in the present invention may be controlled according to size, solubility and heat stability by choosing from among the various additional or auxiliary stabilizing materials described herein. These materials can affect these parameters of the vesicles, especially vesicles formulated from lipids, not only by their physical interaction with the membranes, but also by their ability to modify the viscosity and surface tension of the surface of the gas and gaseous precursor filled vesicle. Accordingly, the gas and gaseous precursor filled vesicles used in the present invention may be favorably modified and further stabilized, for example, by the addition of one or more of a wide variety of (a) viscosity modifiers, including, for example, carbohydrates and their phosphorylated and sulfonated derivatives; polyethers, preferably with molecular weight ranges between 400 and 100,000; and di- and trihydroxy alkanes and their polymers, preferably with molecular weight ranges between 200 and 50,000; (b) emulsifying and/or solubilizing agents including, for example, acacia, cholesterol, diethanolamine, glyceryl monostearate, lanolin alcohols, lecithin, mono- and di-glycerides, mono-ethanolamine, oleic acid, oleyl alcohol, poloxamer, for example, poloxamer 188, poloxamer 184, and poloxamer 181, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax; (c) suspending and/or viscosity-increasing agents, including, for example, acacia, agar, alginic acid, aluminum mono-stearate, bentonite, magma, carbomer 934P, carboxymethylcellulose, calcium and sodium and sodium 12, carrageenan, cellulose, dextran, gelatin, guar gum, locust bean gum, veegum, hydroxyethyl cellulose, hydroxypropyl methylcellulose, magnesium-aluminum-silicate, Zeolites®, methylcellulose, pectin, polyethylene oxide, povidone, propylene glycol alginate, silicon dioxide, sodium alginate, tragacanth, xanthan gum, α-d-gluconolactone, glycerol and mannitol; (d) synthetic suspending agents, such as polyethylene glycol (PEG), polyvinylpyrrolidone (PVP), polyvinylalcohol (PVA), polypropylene glycol (PPG), and polysorbate; and (e) tonicity raising agents which stabilize and add tonicity, including, for example, sorbitol, mannitol, trehalose, sucrose, propylene glycol and glycerol.

As noted above, the compositions of the present invention further comprise a targeting ligand. The targeting ligands are preferably associated with the lipid compounds, proteins, polymers, surfactants and/or vesicles covalently or non-covalently. Thus, in the case of lipid compositions, the targeting ligand may be bound, for example, via a covalent or non-covalent bond, to at least one of the lipids incorporated in the compositions. In the case of vesicles which are formulated from substances other than lipids, for example, clathrates, aerogels, surfactant and albumin vesicles, the targeting ligand may be preferably bound covalently or non-covalently to one or more of the materials incorporated in the vesicle walls. It is generally preferred that the targeting ligand be bound to the lipid and/or vesicles covalently. Preferably, in the case of lipid compositions which comprise cholesterol, the targeting ligand is bound to the cholesterol substantially only non-covalently, and/or that the targeting ligand is bound covalently to a component of the composition, for example, another lipid, such as a phospholipid, other than the cholesterol.

If desired, the targeting ligands may also be bound to other stabilizing materials, for example, biocompatible polymers, which may be present in the compositions. The targeting ligands which are incorporated in the compositions of the present invention are preferably substances which are capable of targeting receptors and/or tissues in vivo. With respect to the targeting of tissue, as noted above, the targeting ligands are desirably capable of targeting heart tissue, including myocardial cells, and membranous tissues, including endothelial and epithelial cells. In the case of receptors, the targeting ligands are desirably capable of targeting GPIIbIIIa receptors. In particularly preferred embodiments, the targeting ligands may be especially suited for targeting cells or receptors associated with coagula, particularly in patients suffering form an arrhythmic disorder. It is contemplated that preferred targeting ligands for use in targeting tissues and/or receptors, including the tissues and receptors exemplified above, are selected from the group consisting of proteins, peptides, saccharides, steroids, steroid analogs, bioactive agents and genetic material, including, for example, antibodies, glycoproteins and lectins, with proteins and peptides being preferred and peptides being more preferred. An example of a protein which may be preferred for use as a targeting ligand is Protein A, which is protein that is produced by most strains of *Staphylococcus aureus*. Protein A is commercially available, for example, from Sigma Chemical Co. (St. Louis, Mo.). Protein A may then be used for binding a variety of IgG antibodies. Generally speaking, peptides which are particularly useful as targeting ligands include natural, modified natural, or synthetic peptides that incorporate additional modes of resistance to degradation by vascularly circulating esterases, amidases, or peptidases. One very useful method of stabilization of peptide moieties incorporates the use of cyclization techniques. As an example, the end-to-end cyclization whereby the carboxy terminus is covalently linked to the amine terminus via an amide bond may be useful to inhibit peptide degradation and increase circulating half-life. Additionally, a side chain-to-side chain cyclization is also particularly useful in inducing stability. In addition, an end-to-side chain cyclization may be a useful modification as well. In addition, the substitution of an L-amino acid for a D-amino acid in a strategic region of the peptide may offer resistance to biological degradation. Suitable targeting ligands, and methods for their preparation, will be readily apparent to one skilled in the art, once armed with the disclosure herein.

In connection with the targeting of endothelial cells, suitable targeting ligands include, for example, one or more of the following: growth factors, including, for example, basic fibroblast growth factor (bFGF), acidic fibroblast growth factor (aFGF), transforming growth factor-alpha (TGF-α), transforming growth factor-beta (TGF-β), platelet-derived endothelial cell growth factor (PD-ECGF) vascular endothelial growth factor (VEGF) and human growth factor (HGF); angiogenin; tumor necrosis factors, including tumor necrosis factor-alpha (TNF-α) and tumor necrosis factor-beta (TNF-β); copper-containing polyribonucleotide angiotropin with a molecular weight of about 4,500, as well as low molecular weight non-peptide angiogenic factors, such as 1-butyryl glycerol; the prostaglandins, including, for example, prostaglandin $E_1$ ($PGE_1$) and prostaglandin $E_2$ ($PGE_2$); nicotinamide; adenosine; dipyridamole; dobutamine; hyaluronic acid degradation products, such as, for example, degradation products resulting from hydrolysis of β linkages, including hyalobiuronic acid; angiogenesis inhibitors, including, for example, collagenase inhibitors; minocycline; medroxyprogesterone; chitin chemically modified with 6-O-sulfate and 6-O-carboxymethyl groups; angiostatic steroids, such as tetrahydrocortisol; and heparin, including fragments of heparin, such as, for example, fragments having a molecular weight of about 6,000, admixed with steroids, such as, for example, cortisone or hydrocortisone; angiogenesis inhibitors, including angioinhibin (AGM-1470—an angiostatic antibiotic); platelet factor 4; protamine; sulfated polysaccharide peptidoglycan complexes derived from the bacterial wall of an Arthobacter species; fungal-derived angiogenesis inhibitors, such as fumagillin derived from *Aspergillus fumigatus;* D-penicillamine; gold thiomalate; thrombospondin; vitamin $D_3$ analogues, including, for example, 1-α, 25-dihydroxyvitamin $D_3$ and a synthetic analogue 22-oxa-1-α, 25-dihydroxyvitamin $D_3$; α-interferon; cytokines, such as the interleukins, including, for example, interleukin-1 (IL-1), interleukin-2 (IL-2), and interleukin-8 (IL-8); granulocyte macrophage colony stimulating factor (GMCSF); heparin, including low molecular weight fragments of heparin or analogues of heparin; simple sulfated polysaccharides, such as cyclodextrins, including α-, β- and γ-cyclodextrin; tetradecasulfate; transferrin; ferritin; platelet factor 4; protamine; Gly-His-Lys complexed to copper; ceruloplasmin; (12R)-hydroxyeicosatrienoic acid; okadaic acid; lectins; antibodies; CD11a/CD18; and Very Late Activation Integrin-4 (VLA4).

Endothelial-eukocyte adhesion molecules (ELAM's) are antigens which are expressed by endothelial cells under conditions of stress which then facilitate the migration of the leukocytes across the endothelium lining the vasculature into the surrounding tissues. It is also the surprising discovery that these same endothelial-leukocyte adhesion molecules may be advantageously exploited as receptors for targeting of vesicles. These endothelial cell adhesion molecules belong to a family known as selectins in which the known members, such as GMP-140, all participate in endothelial-leukocyte adhesion and include ELAM-1, LAM-1 and the granule membrane protein 140 (GMP-140) also known as platelet activation-dependent granule-external membrane protein (PADGEM), VCAM-1/INCAM-110 (Vascular Adhesion Molecule/Inducible Adhesion Molecule) and ICAM-1 (Intercellular Adhesion Molecule). The cadherin family of cell adhesion molecules may also be used as targeting ligands, including for example, the E-, N-, and P-cadherins, cadherin-4, cadherin-5, cadherin-6, cadherin-7, cadherin-8, cadherin-9, cadherin-10, and cadherin-11; and most preferably cadherin C-5. Further, antibodies directed to cadherins, such as, for example, the monoclonal antibody Ec6C10, may be used to recognize cadherins expressed locally by specific endothelial cells.

A wide variety of different targeting ligands can be selected to bind to the cytoplasmic domains of the ELAM molecules. Targeting ligands in this regard may include lectins, a wide variety of carbohydrate or sugar moieties, antibodies, antibody fragments, Fab fragments, such as, for example, Fab'2, and synthetic peptides, including, for example, Arginine-Glycine-Aspartic Acid (R-G-D) which may be targeted to wound healing. While many of these materials may be derived from natural sources, some may be synthesized by molecular biological recombinant techniques and others may be synthetic in origin. Peptides may be prepared by a variety of different combinatorial chemistry techniques as are now known in the art. Targeting ligands derived or modified from human leukocyte origin, such as CD11a/CD18, and leukocyte cell surface glycoprotein (LFA-1), may also be used as these are known to bind to the endothelial cell receptor ICAM-1. The cytokine inducible member of the immunoglobulin superfamily, VCAM-1, which is mononuclear leukocyte-selective, may also be used as a targeting ligand. VLA-4, derived from human monocytes, may be used to target VCAM-1. Antibodies and other targeting ligands may be employed to target endoglin, which is an endothelial cell proliferation marker. Endoglin is upregulated on endothelial cells in miscellaneous solid tumors. A targeting ligand which may be used to target endoglin is the antibody TEC-11. R. E. Thorpe and F. J. Burrows, *Breast Cancer Research and Treatment,* Vol. 36, pp. 237–51 (1995).

Endothelial cell activation in the setting of atherosclerosis is used in this invention to target the compositions to regions of arteriosclerosis including, for example, atherosclerotic plaque. One such target that can be used is the inducible mononuclear leukocyte endothelial adhesion molecule recognized by Rb1/9 as an ATHERO-ELAM. The monoclonal antibodies, H4/18 and H18/7, may be used to target endothelial cell surface antigens which are induced by cytokine mediators. As a preferred embodiment of this invention, gas filled vesicles are targeted to atherosclerotic plaque to non-invasively detect diseased blood vessels before severe damage has occurred, for example, prior to stroke or myocardial infarction, so that appropriate medical or surgical intervention may be implemented. ATHERO-ELAM is a preferred target and ligands, such as antibodies, peptides, or lectins or combinations thereof may be used to target this cell surface epitope expressed on endothelial cells in the context of atherosclerosis. Alternatively, lipoproteins or lipoprotein fragments derived from low or high density lipoprotein proteins may be used as targeting ligands. Additionally, cholesterol may be used to target the endothelial cells and localize the lipids, vesicles, and the like, to regions of atherosclerotic plaque. In embodiments which involve the use of cholesterol as a targeting ligand, the cholesterol is preferably unmodified (non-derivatized) with other chemical groups, moieties, ligands, and the like.

A targeting ligand directed toward thrombotic material in the plaque may be used to differentiate between active and inactive regions of atherosclerotic plaque. Active plaques in the process of generating thrombi are more dangerous as these plaques may ultimately occlude a vessel or result in emboli. In this regard, in addition to low molecular weight heparin fragments, other targeting ligands, such as, for example, anti-fibrin antibody, tissue plasminogen activator (t-PA), anti-thrombin antibody and fibrin antibodies directed to platelet activation factions, may be used to target active plaque with evolving clots. Most preferred targeting ligands are those which will target a plasma membrane associated GPIIbIIIa in activated platelets in addition to targeting P-selectin, and an antibody or associated antibody fragment directed to GPIIbIIIa. The present invention is also useful for detecting regions of acute myocardial infarction. Conveniently, by attaching anti-myosin (particularly cardiomyosin) antibody or anti-actin antibodies to the lipids, polymers or stabilizing materials, infarcted myocardium may be detected by the methods of the present invention. For targeting to granulation tissue (healing wounds), many of the above targeting ligands may be useful. The wound healing tripeptide, arginine-glycine-aspartic acid (RGD), may also be used as a targeting ligand in this regard.

As with the endothelial cells discussed above, a wide variety of peptides, proteins and antibodies may be employed as targeting ligands for targeting epithelial cells. Preferably, a peptide, including synthetic, semi-synthetic or naturally-occurring peptides, with high affinity to the epithelial cell target receptor may be selected, with synthetic peptides being more preferred. In connection with these preferred embodiments, peptides having from about 5 to about 15 amino acid residues are preferred. Antibodies may be used as whole antibody or antibody fragments, for example, Fab or Fab'2, either of natural or recombinant origin. The antibodies of natural origin may be of animal or human origin, or may be chimeric (mouse/human). Human recombinant or chimeric antibodies are preferred and fragments are preferred to whole antibody.

Examples of monoclonal antibodies which may be employed as targeting ligands in the present compositions include CALAM 27, which is formed by immunizing BALB/c mice with whole human squamous cell carcinoma of the tongue and forming hybridomas by crossing extracted spleen cells with those of an NS1 syngeneic myeloma cell line. Gioanni, J. et al., *Cancer Research*, Vol. 47, pp. 4417–4424 (1987). CALAM 27 is directed to surface epitopes of both normal and malignant epithelial cells. Normal lymph nodes generally do not contain cells expressing these epitopes. See *Cancer Research*, Vol. 47, pp. 4417–4424 (1987). Accordingly, lipid and/or vesicle compositions comprising this antibody can be used to target metastases in the lymph nodes. The monoclonal antibody 3C2 may be employed as a targeting ligand for targeting malignant epithelial cells of serious ovarian carcinoma and endometrioid carcinoma. Another exemplary targeting ligand is Mab 4C7 (see *Cancer Research,* Vol. 45, 2358–2362, 1985), which may be used to target mucinous carcinoma, endometriod carcinoma and mesonephroid carcinoma. For targeting squamous cell carcinoma in head and neck cancer, Mab E48 (*Biological Abstract,* Vol. 099 Issue. 066 Ref. 082748) may be used as a targeting ligand. For targeting malignant melanoma, the monoclonal antibody 225.28s (*Pathol. Biol.,* Vol. 38 (8), pp. 866–869, 1990) may be employed.

Targeting ligands may be selected for targeting antigens, including antigens associated with breast cancer, such as epidermal growth factor receptor (EGFR), fibroblast growth factor receptor, erbB2/HER-2 and tumor associated carbohydrate antigens (*Cancer,* Vol. 74 (3) pp. 1006–12 (1994)). CTA 16.88, homologous to cytokeratins 8, 18 and 19, is expressed by most epithelial-derived tumors, including carcinomas of the colon, pancreas, breast, ovary and lung. Thus, antibodies directed to these cytokeratins, such as 16.88 (IgM) and 88BV59 (IgG3k), which recognize different epitopes on CTA 16.88 (*Semin. Nucl. Med.,* Vol. 23 (2), pp. 165–79 (1993)), may be employed as targeting ligands. For targeting colon cancer, anti-CEA IgG Fab' fragments may be employed as targeting ligands. Chemically conjugated bispecific anti-cell surface antigen, anti-hapten Fab'- Fab antibodies may also be used as targeting ligands. The MG series monoclonal antibodies may be selected for targeting, for example, gastric cancer (*Chin. Med. Sci. J.,* Vol. 6 (1), pp. 56–59 (1991).

There are a variety of cell surface epitopes on epithelial cells for which targeting ligands may be selected. For example, the protein human papilloma virus (HPV) has been associated with benign and malignant epithelial proliferations in skin and mucosa. Two HPV oncogenc proteins, E6 and E7, may be targeted as these may be expressed in certain epithelial derived cancers, such as cervical carcinoma See *Curr. Opin. Immunol.* Vol. 6 (5), pp. 746–54 (1994). Membrane receptors for peptide growth factors (PGF-R), which are involved in cancer cell proliferation, may also be selected as tumor antigens. *Anticancer Drugs,* Vol. 5 (4), pp. 379–93 (1994). Also, epidermal growth factor (EGF) and interleukin-2 may be targeted with suitable targeting ligands, including peptides, which bind these receptors. Certain melanoma associated antigens (MAA), such as epidermal growth factor receptor (EGFR) and adhesion molecules (*Tumor Biol.,* Vol. 15 (4), pp. 188–202 (1994)), which are expressed by malignant melanoma cells, can be targeted with the compositions provided herein. The tumor associated antigen FAB-72 on the surface of carcinoma cells may also be selected as a target.

A wide variety of targeting ligands may be selected for targeting myocardial cells. Exemplary targeting ligands include, for example, anticardiomyosin antibody, which may comprise polyclonal antibody, Fab'2 fragments, or be of human origin, animal origin, for example, mouse origin, or of chimeric origin. Additional targeting ligands include dipyridamole; digitalis; nifedipine; apolipoprotein; low density lipoproteins (LDL), including α-LDL, vLDL and methyl LDL; ryanodine; endothelin; complement receptor type 1; IgG Fc; beta 1-adrenergic; dihydropyridine; adenosine; mineralocorticoid; nicotinic acetylcholine and muscarinic acetylcholine; antibodies to the human alpha 1A-adrenergic receptor; bioactive agents, such as drugs, including the alpha 1-antagonist prazosin; antibodies to the anti-beta-receptor; drugs which bind to the anti-beta-receptor; anti-cardiac RyR antibodies; endothelin-1, which is an endothelial cell-derived vasoconstrictor peptide that exerts a potent positive inotropic effect on cardiac tissue (endothelin-1 binds to cardiac sarcolemmal vesicles); monoclonal antibodies which may be generated to the T cell receptor alpha-beta receptor and thereby employed to generate targeting ligands; the complement inhibitor sCR1; drugs, peptides or antibodies which are generated to the dihydropyridine receptor; monoclonal antibodies directed towards the antiinterleukin 2 receptor may be used as targeting ligands to direct the present compositions to areas of myocardial tissue which express this receptor and which may be up-regulated in conditions of inflammation; cyclosporine for directing similarly the compositions to areas of inflamed myocardial tissue; methylisobutyl isonitrile; lectins which bind to specific sugars on membranes of cardiac myocytes and cardiac endothelial cells; adrenomedullin (ADM), which is an endogenous hypotensive and vasorelaxing peptide; atrial natriuretic peptide (ANP); C-type natriuretic peptide (CNP), which is a 22 amino acid peptide of endothelial cell origin and is structurally related to atrial natriuretic peptide but genetically distinct, and possesses vasoactive and antimitogenic activity; vasonatrin peptide (VNP) which is a chimera of atrial natriuretic peptide (ANP) and C-type natriuretic peptide (CNP) and comprises 27 amino acids; thrombin; endothelium-derived relaxing factor (EDRF); neutral endopeptidase 1 (NEP-1);

competitive inhibitors to EDRF, including, for example, NG-monomethyl-L-arginine (L-NMMA); potassium channel antagonists, such as charybdotoxin and glibenclamide; antiheart antibodies, which may be identified in patients with idiopathic dilated cardiomyopathy but which preferably do not elicit cytolysis in the myocardium; antibodies directed against the adenine nucleotide translocator, the branched-chain keto acid dehydrogenase or cardiac myosin; specific antagonists for the endothelin-A receptor, which may be referred to as BQ-123; and antibodies to the angiotensin II receptor.

Two of the major antigens of heart sarcolemmal are calcium binding glycoproteins which copurify with the dihydropyridine receptor. Antisera may be raised, including polyclonal or monoclonal antibodies, against purified sarcolemma. These antibodies may also be employed as targeted ligands. Purified fractions of the calcium binding glycoproteins may be isolated from the plasma membranes of the sarcolemma and then used to generate antibodies. ANP, which, as noted above, may be used as a targeting ligand, can be obtained from cultures of human aortic endothelial cells. ANP is generally localized in endothelium, but also may localize to the endothelial or myocardial tissue. ANP may be prepared, for example, using recombinant techniques, as well as by synthesis of the peptide using peptide synthesis techniques well known to those skilled in the art. It is also possible to use an antibody, either polyclonal or monoclonal, directed towards ANP. Similarly, a peptide directed to ANP may be used for targeting endothelial and/or myocardial cells. Both the P and a forms of atrial natriuretic factor may be used as potential targeting ligands for directing the present compositions to myocardial tissue.

A wide variety of targeting ligands may be employed to direct the present lipid compositions, and particularly vesicle compositions, to the GPIIbIIIa receptor. Compositions which are directed to the GPIIbIIIa receptor may be highly useful for targeting coagulum, including vascular thromboses and/or emboli, and are useful for diagnosing, as well as treating such coagulum, particularly in patients suffering from arrhythmic disorders who may be prone to the development of coagulum. Included among such targeting ligands are, for example, peptides, such as Arg-Gly-Asp-Ser (RGDS), Gly-Arg-Gly-Asp-Ser-Pro (GRGDSP), and Gly-Pro-Arg-Pro (GPRP). Pentapeptides containing the sequence Arg-Gly-Asp (RGD) are also useful including, for example, G4120, which is a cyclic peptide containing the amino acid sequence Arg-Gly-Asp (RGD). Also useful are peptides derived from human coagulation Factor XIIIA including, for example, fragments such as NKLIVRRGQSFYVQIDFSRPYDPRRDL-FRVEYVIGRYPQENKGTYIPVPIVSELQSG KWGAKIVMREDRSVRLSIQSSPKCIVGK-FRMYVAVWTPYGVLRTSRNPETDTYIL FNP-WCEDDAVYLDNEKEREEYVLNDIGVIFYGE VNDIKTRSWSYGQF-R' where R' is —CONH$_2$ or —NH$_2$. In addition, peptides which are fragments of the Factor XIIIA fragment, which include in their sequence the sequence NKLIVRRGOSFYVQIDFSRPYDPRRD or

DDAVYLDNEKEREEYVLNDIGVIFYGEV-NDIKTRSWSYGQF.

Additional peptides which may be useful as targeting ligands for targeting the GPIIbIIIa receptor include, for example, peptides comprising the tripeptide sequence of arginine-tyrosine-aspartic acid (Arg-Tyr-Asp; also abbreviated RGD), linked from amino-to-carboxy-terminus and which may bind to the GPIIbIIIa binding region on activated platelets. Exemplary of such peptides include, for example, peptides of the general formula R$^1$—(X$^1$)$_n$—Arg-Tyr-Asp-(Y)$_o$—(X$^2$)$_m$—R$^2$, wherein each of X$^1$, X$^2$ and Y may independently be one or more amino acid residues while, in certain cases, it is preferred that Y is other than a serine or alanine residue, and each of m, n and o is independently 0 or 1, provided, in certain cases, that when m is 1, then o is 1, and R$^1$ is a protected or unprotected terminal amino group and R$^2$ is a protected or unprotected terminal carboxy group. In a preferred embodiment, X$^1$ is the peptide Ala-Arg-Arg-Ser-Ser-Pro-Ser-Tyr-Tyr and X$^2$ is the peptide Gly-Ala-Gly-Pro-Tyr-Tyr-Ala-Met-Asp-Tyr. Useful peptides include Arg-Ser-Pro-Ser-Tyr-Tyr-Arg-Tyr-Asp-Gly-Ala-Gly-Pro-Tyr-Tyr-Ala-Met-Asp-Tyr and Ala-Arg-Arg-Ser-Pro-Ser-Tyr-Tyr-Arg-Tyr-Asp-Gly-Ala-Gly-Pro-Tyr-Tyr-Ala-Met-Asp-Tyr.

Synthetic compounds which combine a natural amino acid sequence with synthetic amino acids can also be used as the targeting ligand, such as a fibrinogen receptor antagonist compound which comprises the sequence XX-Gly-Asp, wherein XX is a synthetic α-amino acid containing a linear side chain, such as:

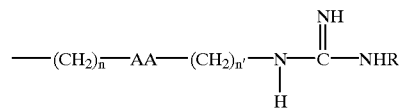

wherein n+n' is 3; AA is a single bond; and R is phenyl or benzyl;

or —(CH$_2$)$_n$—AA—(CH$_2$)$_{n'}$—NHR, wherein n is an integer of 1 to 4; n' is an integer of 2 to 4; AA is oxygen, sulfur or a single bond; and R is H, C$_{1-6}$ alkyl, optionally substituted aryl, optionally substituted arylmethyl or optionally substituted cycloalkyl, provided, in certain cases, that when AA is a single bond and R is H, then n+n' is other than 3 or 4.

Another such compound comprises a fibrinogen receptor antagonist of the formula:

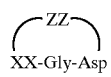

wherein XX is a synthetic a-amino acid containing a linear side chain having the formula:

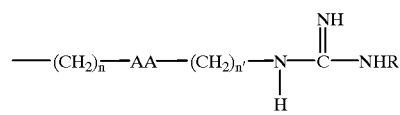

wherein n+n' is 3; AA is a single bond; and R is phenyl or benzyl; or

—(CH$_2$)$_n$—AA—(CH$_2$)$_{n'}$—NHR, wherein n is an integer of 1 to 4; n' is an integer of 2 to 4;

AA is oxygen, sulfur or a single bond; and R is H, C$_{1-6}$ alkyl, optionally substituted cycloalkyl, provided that, in certain cases, when AA is a single bond and R is H, then n+n' is other than 3 or 4, and ZZ is a sequence of 1 to 4 optionally substituted amino acids.

Other useful peptides for use as targeting ligands include, for example, "Elegantin", which has the following sequence: Gly-Glu-Glu-Cys-Asp-Cys-Gly-Ser-Pro-Glu-Asn-Pro-Cys- Cys-Asp-Ala-Ala-Thr-Cys-Lys-Ieu-Arg-Pro-Gly-Ala-Gln-Cys-Ala-Asp-Gly-Leu-Cys-Cys-Asp-Gln-Cys-Arg-Phe-Lys-R-RW-Arg-Thr-Hle-Cys-Arg-Arg-Ala-Arg-Gly-Asp-Asn-Pro-Asp-Asp-Arg-Cys-Thr-Gly-Gln-Ser-Ala-Asp-Cys-Pro-Arg-Asn-Gly-Tyr, wherein each of R and R' is independently any amino acid; "Albolabrin", which has the following sequence: Glu-Ala-Gly-Glu-Asp-Cys-Asp-Cys-Gly-Ser-Pro-Ala-Asn-Pro-Cys-Cys-Asp-Ala-Ala-Thr-Cys-Lys-Leu-Leu-Pro-Gly-Ala-Gln-Cys-Gly-Glu-Gly-Leu-Cys-Cys-Asp-Gln-Cys-Ser-Phe-Met-Lys-Lys-Gly-Thr-Ile-Cys-Arg-Arg-Ala-Arg-Gly-Asp-Asp-Leu-Asp-Asp-Tyr-Cys-Asn-Gly-Ile-Ser-Ala-Gly-Cys-Pro-Arg-Asn-Pro-Leu-His-Ala; "Batroxostatin", which has the following sequence: Glu-Ala-Gly-Glu-Glu-Cys-Asp-Cys-Gly-Thr-Pro-Glu-Asn-Pro-Cys-Cys-Asp-Ala-Ala-Thr-Cys-Lys-Leu-Arg-Pro-Gly-Ala-Gln-Cys-Ala-Glu-Gly-Leu-Cys-Cys-Asp-Gln-Cys-Arg-Phe-Lys-Gly-Ala-Gly-Lys-Ile-Cys-Arg-Arg-Ala-Arg-Gly-Asp-Asn-Pro-Asp-Asp-Cys-Thr-Gly-Gln-Ser-Ala-Asp-Cys-Pro-Arg-Phe; and "Flavoridin", which has the following sequence: Gly-Gly-Glu-Cys-Asp-Cys-Gly-Ser-Pro-Glu-Asn-Pro-Cys-Cys-Asp-Ala-Ala-Thr-Cys-Lys-Leu-Arg-Pro-Gly-Ala-Gln-Cys-Ala-Asp-Gly-Leu-Cys-Cys-Asp-Gln-Cys-Arg-Phe-Lys-R-R'-Arg-Thr-Ile-Cys-Arg-Ile-Ala-Arg-Gly-Asp-Phe-Pro-Asp-Asp-Arg-Cys-Thr-Gly-Leu-Ser-Ala-Asp-Cys-Pro.-Arg-R-Asn-Asp-Leu, wherein each of R and R' is independently any amino acid.

Other ligands useful for targeting the GPIIbIIIa receptor include synthetic compounds, such as Ac-(D)Phe-Pro-boroArg and the cyclic peptidomimetic cyclo(D-2-aminobutyrate-N-Methyl-L-Arginyl-Glycyl-L-Aspartyl-3-amino-methyl-benzoic acid) methanesulfonate salt. Peptides that can also be used include a library of hexapeptides flanked by cysteine residues (capable of forming cyclic disulfides) and cyclic, disulfide-bonded forms of peptides with the sequence Arg-Gly-Asp or Lys-Gly-Asp, as well as the carboxyl-terminal derived peptide, REYVVMWK. Certain matrix glycoproteins such as Thrombospondin are also useful in this regard. Members of the serpin family of serine protease inhibitors, such as Plasminogen activator inhibitor type 1 (PAI-1) are other useful ligands.

Generally speaking, it is preferred to employ as targeting ligands for the GPIIbIIIa receptor a peptide having from about 3 to about 20 amino acids, with peptides having from about 4 to about 15 amino acids being more preferred. Even more preferably, targeting ligands for the GPIIbIIIa receptor may comprise peptides having from about 4 to about 8 amino acids, with peptides having from about 4 to about 6 amino acids or about 5 amino acids being still more preferred. If desired, the peptides may be cyclized, for example, by (1) sidechain-to-sidechain covalent linkages, including, for example, by the formation of a disulfide linkage via the oxidation of two thiol containing amino acids or analogs thereof, including, for example, cysteine or penicillamine; (2) end-to-sidechain covalent linkages, including, for example, by the use of the amino terminus of the amino acid sequence and a sidechain carboxylate group, such as, for example, a non-critical glutamic acid or aspartic acid group. Alternatively, the end-to-sidechain covalent linkage may involve the carboxylate terminus of the amino acid sequence and a sidechain amino, amidine, guanidine, or other group in the sidechain which contains a nucleophilic nitrogen atom, such sidechain groups including, for example, lysine, arginine, homoarginine, homolysine, or the like; (3) end-to-end covalent linkages that are covalent amide linkages, or the like. Such processes are well known to those skilled in the art. In addition, "pseudocyclization" may be employed, in which cyclization occurs via non-covalent interactions, such as electrostatic interactions, which induces a folding of the secondary structure to form a type of cyclic moiety. It is contemplated that metal ions may aid the induction of a "pseudocyclic" formation. This type of pseudocyclic formation may be analogous to "zinc fingers." As known to one of ordinary skill in the art, zinc fingers involve the formation due to electrostatic interactions between a zinc ion ($Zn_{2+}$) and cysteine, penicillamine and/or homocysteine, of a region in the shape of a loop (the finger). In the case of homocysteine, the RGD sequence would reside at the tip of the finger. Of course, it is recognized that, in the context of the present invention, any type of stabilizing cyclization would be suitable as long the recognition and binding peptide ligand, such as, for example, RGD, maintains the proper conformation and/or topography to bind to the appropriate receptor in clots with a reasonable Michaelis-Menten constant ($k_m$) or binding constant. As used herein, the term "conformation" refers to the three-dimensional organization of the backbone of the peptide, peptoid, or pseudopeptide, and the term "topography", as used herein, refers to the three-dimensional organization of the sidechain of the peptide, peptoid, or pseudopeptide.

Other suitable targeting ligands include the following compounds: Ac-Cys-Arg-Gly-Asp-Met-Phe-Gly-Cys-$CONH_2$; Ac-Cys-Arg-Gly-Asp-Met-Leu-Arg-Cys-$CONH_2$; Ac-Cys-Arg-Gly-Asp-Phe-Leu-Asn-Cys-$CONH_2$; Ac-Cys-Asn-Tbr-Leu-Lys-Gly-Asp-Cys-$CONH_2$; Ac-Cys-Asn-Trp-Lys-Arg-Gly-Asp-Cys-$CONH_2$; and Ac-Cys-N-methyl-Arg-Gly-Asp-Pen-$CONH_2$, where "Pen" refers to penicillamine (β,β-dimethylcysteine).

Other compounds which may be used as targeting ligands include peptides, or derivatives thereof, represented by the formula:

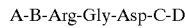

wherein:

A is proline, thioproline, hydroxyproline, dehydroproline, 2-oxo4-thiazolidine carboxylic acid, N-alkyl glycine or an amino acid derivative of the formula:

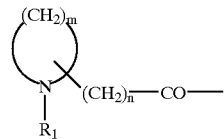

tryptophan, or a tryptophan derivative of the formula:

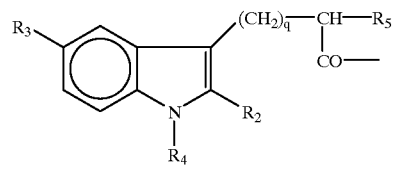

pyroglutamic acid or 2-azetidinone4-carboxylic acid

B is serine, glycine, valine, alanine, threonine or β-alanine;

C is an amino acid group having a hydrophobic functional group; and

D is hydroxy or amino;

wherein:

$R_1$ is hydrogen, —$(CH_2)_pCH_3$ or —CO—$(CH_2)_pCH_3$, $R_2$ is hydrogen or alkyl;

$R_3$ is hydrogen or alkoxy;

$R_4$ is hydrogen or alkyl;

$R_5$ is hydrogen, amino or acylamino;

m is an integer of 2 to 5;

n is an integer of 0 to 2;

p is an integer of 0 to 5; and q is an integer of 0 to 3.

Another targeting ligand which may be suitable for use in connection with the present compositions is a peptide, a peptide derivative, or a salt thereof having the formula:

A-B-Arg-Gly-Asp-C-D wherein:

A is arotic acid or hydroorotic acid;

B is an amino acid;

C is an amino acid having a hydrophobic functional group; and

D is hydroxy or amino.

In the above compounds, examples of amino acids having hydrophobic functional groups in the definition of "C" are tryptophan and phenylalanine.

Various peptides which would be suitable for use as a targeting ligand in connection with the present invention, especially for targeting GPIIbIIIa, are disclosed, for example, in Sato et al., U.S. Pat. No. 5,498,601 and the following published European Patent Applications: 0 368 486 A2, 0 382 451 A2, and 0 422 938 B1, the disclosures of which are hereby incorporated herein by reference, in their entirety. Other targeting ligands which may be used in the compositions of the present invention, in addition to those exemplified above, would be apparent to one of ordinary skill in the art, once armed with the present disclosure. Other suitable targeting ligands include, for example, conjugated peptides, such as, for example, glycoconjugates and lectins, which are peptides attached to sugar moieties. The compositions may comprise a single targeting ligand, as well as two or more different targeting ligands.

There are also provided, in accordance with the present invention, compounds having the formula:

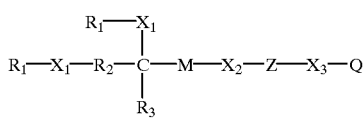

wherein:

each $X_1$ is independently —O—, —S—, —SO—, —SOP$_2$—, —NR$_4$—, —X$_4$—C(=X$_5$)—, —C(=X$_5$)—X$_4$— or —C(=X$_5$)—;

each of $X_2$ and $X_3$ is independently a direct bond, —R$_5$—X$_4$—C(-X$_5$)—, —R$_5$—C(=X$_5$)—X$_4$—, —X$_4$—C(=X$_5$)—R$_5$—, —C(=X$_5$)—X$_4$—R$_5$—, —X$_4$—R$_5$—C(=X$_5$)—X$_4$—, —R$_5$—X$_4$—C(=X$_5$)—R$_5$—C(=X$_5$)—X$_4$— or —R$_5$—C(=X$_5$)—X$_4$—R$_5$—X$_4$—C(=X$_5$)—;

each $X_4$ is independently —O—, —NR$_4$— or —S—;

each $X_5$ is independently O or S;

M is —R$_5$—X$_4$—C(=X$_5$)—, —R$_5$—C(=X$_5$)—X$_4$—, —R$_5$—X$_4$—(YX$_5$)P(=X$_5$)—X$_4$— or —X$_4$—(YX$_5$)P(=X$_5$)—X$_4$—R$_5$—;

Y is hydrogen or a pharmaceutically acceptable counter ion;

Z is a hydrophilic polymer;

Q is a targeting ligand or a precursor thereto;

each $R_1$ is independently alkyl of 1 to about 50 carbons;

each $R_2$ is independently alkylene of 1 to about 30 carbons;

each of $R_3$ and $R_4$ is independently hydrogen or alkyl of 1 to about carbons; and each $R_5$ is independently a direct bond or alkylene of 1 to about 30 carbons.

In the above formula, it is intended that when any symbol appears more than once in a particular formula or substituent, its meaning in each instance is independent of the other.

Also in the above formula, it is intended that when each of two or more adjacent symbols is defined as being a "direct bond" to provide multiple, adjacent direct bonds, the multiple and adjacent direct bonds devolve into a single direct bond.

In the above formula, each $X_1$ is independently —O—, —S—, —SO—, —SO$_2$—, —NR$_4$—, —X$_4$—C(=X$_5$)—, —C(=X$_5$)—X$_4$— or —C(=X$_5$)—. In preferred embodiments, each $X_1$ is independently —X$_4$—C(=X$_5$)—, —C(=X$_5$)—X$_4$— or —C(=X$_5$)—. More preferably, each $X_1$ is independently —X$_4$—C(=X$_5$)— or —C(=X$_5$)—X$_4$—. Even more preferably, $X_1$ is —C(=X$_5$)—X$_4$—, for example, —C(=O)—O—.

In the above formula, each of $X_2$ and $X_3$ is independently a direct bond, —R$_5$—X$_4$—C(=X$_5$)—, —R$_5$—C(=X$_5$)—X$_4$—, —X$_4$—C(=X$_5$)—R$_5$—, —C(=X$_5$)—X$_4$—R$_5$—, —X$_4$—R$_5$—C(=X$_5$)—X$_4$—, —R—X$_4$—C(=X$_5$)—R$_5$—C(=X$_5$)—X$_4$— or —R$_5$—C(=X$_5$)—X$_4$—R$_5$—X$_4$—C(=X$_5$)—. In preferred embodiments, each of $X_2$ and $X_3$ is independently a direct bond, —R$_5$—X$_4$—C(=X$_5$)—, —R$_5$—C(=X$_5$)—X$_4$—, —X$_4$—C(=X$_5$)—R$_5$—, —C(=X$_5$)—X$_4$—R$_5$—, —X$_4$—R$_5$—C(=X$_5$)—X$_4$— or —R$_5$—X$_4$—C(=X$_5$)—R$_5$—C(=X$_5$)—X$_4$—. More preferably, $X_2$ is —CH$_2$CH$_2$—C(=O)—NH— or —CH$_2$CH$_2$NH—C(=O)CH$_2$CH$_2$—C(=O)—NH— and $X_3$ is a direct bond, —C(=O)—NH—, —NH—C(=O)—, —NH—C(=O)—CH$_2$—, —NHCH$_2$—C(=O)—NH— or —NH—C(=O)—CH$_2$CH$_2$.

In the above formula, each $X_4$ is independently —O—, —NR$_4$— or —S—. Preferably, each $X_4$ is independently —O— or —NR$_4$—.

In the above formula, each $X_5$ is independently O or S. Preferably, $X_5$ is O.

In the above formula, M is —R$_5$—X$_4$—C(=X$_5$)—, —R$_5$—C(=X$_5$)—X$_4$—, —R$_5$—X$_4$—(YX$_5$)P(=X$_5$)—X$_4$— or —X$_4$—(YX$_5$)P(=X$_5$)—X$_4$—R$_5$—. In certain preferred embodiments, M is —R$_5$—X$_4$—C(=X$_5$)— or —R$_5$—X$_4$—YX$_5$)P(=X$_5$)—X$_4$—, with M more preferably being —CH$_2$O—C(=O) or —CH$_2$O—(HO)P(=O)—O—. In certain other preferred embodiments, M is —R$_5$—X$_4$—C(=X$_5$)— or —R$_5$—C(=X$_5$)—X$_4$—. In yet other preferred embodiments, M is —R$_5$—X$_4$—(YX$_5$)P(=X$_5$)—X$_4$— or —X$_4$—(YX$_5$)P(=X$_5$)—X$_4$—R$_5$—. wherein at least one of $X_4$ or $X_5$ is S.

In the above formula, Z is a hydrophilic polymer. Preferably, Z is selected from the group consisting of polyalkyleneoxides, polyvinyl alcohol, polyvinylpyrrolidones, polyacrylamides, polymethacrylamides, polyphosphazenes, poly (hydroxyalkylcarboxylic acids) and polyoxazolidines. More preferably, Z comprises a polyalkyleneoxide. Even more preferably, Z is a polyalkyleneoxide selected from the group consisting of polyethylene glycol and polypropylene glycol, with polethylene glycol being still more preferred. In certain other preferred embodiments, Z is a hydrophilic polymer other than polyalkyleneoxides, including polyethylene glycol and polypropylene glycol. The molecular weight of Z may vary, depending, for example, on the particular end-use of the compounds. Preferably, Z is a polymer having a molecular weight which ranges from about 100 to about 10,000, and all combinations and subcombinations of ranges therein. More preferably, Z is a polymer having a molecular weight of from about 1,000 to about 5,000. Also preferred are polymers which exhibit polydispersities ranging from greater than about 1 to about 3, and all combinations and subcombinations of ranges therein. More preferably, Z is a polymer having a polydispersity of from greater than about 1 to about 2, with polydispersities of from greater than about 1 to about 1.5 being even more preferred, and polydispersities of from greater than about 1 to about 1.2 being still more preferred.

In the above formula, Q is a targeting ligand or a precursor thereto. In embodiments where Q is a targeting ligand, Q preferably targets cells or receptors selected from the group consisting of myocardial cells, endothelial cells, epithelial cells, tumor cells and the glycoprotein GPIIbIIIa receptor. In certain preferred embodiments, Q targets cells or receptors selected from the group consisting of myocardial cells, endothelial cells, epithelial cells and the glycoprotein GPIIbIIIa receptor. In addition, in embodiments where Q is a targeting ligand, Q is preferably selected from the group consisting of proteins, peptides, saccharides, steroids, steroid analogs, bioactive agents, and genetic material. In these latter embodiments, Q is preferably selected from the group consisting of proteins, peptides and saccharides. In embodiments where Q comprises a peptide, Q is preferably the peptide -Lys-Gln-Ala-Gly-Asp-Val or a cyclic peptide, such as DMP 728. (See, e.g., Mousa et al., *Thrombosis Research*, Vol. 76 (2), pp. 109–119 (1994), the disclosures of which are hereby incorporated herein by reference, in their entirey.) In embodiments where Q comprises a protein, Q is preferably Protein A. In embodments where Q comprises a saccharide, Q is preferably a monosaccharide, with mannose and glucose being more preferred. In embodiments where Q is a precursor to a targeting ligand, Q preferably comprises a partially unsaturated or aromatic 5- to 7-membered monocyclic ring containing 1 or 2 N, O or S atoms, and more preferably a maleimide moiety or a pyridyl moiety.

In the above formula, each $R_1$ is independently alkyl which ranges from 1 to about 50 carbons, and all combinations and subcombinations of ranges therein, or alkenyl of from about 2 to about 50 carbons, and all combinations and subcombinations of ranges therein. Preferably, each $R_1$ is independently alkyl of greater than 1 to about 40 carbons. More preferably, each $R_1$ is independently alkyl of about 5 to about 30 carbons. Even more preferably, each $R_1$ is independently alkyl of about 10 to about 20 carbons, with alkyl of about 15 carbons being still more preferred. In certain preferred embodiments, $R_1$ is a shorter chain alkyl of from 1 to about 20 carbons. In certain other preferred embodiments, $R_1$ is a longer chain alkyl of from about 20 to about 50 carbons, or about 30 to about 50 carbons.

In the above formula, each $R_2$ is independently alkylene which ranges from 1 to about 30 carbons, and all combinations and subcombinations of ranges therein. Preferably, each $R_2$ is independently alkylene of 1 to about 20 carbons. More preferably, each $R_2$ is independently alkylene of 1 to about 10 carbons. Even more preferably, each $R_2$ is independently alkylene of 1 to about 5 carbons, with methylene being especially preferred.

In the above formula, each of $R_3$ and $R_4$ is independently hydrogen or alkyl which ranges from 1 to about 10 carbons, and all combinations and subcombinations of ranges therein. Preferably, each of $R_3$ and $R_4$ is hydrogen or alkyl of 1 to about 5 carbons. More preferably, each of $R_3$ and $R_4$ is hydrogen.

In the above formula, each $R_5$ is independently a direct bond or alkylene which ranges from 1 to about 30 carbons, and all combinations and subcombinations of ranges therein. Preferably, each $R_5$ is independently a direct bond or alkylene of 1 to about 20 carbons. More preferably, each $R_5$ is independently a direct bond or alkylene of 1 to about 10 carbons. Even more preferably, each $R_5$ is independently a direct bond or alkylene of 1 to about 5 carbons. Still more preferably, each $R_5$ is a direct bond or —$(CH_2)_x$—, where x is 1 or 2.

There are also provided herein compounds of the formula

L-P-T wherein:
L is a lipid, protein or polymer;
P is a hydrophilic polymer; and
T is a targeting ligand.

In preferred embodiments, L is a lipid selected from the group consisting of lecithins, phosphatidylcholines, phosphatidylserines, phosphatidylinositols, cardiolipins, cholesterols, cholesterolamines, lysophosphatides, erythrosphingosines, sphingomyelins, ceramides, cerebrosides, saturated phospholipids, unsaturated phospholipids, and krill phospholipids. More preferably, L is a lipid is selected from the group consisting of lecithins, phosphatidylcholines, phosphatidylserines and phosphatidylinositols. In other preferred embodiments, L is a lipid selected from the group consisting of 1,2-diacyl-sn-glycero-3-phosphocholines, 1,2-diacyl-sn-glycero-3-phosphoethanolamines, 1,2-diacyl-sn-glycero-3-[phospho-rac-(1-glycerols)], 1,2-diacyl-sn-glycero-3-phosphates, 1,2-diacyl-sn-glycero-3-[phosphoserines], lysophosphatidylcholines, lysophosphatidyl-glycerols, 1,2-diacyl-sn-glycerols, 1,2-diacyl-ethylene glycols, N-(n-caproylamine)-1,2-diacyl-sn-glycero-3-phosphoethanolamines, N-dodecanylamine-1,2-diacyl-sn-glycero-3-phosphoethanolamines, N-succinyl-1, 2-diacyl-sn-glycero-3-phosphoethanolamines, N-glutaryl-1, 2-diacyl-sn-glycero-3-phosphoethanolamines and N-dodecanyl-1,2-diacyl-sn-glycero-3-phosphoethanolamines. More preferably, L is a lipid selected from the group consisting of 1,2-diacyl-sn-glycero-3-phosphocholines, 1,2-diacyl-sn-glycero-3-phosphoethanolamines, 1,2-diacyl-sn-glycero-3-[phospho-rac-(1-glycerols)], 1,2-diacyl-sn-glycero-3-phosphates, 1,2-diacyl-sn-glycero-3-[phosphoserines], lysophosphatidylcholines, lysophosphatidylglycerols and 1,2-diacyl-sn-glycerols.

In other preferred embodiments, L is a protein which comprises albumin. In still other preferred embodiments, L is a polymer which comprises synthetic polymers or copolymers prepared from monomers selected from the group consisting of acrylic acid, methacrylic acid, ethyleneimine, crotonic acid, acrylamide, ethyl acrylate, methyl methacrylate, 2-hydroxyethyl methacrylate, lactic acid, glycolic acid, ε-caprolactone, acrolein, cyanoacrylate, bisphenol A, epichlorhydrin, hydroxyalkylacrylates, siloxane, dimethylsiloxane, ethylene oxide, propylene oxide, ethylene glycol, hydroxyalkylmethacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-aminobenzylstyrene, sodium styrene sulfonate, sodium 2-sulfoxyethyl-methacrylate, vinyl pyridine, aminoethyl methacrylates and 2-methacryloyloxytrimethyl-ammonium chloride. Also preferred are compounds where L is a polymer which comprises synthetic polymers or copolymers selected from the group consisting of polyacrylic acid, polyethyleneimine, polymethacrylic acid, polymethylmethacrylate, polysiloxane, polydimethylsiloxane, polylactic acid, poly(ε-caprolactone), epoxy resin, poly(ethylene oxide), poly(propylene oxide), poly(ethylene glycol), polyamide, polyvinylidene-polyacrylonitrile, polyvinylidene-polyacrylonitrile-polymethylmethacrylate and polystyrene-polyacrylonitrile. Preferred among these polymers is polyvinylidene-polyacrylonitrile copolymer.

In the above compounds, P is a hydrophilic polymer. Preferably, P is a hydrophilic polymer selected from the group consisting of polyalkyleneoxides, polyvinyl alcohol, polyvinylpyrrolidones, polyacrylamides, polymethacrylamides, polyphosphazenes, poly(hydroxyalkylcarboxylic acids) and polyoxazolidines. More preferably, P is a polyalkyleneoxide polymer, with polyethylene glycol and polypropylene glycol being even more preferred and polyethylene glycol being particularly preferred.

In the above formula, T is a targeting ligand. Preferably, T is a targeting ligand which targets cells or receptors selected from the group consisting of myocardial cells, endothelial cells, epithelial cells, tumor cells and the glycoprotein GPIIbIIIa receptor. Also in preferred embodiments, T is a targeting ligand selected from the group consisting of proteins, peptides, saccharides, steroids, steroid analogs, bioactive agents and genetic material, with proteins, peptides and saccharides being more preferred. Also preferred are targeting ligands which target regions of arteriosclerosis, especially atherosclerotic plaque.

In the case of targeting ligands which comprise saccharide groups, suitable saccharide moieties include, for example, monosaccharides, disaccharides and polysaccharides. Exemplary monosaccharides may have six carbon atoms and these saccharides include allose, altrose, glucose, mannose, gulose, idose, galactose, talose, fructose, psicose, verbose and tagatose. Five carbon saccharides include ribose, arabinose, xylose, lyxose, ribulose and xylulose. Four carbon saccharides include erythrose, threose and erythrulose. Disaccharides include sucrose, lactose, maltose, isomaltose and cellobiose. Saccharide bearing targeting lipids may be synthesized through a multistep organic synthesis approach, as described more fully hereinafter. For example, lipids bearing targeting glucose moieties may be prepared by reacting, for example, α-glucopyranosyl bromide tetrabenzyl with (-trifluoroacetylaminopolyethyleneglycol to obtain ω-glucopyranosyl tetrabenzyl-ω'-trifluoroacetylaminopolyethyleneglycol. This may then be hydrolyzed in a sodium carbonate or potassium carbonate solution and then hydrogenated to obtain (glucopyranosyl-ω'-amino-polyethyleneglycol. Aminoglycopyranosyl terminated polyethyleneglycol may then react with N-DPGS-succinimide to form the lipid bearing saccharide DPGS-NH-PEG-Glucose. Also preferred are targeting ligands which target infarcted myocardium. In certain embodiments, the targeting ligands target cancer cells.

The foregoing preferred embodiments of the compounds of the present invention are preferred for various reasons, including ease of synthesis, diagnostic efficacy, enhanced biocompatibility, and/or improved targeting efficacy.

The targeting ligand may be incorporated in the present compositions in a variety of ways. Generally speaking, the targeting ligand may be incorporated in the present compositions by being associated covalently or non-covalently with one or more of the materials which are included in the compositions, including, for example, the lipids, proteins, polymers and/or auxiliary stabilizing materials. In preferred form, the targeting ligand is associated covalently with one or more of the aforementioned materials contained in the present compositions. As noted above, preferred compositions of the present invention comprise lipid, protein or polymer compounds. In these compositions, the targeting ligands are preferably associated covalently with the lipid, protein or polymer compounds.

Exemplary covalent bonds by which the targeting ligands are associated with the lipids, proteins, polymers and/or vesicles include, for example, amide (—CONH—); thioamide (—CSNH—); ether (ROR', where R and R' may be the same or different and are other than hydrogen); ester (—COO—); thioester (—COS—); —O—; —S—; —$S_n$—, where n is greater than 1, preferably about 2 to about 8, and more preferably about 2; carbamates; —NH—; —NR—, where R is alkyl, for example, alkyl of from 1 to about 4 carbons; urethane; and substituted inidate; and combinations of two or more of these. Covalent bonds between targeting ligands and, for example, lipids, may be achieved through the use of molecules that may act as spacers to increase the conformational and topographical flexibility of the ligand. Examples of such spacers include, for example, succinic acid, 1,6-hexanedioic acid, 1,8-octanedioic acid, and the like, as well as modified amino acids, such as, for example, 6-aminohexanoic acid, 4-aminobutanoic acid, and the like. In addition, in the case of targeting ligands which comprise peptide moieties, sidechain-to-sidechain crosslinking may be complemented with sidechain-to-end crosslinking and/or end-to-end crosslinking. Also, small spacer molecules, such as dimethylsuberimidate, may be used to accomplish similar objectives. The use of agents, including those used in Schiff's base-type reactions, such as gluteraldehyde, may also be employed. The Schiff's base linkages, which may be reversible linkages, can be rendered more permanent covalent linkages via the use of reductive amination procedures. This may involve, for example, chemical reducing agents, such as lithium aluminum hydride reducing agents or their milder analogs, including lithium aluminum diisobutyl hydride (DIBAL), sodium borohydride (NaBH$_4$) or sodium cyanoborohydride (NaBH$_3$CN).

The covalent linking of the targeting ligands to the materials in the present compositions, including the lipids, proteins and/or polymers, may be accomplished using synthetic organic techniques which would be readily apparent to one of ordinary skill in the art, based on the present disclosure. For example, the targeting ligands may be linked to the materials, including the lipids, via the use of well known coupling or activation agents. As known to the skilled artisan, activating agents are generally electrophilic. This electrophilicity can be employed to elicit the formation of a covalent bond. Exemplary activating agents which may be used include, for example, carbonyldiimidazole (CDI), dicyclohexylcarbodiimide (DCC), diisopropylcarbodiimide (DIC), methyl sulfonyl chloride, Castro's Reagent, and diphenyl phosphoryl chloride.

The covalent bonds may involve crosslinking and/or polymerization. Crosslinking preferably refers to the attachment of two chains of polymer molecules by bridges, composed of either an element, a group, or a compound, which join certain carbon atoms of the chains by covalent chemical bonds. For example, crosslinking may occur in polypeptides which are joined by the disulfide bonds of the cystine residue. Crosslinking may be achieved, for example, by (1) adding a chemical substance (cross-linking agent) and exposing the mixture to heat, or (2) subjecting a polymer to high energy radiation. A variety of crosslinking agents, or "tethers", of different lengths and/or functionalities are described, for example, in R. L. Lunbland, *Techniques in Protein Modification,* CRC Press, Inc., Ann Arbor, Mich., pp. 249–68 (1995), the disclosures of which are hereby incorporated herein by reference, in their entirety. Exemplary crosslinkers include, for example, 3,3'-dithiobis (succinimidylpropionate), dimethyl suberimidate, and its variations thereof, based on hydrocarbon length, and bis-N-maleimido-1,8-octane.

In accordance with preferred embodiments, the targeting ligands may be linked or attached to the lipids, proteins or polymers, or other stabilizing materials, via a linking group. A variety of linking groups are available and would be apparent to one skilled in the art, once armed with the present disclosure. Preferably, the linking group comprises a hydrophilic polymer. Suitable hydrophilic linker polymers include, for example, polyalkyleneoxides such as, for example, polyethylene glycol (PEG) and polypropylene glycol (PPG), polyvinylpyrrolidones, polyvinylmethylethers, polyacrylamides, such as, for example, polymethacrylamides, polydimethylacrylamides and polyhydroxypropylmethacrylamides, polyhydroxyethyl acrylates, polyhydroxypropyl methacrylates, polymethyloxazolines, polyethyloxazolines, polyhydroxyethyloxazolines, polyhyhydroxypropyloxazolines, polyvinyl alcohols, polyphosphazenes, poly(hydroxyalkylcarboxylic acids), polyoxazolidines, and polyaspartamide. The hydrophilic polymers are preferably selected from the group consisting of PEG, PPG, polyvinylalcohol and polyvinylpyrrolidone and copolymers thereof, with PEG and PPG polymers being more preferred and PEG polymers being even more preferred. Thus, in embodiments involving lipid compositions which comprise lipids bearing polymers including, for example, DPPE-PEG, the targeting ligand may be linked directly to the polymer which is attached to the lipid to provide, for example, a conjugate of DPPE-PEG-TL, where TL is a targeting ligand. Thus, using the example DPPE-PEG, such as, for example, DPPE-PEG5000, the aforementioned conjugate may be represented as DPPE-PEG5000-TL. The hydrophilic polymer used as a linking group is preferably a bifunctional polymer, for example, bifunctional PEG, such as diamino-PEG. In this case, one end of the PEG group is linked, for example, to a lipid compound, and is bound at the free end to the targeting ligand via an amide linkage. A hydrophilic polymer, for example, PEG, substituted with a terminal carboxylate group on one end and a terminal amino group on the other end, may also be used. These latter bifunctional hydrophilic polymer may be preferred since they possess various similarities to amino acids.

Standard peptide methodology may be used to link the targeting ligand to the lipid when utilizing linker groups having two unique terminal functional groups. Bifunctional hydrophilic polymers, and especially bifunctional PEGs, may be synthesized using standard organic synthetic methodologies. In addition, many of these materials are available commercially. For example, α-amino, ω-carboxy PEG is commercially available from Shearwater Polymers (Huntsville, Ala.). An advantage of using a PEG material as the linking group is that the size of the PEG can be varied such that the number of monomeric subunits of ethylene glycol may be as few as, for example, about 5, or as many as, for example, about 500 or even greater. Accordingly, the "tether" or length of the linkage may be varied, as desired. This may be important depending, for example, on the particular targeting ligand employed. For example, a targeting ligand which comprises a large protein molecule may require a short tether, such that it will simulate a membrane bound protein. A short tether would also allow for a vesicle to maintain a close proximity to the cell. This can be used advantageously in connection with vesicles which also comprise a bioactive agent, in that the concentration of bioactive agent which is delivered to the cell may be advantageously increased.

Another suitable linking group which may provide a short tether is glyceraldehyde. Glyceraldehyde may be bound, for example, to DPPE via a Schiff's base reaction. Subsequent Amadori rearrangement can provide a substantially short linking group. The β carbonyl of the Schiff's base may then react with a lysine or arginine of the targeting protein or peptide to form the targeted lipid.

More specifically, the compounds employed in the present compositions, including lipids, proteins, polymers and/or surfactants, may contain various functional groups, such as, for example, hydroxy, thio and amine groups, which can react with a carboxylic acid or carboxylic acid derivative of the hydrophilic polymeric linker using suitable coupling conditions which would be apparent to one of ordinary skill in the art, once armed with the present disclosure. After the carboxylic acid group (or derivative thereof) reacts with the functional group, for example, hydroxy, thio or amine group to form an ester, thioester or amide group, any protected functional group may be deprotected utilizing procedures which would be well known to those skilled in the art. The term protecting group, as used herein, refers to any moiety which may be used to block reaction of a functional group and which may be removed, as desired, to afford the unprotected functional group. Any of a variety of protecting groups may be employed and these will vary depending, for example, as to whether the group to be protected is an amine, hydroxyl or carboxyl moiety. If the functional group is a hydroxyl group, suitable protecting groups include, for example, certain ethers, esters and carbonates. Such protecting groups are described, for example, in in Greene, T W and Wuts, PGM "Protective Groups in Organic Synthesis" John Wiley, New York, 2nd Edition (1991), the disclosures of which are hereby incorporated herein by reference, in their entirety. Exemplary protecting groups for amine groups include, for example, t-butyloxycarbonyl (Boc), benzyloxycarbonyl(Cbz), o-nitrobenzyloxycarbonyl and and trifluoroacetate (TFA).

Amine groups which may be present, for example, on a backbone of a polymer which is included in the vesicles, may be coupled to amine groups on a hydrophilic linking polymer by forming a Schiff's base, for example, by using coupling agents, such as glutaraldehyde. An example of this coupling is described by Allcock et al., *Macromolecules* Vol. 19(6), pp. 1502–1508 (1986), the disclosures of which are hereby incorporated herein by reference, in their entirety. If, for example, vesicles are formulated from polylysine, free amino groups may be exposed on the surface of the vesicles, and these free amine groups may be activated as described above. The activated amine groups can be used, in turn, to couple to a functionalized hydrophilic polymer, such as, for example, α-amino-ω-hydroxy-PEG in which the ω-hydroxy group has been protected with a carbonate group. After the reaction is completed, the carbonate group can be cleaved, thereby enabling the terminal hydroxy group to be activated for reaction to a suitable targeting ligand. In certain embodiments, the surface of a vesicle may be activated, for example, by displacing chlorine atoms in chlorine-containing phosphazene residues, such as polydichlorophosphazine. Subsequent addition of a targeting ligand and quenching of the remaining chloride groups with water or aqueous methanol will yield the coupled product.

In addition, poly(diphenoxyphosphazene) can be synthesized (Allcock et al., *Macromolecules* Vol. (1986) 19(6), pp. 1502–1508) and immobilized, for example, on DPPE, followed by nitration of the phenoxy moieties by the addition of a mixture of nitric acid and acetic anhydride. The subsequent nitro groups may then be activated, for example, by (1) treatment with cyanogen bromide in 0.1 M phosphate buffer (pH 11), followed by addition of a targeting ligand containing a free amino moiety to generate a coupled urea analog, (2) formation of a diazonium salt using sodium nitrite/HCl, followed by addition of the targeting ligand to form a coupled ligand, and/or (3) the use of a dialdehyde, for example, glutaraldehyde as described above, to form a Schiff's base. After linking the DPPE to the hydrophilic polymer and the targeting ligand, the vesicles may be formulated utilizing the procedures described herein.

Aldehyde groups on polymers can be coupled with amines as described above by forming a Schiff's base. An example of this coupling procedure is described in Allcock and Austin *Macromolecules* vol 14. p1616 (1981), the disclosures of which are hereby incorporated herein by reference, in their entirety.

In the above procedures, the polymer or terminus of the lipid, for example, phosphatidylglycerol or phosphatidylethanolamine, is preferably activated and coupled to the hydrophilic polymeric linker, the terminus of which has been blocked in a suitable manner. As an example of this strategy, α-amino, ω-carboxy PEG-4000 having a t-Boc protected terminal amino group and a free carboxylate end, may be activated with 1,1'-carbonyldiimidazole in the presence of hydroxybenzotriazole in N-methylpyrollidone. After the addition of phosphatidylethanolamine, the t-Boc group may be removed by using trifluoroacetic acid (TFA), leaving the free amine. The amine may then be reacted with a targeting ligand which may comprise, for example, a peptide, protein, alkaloid, or other moiety, by similar activation of the ligand, to provide the lipid-linker-targeting ligand conjugate. Other strategies, in addition to those exemplified above, may be utilized to prepare the lipid-linker-targeting ligand conjugates. Generally speaking, these methods employ synthetic strategies which are generally known to those skilled in the art of synthetic organic chemistry.

As known to one of ordinary skill in the art, immunoglobulins typically comprise a flexible region which is identified as the "hinge" region. See, e.g., "Concise Encyclopedia of Biochemistry", Second Edition, Walter de Gruyter & Co., pp. 282–283 (1988). Fab' fragments can be linked to the lipids, polymers, proteins and/or vesicles using the well-defined sites of the thiols of the hinge region. This is a preferred region for coupling Fab' fragments as the potential binding site is remote from the antigen-recognition site. Generally speaking, it may be difficult to utilize the thiols of the hinge group unless they are adequately prepared. In particular, as outlined by Shahinian and Salvias (*Biochimica et Biophysica Acta,* Vol 1239 (1995) 157–167) it may be important to reduce the thiol groups so that they are available for coupling, for example, to maleimide derivatized linking groups. Examples of reducing agents commonly used are ethanedithiol, mercaptoethanol, mercaptoethylamine or the more commonly used dithiothreitol, commonly referred to as Cleland's reagent. However, it should be noted that care should be exercised when utilizing certain reducing agents, such as dithiothreitol, as overreduction may result. Discriminating use of reducing agents may be necessary in connection with proteins whose activity or binding capacity may be compromised due to overreduction and subsequent denaturation or conformational change. See, e.g., Shahinian, S. and Salvias, J. R. (1995) Biochim. Biophys. Acta 1239, 157–167.

F(ab')$_2$ antibody fragments may be prepared by incubating the antibodies with pepsin (60 µg/ml) in 0.1M sodium acetate (pH 4.2) for 4 h at 37° C. Digestion may be terminated by adding 2M Tris (pH 8.8) to a final concentration of 80 mM. The F(ab')$_2$ fragments may then be obtained by centrifugation (10,000×g. 30 min. 4° C.). The supernatant may then be dialyzed at 4° C. against 150 mM NaCl, 20 mM phosphate at pH 7.0. This then may be chromatographed on a column of Protein A-Sepharose CL-4B to remove any undigested IgG. The Fab' fragments may then be prepared by extensively degassing the solutions and purging with nitrogen prior to use. The F(ab')$_2$ fragments may be provided at a concentration of 5 mg/ml and reduced under argon in 30 mM cysteine. Alternatively, cysteamine may be employed. 100 mM Tris, pH 7.6 may be used as a buffer for 15 min at 37° C. The solutions may then be diluted 2-fold with an equal volume of the appropriate experimental buffer and spun through a 0.4 ml spin column of Bio-Gel P-6DG. The resulting Fab' fragments may be more efficient in their coupling to maleimide linkers. Note also that the same procedure may be employed with other macromolecules containing cysteine residues for coupling, for example, to the maleimide spacers. Also, peptides may be utilized provided that they contain a cysteine residue. If the peptides have not been made fresh and there is a possibility of oxidation of cysteine residues within the peptide structure, it may be necessary to regenerate the thiol group using the approach outlined above.

Additional linkers would include other derivatives of lipids useful for coupling to a bifunctional spacer. For example, phosphatidylethanolamine (PE) may be coupled to a bifunctional agent. For example N-succinimidyl 4-(p-maleimidophenyl)butyrate (SMPB) and N-succinimidyl 3-(2-pyridyldithiol)propionate (SPDP), N-succinimidyl trans4-(N-maleimidylmethyl)cyclohexane-1-carboxylate (SMCC), and N-succinimidyl 3-maleimidylbenzoate (SMB) may be used among others, to produce, for example the functionalized lipids MPB-PE and PDP-PE.

The free end of the bydrophilic spacer, such as polyethylene glycol ethylamine, which contains a reactive group, such as an amine or hydroxyl group, could be used to bind a cofactor or other targeting ligand. For example, polyethylene glycol ethylamine may be reacted with N-succinimidylbiotin or p-nitrophenylbiotin to introduce onto the spacer a useful coupling group. For example, biotin may be coupled to the spacer and this will readily bind non-covalently proteins. As an example, MPB-PEG-DPPE may be synthesized as follows. DPPE-PEG with a free amino group at the terminus of the PEG will be provided as described previously.. Synthesis of the SMPB:PEG-DPPE may then be carried out with 1 equivalent of triethylamine in chloroform at a molar ratio of 1:5 SMPB:DPPE-PEG. After 3 hours, the reaction mixture will be evaporated to dryness under argon. Excess unreacted SMPB and major by products will be removed by preparative thin layer chromatography (TLC, silica gel developed with 50% acetone in chloroform). The upper portion of the lipid band can be extracted from the silica with about 20–30% methanol in chloroform (V:V) resulting in the isolation of pure intact MPB-Peg-DPPE. Streptavidin may then be coupled to proteins so that the proteins in turn may then be coupled to the MPB-PEG-DPPE. Briefly SPDP would be incubated with streptavidin at room temperature for 30 minutes and chromatography employed to remove unreacted SPDP. Dithiothreitol (DTT) was added to the reaction mixture and 10 minutes later 2-thiopyridone at a concentration of 343 nM. The remainder of the reaction mixture is reduced with DTT (25 mM for 10 min.). The thiolated product is isolated by gel exclusion. The resulting streptavidin labeled proteins may then be used to bind to the biotinylated spacers affixed to the lipid moieties.

In preferred embodiments of the present invention, the targeted compounds, namely, targeted lipids, proteins, polymers and surfactants, are incorporated in compositions which are used to form targeted vesicles, including, for example, targeted lipid coated vesicles, targeted micelles, targeted liposomes, targeted albumin coated microspheres, and/or targeted polymer coated microspheres. The targeting ligand which is attached to the compounds from which the vesicles are prepared may be directed, for example, outwardly from the surface of the vesicle. Thus, there is provided a targeted vesicle which can be used to target receptors and tissues.

In certain embodiments, the targeting ligands may be incorporated in the present compositions via non-covalent associations. As known to those skilled in the art, non-covalent association is generally a function of a variety of factors, including, for example, the polarity of the involved molecules, the charge (positive or negative), if any, of the involved molecules, the extent of hydrogen bonding through the molecular network, and the like. Non-covalent bonds are preferably selected from the group consisting of ionic interaction, dipole-dipole interaction, hydrogen bonds, hydrophilic interactions, van der Waal's forces, and any combinations thereof. Non-covalent interactions may be employed to bind the targeting ligand to the lipid, or directly to the surface of a vesicle. For example, the amino acid sequence Gly-Gly-His may be bound to the surface of a vesicle, preferably by a linker, such as PEG, and copper, iron or vanadyl ion may then be added. Proteins, such as antibodies which contain histidine residues, may then bind to the vesicle via an ionic bridge with the copper ion, as described in U.S. Pat. No. 5,466,467, the disclosures of which are hereby incorporated herein by reference, in their entirety. An example of hydrogen bonding involves cardiolipin lipids which can be incorporated into the lipid compositions.

The amount of the targeting ligand which may be incorporated in the present lipid and/or vesicle compositions may vary depending, for example, on the particular lipids, vesicles and targeting ligands involved, as well as the particular diagnostic and/or therapeutic application. In certain preferred embodiments, the targeted lipid and/or vesicle compositions may comprise as low as about 0.5 mole % of a compound which includes a targeting ligand (for example, a lipid compound linked to a targeting ligand, such as DPGS-PEG-KQAGDV), with the remaining mole % being, for example, lipid compound (such as, for example, DPPC, DPPA and/or DPPE-PEG5000). Preferably, the lipid and/or vesicle compositions may comprise from about 0.5 to about 10 mole %, and all combinations and subcombinations of ranges therein, of a targeted compound and from about 90 to about 99.5 mole %, and all combinations and subcombinations of ranges therein, of lipid. More preferably, the targeted lipid and/or vesicle compositions may comprise from about 2 to about 8 mole % targeted compound and from about 92 to about 98 mole % lipid. In particularly preferred embodiments, the targeted lipid and/or vesicle compositions may comprise about about 5 mole % targeted compound and about 95 mole % lipid.

In preferred embodiments of the present invention, which may involve vesicle compositions, changes, for example, in pH and/or temperature in vivo, may be employed to promote a change in location in the targeting ligands, for example, from a location within the vesicle, to a location external to the outer wall of the vesicle. This may promote binding of the targeting ligands to targeting sites, for example, receptors, such as the GPIIbIIIa receptor, and tissues, including myocardial, endothelial and epithelial cells, since the targeting ligand has a greater likelihood of exposure to such targeting sites. In addition, high energy ultrasound can be used to promote rupturing of the vesicles. This can also expose the targeting ligand to the desired binding site.

As noted above, the present lipid and/or vesicle compositions are desirably formulated in an aqueous environment. This can induce the lipid, because of its hydrophobic/hydrophilic nature, to form vesicles, which may be the most stable configuration which can be achieved in such an environment. The diluents which can be employed to create such an aqueous environment include, for example, water, including deionized water or water containing one or more dissolved solutes, such as salts, which preferably do not interfere with the formation and/or stability of the vesicles or their use as diagnostic agents, such as ultrasound contrast agents, MRI contrast agents or CT contrast agents; and normal saline and physiological saline.

The lipid and/or vesicle compositions of the present invention may also comprise additional contrast agents, including conventional contrast agents, which may serve to increase their effectiveness as contrast agents for diagnostic imaging.

Accordingly, it is within the scope of the present invention to provide vesicle compositions which comprise flexible vesicles, for example, vesicles formulated from lipids, or inflexible vesicles, for example, vesicles prepared from polymethyl methacrylate.

It is contemplated that the compositions of the present invention are particularly useful in connection with ultrasound, including diagnostic and therapeutic ultrasound. The use of the present compositions in ultrasound is described throughout the present disclosure.

As noted above, the present compositions may also be employed in connection with computed tomography (CT) imaging. CT suffers from various drawbacks, and is generally less effective as compared to the diagnostic techniques discussed above. Nevertheless, if a high enough concentration of the present contrast media, and especially gas filled vesicle compositions, is delivered to the region of interest, for example, a blood clot, the clot can be detected on the CT images by virtue of a decrease in the overall density of the clot. In general, a concentration of about 1/10 of 1% of gas filled vesicles or higher (on a volume basis), may be needed to delivered to the region of interest, including the aforementioned blood clot, to be detected by CT.

Exemplary paramagnetic contrast agents suitable for use in the present compositions include, for example, stable free radicals, such as, for example, stable nitroxides, as well as compounds comprising transition, lanthanide and actinide elements, which may, if desired, be in the form of a salt or may be covalently or non-covalently bound to complexing agents, including lipophilic derivatives thereof, or to proteinaceous macromolecules.

Preferable transition, lanthanide and actinide elements include, for example, Gd(III), Mn(II), Cu(II), Cr(III), Fe(II), Fe(III), Co(II), Er(II), Ni(II), Eu(III) and Dy(III). More preferably, the elements may be Gd(III), Mn(II), Cu(II), Fe(II), Fe(III), Eu(III) and Dy(III), especially Mn(II) and Gd(III).

The foregoing elements may, if desired, be in the form of a salt, including inorganic salts, such as a manganese salt, for example, manganese chloride, manganese carbonate, manganese acetate, and organic salts, such as manganese gluconate and manganese hydroxylapatite. Other exemplary salts include salts of iron, for example, iron sulfides and ferric salts such as ferric chloride.

These elements may also, if desired, be bound, for example, through covalent or noncovalent association, to complexing agents, including lipophilic derivatives thereof, or to proteinaceous macromolecules. Preferable complexing agents include, for example, diethylenetriaminepentaacetic acid (DTPA), ethylene-diaminetetraacetic acid (EDTA), 1,4,7,10-tetraazacyclododecane-N,N',N'',N'''-tetraacetic acid (DOTA), 1,4,7,10-tetraazacyclododecane-N,N',N''-triacetic acid (DOTA), 3,6,9-triaza-12-oxa-3,6,9-tricarboxymethylene-10-carboxy-13-phenyl-tridecanoic acid (B-19036), hydroxybenzylethylenediamine diacetic acid (HBED), N,N'-bis(pyridoxyl-5-phosphate)ethylene diamine, N,N'-diacetate (DPDP), 1,4,7-triazacyclononane-N,N',N''-triacetic acid (NOTA), 1,4,8,11-tetraazacyclotetradecane-N,N',N'',N'''-tetraacetic acid (TETA), kryptands (macrocyclic complexes), and desferrioxamine. More preferably, the complexing agents are EDTA, DTPA, DOTA, DO3A and kryptands, most preferably DTPA. Preferable lipophilic complexes include alkylated derivatives of the complexing agents EDTA, DOTA, for example, N,N'-bis-(carboxydecylamidomethyl-N-2,3-dihydroxypropyl)-ethylenediamine-N,N'-diacetate (EDTA-DDP); N,N'-bis-(carboxyoctadecylamido-methyl-N-2,3-dihydroxypropyl)ethylenediamnine-N,N'-diacetate (EDTA-ODP); N,N'-Bis(carboxy-laurylamidomethyl-N-2,3-dihydroxypropyl)ethylenediamine-N,N'-diacetate (EDTA-LDP); and the like, including those described in U.S. Pat. No. 5,312,617, the disclosures of which are hereby incorporated herein by reference, in their entirety. Preferable proteinaceous macromolecules include, for example, albumin, collagen, polyarginine, polylysine, polyhistidine, γ-globulin and β-globulin, with albumin, polyarginine, polylysine, and polyhistidine being more preferred.

Suitable complexes therefore include Mn(II)DTPA, Mn(II)-EDTA, Mn(II)-DOTA, Mn(II)-DO3A, Mn(Il)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine, especially Mn(II)-DTPA or Gd(III)DTPA.

Nitroxides are paramagnetic contrast agents which increase both T1 and T2 relaxation rates on MRI by virtue of the presence of an unpaired electron in the nitroxide molecule. As known to one of ordinary skill in the art, the paramagnetic effectiveness of a given compound as an MRI contrast agent may be related, at least in part, to the number of unpaired electrons in the paramagnetic nucleus or molecule, and specifically, to the square of the number of unpaired electrons. For example, gadolinium has seven unpaired electrons whereas a nitroxide molecule has one unpaired electron. Thus, gadolinium is generally a much stronger MRI contrast agent than a nitroxide. However, effective correlation time, another important parameter for assessing the effectiveness of contrast agents, confers potential increased relaxivity to the nitroxides. When the tumbling rate is slowed, for example, by attaching the paramagnetic contrast agent to a large molecule, it will tumble more slowly and thereby more effectively transfer energy to hasten relaxation of the water protons. In gadolinium, however, the electron spin relaxation time is rapid and will limit the extent to which slow rotational correlation times can increase relaxivity. For nitroxides, however, the electron spin correlation times are more favorable and tremendous increases in relaxivity may be attained by slowing the rotational correlation time of these molecules. The gas filled vesicles of the present invention are ideal for attaining the goals of slowed rotational correlation times and resultant improvement in relaxivity. Although not intending to be bound by any particular theory of operation, it is contemplated that since the nitroxides may be designed to coat the perimeters of the vesicles, for example, by making alkyl derivatives thereof, the resulting correlation times can be optimized. Moreover, the resulting contrast medium of the present invention may be viewed as a magnetic sphere, a geometric configuration which maximizes relaxivity.

If desired, the nitroxides may be alkylated or otherwise derivatized, such as the nitroxides 2,2,5,5-tetramethyl-1-pyrrolidinyloxy, free radical, and 2,2,6,6-tetramethyl-1-piperidinyloxy, free radical (TMPO).

Exemplary superparamagnetic contrast agents suitable for use in the compositions of the present invention include metal oxides and sulfides which experience a magnetic domain, ferro- or ferrimagnetic compounds, such as pure iron, magnetic iron oxide, such as magnetite, $\gamma$-$Fe_2O_3$, $Fe_3O_4$, manganese ferrite, cobalt ferrite and nickel ferrite. Paramagnetic gases can also be employed in the present compositions, such as oxygen 17 gas ($^{17}O_2$). In addition, hyperpolarized xenon, neon, or helium gas may also be employed. MR whole body imaging may then be employed to rapidly screen the body, for example, for thrombosis, and ultrasound may be applied, if desired, to aid in thrombolysis.

The contrast agents, such as the paramagnetic and superparamagnetic contrast agents described above, may be employed as a component within the lipid and/or vesicle compositions. In the case of vesicle compositions, the aforementioned contrast agents may be entrapped within the internal void thereof, administered as a solution with the vesicles, incorporated with any additional stabilizing materials, or coated onto the surface or membrane of the vesicle.

If desired, the paramagnetic or superparamagnetic agents may be delivered as alkylated or other derivatives incorporated into the compositions, especially the lipidic walls of the vesicles. In particular, the nitroxides 2,2,5,5-tetramethyl-1-pyrrolidinyloxy, free radical and 2,2,6,6-tetramethyl-1-piperidinyloxy, free radical, can form adducts with long chain fatty acids at the positions of the ring which are not occupied by the methyl groups via a variety of linkages, including, for example, an acetyloxy linkage. Such adducts are very amenable to incorporation into the lipid and/or vesicle compositions of the present invention.

Mixtures of any one or more of the paramagnetic agents and/or superparamagnetic agents in the present compositions may be used. The paramagnetic and superparamagnetic agents may also be coadministered separately, if desired.

The lipid and/or vesicle compositions of the present invention, and especially the vesicle compositions, may serve not only as effective carriers of the superparamagnetic agents described above, but also may improve the effect of the susceptibility contrast agents. Superparamagnetic contrast agents include metal oxides, particularly iron oxides but including manganese oxides, and as iron oxides, containing varying amounts of manganese, cobalt and nickel which experience a magnetic domain. These agents are nano or microparticles and have very high bulk susceptibilities and transverse relaxation rates. The larger particles, for example, particles having diameters of about 100 nm, have much higher R2 relaxivities as compared to R1 relaxivities. The smaller particles, for example, particles having diameters of about 10 to about 15 nm, have somewhat lower R2 relaxivities, but much more balanced R1 and $R_2$ values. Much smaller particles, for example, monocrystalline iron oxide particles having diameters of about 3 to about 5 nm, have lower R2 relaxivities, but probably the most balanced R1 and R2 relaxation rates. Ferritin can also be formulated to encapsulate a core of very high relaxation rate superparamagnetic iron. It has been discovered that the lipid and/or vesicle compositions, especially vesicle compositions, including gas filled vesicles, can increase the efficacy and safety of these conventional iron oxide based MRI contrast agents.

The iron oxides may simply be incorporated into the lipid and/or vesicle compositions. Preferably, in the case of vesicles formulated from lipids, the iron oxides may be incorporated into the walls of the vesicles, for example, by being adsorbed onto the surfaces of the vesicles, or entrapped within the interior of the vesicles as described in U.S. Pat. No. 5,088,499, the disclosures of which are hereby incorporated herein by reference in their entirety.

Without being bound to any particular theory or theories of operation, it is believed that the vesicles of the present invention increase the efficacy of the superparamagnetic contrast agents by several mechanisms. First, it is believed that the vesicles function to increase the apparent magnetic concentration of the iron oxide particles. Also, it is believed that the vesicles increase the apparent rotational correlation time of the MRI contrast agents, including paramagnetic and superparamagnetic agents, so that relaxation rates are increased. In addition, the vesicles appear to increase the apparent magnetic domain of the contrast medium according to the manner described hereinafter.

Certain of the vesicles of the present invention, and especially vesicles formulated from lipids, may be visualized as flexible spherical domains of differing susceptibility from the suspending medium, including, for example, the aqueous suspension of the contrast medium or blood or other body fluids, for example, in the case of intravascular injection or injection into other body locations. In the case of ferrites or iron oxide particles, it should be noted that the contrast provided by these agents is dependent on particle size. This phenomenon is very common and is often referred to as the "secular" relaxation of the water molecules. Described in more physical terms, this relaxation mechanism is dependent upon the effective size of the molecular complex in which a paramagnetic atom, or paramagnetic molecule, or molecules, may reside. One physical explanation may be described in the following Solomon-Bloembergen equations which define the paramagnetic contributions as a function of the $T_1$ and $T_2$ relaxation times of a spin ½ nucleus with gyromagnetic ratio g perturbed by a paramagnetic ion:

$$1/T_1M=(2/15)S(S+1)\gamma^2g^2\beta^2/r^6[3\tau_c/(1+\omega_I^2\tau_c^2)+7\tau_c/(1+\omega_s^2\tau_c^2)]+(2/3)S(S+1)A^2/h^2[\tau_e/(1+\omega_2 2\tau_e^2)]$$

and $$1/T_2M=(1/15)S(S+1)\gamma^2g^2\beta^2/r^6[4\tau_c+3\tau c/(1+\omega_1^2\tau_c^2)+13\tau_c(1+w_s^2\tau_c^2)]+(1/3)S(S+1)A^2/h^2[\tau_e/(1+\omega_s 2\tau_e^2)]$$

where:

S is the electron spin quantum number;

g is the electronic g factor;

β is the Bohr magneton;

ωI and $\omega_s$ (657 $\omega_1$) is the Larmor angular precession frequencies for the nuclear spins and electron spins;

r is the ion-nucleus distance;

A is the hyperfine coupling constant;

$\tau_c$ and $\tau_e$ are the correlation times for the dipolar and scalar interactions, respectively; and h is Planck's constant.

See, e.g., Solomon, I. *Phys. Rev.* Vol. 99, p. 559 (1955) and Bloembergen, N. *J. Chem. Phys.* Vol. 27, pp. 572, 595 (1957).

A few large particles may have a much greater effect than a larger number of much smaller particles, primarily due to a larger correlation time. If one were to make the iron oxide particles very large however, increased toxicity may result, and the lungs may be embolized or the complement cascade system may be activated. Furthermore, it is believed that the total size of the particle is not as important as the diameter of the particle at its edge or outer surface. The domain of magnetization or susceptibility effect falls off exponentially from the surface of the particle. Generally speaking, in the case of dipolar (through space) relaxation mechanisms, this exponential fall off exhibits an $r^6$ dependence for a paramagnetic dipole-dipole interaction. Interpreted literally, a water molecule that is 4 angstroms away from a paramagnetic surface will be influenced 64 times less than a water molecule that is 2 angstroms away from the same paramagnetic surface. The ideal situation in terms of maximizing the contrast effect would be to make the iron oxide particles hollow, flexible and as large as possible. It has not been possible to achieve this heretofore and it is believed that the benefits have been unrecognized heretofore also. By coating the inner or outer surfaces of the vesicles with the contrast agents, even though the individual contrast agents, for example, iron oxide nanoparticles or paramagnetic ions, are relatively small structures, the effectiveness of the contrast agents may be greatly enhanced. In so doing, the contrast agents may function as an effectively much larger sphere wherein the effective domain of magnetization is determined by the diameter of the vesicle and is maximal at the surface of the vesicle. These agents afford the advantage of flexibility, namely, compliance. While rigid vesicles might lodge in the lungs or other organs and cause toxic reactions, these flexible vesicles slide through the capillaries much more easily.

In contrast to the flexible vesicles described above, it may be desirable, in certain circumstances, to formulate vesicles from substantially impermeable polymeric materials including, for example, polymethyl methacrylate. This would generally result in the formation of vesicles which may be substantially impermeable and relatively inelastic and brittle. In embodiments involving diagnostic imaging, for example, ultrasound, contrast media which comprise such brittle vesicles would generally not provide the desirable reflectivity that the flexible vesicles may provide. However, by increasing the power output on ultrasound, the brittle microspheres can be made to rupture, thereby causing acoustic emissions which can be detected by an ultrasound transducer.

Nuclear Medicine Imaging (NMI) may also be used in connection with the diagnostic and therapeutic method aspects of the present invention. For example, NMI may be used to detect radioactive gases, such as $Xe^{133}$, which may be incorporated in the present compositions in addition to, or instead of, the gases discussed above. Such radioactive gases may be entrapped within vesicles for use in detecting, for example, thrombosis. Preferably, bifunctional chelate derivatives are incorporated in the walls of vesicles, and the resulting vesicles may be employed in both NMI and ultrasound. In this case, high energy, high quality nuclear medicine imaging isotopes, such as technetium$^{99m}$ or indium$^{111}$ can be incorporated in the walls of vesicles. Whole body gamma scanning cameras can then be employed to rapidly localize regions of vesicle uptake in vivo. If desired, ultrasound may also be used to confirm the presence, for example, of a clot within the blood vessels, since ultrasound generally provides improved resolution as compared to nuclear medicine techniques. NMI may also be used to screen the entire body of the patient to detect areas of vascular thrombosis, and ultrasound can be applied to these areas locally to promote rupture of the vesicles and treat the clot.

For optical imaging, optically active gases, such as argon or neon, may be incorporated in the present compositions. In addition, optically active materials, for example, fluorescent materials, including porphyrin derivatives, may also be used. Elastography is an imaging technique which generally employs much lower frequency sound, for example, about 60 KHz, as compared to ultrasound which can involve over frequencies of over 1 MHz. In elastography, the sound energy is generally applied to the tissue and the elasticity of the tissue may then be determined. In connection with preferred embodiments of the invention, which involve highly elastic vesicles, the deposition of such vesicles onto, for example, a clot, increases the local elasticity of the tissue and/or the space surrounding the clot. This increased elasticity may then be detected with elastography. If desired, elastography can be used in conjunction with other imaging techniques, such as MRI and ultrasound.

In addition to the aforementioned diagnostic imaging techniques and thrombolysis of clots, the present compositions can be used in a variety of therapeutic treatment modalities. For example, bioactive agents, for example, drugs, may be incorporated in the present compositions. In the case of vesicle compositions, the bioactive agents may be advantageously incorporated within the internal void(s). Useful drugs include, for example, heparin sulfate, tissue plasminogen activator, streptokinase, urokinase and hirudin. In connection with therapeutic applications, complementary agents can also be used including, for example, dihydroergotamine, which can be used with heparin sulfate to decrease venostasis. In addition, as noted above, anticoagulants may be used as an adjunct to anticoagulation therapy. Suitable anticoagulants include, for example, derivatives of 4-hydroxycoumarin, such as warfarin, phenprocoumon, acenocoumarol and dicumarol, as well as derivatives of indan-1,3-dione, such as anisindione, with warfarin being preferred. Genetic materials may also be incorporated in the present compositions. In the case of vesicle compositions, the genetic material can be incorporated into the walls of the vesicles or within the central gas-filled void of the vesicles. This may be conveniently accomplished when cationic lipids are employed in the vesicle walls. Genes, such as vascular endothelial growth factor, or antisense gene fragments directed to basic fibroblast growth factor, may be used. This invention can be useful for treating underlying atherosclerosis or to decrease the tendency toward fibrointimal hyperplasia.

The lipid and/or vesicle compositions of the present invention may be prepared using any of a variety of suitable methods. These are described below separately for the embodiments involving lipid compositions and a gas, including gas filled vesicles, and embodiments involving lipid compositions and a gaseous precursor, including gaseous precursor filled vesicles, although compositions comprising both a gas and gaseous precursor form a part of the present invention.

A targeting ligand may be attached to the gas or gaseous precursor filled vesicle by bonding to one or more of the materials employed in the compositions from which they are made, including the lipids, proteins, polymers, and/or auxiliary stabilizing materials, as described above.

A wide variety of methods are available for the preparation of the compositions, including vesicle compositions, such as micelles and/or liposomes. Included among these methods are, for example, shaking, drying, gas-installation, spray drying, and the like. Suitable methods for preparing vesicle compositions are described, for example, in U.S. Pat. No. 5,469,854, the disclosures of which are incorporated herein by reference. As noted above, the vesicles are preferably prepared from lipids which remain in the gel state.

With particular reference to the preparation of micelle compositions, the following discussion is provided. Micelles may be prepared using any one of a variety of conventional micellar preparatory methods which will be apparent to those skilled in the art. These methods typically involve suspension of the lipid compound in an organic solvent, evaporation of the solvent, resuspension in an aqueous medium, sonication and centrifugation. The foregoing methods, as well as others, are discussed, for example, in Canfield et al., *Methods in Enzymology,* Vol. 189, pp. 418–422 (1990); El-Gorab et al, *Biochem. Biophys. Acta,* Vol. 306, pp. 58–66 (1973); *Colloidal Surfactant,* Shinoda, K., Nakagana, Tamamushi and Isejura, Academic Press, NY (1963) (especially "The Formation of Micelles", Shinoda, Chapter 1, pp. 1–88); *Catalysis in Micellar and Macromolecular Systems,* Fendler and Fendler, Academic Press, NY (1975). The disclosures of each of the foregoing publications are incorporated by reference herein, in their entirety.

As noted above, the vesicle composition may comprise liposomes. In any given liposome, the lipid compound(s) may be in the form of a monolayer or bilayer, and the mono- or bilayer lipids may be used to form one or more mono- or bilayers. In the case of more than one mono- or bilayer, the mono- or bilayers are generally concentric. Thus, the lipids may be used to form unilamellar liposomes (comprised of one monolayer or bilayer), oligolamellar liposomes (comprised of two or three monolayers or bilayers) or multilamellar liposomes (comprised of more than three monolayers or bilayers).

A wide variety of methods are available in connection with the preparation of liposome compositions. Accordingly, the liposomes may be prepared using any one of a variety of conventional liposomal preparatory techniques which will be apparent to those skilled in the art. These techniques include, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, French pressure cell technique, controlled detergent dialysis, and others, each involving the preparation of the vesicles in various fashions. See, e.g., Madden et al., *Chemistry and Physics of Lipids,* 1990 53, 37–46, the disclosures of which are hereby incorporated herein by reference in their entirety. Suitable freeze-thaw techniques are described, for example, in International Application Serial No. PCT/US89/05040, filed Nov. 8, 1989, the disclosures of which are incorporated herein by reference in their entirety. Methods which involve freeze-thaw techniques are preferred in connection with the preparation of liposomes. Preparation of the liposomes may be carried out in a solution, such as an aqueous saline solution, aqueous phosphate buffer solution, or sterile water. The liposomes may also be prepared by various processes which involve shaking or vortexing. This may be achieved, for example, by the use of a mechanical shaking device, such as a Wig-L-Bug™ (Crescent Dental, Lyons, Ill.), a Mixomat, sold by Degussa AG, Frankfurt, Germany, a Capmix, sold by Espe Fabrik Pharmazeutischer Praeparate GMBH & Co., Seefeld, Oberay Germany, a Silamat Plus, sold by Vivadent, Lechtenstein, or a Vibros, sold by Quayle Dental, Sussex, England. Conventional microemulsification equipment, such as a Microfluidizer™ (Microfluidics, Woburn, Mass.) may also be used.

Spray drying may be also employed to prepare the gas-filled vesicles. Utilizing this procedure, the lipids may be pre-mixed in an aqueous environment and then spray dried to produce gas-filled vesicles. The vesicles may be stored under a headspace of a desired gas.

Many liposomal preparatory techniques which may be adapted for use in the preparation of vesicle compositions are discussed, for example, in U.S. Pat. No. 4,728,578; U.K. Patent Application GB 2193095 A; U.S. Pat. No. 4,728,575; U.S. Pat. No. 4,737,323; International Application Serial No. PCT/US85/01161; Mayer et al., *Biochimica et Biophysica Acta,* Vol. 858, pp. 161–168 (1986); Hope et al., *Biochimica et Biophysica Acta,* Vol. 812, pp. 55–65 (1985); U.S. Pat. No. 4,533,254; Mayhew et al., *Methods in Enzymology,* Vol. 149, pp. 64–77 (1987); Mayhew et al., *Biochimica et Biophysica Acta,* Vol 755, pp. 169–74 (1984); Cheng et al, *Investigative Radiology,* Vol. 22, pp. 47–55 (1987); International Application Serial No. PCT/US89/05040; U.S. Pat. No. 4,162,282; U.S. Pat. No. 4,310,505; U.S. Pat. No. 4,921,706; and *Liposome Technology,* Gregoriadis, G., ed., Vol. I, pp. 29–31, 51–67 and 79–108 (CRC Press Inc., Boca Raton, Fla. 1984), the disclosures of each of which are hereby incorporated by reference herein, in their entirety.

Lipid compositions comprising a gas can be prepared by agitating an aqueous solution containing, if desired, a stabilizing material, in the presence of a gas. The term "agitating," as used herein, means any shaking motion of an aqueous solution such that gas is introduced from the local ambient environment into the aqueous solution. This agitation is preferably conducted at a temperature below the gel to liquid crystalline phase transition temperature of the lipid. The shaking involved in the agitation of the solutions is preferably of sufficient force to result in the formation of a lipid composition, including vesicle compositions, and particularly vesicle compositions comprising gas filled vesicles. The shaking may be by swirling, such as by vortexing, side-to-side, or up and down motion. Different types of motion may be combined. Also, the shaking may occur by shaking the container holding the aqueous lipid solution, or by shaking the aqueous solution within the container without shaking the container itself.

The shaking may occur manually or by machine. Mechanical shakers that may be used include, for example, a shaker table such as a VWR Scientific (Cerritos, Calif.) shaker table, as well as any of the shaking devices described hereinbefore, with the Capmix (Espe Fabrik Pharmazeutischer Praeparate GMBH & Co., Seefeld, Oberay Germany) being preferred. It has been found that certain modes of shaking or vortexing can be used to make vesicles within a preferred size range. Shaking is preferred, and it is preferred that the shaking be carried out using the Espe Capmix mechanical shaker. In accordance with this preferred method, it is preferred that a reciprocating motion be utilized to generate the lipid compositions, and particularly vesicle compositions. It is even more preferred that the motion be reciprocating in the form of an arc. It is contemplated that the rate of reciprocation, as well as the arc thereof, is particularly important in connection with the formation of vesicles. Preferably, the number of reciprocations or full cycle oscillations is from about 1000 to about 20,000 per minute. More preferably, the number of reciprocations or oscillations is from about 2500 to about 8000, with reciprocations or oscillations of from about 3300 to about 5000 being even more preferred. Of course, the number of oscillations can be dependent upon the mass of the contents being agitated. Generally speaking, a larger mass requires fewer oscillations. Another means for producing shaking includes the action of gas emitted under high velocity or pressure.

It will also be understood that preferably, with a larger volume of aqueous solution, the total amount of force will be correspondingly increased. Vigorous shaking is defined as at least about 60 shaking motions per minute, and is preferred. Vortexing at about 60 to about 300 revolutions per minute is more preferred. Vortexing at about 300 to about 1800 revolutions per minute is even more preferred.

In addition to the simple shaking methods described above, more elaborate methods can also be employed. Such elaborate methods include, for example, liquid crystalline shaking gas instillation processes and vacuum drying gas instillation processes, such as those described in U.S. Pat. No. 5,580,575, the disclosures of which are incorporated herein by reference, in their entirety. Although any of a number of varying techniques can be used, the vesicle compositions employed in the present invention are preferably prepared using a shaking technique. Preferably, the shaking technique involves agitation with a mechanical shaking apparatus, such as an Espe Capmix (Seefeld, Oberay Germany), using, for example, the techniques disclosed in U.S. Pat. No. 5,542,935, the disclosures of which are hereby incorporated herein by reference in their entirety.

The size of gas filled vesicles can be adjusted, if desired, by a variety of procedures, including, for example, microemulsification, vortexing, extrusion, filtration, sonication, homogenization, repeated freezing and thawing cycles, extrusion under pressure through pores of defined size, and similar methods. Gas filled vesicles prepared in accordance with the methods described herein can range in size from less than about 1 μm to greater than about 100 μm. In addition, after extrusion and sterilization procedures, which are discussed in detail below, agitation or shaking provides vesicle compositions which provide substantially no or minimal residual anhydrous lipid phase in the remainder of the solution. (Bangham, A. D., Standish, M. M, & Watkins, J. C., *J. Mol. Biol.* Vol. 13, pp. 238–252 (1965). If desired, the vesicles of the present invention may be used as they are formed, without any attempt at further modification of the size thereof. For intravascular use, the vesicles preferably have diameters of less than about 30 μm, and more preferably, less than about 12 μm. For targeted intravascular use including, for example, binding to certain tissue, such as cancerous tissue, the vesicles can be significantly smaller, for example, less than about 100 nm in diameter. For enteric or gastrointestinal use, the vesicles can be significantly larger, for example, up to a millimeter in size. Preferably, the vesicles are sized to have diameters of from about 2 μm to about 100 μm.

The gas filled vesicles may be sized by a simple process of extrusion through filters wherein the filter pore sizes control the size distribution of the resulting gas filled vesicles. By using two or more cascaded or stacked set of filters, for example, a 10 μm filter followed by an 8 μm filter, the gas filled vesicles can be selected to have a very narrow size distribution around 7 to 9 μm. After filtration, these gas filled vesicles can remain stable for over 24 hours.

The sizing or filtration step may be accomplished by the use, for example, of a filter assembly when the composition is removed from a sterile vial prior to use, or more preferably, the filter assembly may be incorporated into a syringe during use. The method of sizing the vesicles will then comprise using a syringe comprising a barrel, at least one filter, and a needle; and will be carried out by a step of extracting which comprises extruding the vesicles from the barrel through the filter fitted to the syringe between the barrel and the needle, thereby sizing the vesicles before they are administered to a patient. The step of extracting may also comprise drawing the vesicles into the syringe, where the filter will function in the same way to size the vesicles upon entrance into the syringe. Another alternative is to fill such a syringe with vesicles which have already been sized by some other means, in which case the filter now functions to ensure that only vesicles within the desired size range, or of the desired maximum size, are subsequently administered by extrusion from the syringe.

In certain preferred embodiments, the vesicle compositions may be heat sterilized or filter sterilized and extruded through a filter prior to shaking. Generally speaking, vesicle compositions comprising a gas may be heat sterilized, and vesicle compositions comprising gaseous precursors may be filter sterilized. Once gas filled vesicles are formed, they may be filtered for sizing as described above. Performing these steps prior to the formation of gas and gaseous precursor filled vesicles provide sterile gas filled vesicles ready for administration to a patient. For example, a mixing vessel such as a vial or syringe may be filled with a filtered lipid composition, and the composition may be sterilized within the mixing vessel, for example, by autoclaving. Gas may be instilled into the composition to form gas filled vesicles by shaking the sterile vessel. Preferably, the sterile vessel is equipped with a filter positioned such that the gas filled vesicles pass through the filter before contacting a patient.

The step of extruding the solution of lipid compound through a filter decreases the amount of unhydrated material by breaking up any dried materials and exposing a greater surface area for hydration. Preferably, the filter has a pore size of about 0.1 to about 5 μm, more preferably, about 0.1 to about 4 μm, even more preferably, about 0.1 to about 2 μm, and still more preferably, about 1 μm. Unhydrated compound, which is generally undesirable, appears as amorphous clumps of non-uniform size.

The sterilization step provides a composition that may be readily administered to a patient for diagnostic imaging including, for example, ultrasound or CT. In certain preferred embodiments, sterilization may be accomplished by heat sterilization, preferably, by autoclaving the solution at a temperature of at least about 100° C., and more preferably, by autoclaving at about 100° C. to about 130° C., even more preferably, about 110° C. to about 130° C., still more preferably, about 120° C. to about 130° C., and even more preferably, about 130° C. Preferably, heating occurs for at least about 1 minute, more preferably, about 1 to about 30 minutes, even more preferably, about 10 to about 20 minutes, and still more preferably, about 15 minutes.

If desired, the extrusion and beating steps, as outlined above, may be reversed, or only one of the two steps can be used. Other modes of sterilization may be used, including, for example, exposure to gamma radiation.

In addition to the aforementioned embodiments, gaseous precursors contained in vesicles can be formulated which, upon activation, for example, by exposure to elevated temperature, varying pH, or light, undergo a phase transition from, for example, a liquid, including a liquid entrapped in a vesicle, to a gas, expanding to create the gas filled vesicles described herein. This technique is described in detail in U.S. Pat. No. 5,542,935 and U.S. Pat. No. 5,585,112, the disclosures of which are incorporated herein by reference, in their entirety.

The preferred method of activating the gaseous precursor is by exposure to elevated temperature. Activation or transition temperature, and like terms, refer to the boiling point of the gaseous precursor and is the temperature at which the liquid to gaseous phase transition of the gaseous precursor takes place. Useful gaseous precursors are those materials which have boiling points in the range of about −100° C. to about 70° C. The activation temperature is particular to each gaseous precursor. An activation temperature of about 37° C., or about human body temperature, is preferred for gaseous precursors in the context of the present invention. Thus, in preferred form, a liquid gaseous precursor is activated to become a gas at about 37° C. or below. The gaseous precursor may be in liquid or gaseous phase for use in the methods of the present invention.

The methods of preparing the gaseous precursor filled vesicles may be carried out below the boiling point of the gaseous precursor such that a liquid is incorporated, for example, into a vesicle. In addition, the methods may be conducted at the boiling point of the gaseous precursor, such that a gas is incorporated, for example, into a vesicle. For gaseous precursors having low temperature boiling points, liquid precursors may be emulsified using a microfluidizer device chilled to a low temperature. The boiling points may also be depressed using solvents in liquid media to utilize a precursor in liquid form. Further, the methods may be performed where the temperature is increased throughout the process, whereby the process starts with a gaseous precursor as a liquid and ends with a gas.

The gaseous precursor may be selected so as to form the gas in situ in the targeted tissue or fluid, in vivo upon entering the patient or animal, prior to use, during storage, or during manufacture. The methods of producing the temperature-activated gaseous precursor filled vesicles may be carried out at a temperature below the boiling point of the gaseous precursor. In this embodiment, the gaseous precursor is entrapped within a vesicle such that the phase transition does not occur during manufacture. Instead, the gaseous precursor filled vesicles are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the vesicles upon attaining the gaseous state may be determined.

Alternatively, the gaseous precursors may be utilized to create stable gas filled vesicles which are pre-formed prior to use. In this embodiment, the gaseous precursor is added to a container housing a lipid composition at a temperature below the liquid-gaseous phase transition temperature of the respective gaseous precursor. As the temperature is increased, and an emulsion is formed between the gaseous precursor and liquid solution, the gaseous precursor undergoes transition from the liquid to the gaseous state. As a result of this heating and gas formation, the gas displaces the air in the head space above the liquid mixture so as to form gas filled vesicles which entrap the gas of the gaseous precursor, ambient gas (e.g. air), or coentrap gas state gaseous precursor and ambient air. This phase transition can be used for optimal mixing and formation of the contrast agent. For example, the gaseous precursor, perfluorobutane, can be entrapped in the lipid vesicles and as the temperature is raised beyond the boiling point of perfluorobutane (4° C.), perfluorobutane gas is entrapped in the vesicles.

Accordingly, the gaseous precursors may be selected to form gas filled vesicles in vivo or may be designed to produce the gas filled vesicles in situ, during the manufacturing process, on storage, or at some time prior to use. A water bath, sonicator or hydrodynamic activation by pulling back the plunger of a syringe against a closed stopcock may be used to activate targeted gas-filled vesicles from temperature-sensitive gaseous precursors prior to I.V. injection.

As a further embodiment of this invention, by preforming the gaseous precursor in the liquid state into an aqueous emulsion, the maximum size of the vesicle may be estimated by using the ideal gas law, once the transition to the gaseous state is effectuated. For the purpose of making gas filled vesicles from gaseous precursors, the gas phase is assumed to form instantaneously and substantially no gas in the newly formed vesicle has been depleted due to diffusion into the liquid, which is generally aqueous in nature. Hence, from a known liquid volume in the emulsion, one would be able to predict an upper limit to the size of the gas filled vesicle.

In embodiments of the present invention, a mixture of a lipid compound and a gaseous precursor, containing liquid droplets of defined size, may be formulated such that upon reaching a specific temperature, for example, the boiling point of the gaseous precursor, the droplets will expand into gas filled vesicles of defined size. The defined size represents an upper limit to the actual size because the ideal gas law cannot account for such factors as gas diffusion into solution, loss of gas to the atmosphere, and the effects of increased pressure.

The ideal gas law, which can be used for calculating the increase in the volume of the gas bubbles upon transitioning from liquid to gaseous states, is as follows:

$$PV=nRT$$

where

P is pressure in atmospheres (atm);

V is volume in liters (L);

n is moles of gas;

T is temperature in degrees Kelvin (K.); and

R is the ideal gas constant (22.4 L-atm/K-mole).

With knowledge of volume, density, and temperature of the liquid in the mixture of liquids, the amount, for example, in moles, and volume of liquid precursor may be calculated which, when converted to a gas, will expand into a vesicle of known volume. The calculated volume will reflect an upper limit to the size of the gas filled vesicle, assuming instantaneous expansion into a gas filled vesicle and negligible diffusion of the gas over the time of the expansion.

Thus, for stabilization of the precursor in the liquid state in a mixture wherein the precursor droplet is spherical, the volume of the precursor droplet may be determined by the equation:

$$\text{Volume (spherical vesicle)}=4/3\pi r^3$$

where r is the radius of the sphere.

Thus, once the volume is predicted, and knowing the density of the liquid at the desired temperature, the amount of liquid gaseous precursor in the droplet may be determined. In more descriptive terms, the following can be applied:

$$V_{gas}=4/3\pi(r_{gas})^3$$

by the ideal gas law, $$PV=nRT$$

substituting reveals, $$V_{gas}=nRT/P_{gas}$$

or, $$n=4/3[\pi r_{gas}^3]P/RT \qquad (A)$$

amount $n=4/3 [\pi r_{gas}^3 P/RT] \cdot MW_n$
Converting back to a liquid volume $$V_{liq}=[4/3[\pi r_{gas}^3]P/RT \cdot MW_n/D] \qquad (B)$$

where D is the density of the precursor.
Solving for the diameter of the liquid droplet, $$\text{diameter}/2=[3/4\pi[4/3 \cdot [\pi r_{gas}^3]P/RT]MW_n/D]^{1/3} \qquad (C)$$

which reduces to $$\text{Diameter}=2[[r_{gas}^3]P/RT [MW_n/D]]^{1/3}.$$

As a further means of preparing vesicles of the desired size for use in the methods of the present invention, and with a knowledge of the volume and especially the radius of the liquid droplets, one can use appropriately sized filters to size the gaseous precursor droplets to the appropriate diameter sphere.

A representative gaseous precursor may be used to form a vesicle of defined size, for example, 10 μm diameter. In this example, the vesicle is formed in the bloodstream of a human being, thus the typical temperature would be 37° C. or 310 K. At a pressure of 1 atmosphere and using the equation in (A), $7.54 \times 10^{-17}$ moles of gaseous precursor would be required to fill the volume of a 10 μm diameter vesicle.

Using the above calculated amount of gaseous precursor and 1-fluorobutane, which possesses a molecular weight of 76.11, a boiling point of 32.5° C. and a density of 0.7789 g/mL at 20° C., further calculations predict that $5.74 \times 10^{-15}$ grams of this precursor would be required for a 10 μm vesicle. Extrapolating further, and with the knowledge of the density, equation (B) further predicts that $8.47 \times 10^{-16}$ mL of liquid precursor is necessary to form a vesicle with an upper limit of 10 μm.

Finally, using equation (C), a mixture, for example, an emulsion containing droplets with a radius of 0.0272 μm or a corresponding diameter of 0.0544 μm, is formed to make a gaseous precursor filled vesicle with an upper limit of a 10 μm vesicle.

An emulsion of this particular size could be easily achieved by the use of an appropriately sized filter. In addition, as seen by the size of the filter necessary to form gaseous precursor droplets of defined size, the size of the filter would also suffice to remove any possible bacterial contaminants and, hence, can be used as a sterile filtration as well.

This embodiment for preparing gas filled vesicles may be applied to all gaseous precursors activated by temperature. In fact, depression of the freezing point of the solvent system allows the use of gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be determined by physical methods as well. When substances, solid or liquid, herein referred to as solutes, are dissolved in a solvent, such as water based buffers, the freezing point is lowered by an amount that is dependent upon the composition of the solution. Thus, as defined by Wall, one can express the freezing point depression of the solvent by the following equation:

$$lnx_a = ln(1-x_b) = \Delta H_{fus}/R(1/T_o - 1/T)$$

where:

$x_a$ is the mole fraction of the solvent;

$x_b$ is the mole fraction of the solute;

$\Delta H_{fus}$ is the heat of fusion of the solvent; and $T_o$ is the normal freezing point of the solvent.

The normal freezing point of the solvent can be obtained by solving the equation. If $x_b$ is small relative to $x_a$, then the above equation may be rewritten as follows.

$$x^b = \Delta H_{fus}/R[T-T_o/T_oT] \approx \Delta H_{fus}\Delta T/RT_o^2$$

The above equation assumes the change in temperature $\Delta T$ is small compared to $T_2$. This equation can be simplified further by expressing the concentration of the solute in terms of molality, m (moles of solute per thousand grams of solvent). Thus, the equation can be rewritten as follows.

$$X_b = m/[m+1000/m_a] = mMa/1000$$

where Ma is the molecular weight of the solvent.

Thus, substituting for the fraction $x_b$:

$$\Delta T = [M_a RT_o^2/1000\Delta H_{fus}]m$$

or $$\Delta T = K_f m,$$

where $$K_f = M_a RT_o^2/1000\Delta H_{fus}$$

$K_f$ is the molal freezing point and is equal to 1.86 degrees per unit of molal concentration for water at one atmosphere pressure. The above equation may be used to accurately determine the molal freezing point of solutions of gaseous-precursor filled vesicles. Accordingly, the above equation can be applied to estimate freezing point depressions and to determine the appropriate concentrations of liquid or solid solute necessary to depress the solvent freezing temperature to an appropriate value.

Methods of preparing the temperature activated gaseous precursor filled vesicles include:

(a) vortexing and/or shaking an aqueous mixture of gaseous precursor and additional materials as desired, including, for example, stabilizing materials, thickening agents and/or dispersing agents. Optional variations of this method include autoclaving before vortexing or shaking; heating an aqueous mixture of gaseous precursor; venting the vessel containing the mixture/suspension; shaking or permitting the gaseous precursor filled vesicle to form spontaneously and cooling down the suspension of gaseous precursor filled vesicles; and extruding an aqueous suspension of gaseous precursor through a filter of about 0.22 μm. Alternatively, filtering may be performed during in vivo administration of the vesicles such that a filter of about 0.22 μm is employed;

(b) microemulsification whereby an aqueous mixture of gaseous precursor is emulsified by agitation and heated to form, for example, vesicles prior to administration to a patient;

(c) heating a gaseous precursor in a mixture, with or without agitation, whereby the less dense gaseous precursor filled vesicles float to the top of the solution by expanding and displacing other vesicles in the vessel and venting the vessel to release air; and (d) utilizing in any of the above methods a sealed vessel to hold the aqueous suspension of gaseous precursor and maintaining the suspension at a temperature below the phase transition temperature of the gaseous precursor, followed by autoclaving to raise the temperature above the phase transition temperature, optionally with shaking, or permitting the gaseous precursor vesicle to form spontaneously, whereby the expanded gaseous precursor in the sealed vessel increases the pressure in the vessel, and cooling down the gas filled vesicle suspension, after which shaking may also take place.

Freeze drying is useful to remove water and organic materials prior to the shaking installation method. Drying installation methods may be used to remove water from vesicles. By pre-entrapping the gaseous precursor in the dried vesicles (i.e. prior to drying) after warming, the gaseous precursor may expand to fill the vesicle. Gaseous precursors can also be used to fill dried vesicles after they have been subjected to vacuum. As the dried vesicles are kept at a temperature below their gel state to liquid crystalline temperature, the drying chamber can be slowly filled with the gaseous precursor in its gaseous state. For example, perfluorobutane can be used to fill dried vesicles at temperatures above 4° C. (the boiling point of perfluorobutane).

Preferred methods for preparing the temperature activated gaseous precursor filled vesicles comprise shaking an aqueous solution having a lipid compound in the presence of a gaseous precursor at a temperature below the liquid state to gas state phase transition temperature of the gaseous precursor. This is preferably conducted at a temperature below the gel state to liquid crystalline state phase transition temperature of the lipid. The mixture is then heated to a temperature above the liquid state to gas state phase transition temperature of the gaseous precursor which causes the precursor to volatilize and expand. Heating is then discontinued, and the temperature of the mixture is then allowed to drop below the liquid state to gas state phase transition temperature of the gaseous precursor. Shaking of the mixture may take place during the heating step, or subsequently after the mixture is allowed to cool.

Other methods for preparing gaseous precursor filled vesicles can involve shaking an aqueous solution of, for example, a lipid and a gaseous precursor, and separating the resulting gaseous precursor filled vesicles.

Conventional, aqueous-filled liposomes of the prior art are routinely formed at a temperature above the phase transition temperature of the lipids used to make them, since they are more flexible and thus useful in biological systems in the liquid crystalline state. See, for example, Szoka and Papahadjopoulos, *Proc. Natl. Acad. Sci.* 1978, 75, 4194–4198. In contrast, the vesicles made according to certain preferred embodiments described herein are gaseous precursor filled, which imparts greater flexibility, since gaseous precursors after gas formation are more compressible and compliant than an aqueous solution.

The methods contemplated by the present invention provide for shaking an aqueous solution comprising a lipid, in the presence of a temperature activatable gaseous precursor. Preferably, the shaking is of sufficient force such that a foam is formed within a short period of time, such as about 30 minutes, and preferably within about 20 minutes, and more preferably, within about 10 minutes. The shaking may involve microemulsifying, microfluidizing, swirling (such as by vortexing), side-to-side, or up and down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself Further, the shaking may occur manually or by machine. Mechanical shakers that may be used include, for example, the mechanical shakers described hereinbefore, with an Espe Capmix (Seefeld, Oberay Germany) being preferred. Another means for producing shaking includes the action of gaseous precursor emitted under high velocity or pressure.

According to the methods described herein, a gas, such as air, may also be provided by the local ambient atmosphere. The local ambient atmosphere can include the atmosphere within a sealed container, as well as the external environment. Alternatively, for example, a gas may be injected into or otherwise added to the container having the aqueous lipid solution or into the aqueous lipid solution itself to provide a gas other than air. Gases that are lighter than air are generally added to a sealed container, while gases heavier than air can be added to a sealed or an unsealed container. Accordingly, the present invention includes co-entrapment of air and/or other gases along with gaseous precursors.

Hence, the gaseous precursor filled vesicles can be used in substantially the same manner as the gas filled vesicles described herein, once activated by application to the tissues of a host, where such factors as temperature or pH may be used to cause generation of the gas. It is preferred that the gaseous precursors undergo phase transitions from liquid to gaseous states at near the normal body temperature of the host, and are thereby activated, for example, by the in vivo temperature of the host so as to undergo transition to the gaseous phase therein. Alternating, activation prior to I.V. injection may be used, for example, by thermal, mechanical or optical means. This activation can occur where, for example, the host tissue is human tissue having a normal temperature of about 37° C. and the gaseous precursors undergo phase transitions from liquid to gaseous states near 37° C.

As noted above, the lipid and/or vesicle compositions may be sterilized by autoclave or sterile filtration if these processes are performed before the installation step or prior to temperature mediated conversion of the temperature sensitive gaseous precursors within the compositions. Alternatively, one or more anti-bactericidal agents and/or preservatives may be included in the formulation of the compositions, such as sodium benzoate, quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized vesicles are used for imaging under invasive circumstances, e.g., intravascularly or intraperitonealy. The appropriate means of sterilization will be apparent to the artisan based on the present disclosure.

Vesicle compositions which comprise vesicles formulated from proteins (also referred to as protein encapsulated microbubbles), such as albumin vesicles, may be prepared by various processes, as will be readily apparent to those skilled in the art, once armed with the present disclosure. Suitable methods include those described, for example, in Feinstein, U.S. Pat. Nos. 4,572,203, 4,718,433 and 4,774, 958, and Cerny et al., U.S. Pat. No. 4,957,656, the disclosures of which are hereby incorporated herein by reference, in their entirety. Included among the methods described in the aforementioned patents for the preparation of protein-based vesicles are methods which involve sonicating a solution of a protein. In preferred form, the starting material may be an aqueous solution of a heat-denaturable, water-soluble biocompatible protein. The encapsulating protein is preferably heat-sensitive so that it can be partially insolubilized by heating during sonication. Suitable heat-sensitive proteins include, for example, albumin, hemoglobin, collagen, and the like. Preferably, the protein is a human protein, with human serum albumin (HSA) being more preferred. HSA is available commercially as a sterile 5% aqueous solution, which is suitable for use in the preparation of protein-based vesicles. Of course, as would be apparent to one of ordinary skill in the art, other concentrations of albumin, as well as other proteins which are heat-denaturable, can be used to prepare the vesicles. Generally speaking, the concentration of HSA can vary and may range from about 0.1 to about 25% by weight, and all combinations and subcombinations of ranges therein. It may be preferable, in connection with certain methods for the preparation of protein-based vesicles, to utilize the protein in the form of a dilute aqueous solution. For albumin, it may be preferred to utilize an aqueous solution containing from about 0.5 to about 7.5% by weight albumin, with concentrations of less than about 5% by weight being preferred, for example, from about 0.5 to about 3% by weight.

The protein-based vesicles may be prepared using equipment which is commercially available. For example, in connection with a feed perparation operation as disclosed, for example, in Cerny, et al., U.S. Pat. No. 4,957,656, stainless steel tanks which are commercially available from Walker Stainless Equipment Co. (New Lisbon, Wis.), and process filters which are commercially available from Millipore (Bedford, Mass.), may be utilized.

The sonication operation may utilize both a heat exchanger and a flow through sonciating vessel, in series. Heat exhanger equipment of this type may be obtained from ITT Standard (Buffalo, N.Y.). The heat exchanger maintains operating temperature for the sonication process, with temperature controls ranging from about 65° C. to about 80° C., depending on the makeup of the media. The vibration frequency of the sonication equipment may vary over a wide range, for example, from about 5 to about 40 kilohertz (kHz), with a majority of the commerically available sonicators operating at about 10 or 20 kHz. Suitable sonicating equipment include, for example, a Sonics & Materials Vibra-Cell, equipped with a flat-tipped sonicator horn, commercially available from Sonics & Materials, Inc. (Danbury, Conn.). The power applied to the sonicator horn can be varied over power settings scaled from 1 to 10 by the manufacturer, as with Sonics & Materials Vibra-Cell Model VL1500. An intermediate power setting, for example, from 5 to 9, can be used. It is preferred that the vibrational frequency and the power supplied be sufficeint to produce cavitation in the liquid being sonicated. Feed flow rates may range from about 50 mL/min to about 1000 mL/min, and all combinations and subcombinations of ranges therein. Residence times in the sonication vessel can range from about 1 second to about 4 minutes, and gaseous fluid addition rates may range from about 10 cubic centimeters (cc) per minute to about 100 cc/min, or 5% to 25% of the feed flow rate, and all combinations and subcombinations of ranges therein.

It may be preferable to carry out the sonication in such a manner to produce foaming, and especially intense foaming, of the solution. Generally speaking, intense foaming and aerosolating are important for obtaining a contrast agent having enhanced concentration and stability. To promote foaiming, the power input to the sonicator horn may be increased, and the process may be operated under mild pressure, for example, about 1 to about 5 psi. Foaming may be easily detected by the cloudy appearance of the solution, and by the foam produced.

Suitable methods for the preparation of protein-based vesicles may also involve physically or chemically altering the protein or protein derivative in aqueous solution to denature or fix the material. For example, protein-based vesicles may be prepared from a 5% aqueous solution of HSA by heating after formation or during formation of the contrast agent via sonication. Chemical alteration may involve chemically denaturing or fixing by binding the protein with a difunctional aldehyde, such as gluteraldehyde. For example, the vesicles may be reacted with 0.25 grams of 50% aqueous gluteradehyde per gram of protein at pH 4.5 for 6 hours. The unreacted gluteraldehyde may then be washed away from the protein.

In any of the techniques described above for the preparation of protein-based vesicles, the targeting ligands may be incorporated with the proteins before, during or after formation of the vesicles, as would be apparent to one of ordinary skill in the art, once armed with the present disclosure.

Vesicle compositions which comprise vesicles formulated from polymers may be prepared by various processes, as will be readily apparent to those skilled in the art, once armed with the present disclosure. Exemplary processes include, for example, interfacial polymerization, phase separation and coacervation, multiorifice centrifugal preparation, and solvent evaporation. Suitable procedures which may be employed or modified in accordance with the present disclosure to prepare vesicles from polymers include those procedures disclosed in Garner et al., U.S. Pat. No. 4,179,546, Garner, U.S. Pat. No. 3,945,956, Cohrs et al., U.S. Pat. No. 4,108,806, Japan Kokai Tokkyo Koho 62 286534, British Patent No. 1,044,680, Kenaga et al., U.S. Pat. No. 3,293,114, Morehouse et al., U.S. Pat. No. 3,401,475, Walters, U.S. Pat. No. 3,479,811, Walters et al., U.S. Pat. No. 3,488,714, Morehouse et al., U.S. Pat. No. 3,615,972, Baker et al., U.S. Pat. No. 4,549,892, Sands et al., U.S. Pat. No. 4,540,629, Sands et al., U.S. Pat. No. 4,421,562, Sands, U.S. Pat. No. 4,420,442, Mathiowitz et al., U.S. Pat. No. 4,898,734, Lencki et al., U.S. Pat. No. 4,822,534, Herbig et al., U.S. Pat. No. 3,732,172, Himmel et al., U.S. Pat. No. 3,594,326, Sommerville et al., U.S. Pat. No. 3,015,128, Deasy, *Microencapsulation and Related Drug Processes,* Vol. 20, Chs. 9 and 10, pp. 195–240 (Marcel Dekker, Inc., N.Y., 1984), Chang et al., *Canadian J. of Physiology and Pharmacology,* Vol 44, pp. 115–129 (1966), and Chang, *Science,* Vol. 146, pp. 524–525 (1964), the disclosures of each of which are incorporated herein by reference in their entirety.

In accordance with a preferred synthesis protocol, the vesicles may be prepared using a heat expansion process, such as, for example, the process described in Garner et al., U.S. Pat. No. 4,179,546, Garner, U.S. Pat. No. 3,945,956, Cohrs et al., U.S. Pat. No. 4,108,806, British Patent No. 1,044,680, and Japan Kokai Tokkyo Koho 62 286534. In general terms, the heat expansion process may be carried out by preparing vesicles of an expandable polymer or copolymer which may contain in their void (cavity) a volatile liquid (gaseous precursor). The vesicle is then heated, plasticising the vesicle and converting the volatile liquid into a gas, causing the vesicle to expand to up to about several times its original size. When the heat is removed, the thermoplastic polymer retains at least some of its expanded shape. Vesicles produced by this process tend to be of particularly low density, and are thus preferred. The foregoing described process is well known in the art, and may be referred to as the heat expansion process for preparing low density vesicles.

Polymers useful in the heat expansion process will be readily apparent to those skilled in the art and include thermoplastic polymers or copolymers, including polymers or copolymers of many of the monomers described above. Preferable of the polymers and copolymers described above include the following copolymers: polyvinylidene-polyacrylonitrile, polyvinylidene-polyacrylonitrile-polymethyl-methacrylate, and polystyrene-polyacrylonitrile. A most preferred copolymer is polyvinylidene-polyacrylonitrile.

Volatile liquids useful in the heat expansion process will also be well known to those skilled in the art and include: aliphatic hydrocarbons such as ethane, ethylene, propane, propene, butane, isobutane, neopentane, acetylene, hexane, heptane; chlorofluorocarbons such as $CCl_3F$, $CCl_2F_3$, $CClF_3$, $CClF_2$—$CCl_2F_2$, chloroheptafluoro-cyclobutane, and 1,2-dichlorohexafluorocyclobutane; tetraalkyl silanes, such as tetramethyl silane, trimethylethyl silane, trimethylisopropyl silane, and trimethyl n-propyl silane; as well as perfluorocarbons, including the perfluorocarbons described above. In general, it is important that the volatile liquid not be a solvent for the polymer or copolymer being utilized. It is also preferred that the volatile liquid have a boiling point that is below the softening point of the involved polymer or co-polymer. Boiling points of various volatile liquids and softening points of various polymers and copolymers will be readily ascertainable to one skilled in the art, and suitable combinations of polymers or copolymers and volatile liquids will be easily apparent to the skilled artisan. By way of guidance, and as one skilled in the art would recognize, generally as the length of the carbon chain of the volatile liquid increases, the boiling point of that liquid increases also. Also, mildly preheating the vesicles in water in the presence of hydrogen peroxide prior to definitive heating and expansion may pre-soften the vesicle to allow expansion to occur more readily.

For example, to produce vesicles from synthetic polymers, vinylidene and acrylonitrile may be copolymerized in a medium of isobutane liquid using one or more of the foregoing modified or unmodified literature procedures, such that isobutane becomes entrapped within the vesicles. When such vesicles are then heated to a temperature of from about 80° C. to about 120° C., the isobutane gas expands, which in turn expands the vesicles. After heat is removed, the expanded polyvinylidene and acrylo-nitrile copolymer vesicles remain substantially fixed in their expanded position. The resulting low density vesicles are extremely stable both dry and suspended in an aqueous media. Isobutane is utilized herein merely as an illustrative liquid, with the understanding that other liquids which undergo liquid/gas transitions at temperatures useful for the synthesis of these vesicles and formation of the very low density vesicles upon heating can be substituted for isobutane. Similarly, monomers other than vinylidene and acrylonitrile may be employed in preparing the vesicles.

In certain preferred embodiments, the vesicles which are formulated from synthetic polymers and which may be employed in the methods of the present invention are commercially available from Expancel, Nobel Industries (Sundsvall, Sweden), including EXPANCEL 551 DE™ microspheres. The EXPANCEL 551 DE™ microspheres are composed of a copolymer of vinylidene and acrylonitrile which have encapsulated therein isobutane liquid. Such microspheres are sold as a dry composition and are approximately 50 microns in size. The EXPANCEL 551 DE™ microspheres have a specific gravity of only 0.02 to 0.05, which is between one-fiftieth and one-twentieth the density of water.

In any of the techniques described above for the preparation of polymer-based vesicles, the targeting ligands may be incorporated with the polymers before, during or after formation of the vesicles, as would be apparent to one of ordinary skill in the art, once armed with the present disclosure.

As with the preparation of lipid and/or vesicle compositions, a wide variety of techniques are available for the preparation of lipid formulations. For example, the lipid and/or vesicle formulations may be prepared from a mixture of lipid compounds, bioactive agent and gas or gaseous precursor. In this case, lipid compositions are prepared as described above in which the compositions also comprise bioactive agent. Thus, for example, micelles can be prepared in the presence of a bioactive agent. In connection with lipid compositions which comprise a gas, the preparation can involve, for example, bubbling a gas directly into a mixture of the lipid compounds and one or more additional materials. Alternatively, the lipid compositions may be preformed from lipid compounds and gas or gaseous precursor. In the latter case, the bioactive agent is then added to the lipid composition prior to use. For example, an aqueous mixture of liposomes and gas may be prepared to which the bioactive agent is added and which is agitated to provide the liposome formulation. The liposome formulation can be readily isolated since the gas and/or bioactive agent filled liposome vesicles generally float to the top of the aqueous solution. Excess bioactive agent can be recovered from the remaining aqueous solution.

As those skilled in the art will recognize, any of the lipid and/or vesicle compositions and/or lipid and/or vesicle formulations may be lyophilized for storage, and reconstituted, for example, with an aqueous medium (such as sterile water, phosphate buffered solution, or aqueous saline solution), with the aid of vigorous agitation. To prevent agglutination or fusion of the lipids and/or vesicles as a result of lyophilization, it may be useful to include additives which prevent such fusion or agglutination from occurring. Additives which may be useful include sorbitol, mannitol, sodium chloride, glucose, trehalose, polyvinylpyrrolidone and poly(ethylene glycol) (PEG), for example, PEG 400. These and other additives are described in the literature, such as in the U.S. Pharmacopeia, USP XXII, NF XVII, The United States Pharmacopeia, The National Formulary, United States Phannacopeial Convention Inc., 12601 Twinbrook Parkway, Rockville, Md. 20852, the disclosures of which are hereby incorporated herein by reference in their entirety. Lyophilized preparations generally have the advantage of greater shelf life.

As discussed above, the compositions of the present invention, including gas and/or gaseous precursor filled vesicles, are useful as contrast agents for diagnostic imaging, including, for example, ultrasound imaging (US), computed tomography (CT) imaging, including CT angiography (CTA) imaging, magnetic resonance (MR) imaging, magnetic resonance angiography (MRA), nuclear medicine, optical imaging and elastography.

In accordance with the present invention, there are provided methods of imaging one or more regions of a patient. The present invention also provides methods for diagnosing the presence or absence of diseased tissue in a patient. The methods of the present invention involve the administration of a contrast medium, in the form of a lipid and/or vesicle composition, to a patient. The patient is scanned using diagnostic imaging including, for example ultrasound imaging, to obtain visible images of an internal region of a patient. The methods are especially useful in providing images of the heart region, the gastrointestinal region or the lymphatic system, but can also be employed more broadly to image other internal regions of the patient including, for example, the vasculature. The phrase "gastrointestinal region" or "gastrointestinal tract," as used herein, includes the region of a patient defined by the esophagus, stomach, small and large intestines and rectum. The methods are also especially useful in providing images of regions of a patient, for example, to detect the presence or absence of coagula, including emboli or thrombi. The present methods can also be used in connection with the delivery of a bioactive agent to an internal region of a patient including, for example, regions characterized by the presence of one or more coagula.

As one skilled in the art would recognize, administration of the lipid and/or vesicle compositions of the present invention can be carried out in various fashions, namely, parenterally, orally, or intraperitoneally. Parenteral administration, which is preferred, includes administration by the following routes: intravenous; intramuscular; interstitially; intra-arterially; subcutaneous; intraocular; intrasynovial; transepithelial, including transdermal; pulmonary via inhalation; ophthalmic; sublingual and buccal; topically, including ophthalmic; dermal; ocular; rectal; and nasal inhalation via insufflation. Intravenous administration is preferred among the routes of parenteral administration. The useful dosage to be administered and the particular mode of administration will vary depending upon the age, weight and the particular mammal and region thereof to be scanned, and the particular contrast agent employed. Typically, dosage may be initiated at lower levels and increased until the desired contrast enhancement is achieved. Similarly, in connection with therapeutic applications, dosage may be initiated at lower levels and increased until the desired therapeutic effect is achieved. Various combinations of the lipid compositions may be used to alter properties as desired, including viscosity, osmolarity or palatability. In carrying out the imaging methods of the present invention, the contrast medium can be used alone, or in combination with diagnostic, therapeutic or other agents. Such other agents include excipients such as flavoring or coloring materials. CT imaging techniques which are employed are conventional and are described, for example, in *Computed Body Tomography*, Lee, J. K. T., Sagel, S. S., and Stanley, R. J., eds., 1983, Ravens Press, New York, N.Y., especially the first two chapters thereof entitled "*Physical Principles and Instrumentation*", Ter-Pogossian, M. M., and "*Techniques*", Aronberg, D. J., the disclosures of which are incorporated by reference herein in their entirety.

In the case of diagnostic applications, such as ultrasound and CT, energy, such as ultrasonic energy, is applied to at least a portion of the patient to image the target tissue. A visible image of an internal region of the patient is then obtained, such that the presence or absence of diseased tissue can be ascertained. With respect to ultrasound, ultrasonic imaging techniques, including second harmonic imaging, and gated imaging, are well known in the art, and are described, for example, in Uhlendorf, "Physics of Ultrasound Contrast Imaging: Scattering in the Linear Range", *IEEE Transactions on Ultrasonics, Ferroelectrics, and Frequency Control*, Vol. 14(1), pp. 70–79 (1994) and Sutherland, et al., "Color Doppler Myocardial Imaging: A New Technique for the Assessment of Myocardial Function", *Journal of the American Society of Echocardiography*, Vol. 7(5), pp. 441–458 (1994), the disclosures of which are hereby incorporated herein by reference in their entirety.

Ultrasound can be used for both diagnostic and therapeutic purposes. In diagnostic ultrasound, ultrasound waves or a train of pulses of ultrasound may be applied with a transducer. The ultrasound is generally pulsed rather than continuous, although it may be continuous, if desired. Thus, diagnostic ultrasound generally involves the application of a pulse of echoes, after which, during a listening period, the ultrasound transducer receives reflected signals. Harmonics, ultraharmonics or subharmonics may be used. The second harmonic mode may be beneficially employed, in which the 2x frequency is received, where x is the incidental frequency. This may serve to decrease the signal from the background material and enhance the signal from the transducer using the targeted contrast media of the present invention which may be targeted to the desired site, for example, blood clots. Other harmonics signals, such as odd harmonics signals, for example, 3x or 5x, would be similarly received using this method. Subharmonic signals, for example, x/2 and x/3, may also be received and processed so as to form an image.

In addition to the pulsed method, continuous wave ultrasound, for example, Power Doppler, may be applied. This may be particularly useful where rigid vesicles, for example, vesicles formulated from polymethyl methacrylate, are employed. In this case, the relatively higher energy of the Power Doppler may be made to resonate the vesicles and thereby promote their rupture. This can create acoustic emissions which may be in the subharmonic or ultraharmonic range or, in some cases, in the same frequency as the applied ultrasound. It is contemplated that there will be a spectrum of acoustic signatures released in this process and the transducer so employed may receive the acoustic emissions to detect, for example, the presence of a clot. In addition, the process of vesicle rupture may be employed to transfer kinetic energy to the surface, for example of a clot to promote clot lysis. Thus, therapeutic thrombolysis may be achieved during a combination of diagnostic and therapeutic ultrasound. Spectral Doppler may also be employed. In general, the levels of energy from diagnostic ultrasound are insufficient to promote the rupture of vesicles and to facilitate release and cellular uptake of the bioactive agents. As noted above, diagnostic ultrasound may involve the application of one or more pulses of sound. Pauses between pulses permits the reflected sonic signals to be received and analyzed. The limited number of pulses used in diagnostic ultrasound limits the effective energy which is delivered to the tissue that is being studied.

Higher energy ultrasound, for example, ultrasound which is generated by therapeutic ultrasound equipment, is generally capable of causing rupture of the vesicle species. In general, devices for therapeutic ultrasound employ from about 10 to about 100% duty cycles, depending on the area of tissue to be treated with the ultrasound. Areas of the body which are generally characterized by larger amounts of muscle mass, for example, backs and thighs, as well as highly vascularized tissues, such as heart tissue, may require a larger duty cycle, for example, up to about 100%.

In therapeutic ultrasound, continuous wave ultrasound is used to deliver higher energy levels. For the rupture of vesicles, continuous wave ultrasound is preferred, although the sound energy may be pulsed also. If pulsed sound energy is used, the sound will generally be pulsed in echo train lengths of from about 8 to about 20 or more pulses at a time. Preferably, the echo train lengths are about 20 pulses at a time. In addition, the frequency of the sound used may vary from about 0.025 to about 100 megahertz (MHz). In general, frequency for therapeutic ultrasound preferably ranges between about 0.75 and about 3 MHz, with from about 1 and about 2 MHz being more preferred. In addition, energy levels may vary from about 0.5 Watt (W) per square centimeter ($cm^2$) to about 5.0 $W/cm^2$, with energy levels of from about 0.5 to about 2.5 $W/cm^2$ being preferred. Energy levels for therapeutic ultrasound involving hyperthermia are generally from about 5 $W/cm^2$ to about 50 $W/cm^2$. For very small vesicles, for example, vesicles having a diameter of less than about 0.5 $\mu$m, higher frequencies of sound are generally preferred. This is because smaller vesicles are capable of absorbing sonic energy more effectively at higher frequencies of sound. When very high frequencies are used, for example, greater than about 10 MHz, the sonic energy will generally penetrate fluids and tissues to a limited depth only. Thus, external application of the sonic energy may be suitable for skin and other superficial tissues. However, it is generally necessary for deep structures to focus the ultrasonic energy so that it is preferentially directed within a focal zone. Alternatively, the ultrasonic energy may be applied via interstitial probes, intravascular ultrasound catheters or endoluminal catheters. Such probes or catheters may be used, for example, in the esophagus for the diagnosis and/or treatment of esophageal carcinoma. In addition to the therapeutic uses discussed above, the present compositions can be employed in connection with esophageal carcinoma or in the coronary arteries for the treatment of atherosclerosis, as well as the therapeutic uses described, for example, in U.S. Pat. No. 5,149,319, the disclosures of which are hereby incorporated herein by reference, in their entirety.

A therapeutic ultrasound device may be used which employs two frequencies of ultrasound. The first frequency may be x, and the second frequency may be 2x. In preferred form, the device would be designed such that the focal zones of the first and second frequencies converge to a single focal zone. The focal zone of the device may then be directed to the targeted compositions, for example, targeted vesicle compositions, within the targeted tissue. This ultrasound device may provide second harmonic therapy with simultaneous application of the x and 2x frequencies of ultrasound energy. It is contemplated that, in the case of ultrasound involving vesicles, this second harmonic therapy may provide improved rupturing of vesicles as compared to ultrasound energy involving a single frequency. Also, it is contemplated that the preferred frequency range may reside within the fundamental harmonic frequencies of the vesicles. Lower energy may also be used with this device. An ultrasound device which may be employed in connection with the aforementioned second harmonic therapy is described, for example, in Kawabata, K. et al., *Ultrasonics Sonochemistry*, Vol. 3, pp. 1–5 (1996), the disclosures of which are hereby incorporated herein by reference, in their entirety.

In connection with methods involving ultrasonic imaging, particularly in embodiments involving vesicles, diagnostic ultrasound imaging may be carried out simultaneously with the application of therapeutic ultrasonic waves so as to rupture the vesicles for purposes, such as, for example, enhanced cavitation or the targeted release of a bioactive agent combined with the vesicles. The method comprises the steps of (i) administering to the patient a quantity of vesicles; (ii) insonating the vesicles in a region of the patient with therapeutic ultrasonic waves at a frequency and energy to cause the vesicles to rupture; and (iii) simultaneously receiving ultrasonic emissions from the insonated vesicles at a harmonic of the frequency of the therapeutic ultrasonic waves and generating an image of said region from the received ultrasonic emissions. Simultaneous imaging allows an operator to monitor the rupture of the vesicles in real time.

In accordance with a preferred embodiment of the present invention, there are provided methods for providing an image of an internal region of a patient which may comprise (a) administering to the patient a contrast agent comprising, in an aqueous carrier, a lipid, protein or polymer, and a gas, and (b) scanning the patient using ultrasound imaging to obtain a visible image of the region. In preferred form, the scanning step (b) may comprise (i) applying a first quantity of ultrasound energy to the patient to provide a first image, and (ii) substantially immediately thereafter applying a second quantity of ultrasound energy to the patient to provide a second image. In preferred form, the first and second quantities of ultrasound energy may comprise pulses of ultrasound energy. It is also preferred that the first and second applications of ultrasound energy occur, and that the first and second images be obtained, during the same cardiac cycle. In certain particularly preferred embodiments, the first quantity of ultrasound energy may be applied at end systole, i.e., at about the end of the T-wave in the patient's ECG. In certain alternate particularly preferred embodiments, the first quantity of ultrasound energy may be applied at end diastole, i.e., at about the end of the R-wave in the patient's ECG. As noted above, the first and second images may then be processed. Generally speaking, this involves subtracting the second image from the first image.

As would be apparent to one skilled in the art, once armed with the teachings of the present disclosure, the methods described herein may be used to obtain images of myocardial perfusion at different points in the cardiac cycle. For example, the images may be obtained during ancillary. Alternatively, by changing the position of acquisition of the imaging pulses relative to the ECG (QRST-complex), images can be produced at different points in the cardiac cycle. For example, to obtain an image during late diastole, a first quantity of ultrasound energy may be applied at the end of the P-wave antecedent to the QRS-complex. A second quantity of ultrasound energy may then be applied substantially immediately thereafter, for example, within about 100 milliseconds of application of the first quantity of ultrasound energy. In doing so, excellent registration may be realized between the first and second images.

While the inventors do not wish to be bound by any theory or theories of operation, it is believed that the improved ultrasound images which may be obtained with the methods of the present invention involving vesicles, particularly lipid vesicles, may be due, at least in part, to the following phenomenon. Vesicles which have been administered to the patient and which are located in a region of interest, for example, myocardial tissue, may be ruptured by application of the first quantity of ultrasound energy. Accordingly, contrast is not observed upon application of the second quantity of ultrasound energy. Subtraction of the two images reveals a highly enhanced image of the region of interest, for example, myocardial perfusion in a single frame of a single cardiac cycle. Accordingly, excellent images, particularly myocardial perfusion images, may be produced on-line by subtracting the two data sets which already have perfect or nearly perfect registration. If desired, multiple averages can be obtained from different cardiac cycles to increase the signal-to-noise ratio.

The images produced according to the methods of the present invention may be viewed as gray scale or as colorized images. As would be apparent to one of ordinary skill in the art, once armed with the teachings of the present disclosure, various different colorization schemes may be employed, such as, for example, heated object or hot/cold displays. In addition, video densitometry or backscatter measurements, spectral analysis or speckle analysis may also be employed on the resulting ultrasound image, including the enhanced perfusion images, to obtain quantitative images.

Highly advantageous and superior ultrasound images may be obtained by employing imaging methods according to the present invention. This is depicted dramatically in FIGS. 1 and 2. With particular reference to the figures, FIG. 1 includes photographs which may be typical of ultrasound images of the cardiovascular region which may be obtained according to aspects of the present invention. In particular, photograph A in FIG. 1 is a photograph of a generally standard ultrasound image of the cardiovascular region, including the left ventricular area and the myocardium, which may be obtained after administration to a patient of a contrast agent comprising gas filled vesicles and at a time corresponding to about end systole on an ECG waveform. The image in photograph A shows contrast in the left ventricular cavity and the myocardium. Photograph B is a photograph of an ultrasound image which may be obtained about 40 milliseconds after application of ultrasound energy which resulted in the image in photograph A. The image in photograph B shows markedly decreased contrast in the left ventricular area and the myocardium. As discussed above, this reduction in contrast is believed to be due, at least in part, to the rupturing of the gas filled vesicles caused by the application of ultrasound energy in photograph A. Representative locations in an ECG waveform at which ultrasound images exemplified in photographs A and B may be obtained, according to an embodiment of the present invention, are also included in FIG. 1.

Figure 2:
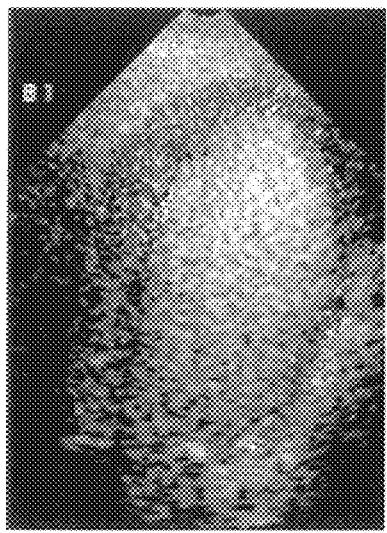
FIG. 2 includes photographs (photographs C and D) which are typical of ultrasound images of the cardiovascular region that may be obtained employing methods according to the present invention (see photograph C) and images that may be obtained employing methods according to the prior art (see photograph D). Specifically, photograph C corresponds to an image obtained after subtracting the image in photograph B from the image in photograph A in FIG. 1. Photograph D is a comparative view of the cardiovascular region employing the prior art myocardial perfusion imaging agent Cardiolite™ ($^{99m}$Tc Sestamibi).
Figure 2:
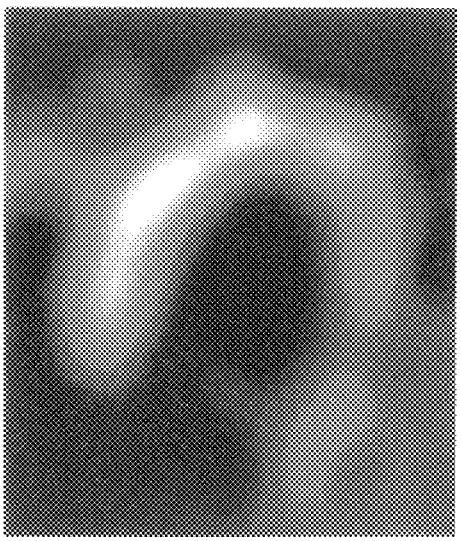

The images depicted in FIG. 1 may then be processed according to methods of the present invention. The resulting processed image, which shows dramatically improved contrast, is depicted in photograph C in FIG. 2. Specifically, photograph C corresponds to a computer generated, color enhanced image of myocardial contrast echography (MCE), obtained after subtracting the image in photograph B from the image in photograph A in FIG. 1. This subtraction of images may involve, for example, a computer analysis in which the differences between the images are determined, pixel by pixel, and designating a color intensity proportional to these differences. The differences between the two ultrasound images is exemplified in color in photograph C. Photograph D in FIG. 2 is a comparative view of the cardiovascular region employing Cardiolite™ ($^{99m}$Tc Sestamibi), which is a myocardial perfusion imaging agent of the prior art. A comparison of the photographs, especially photographs C and D and C and A reveals that significantly improved contrast may be observed by employing methods of the present invention as compared to methods of the prior art.

As one skilled in the art would recognize, once armed with the teachings in the present disclosure, widely varying amounts of vesicles may be employed in the practice of the methods described herein. As used herein, the term "quantity of vesicles" is intended to encompass all such amounts.

It is known that bubbles suspended in a liquid, such as the administered vesicles described herein, can be made to emit ultrasonic energy when exposed to ultrasonic waves. See, e.g., D. L. Miller, "Ultrasonic Detection of Resonant Cavitation Bubbles in a Flow Tube by their Second Harmonic Emissions," *Ultrasonics*, pp. 217–224 (September 1981), the disclosure of which is hereby incorporated by reference. Emission of ultrasonic energy occurs at harmonics of the incident frequency. Methods provided herein take advantage of this known property to allow an operator to image the vesicles of a vesicle formulation simultaneously with the application of therapeutic ultrasonic waves for the purpose of rupturing the vesicles. The therapeutic ultrasonic waves serve to produce the harmonic emissions in the vesicles prior to their rupture.

Emission at twice the frequency of the incident ultrasonic waves, called second harmonic emissions, are the strongest harmonic emissions at low amplitudes. Preferably, it is these so-called second harmonic emissions that are received in the aforementioned receiving step. It is desirable, where possible, to insonate the vesicles at a frequency which is close to optimal for eliciting maximal second harmonic signals, and this will vary depending upon the diameter, elasticity, and density of the vesicles. Of course, imaging can be performed at other harmonic frequencies, including both even and odd harmonic frequencies, if desired. Imaging at harmonics and sub-harmonics of an excitation frequency is described in U.S. Pat. No. 5,410,516, the disclosure of which is hereby incorporated by reference in its entirety.

In order to achieve desirable rupture of the vesicles, continuous wave therapeutic ultrasound is preferred, although the sound energy may be pulsed also. If pulsed sound energy is used, the sound will generally be pulsed in echo train lengths of about 8 to about 20 or more pulses at a time. Preferably, the echo train lengths are about 20 pulses at a time.

Energy levels of the therapeutic ultrasonic waves used to insonate the vesicles are preferably in the range of about 0.05 Watt (W) per square centimeter ($cm^2$) to about 5.0 W/$cm^2$, with energy levels of about 0.2 to about 2.5 W/$cm^2$ being preferred. For very small vesicles, for example, vesicles having a diameter of less than about 0.5 micron, higher frequency ultrasonic waves are generally preferred. This is because smaller vesicles are capable of absorbing ultrasonic energy more effectively at higher frequencies. External application may be preferred for the skin and other superficial tissues, but for deep structures, the application of sonic energy via interstitial probes or intracavitary probes of the type described above may be preferred.

Experiments have shown that the onset of vesicle rupture occurs at the following spatial peak temporal average intensities ($I_{SPTA}$), in milli-Watts (mW) per centimeter squared ($cm^2$), for continuous-wave and selected duty cycles of ultrasonic waves. All values were obtained using a ultrasonic waves having a frequency of 1.0 MHZ.

| Duty Cycles | $I_{SPTA}$(mW/$cm^2$) |
|---|---|
| 5.3% | 290 |
| 10.4% | 100 |
| 21.9% | 70 |
| Continuous Wave | 35 |

As these data reveal, rupture occurs most easily with continuous wave ultrasound.

The methods of the present invention can also be carried out in vitro. For example, in cell culture applications, the vesicles may be added to the cells in cultures and then incubated. Therapeutic ultrasonic waves can then be applied to the culture media containing the cells and vesicles.

Further discussion regarding methods and apparatus for performing simultaneous diagnostic and therapeutic ultrasound, which may be adapted for use with the methods and compositions of the present invention, in addition to those exemplified above, are disclosed in U.S. Pat. No. 5,558,092, the disclosures of which are incorporated herein by reference, in their entireties.

The concentration of lipid required to form a desired stabilized vesicle level will vary depending upon the type of lipid used, and may be readily determined by routine experimentation. For example, in preferred embodiments, the concentration of 1,2-dipalmitoylphosphatidylcholine (DPPC) used to form stabilized vesicles according to the methods of the present invention is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution. The concentration of distearoylphosphatidylcholine (DSPC) used in preferred embodiments is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution. The amount of composition which is administered to a patient can vary. Generally speaking, lower doses may be used initially and increased until the desired therapeutic and/or diagnostic effect is achieved. Typically, the IV dose may be less than about 10 mL for a 70 Kg patient, with lower doses being preferred.

In addition to the methods disclosed above, another embodiment of preparing a targeted contrast medium comprises combining at least one biocompatible lipid and a gaseous precursor; agitating until gas filled vesicles are formed; adding a targeting ligand to said gas filled vesicles such that the targeting ligand binds to said gas filled vesicle by a covalent bond or non-covalent bond; and agitating until a contrast agent comprising gas filled vesicles and a targeting ligand result Rather than agitating until gas filled vesicles are formed before adding the targeting ligand, the gaseous precursor may remain a gaseous precursor until the time of use. That is, the gaseous precursor is used to prepare the contrast medium and the precursor is activated in vivo, by temperature for example.

Alternatively, a method of preparing a contrast medium targeted to endothelial cells may comprise combining at least one biocompatible lipid and a targeting ligand such that the targeting ligand binds to said lipid by a covalent bond or non-covalent bond, adding a gaseous precursor and agitating until a contrast medium comprising gas filled vesicles and a targeting ligand result. In addition, the gaseous precursor may be added and remain a gaseous precursor until the time of use. That is, the gaseous precursor is used to prepare the contrast medium having gaseous precursor filled vesicles and a targeting ligand which result for use in vivo.

Alternatively, the gaseous precursors may be utilized to create stable gas filled vesicles with targeting ligands which are pre-formed prior to use. In this embodiment, the gaseous precursor and targeting ligand are added to a container housing a suspending and/or stabilizing medium at a temperature below the liquid-gaseous phase transition temperature of the respective gaseous precursor. As the temperature is then exceeded, and an emulsion is formed between the gaseous precursor and liquid solution, the gaseous precursor undergoes transition from the liquid to the gaseous state. As a result of this heating and gas formation, the gas displaces the air in the head space above the liquid suspension so as to form gas filled lipid spheres which entrap the gas of the gaseous precursor, ambient gas for example, air, or coentrap gas state gaseous precursor and ambient air. This phase transition can be used for optimal mixing and stabilization of the contrast medium. For example, the gaseous precursor, perfluorobutane, can be entrapped in the biocompatible lipid or other stabilizing compound, and as the temperature is raised, beyond 4° C. (boiling point of perfluorobutane) stabilizing compound entrapped fluorobutane gas results. As an additional example, the gaseous precursor fluorobutane, can be suspended in an aqueous suspension containing emulsifying and stabilizing agents such as glycerol or propylene glycol and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents, surprisingly stable gas filled vesicles and targeting ligand result.

Accordingly, the gaseous precursors may be selected to form a gas filled vesicle in vivo or may be designed to produce the gas filled vesicle in situ, during the manufacturing process, on storage, or at some time prior to use.

It will be understood by one skilled in the art, once armed with the present disclosure, that the lipids, proteins, polymers, surfactants and other stabilizing compounds used as starting materials, or the vesicle final products, may be manipulated prior and subsequent to being subjected to the methods contemplated by the present invention. For example, the stabilizing compound such as a biocompatible lipid may be hydrated and then lyophilized, processed through freeze and thaw cycles, or simply hydrated. In preferred embodiments, the lipid is hydrated and then lyophilized, or hydrated, then processed through freeze and thaw cycles and then lyophilized, prior to the formation of gaseous precursor filled vesicles.

According to the methods contemplated by the present invention, the presence of gas, such as and not limited to air, may also be provided by the local ambient atmosphere. The local ambient atmosphere may be the atmosphere within a sealed container, or in an unsealed container, may be the external environment. Alternatively, for example, a gas may be injected into or otherwise added to the container having the aqueous lipid solution or into the aqueous lipid solution itself in order to provide a gas other than air. Gases that are not heavier than air may be added to a sealed container while gases heavier than air may be added to a sealed or an unsealed container. Accordingly, the present invention includes co-entrapment of air and/or other gases along with gaseous precursors.

As already described above in the section dealing with the stabilizing compound, the preferred methods contemplated by the present invention are carried out at a temperature below the gel state to liquid crystalline state phase transition temperature of the lipid employed. By "gel state to liquid crystalline state phase transition temperature", it is meant the temperature at which a lipid bilayer will convert from a gel state to a liquid crystalline state. See, for example, Chapman et al., *J. Biol. Chem.* 1974, 249, 2512–2521.

Hence, the stabilized vesicle precursors described above, can be used in the same manner as the other stabilized vesicles used in the present invention, once activated by application to the tissues of a host, where such factors as temperature or pH may be used to cause generation of the gas. It is preferred that this embodiment is one wherein the gaseous precursors undergo phase transitions from liquid to gaseous states at near the normal body temperature of said host, and are thereby activated by the temperature of said host tissues so as to undergo transition to the gaseous phase therein. More preferably still, this method is one wherein the host tissue is human tissue having a normal temperature of about 37° C., and wherein the gaseous precursors undergo phase transitions from liquid to gaseous states near 37° C.

All of the above embodiments involving preparations of the stabilized gas filled vesicles used in the present invention, may be sterilized by autoclave or sterile filtration if these processes are performed before either the gas instillation step or prior to temperature mediated gas conversion of the temperature sensitive gaseous precursors within the suspension. Alternatively, one or more antibactericidal agents and/or preservatives may be included in the formulation of the contrast medium, such as sodium benzoate, all quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized microspheres are used for imaging under invasive circumstances, for example, intravascularly or intraperitoneally. The appropriate means of sterilization will be apparent to the artisan instructed by the present description of the stabilized gas filled vesicles and their use. The contrast medium is generally stored as an aqueous suspension but in the case of dried vesicles or dried lipidic spheres the contrast medium may be stored as a dried powder ready to be reconstituted prior to use.

The novel compositions of the present invention, and especially the vesicle compositions, are useful as contrast media in diagnostic imaging, and are also suitable for use in all areas where diagnostic imaging is employed. However, the stabilized vesicles are particularly useful for perfusion imaging.

Diagnostic imaging is a means to visualize internal body regions of a patient. Diagnostic imaging includes, for example, ultrasound (US), magnetic resonance imaging (MRI), nuclear magnetic resonance (NMR), computed tomography (CT), electron spin resonance (ESR); nuclear medicine when the contrast medium includes radioactive material; and optical imaging, particularly with a fluorescent contrast medium. Diagnostic imaging also includes promoting the rupture of the vesicles via the methods of the present invention. For example, ultrasound may be used to visualize the vesicles and verify the localization of the vesicles in certain tissue. In addition, ultrasound may be used to promote rupture of the vesicles once the vesicles reach the intended target, including tissue and/or receptor destination, thus releasing a bioactive agent and/or diagnostic agent.

In accordance with the present invention, there are provided methods of imaging a patient generally, and/or in specifically diagnosing the presence of diseased tissue in a patient. The imaging process of the present invention may be carried out by administering a contrast medium of the invention to a patient, and then scanning the patient using, for example, ultrasound, computed tomography, and/or magnetic resonance imaging, to obtain visible images of an internal region of a patient and/or of any diseased tissue in that region. By region of a patient, it is meant the whole patient or a particular area or portion of the patient. The contrast medium may be particularly useful in providing images of tissue, such as myocardial, endothelial, and/or epithelial tissue, as well as the gastrointestinal and cardiovascular regions, but can also be employed more broadly, such as in imaging the vasculature or in other ways as will be readily apparent to those skilled in the art. Cardiovascular region, as that phrase is used herein, denotes the region of the patient defined by the heart and the vasculature leading directly to and from the heart. The phrase vasculature, as used herein, denotes the blood vessels (arteries, veins, etc.) in the body or in an organ or part of the body. The patient can be any type of mammal, but most preferably is a human.

The present invention also provides a method of diagnosing the presence of diseased tissue. Diseased tissue includes, for example, endothelial tissue which results from vasculature that supports diseased tissue. As a result, the localization and visualization of endothelial tissue to a region of a patient which under normal circumstances is not associated with endothelial tissue provides an indication of diseased tissue in the region.

In carrying out the magnetic resonance imaging method of the present invention, the contrast medium can be used alone, or in combination with other diagnostic, therapeutic or other agents. Such other agents include excipients such as flavoring or coloring materials. The magnetic resonance imaging techniques which are employed are conventional and are described, for example, in D. M. Kean and M. A. Smith, *Magnetic Resonance Imaging: Principles and Applications,* (William and Wilkins, Baltimore 1986). Contemplated MRI techniques include, but are not limited to, nuclear magnetic resonance (NMR) and electronic spin resonance (ESR). The preferred imaging modality is NMR.

The concentration of vesicles, especially the concentration of echogenic vesicles, referred to herein as "vesicle concentration," may be important with respect to the effectiveness of contrast agents based on vesicles. It is preferred that the vesicle compositions described herein have a vesicle concentration of at least about $1\times10^8$ vesicles/mL, as measured with a Model 770 AccuSizer (Particle Sizing Systems, Santa Barbara, Calif.). More preferably, the vesicle compositions have vesicle concentrations of at least about $1\times10^9$ vesicles/mL, with concentrations of about $1.5\times10^9$ vesicles/mL being even more preferred. In certain circumstances, compositions comprising vesicle concentrations of even more than $1.5\times10^9$ vesicles/mL may be desirable. However, these highly concentrated vesicle compositions may be difficult to administer, for example, in the case of administration by injection.

In connection with the diagnostic method aspects of the present invention, it has been surprisingly and unexpectedly found that the rate at which the lipid and/or vesicle compositions are administered to a patient may have a profound effect on the quality of the resulting diagnostic image. Specifically, it has been found that the occurrence of diagnostic artifacts in diagnostic images may be directly related to the rate at which the lipid and/or vesicle compositions are administered. Thus, the administration of a lipid and/or vesicle composition at too high a rate can result in an excess concentration of lipid and/or vesicle composition at the region of interest. In the case of ultrasound imaging, the application of energy (sound waves) can result in the reflection of an excess amount of sound energy, thereby resulting, for example, in shadowing in the resulting ultrasound image. Conversely, the administration of a lipid and/or vesicle composition at too low a rate can result in an insufficient concentration of lipid and/or vesicle composition at the region of interest. In the case of ultrasound imaging involving, for example, gas filled vesicles, the application of energy (sound waves) can result in too little sound energy being reflected, thereby resulting, for example, in inadequate contrast in the resulting ultrasound image.

In accordance with certain preferred embodiments of the present invention, the rate at which lipid and/or vesicle compositions which comprise a gas or gaseous precursor are administered may be determined and regulated as follows. The compositions may be administered to a patient at a dose of, for example, about 10 microliters ($\mu$L) of composition per kilogram (Kg) of patient body weight (10 $\mu$L/Kg). In certain preferred embodiments, the compositions may contain gas in a concentration which provides a dose of gas ranging from about $1\times10^{-4}$ to about $5\times10^{-3}$ cubic centimeters (cc) of gas per kilogram (Kg) of patient body weight, and all combinations and subcombinations of ranges therein. This gas dose may be employed to provide an administration rate of gas to a patient, referred to herein as the "gas administration rate."

The compositions may be administered over a period of time which can vary and depends upon a variety of factors including, for example, the volume of the composition being administered, the age and weight of the patient, the particular materials employed in the compositions, including, for example, lipids, polymers, proteins, surfactants, vesicles, gases and/or gaseous precursors, the purpose for the administration (for example, diagnostic or therapeutic), the region of interest, the mode of administration, the size of the vesicles (in the case of vesicle compositions), and the like. An exemplary administration time for the compositions described above is about 5 seconds. Dividing the gas dose by this time period provides a gas administration rate which can be expressed as cc gas/Kg-sec. Thus, a gas dose of, for example, about $1\times10^{-4}$ cc gas/Kg and an administration time of 5 sec provides a gas administration rate of about $2\times10^{-5}$ cc gas/Kg-sec.

It is to be understood that the foregoing specific gas concentrations, composition doses, administration times and administration rates are for purposes of illustration only, and not for purposes of limitation.

In connection with preferred embodiments of the invention, the lipid and/or vesicle compositions may be administered to a patient, preferably as a constant infusion, to provide a gas administration rate which ranges from about $1\times10^{-7}$ to about $3\times10^{-3}$ cc gas/Kg-sec, and all combinations and subcombinations of ranges therein including, for example, from about $4\times10^{-7}$, $8\times10^{-7}$, $1\times10^{-6}$, $2\times10^{-6}$ or about $3\times10^{-6}$ to about $3\times10^{-3}$ cc gas/Kg-sec. More preferably, the lipid and/or vesicle compositions may be administered to provide a gas administration rate of from about $4\times10^{-6}$ to about $2\times10^{-3}$ cc gas/Kg-sec, with gas administration rates of from about $5\times10^{-6}$, $6\times10^{-6}$, $7\times10^{-6}$ or $8\times10^{-6}$ to about $2\times10^{-3}$ cc gas/Kg-sec being even more preferred. Still more preferably, the lipid and/or vesicle compositions may be administered to provide a gas administration rate of from about $9\times10^{-6}$ or $1\times10^{-5}$ to about $1\times10^{-3}$ cc gas/Kg-sec, with gas administration rates of from about $2\times10^{-5}$, $3\times10^{-5}$, $4\times10^{-5}$ or $5\times10^{-5}$ to about $1\times10^{-3}$ cc gas/Kg-sec being still more preferred. Yet more preferably, the lipid and/or vesicle compositions may be administered to a patient at a gas administration rate of from about $6\times10^{-5}$, $7\times10^{-5}$, $8\times10^{-5}$ or $9\times10^{-5}$ to less than about $1\times10^{-3}$ cc gas/Kg-sec, with gas administration rates of from about $1\times10^{-4}$ to about $9\times10^{-4}$ cc gas/Kg-sec being even still more preferred.

In connection with an alternate preferred embodiment of the invention, the lipid and/or vesicle compositions may be administered to a patient, preferably as a constant infusion, to provide a gas administration rate which ranges from about $5\times10^{-6}$ to about $9\times10^{-4}$ cc gas/Kg-sec, and all combinations and subcombinations of ranges therein.

Gaseous precursors may be incorporated in the compositions described herein and may be, for example, liquids or solids, which are converted to a gas after administration (that is, in vivo), or prior to administration. As would be apparent to one of ordinary skill in the art, once armed with the present disclosure, concentrations of gaseous precursors may be employed in the compositions, and administration rates of compositions which contain gaseous precursors may be employed, preferably as a constant infusion, to provide the foregoing gas administration rates upon conversion of the gaseous precursor into a gas.

As noted above, vesicle compositions represent a preferred form of the compositions employed in the methods of the present invention. Also as noted above, the concentration of vesicles in the vesicle compositions is preferably at least about $1.5\times10^8$ vesicles per mL of vesicle composition (vesicles/mL), more preferably at least about $1\times10^9$ vesicles/mL, and even more preferably at least about $1.5\times10^9$ vesicles/mL. This vesicle concentration may be employed to provide an administration rate of vesicles to a patient, referred to herein as the "vesicle administration rate." In this connection, the vesicle compositions may be administered to a patient at a dose of, for example, about 10 microliters ($\mu$L) of vesicle composition per kilogram (Kg) of patient body weight (10 $\mu$L/Kg). The product of the vesicle concentration (vesicles/mL) and the dose of the vesicle composition ($\mu$L/Kg) provides a vesicle dose which can be expressed as vesicles/Kg. Thus, the highly preferred vesicle concentration ($1.5\times10^9$ vesicles/mL) and the vesicle composition dose (10 $\mu$L/Kg) described above provides a vesicle dose of about $1.5\times10^7$ vesicles/Kg.

The vesicle compositions are generally administered over a period of time which may vary and depends upon a variety of factors including, for example, the volume of the vesicle composition being administered, the weight of the patient, the particular lipids, polymers, proteins, surfactants, vesicles, gases or gaseous precursors employed in the composition, the purpose for the administration (for example, diagnostic or therapeutic), the region of interest, the mode of administration, the size of the vesicles, and the like. An exemplary administration time for the vesicle compositions is about 5 seconds. Dividing the vesicle dose by this time period provides an administration rate which may be expressed as vesicles/Kg-sec. Thus, the vesicle dose ($1.5\times10^7$ vesicles/Kg) and administration time (5 sec) described above provides a vesicle administration rate of about $3\times10^6$ vesicles/Kg-sec.

It is to be understood that the foregoing specific vesicle concentrations, composition doses, administration times and administration rates are for purposes of illustration only, and not for purposes of limitation.

It has been observed that diagnostic images obtained using methods which involve the administration of vesicle compositions at a rate of about $8\times10^6$ vesicles/Kg-sec or greater generally may contain substantial diagnostic artifacts. For example, in connection with ultrasound imaging, the administration of a vesicle composition at an administration rate of about $8\times10^6$ vesicles/Kg-sec or greater may result in significant shadowing in the resulting ultrasound image. In certain circumstances, the shadowing may be so severe as to prohibit visualization of the region of interest, thereby rendering the ultrasound image substantially unusable as a diagnostic tool. Delaying the application of energy or prolonging the period of time that energy is applied to the region of interest, in an effort to permit the concentration of lipid and/or vesicle composition at the region of interest to diminish, for example, by being carried away in the bloodstream, generally does not result in an improvement in the quality of the diagnostic image. Instead, it has been observed that as the diagnostic artifacts diminish, the contrast provided by the lipid and/or vesicle composition may diminish also.

In connection with preferred embodiments of the present invention, the vesicle compositions may be administered to a patient, preferably as a constant infusion, to provide a vesicle administration rate of less than about $8\times10^6$ vesicles/Kg-sec. More preferably, the vesicle compositions may be administered to a patient to provide a vesicle administration rate which ranges from about $1\times10^6$ to less than about $8\times10^6$ vesicles/Kg-sec, and all combinations and subcombinations of ranges therein, for example, from about $1\times10^6$ to about $7.5\times10^6$, about $7\times10^6$ or about $6.5\times10^6$ vesicles/Kg-sec. Even more preferably, the vesicle compositions may be administered to a patient to provide a vesicle administration rate of from about $1.5\times10^6$ to about $6\times10^6$ vesicles/Kg-sec, with vesicle administration rates of from about $2\times10^6$ to about $5.5\times10^6$ vesicles/Kg-sec being still more preferred. Yet more preferably, the vesicle compositions may be administered to provide a vesicle administration rate of from about $2.5\times10^6$ to about $5\times10^6$ vesicles/Kg-sec, with vesicle administration rates of from about $3\times10^6$ to about $4.5\times10^6$ vesicles/Kg-sec being even more preferred.

In connection with an alternate preferred embodiment of the invention, the lipid and/or vesicle compositions may be administered to a patient, preferably as a constant infusion, to provide a gas administration rate of up to about $1\times10^6$ vesicles/Kg-sec. Preferably, the lipid and/or vesicle compositions may be administered to a patient to provide a gas administration rate which ranges from about $6\times10^4$ to about $1\times10^6$ vesicles/Kg-sec, and all combinations and subcombinations of ranges therein.

As would be apparent to one skilled in the art, based on the present disclosure, the rate at which the lipid and/or vesicle compositions are preferably administered can vary, depending, for example, on the lipids, polymers, proteins, vesicles, gases and/or gaseous precursors employed, the age and weight of the patient, the mode of administration, the size of the vesicles (in the case of vesicle compositions), and the like. Typically, administration may be carried out at lower rates and the rate can be increased until a desired effect is achieved.

In preferred embodiments of the present invention, the lipid and/or vesicle compositions may be administered by syringe, that is, by intravenous (IV) injection. Accordingly, the gas and/or vesicle administration rates provided herein generally correspond to injection rates, preferably as constant infusion injection rates. As would be apparent to one of ordinary skill in the art, once armed with the present disclosure, the location on the body of the patient at which the lipid and/or vesicle compositions are injected may vary and depends upon a variety of factors, including, for example, the particular lipid and/or vesicle composition employed, the contemplated application, such as diagnostic or therapeutic application, and the particular region of interest. For example, in the case of diagnostic ultrasound of myocardial tissue, the lipid and/or vesicle compositions may be injected intravenously, for example, in the arm of a patient.

The IV administration of the contrast agents described herein including, for example, the vesicle compositions, may involve administration via syringe. This may be achieved, for example, by an appropriate medical technician who handles the syringe or syringes manually. Alternatively, administration by syringe may be achieved mechanically, for example, via a mechanical injector, such as a mechanical injector which operates using pneumatic or hydraulic pressure. Mechanical administration may be preferred, in certain embodiments, in that it may assist in achieving the desirable and advantageous administration of the lipid and/or vesicle compositions in the form of a constant infusion. Suitable mechanical injectors which may be used in the methods of the present invention include a Syringe Pump Model 351, commercially available from Sage Instruments (a division of Orion Research Inc., Boston, Mass.), a MedRad™ power injector, commercially available from Medrad, Inc. (Pittsburgh, Pa.) or a Liebel Flarsheim, commercially available from Liebel Flarsheim Co. (Cincinnati, Ohio).

In connection with lipid and/or vesicle compositions which are administered via injection, it may be desirable, and sometimes preferable, to facilitate the movement through the circulating bloodstream of the injected composition. As would be apparent to one of ordinary skill in the art, once armed with the present disclosure, administration by injection generally involves injection of the compositions into a blood vessel. Also as known to the skilled artisan, the blood flow in many blood vessels, and especially smaller blood vessels, may be limited. Due to this limited blood flow, the injected lipid and/or vesicle compositions may pool or accumulate at or near the site of injection. To promote the transport of the lipid and/or vesicle composition from the injection site into the bloodstream and, thereafter, to the region of interest, a flush may be administered. The flush may act, generally by mechanical action, to "push" or "wash" the injected compositions into the bloodstream. Thus, in embodiments which may involve, for example, diagnostic ultrasound of myocardial tissue with a contrast agent that comprises a lipid and/or vesicle composition, a flush may be administered after injection of the lipid and/or vesicle composition to facilitate its movement through the circulatory system and delivery to the region of interest, for example, the heart region.

In embodiments which involve the flush of lipid and/or vesicle compositions, it has been surprisingly and unexpectedly found that, as with the administration rates discussed hereinbefore, the rate at which the lipid and/or vesicle compositions are flushed may have a profound effect on the quality of the resulting diagnostic image. For example, flushing at too high a rate may result in an excess concentration of lipid and/or vesicle composition at the region of interest. Thus, in the case of diagnostic imaging, such as ultrasound, involving, for example, gas filled vesicles, the application of energy, for example, sound waves, may result in the reflection of excess energy from the vesicles. As discussed in detail above, this may cause diagnostic artifacts, for example, shadowing, in the resulting image. Conversely, flushing at too low a rate may result in an insufficient concentration of lipid and/or vesicle composition at the region of interest. It is contemplated that in this case, the lipid and/or vesicle compositions may become highly diluted in the bloodstream. In the case of diagnostic imaging, such as ultrasound, involving, for example, gas filled vesicles, the application of energy, for example, sound waves, may result in the reflection of an insufficient quantity of energy from the vesicles. This may cause diagnostic artifacts, for example, lightening and/or brightening, which are associated with insufficient contrast. As would be apparent to one skilled in the art, based on the present disclosure, the rate at which the lipid and/or vesicle compositions are preferably flushed may vary, depending, for example, on the lipids, vesicles, polymers, proteins, gases and/or gaseous precursors employed, the age and weight of the patient, the mode of administration, the size of the vesicles (in the case of vesicle compositions), and the like.

In accordance with the present invention, the rate at which the lipid compositions may be flushed can be determined as follows. After administration of a lipid and/or vesicle composition, a flush may be administered which can be expressed as the volume of flush (mL) that is administered per unit time (sec). An exemplary flush for the dosages described above can involve a volume of about 5 mL which may be administered over a period of about 10 seconds, providing a flush of about 0.5 mL/sec.

It is to be understood that the foregoing specific flush rate is for purposes of illustration only, and not for purposes of limitation.

In embodiments of the present invention which involve flushing, it has been observed that diagnostic images obtained using methods which involve flushing at a rate of about 2.5 mL/sec or greater may contain substantial diagnostic artifacts. In certain circumstances, the shadowing may be so severe as to prohibit visualization of the region of interest, thereby rendering the ultrasound image substantially unusable as a diagnostic tool. Thus, the flush may preferably be administered at rates of less than about 2.5 mL/sec, for example, from about 0.01 to about 2.4 mL/sec, and all combinations and subcombinations of ranges therein. More preferably, the flush may be administered at a rate of from about 0.02 to about 2.3 mL/sec, with flush rates of from about 0.03 to about 2.2 mL/sec, about 0.04 to about 2.1 mL/sec, about 0.05 to about 2 mL/sec, about 0.06 to about 1.9 mL/sec, about 0.07 to about 1.8 mL/sec, about 0.08 to about 1.7 mL/sec, about 0.09 to about 1.6 mL/sec, or about 0.1 to about 1.5 mL/sec being even more preferred. Still more preferably, the flush may be administered at a rate of from about 0.2 to about 1.4 mL/sec, with flush rates of from about 0.3 to about 1.3 mL/sec, about 0.4 to about 1.2 mL/sec or about 0.5 to about 1.1 mL/sec being yet more preferred.

In connection with an alternate preferred embodiment of the invention, the flush may be administered to a patient at a rate of up to about 1 mL/sec. Preferably, the flush may be administered to a patient at a rate which ranges from about 0.05 to about 1 mL/sec, and all combinations and subcombinations of ranges therein.

As would be apparent to one of ordinary skill in the art, once armed with the present disclosure, the gas and/or vesicle administration rates and flush rates described above may be used in connection with the administration to a patient of lipid and/or vesicle formulations. The particular administration and/or flush rates employed with lipid and/or vesicle formulations may vary and depends on a variety of factors, including, for example, the specific bioactive agents and lipids, vesicles, proteins, surfactants and/or polymers involved, the particular disorder being treated, and the like. Typically, a lower flush rate may be employed initially, and then increased until a desired diagnostic effect is achieved.

As with the IV administration of the contrast agents, the administration of the flush may be achieved via syringe. This may involve, for example, manual manipulation of a syringe by an appropriate medical technician. Also, as noted above in connection with the administration of the vesicle compositions, the administration of the flush may be done mechanically, for example, via a mechanical syringe pump, including mechanical pumps which operate using hydraulic and/or pneumatic power, such as, for example, a Syringe Pump Model 351 (Sage Instruments, a division of Orion Research Inc., Boston, Mass.), or a mechanical power injector, such as a MedRad™ Power Injector (Medrad, Inc., Pittsburgh, Pa.) or a Liebel Flarsheim (Liebel Flarsheim Co., Cincinnati, Ohio).

Further discussion regarding methods and apparatus for administering the compositions of the present invention, in addition to those exemplifed above, are disclosed in U.S. application Ser. No. 08/666,129, filed Jun. 19, 1996, the disclosures of which are incorporated herein by reference, in their entireties. The invention is further demonstrated in the following examples. Examples 1 to 8, 13 to 15, 20 to 22, 27, 28, 42, 43 to 45, 47, 48 and 60 are actual examples and Examples 9 to 12, 16 to 19, 23 to 26, 29 to 41, 49 to 59 and 61 are prophetic examples. Example 46 is both actual (in part) and prophetic (in part). The examples are for purposes of illustration and are not intended to limit the scope of the present invention.

EXAMPLES

Example 1

This example is directed to the preparation of N,N'-bis(hexadecylaminocarbonylmethylene)-(β-N,N,N-trimethylammonium ethylaminocarbonylmethylene)-N,N'-dimethyl-N-N'-ethylenediamine tetraiodide (EDTA-HA-TMA tetraiodide), which has the following formula.

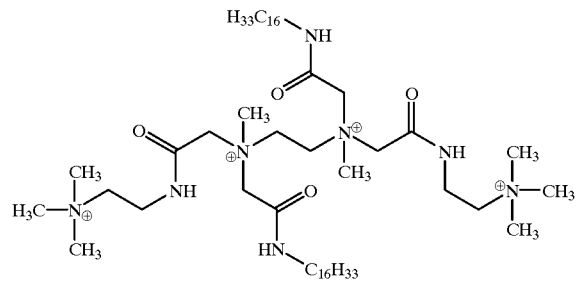

A. Preparation of N,N'-bis-(hexadecylaminocarbonylmethylene)-ethylenediamine-N,N'-diacetic acid (EDTA-HA).

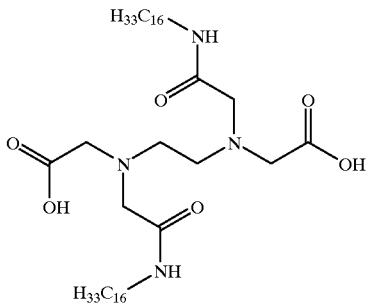

Ethylenediaminetetraacetic acid dianhydride (2.56 g, 0.01 mole) in dry methanol (30 mL) and hexadecylamine (4.82 g, 0.02 mole) in dry methanol (60 mL) were combined and stirred at 50° C. for 6 hours. The resulting white solid was isolated by filtration and dried at room temperature under vacuum to yield 3.43 g (64%) of EDTA-HA.

IR: 3320 cm$^{-1}$ for OH, 1670 cm$^{-1}$ for C=O (carbonyl).

B. Preparation of N,N'-bis-(hexadecylaminocarbonylmethylene)-N,N'-β-N,N-dimethylamino-ethylaminocarbonylmethylene) ethylenediamine (EDTA-HA-DMA).

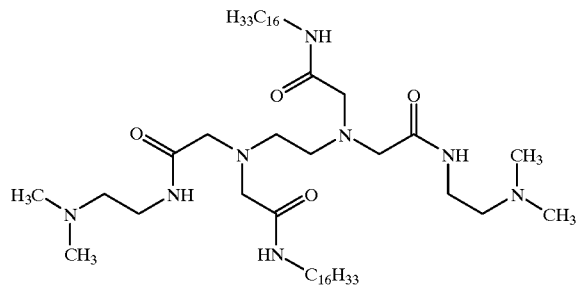

To a cooled (5° C.) solution of EDTA-HA from Step A (3.69 g, 0.005 mole), N,N-dimethylethylenediamine (0.88 g, 0.01 mole) and CHCl$_3$ (100 mL) was added dropwise a solution of DCC (2.227 g, 0.011 mole) in CHCl$_3$ (20 mL). The resulting emulsion was stirred at room temperature for about 24 hours and filtered. The filtrate was washed with 0.5% acetic acid (100 mL) to decompose any excess DCC. A white milky solution was observed which separated into two layers. The lower organic layer was dried overnight (Na$_2$SO$_4$) and concentrated in vacuo to provide 3.81 g of EDTA-HA-DMA as a soft solid.

IR: 3280 cm$^{-1}$, 2900 cm$^{-1}$, 1640 cm$^{-1}$, 1530 cm$^{-1}$

C. Preparation of EDTA-HA-TMA tetraiodide.

EDTA-HA-DMA from Step B (4.22 g, 4.77 mmole), iodomethane (3.41 g, 24 mmole) and ethanol (30 mL) were combined and refluxed for 2 hours. The reaction mixture was concentrated and the residue was lyophilized overnight. 4.98 g of the title product (EDTA-HA-TMA tetraiodide) was obtained as a yellow solid.

IR: 3260 cm$^{-1}$, 1650 cm$^{-1}$.

Example 2

This example is directed to the preparation of N,N'-bis(hexadecyloxycarbonylmethylene)-N-(β-N,N,N-trimethylammoniumethyl-aminocarbonylmethylene)-N- methyl-N'-(carboxymethylene)ethylenediamine diiodide (EDTA-HAL-DMA diiodide), which has the following formula.

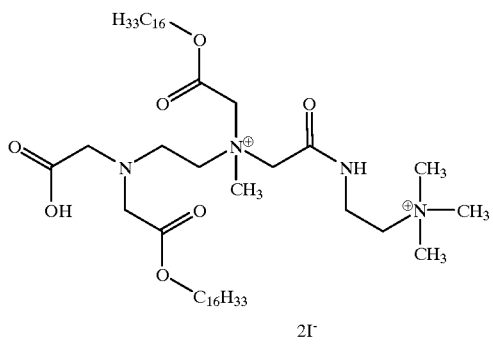

A. Preparation of N,N'-bis-(hexadecyloxycarbonylmethylene)-ethylenediamine-N,N'-diacetic acid (EDTA-HAL).

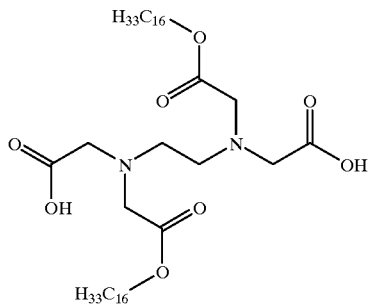

Hexadecyl alcohol (4.84 g, 0.02 mole), dry dimethylformamide (20 mL), dry triethylamine (3.3 g) and ethylenediaminetetraacetic acid dianhydride (2.56 g, 0.01 mole) were combined and stirred at 50° C. for 2 hrs. The reaction mixture was poured into cold water (200 mL) and the resulting aqueous mixture was acidified with HCl. The resulting white precipitate was isolated by filtration and the filter cake was washed with water. Recrystallization of the white solid from ethanol yielded 7 g of EDTA-HAL. m.p. 103° C.

B. Preparation of N,N'-bis(hexadecyloxycarbonylmethylene)-N-(β-N-dimethylaminoethylaminocarbonyl)-N'-acetic acid (EDTA-HAL-DMA).

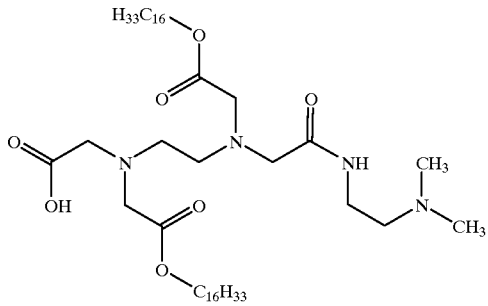

To a cooled (5° C.) solution of EDTA-HAL from Step A (3.70 g, 0.005 mole), N,N-dimethylethylenediamine (1.598 g, 0.0175 mole) and CHCl$_3$ (100 mL) was added dropwise a solution of (DCC) (3.60 g, 0.0175 mole) in CHCl$_3$ (20 mL). A precipitate formed, and the reaction mixture was stirred at room temperature for about 24 hours. The reaction mixture was filtered and the filtrate was washed with 0.5% acetic acid (100 mL) to decompose any excess DCC. A white milky solution formed which separated into two layers. The bottom organic layer was dried and concentrated in vacuo to yield 3.85 g of EDTA-HAL-DMA as a viscous liquid.

C. Preparation of EDTA-HAL-DMA diiodide.

EDTA-HAL-DMA from Step B (2.36 g, 0.0027 mole), iodomethane (3.81 g) and ethanol (50 mL) were combined and refluxed for 2 hrs. The solution was concentrated in vacuo and the resulting residue was lyophilized overnight. 2.96 g of the title compound (EDTA-HAL-DMA diiodide) was obtained as a yellowish solid.

Example 3

This example is directed to the preparation of N,N'-bis(hexadecyloxycarbonylmethylene)-N-β-N,N,N-trimethylammoniumethyl-aminocarbonylmethylene)-N-methyl-N'-(carboxymethylene)ethylenediamine diiodide (EDTA-HA-DMA diiodide), which has the following formula.

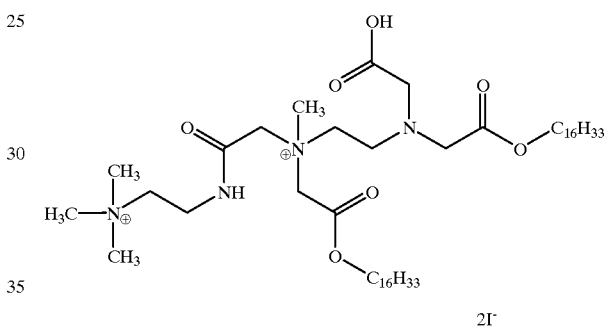

A. Preparation of N,N'-bis(hexadecylaminocarbonylmethylene)-ethylenediamine-N,N'-diacetic acid (EDTA-HA).

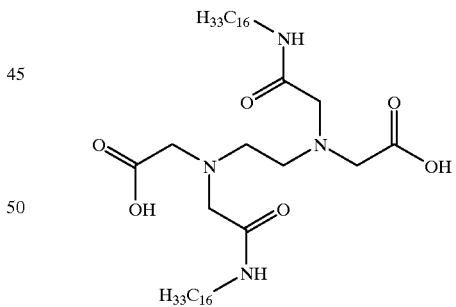

Hexadecylamine (4.82 g, 0.02 mole) in dry methanol (60 mL) was added to a suspension of ethylenediaminetetraacetic acid dianhydride (2.56 g, 0.01 mole) in dry methanol (30 mL). The mixture was stirred at 50° C. for 6 hours. The resulting white solid precipitate was isolated by filtration and dried under vacuum at room temperature to yield 3.43 g (64%) of EDTA-HA. m.p. 156–158° C.

IR: 3320 cm$^{-1}$ for OH; 1670cm$^{-1}$ for —C(=O)—.

B. Preparation of N,N'-bis(hexadecylaminocarbonylmethylene)-N,N'-bis(β-N,N-dimethylaminoethylaminocarbonylmethylene)ethylenediamine (EDTA-HA-DMA).

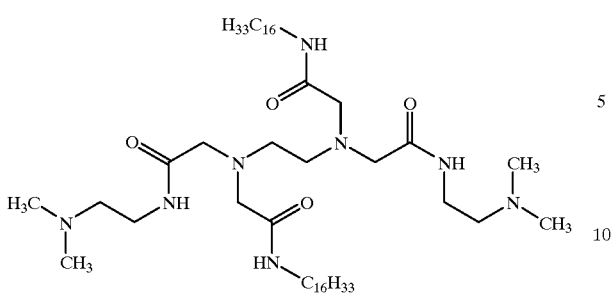

A. Preparation of N-(1,2-dipalmitoyl-sn-glycero-3-succinyl)-succinimide (N-DPGS-succinimide).

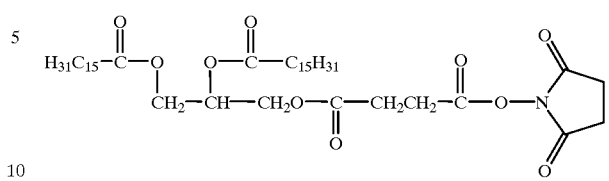

To a cooled (5° C.) solution of EDTA-HA from Step A (3.69 g, 0.005 mole), N,N-dimethylethylenediamine (0.88 g, 0.01 mole) and CHCl$_3$ (100 mL) was added dropwise a solution of 1,3-dicyclohexylcarbodiimide (DCC) (2.227 g, 0.011 mole) in CHCl$_3$ (20 mL). A precipitate was observed and the reaction mixture was stirred at room temperature for about 24 hours. The reaction mixture was filtered and the filtrate was washed with 0.5% acetic acid (100 mL) to decompose any excess DCC. A white milky solution was formed which separated into two layers. The bottom organic layer was dried (Na$_2$SO$_4$) and concentrated in vacuo to yield 3.81 g of EDTA-HA-DMA as a soft solid.

IR: 3280 cm–1; 2900 cm$^{-1}$; 1640 cm$^{-1}$; 1530 cm$^{-1}$.

C. Preparation of EDTA-HA-DMA diiodide.

A solution of EDTA-HA-DMA from Step B (4.2 g, 4.77 mmole), iodomethane (3.41 g, 24 mmole) and ethanol (30 mL) was refluxed for 2 hours. The ethanolic solution was concentrated in vacuo and the resulting residue was lyophilized overnight. 3.98 g of the title compound (EDTA-LA-DMA diiodide) was obtained as a yellow solid.

IR: 3260 cm$^{-1}$; 1650 cm$^{-1}$.

Example 4

This example is directed to the preparation of DPGS-PEG-Lys-Gln-Ala-Gly-Asp-Val which has the following formula.

To a cooled (0 to 5° C.) solution of DCC (20.6 mg) and acetonitrile (10 mL) was added dropwise a solution of 1,2-dipalmitoyl-sn-glycero-3-succinate (Avanti Polar Lipids, Alabaster, Ala.) (66.8 mg), N-hydroxysuccinimide (11.5 mg), dimethylaminopyridine (DMAP) (2 mg) and acetonitrile (40 mL). The reaction mixture was stirred for 5 hours and the resulting solid was removed by filtration. The filtrate was concentrated in vacuo to provide 78 mg of N-DPGS-succinimide as a white product.

B. Preparation of 3-ω-carboxy-polyethyleneglycoliminosuccinate-1,2-dipamitoyl-sn-glycerol (DPGS-ω-carboxy-PEG).

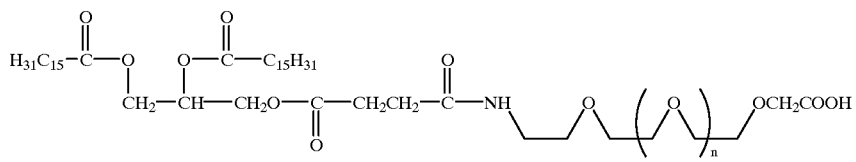

To a cooled (0 to 5° C.) solution of ω-amino-ω'-carboxy-polyethyleneglycol (Shearwater Polymers, Huntsville, Ala.) (0.3 g) and triethylamine (40 mg) in CHCl$_3$ (20 mL) was added dropwise a solution of N-DPGS-succinimide from Step A (78 mg) in CHCl$_3$ (10 mL). The resulting solution was stirred for about 5 hours at 10° C. and allowed to stand overnight. The reaction mixture was poured into ice water and neutralized with 10% HCl to a pH of less than 3. The organic layer was isolated, washed with water and dried (NaSO$_4$). Filtration and concentration in vacuo provided 0.34 g of DPGS-ω-carboxy-PEG as a white solid.

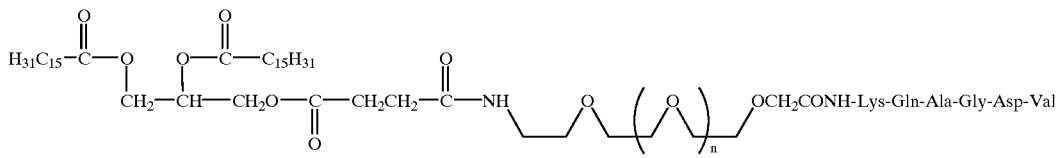

IV C. Preparation of 3-succinamoyloxycarbonyl-polyethyleneglycol-imino-succinate-1,2-dipalmitoyl-sn-glycerol (DPGS-ω-carboxy-PEG-succinimide).

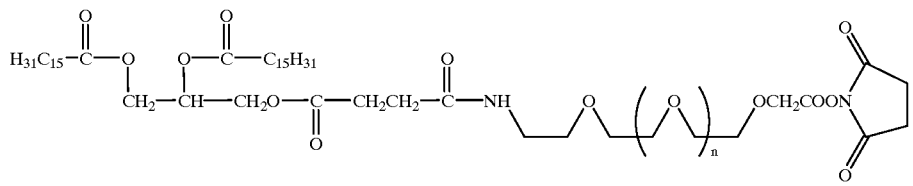

To a cooled (0 to 5° C.) solution of DCC (12 mg) in acetonitrile (10 mL) was added a solution of DPGS-ω-carboxy-PEG from Step B (200 mg), N-hydroxysuccinimide (6 mg) and dimethylaminopyridine (2 mg). The resulting reaction mixture was stirred for 5 hours. The white solid which formed was removed from the reaction mixture by filtration, and the filtrate was concentrated in vacuo. DPGS-ω-carboxy-PEG-succinimide was obtained as a white solid (200 mg).

D. Preparation of DPGS-PEG-Lys-Gln-Ala-Gly-Asp-Val conjugate.

To a cooled (0 to 5° C.) solution of the peptide Lys-Gln-Ala-Gly-Asp-Val (5 mg) in a buffer solution at pH 8.5 (20 mL) was added dropwise a solution of DPGS-ω-carboxy-PEG-succinimide from Step C (40 mg) in acetonitrile (0.1 mL). The resulting reaction mixture was stirred at room temperature for about 48 hours. The reaction mixture was concentrated in vacuo and the mineral salt was dialyzed through a membrane having a molecular weight cutoff of about 1,000 and dried on a lyophilizer. The title compound (DPGS-PEG-Lys-Gln-Ala-Gly-Asp-Val) was obtained as a white solid (24 mg).

Example 5

This example is directed to the preparation of DPPE-PEG-Lys-Gln-Ala-Gly-Asp-Val), which has the following formula.

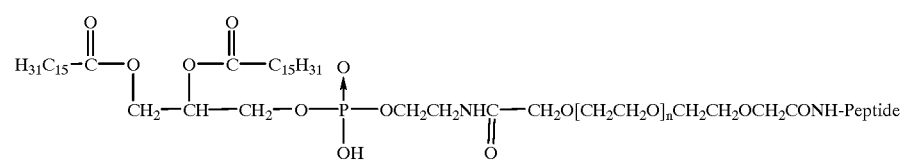

where "Peptide" is -Lys-Gln-Ala-Gly-Asp-Val

A. Preparation of ω,ω'-dimethylenecarboxy-polyethylene glycol anhydride.

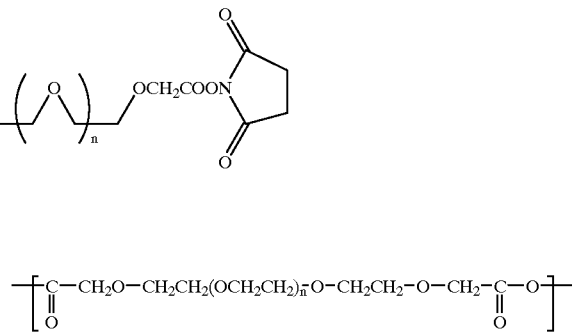

To a cooled (0 to 5° C.) solution of chlorosulfonyl isocyanate (14.2 mg) in CHCl₃ (5 mL) was added a solution of ω,ω'-dimethylenecarboxypolyethylene glycol (0.34 g) and triethylamine (20 mg) in CHCl₃ (20 mL). The reaction mixture was stirred overnight and poured into ice water. The organic layer was isolated and dried (NaSO₄). Filtration and concentration of the organic layer in vacuo yielded the title anhydride compound as a white solid (0.2 g).

B. Preparation of 1,2-dipalmitoyl-sn-glycerol-3-phosphoethanolamine-N-carboxymethylene-ω'-carboxy-polyethylene glycol (DPPE-ω-carboxy-PEG).

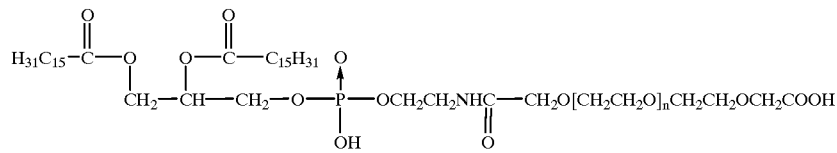

To a cooled (0 to 10° C.) solution of the anhydride compound from Step A (0.3 g) in CH₂Cl₂ (10 mL) was added a solution of DPPE (0.07 g) and triethylamine (0.05 g) in CH₂Cl₂ (15 mL). The resulting reaction mixture was stirred overnight, poured into ice water and neutralized with 10% HCl to a pH of less than 3. The organic layer was isolated and dried (NaSO₄). Filtration and concentration of the organic layer in vacuo provided 0.45 g of DPPE-ω-carboxy-PEG as a dark white solid.

C. Preparation of 1,2-dipalmitoyl-sn-glycerol-3-phosphoethanolamine-N-carbonylmethylene-polyethylene glycol-succinimide (DPPE-ω-carboxy-PEG-succinimide).

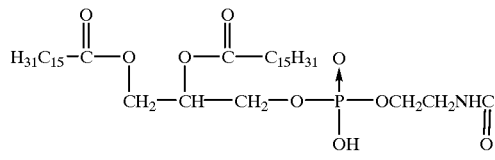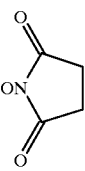

To a cooled (0 to 5° C.) solution of DCC (3 mg) in acetonitrile (2 mL) was added a solution of DPPE-ω-carboxy-PEG from Step B (60 mg), N-hydroxysuccinimide (1.8 mg) and dimethylaminopyridine (0.2 mg) in acetonitrile (6 mL). The resulting mixture was stirred for 3 hours at 0 to 5° C. and then overnight at room temperature. The solid which formed was removed by filtration and the filtrate was concentrated in vacuo to provide 60 mg of DPPE-ω-carboxy-PEG-succinimide.

D. Preparation of DPPE-PEG-Lys-Gln-Ala-Gly-Asp-Val conjugate.

To a cooled (0 to 5° C.) solution of Lys-Gln-Ala-Gly-Asp-Val (5 mg) in a buffer solution at pH 8.5 was added dropwise DPPE-ω-carboxy-PEG-succinimide (40 mg) in acetonitrile (10 mL). The resulting mixture was stirred at room temperature for about 48 hours. The acetonitrile was removed in vacuo, and the mineral salt was dialyzed out through a membrane having a molecular weight cutoff of 1000. Lyophilization afforded 35 mg of the title compound (DPPE-PEG-Lys-Gln-Ala-Gly-Asp-Val) as a white solid.

Example 6

To a solution of saline, propylene glycol and glycerol (8:1:1) were added DPPC, DPPE-PEG5000 and DPPA in a molar ratio of 82:8:10. The resulting mixture was heated to about 45° C. and filtered (0.22 μM). The filtered mixture was placed in a vial and allowed to cool to room temperature. The vial was placed under vacuum to evacuate any gas, after which the vial was pressurized with PFP. The vial was then sealed, placed on a shaker and agitated at room temperature to provide a solution of PFP-filled vesicles having a mean diameter of about 2.5 μm.

Example 7

This example is directed to the preparation of targeted vesicles within the scope of the present invention.

GPIIbIIIa binding peptide (Integrated Biomolecule Corporation, Tucson, Ariz.) was covalently bonded to DPPE-PEG 3400 utilizing the procedure described above in Example 5. This peptide conjugate was then combined with a dried lipid mixture of DPPC (82 mole %), DPPE-PEG5000 (8 mole %) and DPPA (8 mole %). This mixture was hydrated and lyophilized on a Labconco Lyph-Lock 12 lyophilizer (Kansas City, Mo.). The lyophilized material was resuspended in 8:1:1 normal saline:propylene glycol:glycerol at a concentration of 1 mg/mL. Aliquots of this mixture were placed into 2 mL Wheaton vials (Millville, N.J.), capped and the headspace replaced with perfluorobutane gas (Flura, Newport, Tenn.). The vials were agitated to provide a vesicle composition targeted to the GPIIbIIIa receptor.

Example 8

This example includes a description of peptide binding experiments utilizing the vesicle compositions prepared in Examples 6 and 7.

Unheparinized human blood was placed in Vacutainer tubes (Becton Dickinson, Rutherford, N.J.) and allowed to clot. The clot was collected by centrifugation in a Beckman TJ-6 centrifuge (Palo Alto, Calif.). The clot was then placed on positively charged microscope slides (Fisher Scientific, Pittsburgh, Pa.). Nine slides were coated with clotted blood. Six uncoated slides were also used as control studies. Binding studies were then conducted by applying the vesicle compositions from Examples 6 and 7 (200 μL) to the aforementioned slides as follows: (A) blood clot alone (control); (B) vesicle composition from Example 6 without blood clot; (C) vesicle composition from Example 6 with blood clot; (D) vesicle composition from Example 7 without blood clot; and (E) vesicle composition from Example 3 with blood clot. The slides were incubated for 20 minutes and then unbound material was washed off using phosphate buffered saline. The slides were then observed using a Nikon Diaphot (Tokyo, Japan) microscope. The results are set forth in the following table.

TABLE 3

| Binding Study | Binding |
| --- | --- |
| (A) | no |
| (B) | no |
| (C) | no |
| (D) | no |
| (E) | yes |

As can be seen from the above table, binding was observed only with the vesicle composition prepared in Example 7 which contains GPIIbIIIa targeting peptide.

Example 9

This example is directed to the preparation of vesicles based on human serum albumin that bear targeting ligands directed to the GPIIbIIIa receptor.

Into a vessel will be introduced a suspension of 5% human serum albumin. The suspension will be deaerated under continuous vacuum and a headspace of perfluoropropane gas will be introduced, as described in Published International Application WO 95/29705, the disclosures of which are hereby incorporated by reference, in their entirety. The resulting gas-filled albumin vesicles will be separated from any free albumin by repeated washing with normal saline. The gas-filled vesicles will be resuspended in a mixture of normal saline:propylene glycol:glycerol (6:2:2, v:v:v) and the suspension will be mixed gently. To this suspension will be added 1% glutaraldehyde and 1% by weight of the peptide Lys-Gln-Ala-Gly-Asp-Val resulting in crosslinked perfluoropropane vesicles bearing GPIIbIIIa binding peptide.

Example 10

This example is directed to the preparation of vesicles stabilized by polymerizable acryloyl/styryl lipid analogs binding targeting ligands directed to the GPIIbIIIa receptor.

99

12-Hydroxydodecanoic acid will be esterified with methacryloyl chloride and the ester will be converted to the anhydride to provide 12-(methacryloyloxy)dodecanoic anhydride. L-alpha-Glycerophosphocholine, derived from egg lecithin, will be acylated with the 12-(methacryloyloxy) dodecanoic anhydride to afford bis[12-(methacryloyl) oxydodecanoyl]-L-alpha-phosphatidylcholine (1). Compound (1) will be hydrolyzed enzymatically with phospholipase A$_2$, derived from crude rattle snake venom (*Crotalus adamanteus*), followed by acylation with palmitoyl anhydride to provide 1-[2-(methacryloyloxy) dodecanoyl]-2-palmitoyl-L-alpha-phosphatidylcholine (2). Similar methods will be employed to convert dipalmitoyl-L-alpha-phosphatidylcholine into 1-palmitoyl-2-[12-(methacryloyloxy)-dodecanoyl]-L-alpha-phosphatidylcholine (3).

To a solution in normal saline of DPPE-PEG 5000 (1.8 mg/mL) and 10% by weight DPPE-PEG-5000 labelled with GPIIbIIIa binding peptide (Lys-Gln-Ala-Gly-Asp-Val), which will be prepared using the procedure described above in Example 5, will be added compound (3) prepared above. An aliquot of this solution will be placed in a sterile 3 mL vial. The headspace of the vial will be evacuated and a mixture of nitrogen and perfluoroethane gas (20:80, v/v) will be filled into the headspace of the vial to ambient pressure. The vial will be shaken on an ESPE Capmix (Seefeld, Oberay Germany) at room temperature for about 1 minute. The vesicle composition will be irradiated (254 nm) to provide polymerized gas-filled vesicles bearing GPIIbIIIa binding peptide. The mean diameter of the vesicles will be about 3 μm.

Example 11

This example is directed to the preparation of synthetic polybis(carboxylatophenoxy)phosphazene) (PCPP) gas-filled vesicles targeted to the GPIIbIIIa receptor.

PCPP-PEG2000-Lys-Gln-Ala-Gly-Asp-Val will be prepared utilizing the procedure described above in Example 5. PCPP vesicles will then be prepared as described as in U.S. Pat. No. 5,487,390, the disclosures of which are hereby incorporated by reference herein, in their entirety. The PCPP vesicles (100 mg) will be added to 1 mL of a Na$_2$CO$_3$ solution (30 mg/mL) and will be dissolved by stirring overnight at room temperature. The solution will be diluted with phosphate-buffered saline (pH 7.4) to provide a final polymer concentration of 2.5% (w/v) and a solution pH of 7.4. The pH will be adjusted, as needed, with 1N HCl.

A solution of PCPP (2.5% w/v) containing 0.2% Tween 20 will be mixed with perfluoropropane gas in a colloid mill to produce a gassed PCPP solution that is stable for several hours. Ten mole % of the PCPP utilized in the solution will be PCPP-PEG2000-Lys-Gln-Ala-Gly-Asp-Val. The gassed solution will be extruded from a syringe pump at 150 μL/min into an air-atomizing device under an atmosphere of perfluoropropane gas and sprayed into a pan containing 250 mL of a 7.5% CaCl$_2$ solution containing 0.5% Tween 20. Upon contact with the CaCl$_2$ solution, PCPP will be crosslinked by the divalent calcium ions to produce a relatively homogeneous population of spherical gel vesicles, targeted to the GPIIbIIIa and filled with perfluoropropane. The presence of entrapped perfluoropropane will be demonstrated by observation of the vesicles using an inverted microscope.

Example 12

This example is directed to the preparation of a vesicles targeted to the GPIIbIIIa receptor formulated form a fluorinated lipid.

100

The amino group in α-amino, ω-carboxy-PEG3400 (Shearwater Polymer, Huntsville, Ala.) will be protected by dissolving one equivalent of the α-amino, ω-carboxy-PEG3400 in a solution of water:dioxane (1:1, v:v). To this stirring solution will be added one molar equivalent each of t-Boc-anhydride (Bachem, Gardena, Calif.) and triethylamine (Aldrich Chemical, Milwaukee, Wis.). The resulting solution will be stirred overnight and concentrated in vacuo to remove the volatile dioxane. To concentrated material will be added ten volume equivalents, relative to water, of ethyl acetate and the resulting mixture will be cooled with an ice bath. The pH of the mixture will be adjusted to pH 2 with aqueous 2N sulfuric acid, and the lower aqueous layer will be removed using a separatory funnel. The ethyl acetate layer will be washed with saturated brine, dried (MgSO$_4$), filtered, and concentrated in vacuo to afford a syrup.

The t-BOC-α-amino, ω-carboxyl PEG3400, one molar equivalent of diisopropylcarbodiimide (DIC) (Sigma Chemical Co., St. Louis, Mo.) and dry DMF will be combined. The solution will be stirred and one equivalent each of diisopropylethylamine (DIEA) (Sigma Chemical Co., St. Louis, Mo.), hydroxybenzotriazole (HOBT) and 1,2-di-(15, 16,17,18-nonafluoro)stearoylphosphatidylethanolamine (fluoro-DSPE) will be added. The resulting solution will be stirred for 2 hours and concentrated in vacuo. The fluoro-DSPE-t-BOC-α-amino, ω-amido PEG3400 will be suspended in a solution of trifluoroacetic acid and CH$_2$Cl$_2$ (4:6, v:v), followed by stirring an additional 20 minutes. The solution will then be neutralized with DIEA and concentrated in vacuo. The product will be resuspended in CH$_2$Cl$_2$ and aqueous HCl will be added to a pH of about 2. The aqueous layer will be separated and the pH readjusted to pH 10 with 1.0% NaOH. To the aqueous mixture will be added ethyl acetate which will be separated, washed with saturated brine, and dried (MgSO$_4$). Filtration and concentration in vacuo will provide the fluoro-DSPE α-amino, ω-amido PEG3400 as a yellow oil.

The yellow oil obtained above, one equivalent of N-bromosuccinimide (NBS), (Sigma Chemical, St. Louis, Mo.) and DMF will be combined. The resulting mixture will be stirred for 3 hours and concentrated in vacuo overnight. The concentrated material will be suspended in phosphate-buffered saline at a pH of 7. The peptide Arg-Gly-Asp-Ser (RGDS), which is targeted to the GPIIbIIIa receptor, will be added to the suspension. After stirring overnight, the reaction mixture will be concentrated with an Amicon filter concentrator (Amicon, Beverly, Mass.) to a volume of −300 mL. The concentrated solution will be purified by size exclusion chromatography to yield the fluoro-DSPE-α-amino, ω-amido PEG3400-Arg-Gly-Asp-Ser. This product will be added to a mixture of DPPC and DPPA to provide a ratio of DPPC:fluoro-DSPE:DPPA of 40:54:6, w:w:w. This lipid mixture will be added to a diluent comprising normal saline:glycerol:propylene glycol (8:1:1, v:v:v) to provide a final lipid concentration of 1 mg/mL of diluent. An aliquot of this solution will be introduced into a 2 mL vial (Wheaton Industries, Chicago, Ill.) and the headspace will be filled with perfluoropropane. The vial will be agitated on an ESPE Capmix (ESPE, Seefeld, Germany) at 4300 rpm for 1 minute to yield the fluorinated vesicle targeted to the GPIIbIIIa receptor.

Example 13

This example is directed to the preparation of N-(1,2-dipalmitoyl-sn-glycero-3-succinyl)-PEG-Protein A conjugate, which has the following formula.

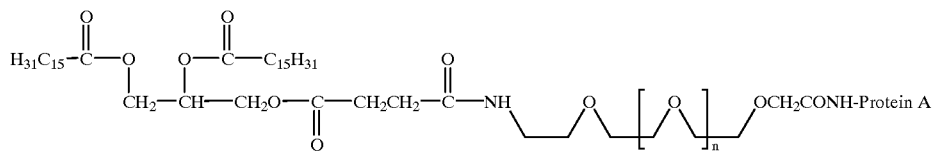

A. Preparation of N-DPGS-succinimide.

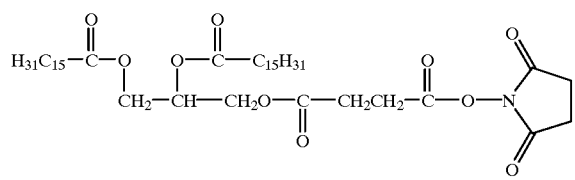

To a cooled (0 to 5° C.) solution of 1,2-dipalmitoyl-sn-glycero-3-succinate (66.8 mg), N-hydroxy-succinimide (11.5 mg), DMAP (2 mg) and acetonitrile (40 mL) in a 100 mL round bottom flask was added dropwise a solution of DCC (20.6 mg) in acetonitrile (10 mL). The resulting mixture was stirred for 5 hours. The solid material which formed during the reaction (dicyclohexylurea) was removed by filtration and the filtrate was concentrated in vacuo to yield 78 mg of N-DPGS-succinimide as a white product.

B. Preparation of 3-ω-carboxy-polyethyleneglycol-imino-succinat-1,2-dipalmitoyl-sn-glycerol (DPGS-ω-carboxy-PEG).

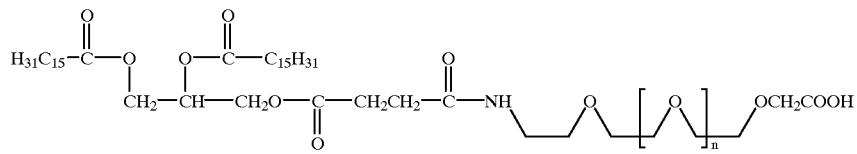

To a cooled (0 to 5° C.) solution of N-DPGS-succinimide from Step A (78 mg) and CHCl$_3$ (10 mL) (Mallinckrodt, St. Louis, Mo.) in a 100 mL round bottom flask was added dropwise a solution of ω-amino-ω'-carboxy-polyethyleneglycol (0.3 g) and triethylamine (40 mg) in CHCl$_3$ (20 mL). The resulting mixture was stirred for 5 hours at 10° C. After stirring overnight, the reaction mixture was poured into ice water and neutralized with 10% HCl to a pH of about 3 or less. The lower organic layer was removed using a separatory funnel and washed three times with water. The organic layer was collected and dried (NaSO$_4$). Filtration and concentration in vacuo yield 0.34 g of DPGS-ω-carboxy-PEG as a white solid.

C. Preparation of 3-succinamoyl-oxy-carbonyl-polyethyleneglycol-imino-succinate-1,2-dipalmitoyl-sn-glycerol (DPGS-ω-carboxy-PEG-succinimide).

To a cooled (0 to 5° C.) solution of DPGS-ω-carboxy-PEG (200 mg) from Step B, N-hydroxysuccinimide (6 mg), DMAP (2 mg) and acetonitrile (40 mL) in a 250 mL round bottom flask was added dropwise a solution of DCC (12 mg) in acetonitrile (10 mL). The resulting mixture was stirred for 5 hours and the white solid which formed (dicyclohexylurea) was removed by filtration. The filtrate was concentrated in vacuo to afford 200 mg of DPGS-ω-carboxy-PEG-succinimide as a white solid.

D. Preparation of DPGS-PEG-Protein A conjugate.

To a cooled (5 to 10° C.), stirred solution of Protein A (Sigma Chemical Co., St. Louis, Mo.) (20 mg) in aqueous buffer (20 mL) at a pH of 8.5 was added dropwise a solution of DPGS-(carboxy-PEG-succinimide from Step C (4 mg) and acetonitrile (10 mL). The temperature of the resulting mixture was equilibrated to room temperature and the reaction mixture was stirred for about 48 hours. The mixture was concentrated in vacuo and the residual salts were dialyzed away using a dialysis bag having a molecular weight cutoff of about 3500, equilibrated against water. The resulting dialyzed solution was frozen and lyophilized to yield 12 mg of the title material (DPGS-PEG-Protein A conjugate) as a white solid.

Example 14

This example is directed to the preparation of DPPE-PEG-protein A conjugate, which has the following formula.

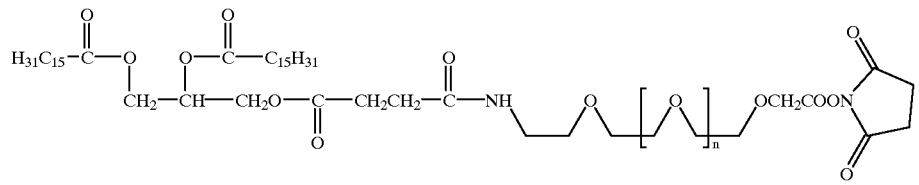

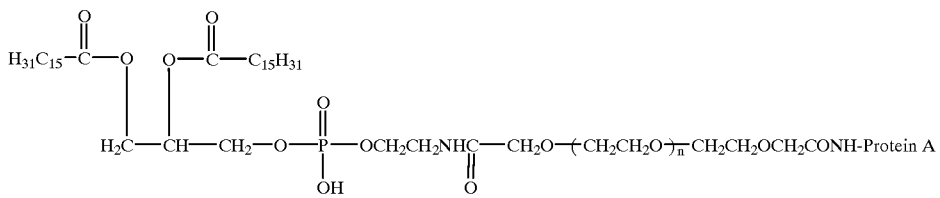

A. Preparation of ω,ω'-dimethylenecarboxy-polyethyleneglycol anhydride.

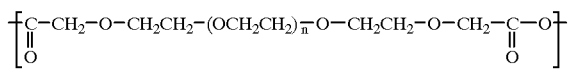

To a cooled (0 to 5° C.) solution of ω,ω'-dimethylenecarboxypolyethyleneglycol (0.34 g) and CHCl$_3$ (20 mL) in a 100 mL round bottom flask was added a solution of DCC (0.02 g) in CHCl$_3$ (5 mL). This solution was stirred overnight, and the resulting white solid precipitate (dicyclohexylurea) was removed by filtration. The filtrate was concentrated in vacuo to provide 0.3 g of the anhydride as a white solid.

B. Preparation of 1,2-dipalmitoyl-sn-glycerol-3-phosphoethanolamine-N-carbonyl-methylene-ω'-carboxy-polyethyleneglycol (DPPE-ω-carboxy-PEG).

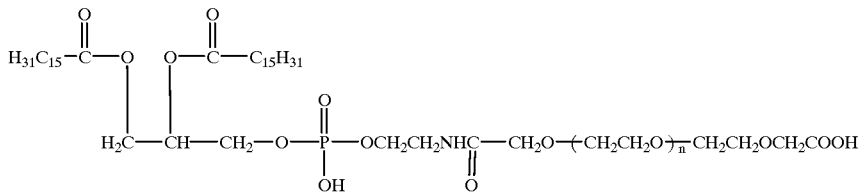

To a cooled (0 to 10° C.) solution of the anhydride from Step A (0.3 g) and CH$_2$Cl$_2$ (10 mL) in a 100 mL round bottom flask was added a solution of DPPE (0.07 g) and triethylamine (0.05 g) in CH$_2$Cl$_2$ (15 mL). After stirring overnight, the reaction mixture was poured into ice water and acidified with 10% HCl to a pH of about 3 or less. The bottom organic layer was then separated using a 250 mL separatory funnel and dried (NaSO$_4$). Filtration and concentration of the CH$_2$Cl$_2$ solution in vacuo yielded 0.45 g of DPPE-ω-carboxy-PEG as an off-white solid.

C. Preparation of 1,2-dipalmitoyl-sn-glycerol-3-phosphoethylamine-N-carbonylmethylene-polyethyleneglycol-succinimide (DPPE-ω-carboxy-PEG-succinmide).

To a cooled (0 to 5° C.) solution of DCC (3 mg) and acetonitrile (2 mL) was added a solution of DPPE-ω-carboxy-PEG from Step B (60 mg), N-hydroxy-succinimide (1.8 mg) and DMAP (0.2 mg) in acetonitrile (6 mL). After stirring for 3 hours at 0 to 5° C., the temperature of the reaction mixture was equilibrated to room temperature. After stirring overnight, the white solid precipitate which formed (dicycohexylurea) was removed by filtration, and the filtrate was concentrated in vacuo to yield 60 mg of DPPE-ω-carboxy-PEG-succinimide.

D. Preparation of DPPE-PEG-protein A conjugate.

To a cooled (5 to 10° C.) solution of Protein A (20 mg) in 15 ml aqueous buffer (15 mL) at a pH of 8.5 was added dropwise DPPE-ω-carboxy-PEG-succinimide from Step C (4 mg) in acetonitrile (8 mL). The temperature of the reaction mixture was equilibrated to room temperature and stirring was continued for 48 hours. The mixture was concentrated in vacuo and the remaining salts were dialyzed against water using a dialysis membrane having a molecular weight cutoff of about 3500. The aqueous dialyzed sample was lyophilized to yield 15 mg of the title product (DPPE-PEG-protein A conjugate) as a white solid.

Example 15

This example is directed to the preparation and use of a targeted vesicle composition for targeting epithelial cells.

A. Preparation of vesicle composition.

The DPGS-PEG-Protein A conjugate product from Example 13 (1% by weight) was combined with a dried lipid mixture of DPPC (82 mole %), DPPA (10 mole %), and DPPE (8 mole %). This dry lipid mixture was hydrated and lyophilized on a Labconco (Kansas City, Mo.) Lyph-Lock

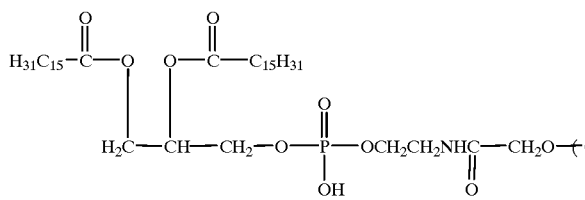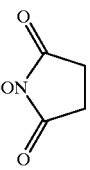

12 lyophilizer. The lyophilized mixture was -resuspended in normal saline:propylene glycol:glycerol (8:1:1) at a lipid concentration of 1 mg/mL. The mixture was aliquoted into 2 mL Wheaton vials (Millville, N.J.). The vials were capped and the headspace in the vials was replaced with perfluorobutane gas (Flura, Newport, Tenn.). The vials were then shaken for one minute on an Espe Capmix® (Seefeld, Germany) to provide gas-filled vesicles. Rabbit anti-keratin antibody (Calbiochem, San Diego, Calif.) (100 µL) was added to a sample of the vials and these vials were inverted to mix the antibody with the gas filled vesicles. The vials were incubated at room temperature for about 1 hour. A bicinchoninic acid protein assay (Pierce, Rockford, Ill.) was performed on the vesicle compositions both before and after washing with PBS. This assay showed that the anti-keratin antibody was bound to the vesicles via Protein A and remained bound during washing.

B. Targeting experiments with the vesicle composition.

HeLa cells (an epithelial cervical cancer cell line which express keratin) were plated in flat sided tissue culture tubes (Nunc, Roskilde, Denmark) in EMEM media (Cellgro, Washington, D.C.). The cells were grown overnight and aliquots of vesicle compositions were added to each tube. The vesicle compositions employed were: (i) vesicles from Example 6; (ii) vesicles prepared in Step A which contained no rabbit anti-keratin antibody; and (iii) vesicles prepared in Step A which contained rabbit anti-keratin antibody. Only the vesicles in (iii), which included the antibody, binded to the HeLa cells.

Example 16

A pegylated lipid will be prepared from distearoylphosphatidylethanolamine (DSPE), (Avanti Polar Lipids, Alabaster, Ala.) and α-amino, ω-carboxy-PEG3400 (Shearwater Polymer, Huntsville, Ala.). The amino group will be protected by combining in water:dioxane (1:1, v:v) α-amino ω-amido PEG and one molar equivalent each of t-Boc-anhydride (Bachem, Gardena, Calif.) and triethylamine (Aldrich Chemical, Milwaukee, Wis.). The resulting solution will be stirred overnight and the dioxane will be removed in vacuo. To the aqueous residue will be added ten volume equivalents, relative to water, of ethyl acetate (Mallincrodt, St. Louis, Mo.), and this mixture will be cooled in an ice bath. The pH will be adjusted to pH 2 with aqueous sulfuric acid (2 N) and the aqueous layer will be separated using a separatory funnel. The ethyl acetate layer will be washed with brine, dried (MgSO$_4$) and concentrated in vacuo to yield a syrup.

The yellow oil, DSPE-t-Boc-α-amino, ω-amido-PEG3400, one molar equivalent of diisopropylcarbodiimide (DIC) (Sigma Chemical Co., St. Louis, Mo.) and dry dimethylformamide (DMF) will be combined. The solution will be stirred and one molar equivalent each of diisopropylethylamine (DIEA), (Sigma Chemical Co., St. Louis, Mo.) and hydroxylbenzotriazole (HOBT) will be added. The solution will be stirred for two hours and concentrated in vacuo. The concentrated residue DSPE-t-BOC-α-amino, ω-amido-PEG3400 will be combined with trifluoroacetic acid and methylene chloride (4:6, v:v) and the resulting mixture will be stirred an additional 20 minutes. The solution will be neutralized with DIEA and concentrated in vacuo. This residue will be resuspended in methylene chloride and aqueous hydrochloric acid will be added until a pH of 2 is obtained. The aqueous layer will be separated and the pH will be adjusted with 1.0% NaOH to a pH of 10. To this aqueous mixture will be added ethyl acetate which will be separated, washed with saturated brine, and dried (MgSO$_4$). The ethyl acetate solution will be concentrated in vacuo to yield a yellow oil.

To a solution of the yellow oil, DSPE-α-amino, ω-amido-PEG3400 in DMF will be added one equivalent of N-bromosuccinimide (NBS), (Sigma Chemical, St. Louis, Mo.). After stirring for 3 hours, the reaction mixture will be concentrated overnight in vacuo. To a suspension of the resulting concentrated residue in a phosphate-buffered saline (PBS) at a pH of about 7 will be added anti-carcinoembryonic antigen (anti-CEA) which is a monoclonal antibody of mouse/human chimeric origin. After stirring overnight, the solution will be concentrated with an Amicon filter concentrator (Amicon, Beverly, Mass.) to a volume of ~300 mL. The concentrated solution will be purified by size exclusion chromatography to yield the final product.

Example 17

A vesicle formulation will be prepared by repeating Example 6, except that about 1 nanomole of recombinant human growth hormone will be added to the lipid composition, prior to vesicle formation.

Example 18

Example 17 will be repeated except that the DPPA is replaced with the cationic lipid dipalmitoylphosphocholine (Avanti) and the DPPC is replaced with the neutral lipid DPPE. This will provide cationic vesicles to which bioactive agents, especially genetic material, such as the gene for vascular endothelial growth factor (VEGF), can be bound. The incorporation of a targeting ligand, such as an antimyocardial antibody lipid conjugate, will provide targeted vesicles which can be directed to the infarcted and/or ischemic tissue. A burst of high energy ultrasound, for example, 1 MHz continuous wave 200 mW, can be applied with varying pulse duration to promote the rupture of the vesicles. As a result, the VEGF can be substantially delivered directly to the infarcted and/or ischemic tissue.

Example 19

This example is directed to the preparation of a vesicle composition targeted for neuroendocrine tumors of the pancreas.

Example 16 will be repeated except that Somatostatin peptide will be employed instead of anti-CEA. A therapeutic anti-cancer agent, Streptozocin, will also be incorporated in the vesicle composition. The resulting vesicle composition will be injected intravenously into a patient who has been diagnosed with a neuroendocrine tumor. The vesicles will be preferentially absorbed in the region of the pancreas proximate the tumor, thereby resulting in the enhanced delivery of the anti-cancer agent to the tumor.

Example 20

Example 15 was repeated except that, in addition to HeLa cells, the targeted vesicles were also added to an epithelial cell line comprising mouse normal liver cells. Only the vesicles containing the antibodies were bound to the liver cells.

Example 21

This example is directed to the preparation and use of a vesicle composition targeted for myocardial cells (cardiomyocites).

A. Preparation of targeted vesicles.

Example 15 was repeated except that rabbit anti-keratin antibody was replaced with rabbit anti-human skeletal myosin antibody (Biomakor™, Kiryat Weizmann, Rehovot, Israel) (100 μL).

B. Targeting of myocardial cells.

Rat heart myoblasts (American Type Culture Collection, Rockville, Md.) were plated in flat sided tissue culture tubes (Nunc, Roskilde, Denmark) in EMEM media (Cellgro, Washington, D.C.). The cells were grown overnight and aliquots of vesicle compositions were added to each tube. The vesicle compositions employed were: (i) vesicles from Example 6; (ii) vesicles prepared in Step A above which contained no rabbit anti-myosin antibody; and (iii) vesicles prepared in Step A above which contained rabbit anti-myosin antibody. Only the vesicles in (iii), which included the antibody, binded to the myoblast cells.

Example 22

This example is directed to the preparation and use of a vesicle composition targeted for myocardial cells (cardiomyocites).

A. Preparation of targeted vesicles.

Example 15 was repeated except that rabbit anti-keratin antibody was replaced with rabbit anti-myosin (skeletal) antibody (Accurate Chemical, Westbury, N.Y.) (100 μL).

B. Targeting of myocardial cells.

H9C2, a rat cardiac myocite line which expresses cardiac myosin, was employed. (Skeletal muscle myosin and cardiac muscle myosin are substantially similar.) The control cell line was INT407, which is a human intestinal cell line. The cells were plated in flat sided tissue culture tubes (Nunc, Roskilde, Denmark) in EMEM media (Cellgro, Washington, D.C.). The cells were grown overnight and aliquots of vesicle compositions were added to each tube. The vesicle compositions employed were: (i) -vesicles from Example 6; (ii) vesicles prepared in Step A above which contained no rabbit anti-myosin antibody; and (iii) vesicles prepared in Step A above which contained rabbit anti-myosin antibody. Three experimental cell types were employed: (a) INT407; (b) H9C2; and (c) H9C2 that was exposed to 10% glucose for 10 minutes to shock the cells and open pores to allow binding of the antimyosin to the cytoplasmic myosin. No binding was observed with vesicle compositions (i) or (ii) in any of cell types (a), (b) or (c). Vesicle composition (iii) also did not bind to cell type (a). Some binding of vesicle composition (iii) to cell type (b) was observed, whereas substantial binding of vesicle composition (iii) to cell type (c) was observed.

Example 23

Dipyridamole (see, e.g., *The Merck Index,* 10th Ed., p.489 (1983)) is a bioactive agent in the context of the present invention in that it is a coronary vasodilator. Dipyridamole is also a targeting ligand within the context of the present invention since it can bind to one or more receptors in heart tissue, and can also be attached to phospholipids to provide membrane compatible derivatives. Specifically, N-succinyl-DPPE will bind with dipyridamole using dicyclohexylcarbodiimide and a catalyst as a condensation agent to form N-dipyridamolylsuccinate-DPPE. This lipid bound dipyridamole derivative will be employed in a lipid composition for the preparation of vesicles for targeting heart tissue.

Example 24

A balloon catheter will be placed percutaneously via a femoral arterial access into the left circumflex coronary artery of a laboratory animal. The balloon will be inflated for a period of three hours, preventing blood flow to the anterolateral myocardium and resulting in a myocardial infarction. Echocardiography will be performed with a 5 MHz transducer and will reveal a persistent wall motion abnormality, as well as myocardial thinning of the anterolateral wall of the left ventricle. The balloon will be deflated and a dose of 30 μL/Kg of anti-cardiomyosin antibody labeled vesicles similar to those prepared, for example, in Step A of Example 22, filled with dodecafluoropentane gas will be injected intravenously. Echocardiography will be performed thirty minutes after injection. Imaging will show an area of increased echogenicity in the anterolateral wall corresponding to the region of the infarct. The periphery of the infarct (reperfused region) appears brightest with less intensity centrally (region of persistent absence of flow). In comparison, the central ventricular cavity is relatively dark, with a majority of the vesicles having been cleared by this time.

Example 25

A patient suffering from chest pains will be admitted to the emergency room of a hospital. An ultrasound study will be performed and will indicate a wall motion abnormality in the anterior wall of the left ventricle. The patient will be administered a dose of 5 μL/Kg of anticardiomyosin antibody labeled vesicles similar to those prepared, for example, in Step A of Example 22, filled with perfluorobutane gas. Ten minutes after administration, ultrasound imaging will be repeated and will show an area of increased echogenicity in the left ventricle anterior wall. This will confirm the diagnosis of myocardial infarction, and the patient will be treated with tissue plasminogen activator.

Example 26

A patient will undergo a stress echocardiography examination to diagnose the presence or absence of coronary artery disease. During peak exercise, the patient will be administered 5 μL/Kg of perfluoropropane filled vesicles labeled with dipyridamole as described in Example 23 above. The dipyridamole will be combined with the vesicles through the use of (a) a bifunctional linking group; (b) a small spanning molecule; (c) a Schiff's base with or without reductive amination; or (d) a maleimidyl linker. The vesicles will bind to perfused regions of myocardium. As the background vesicles clear, which takes about 5 minutes, the labeled vesicles will persist within the myocardium. Delayed imaging will show the ischemic myocardium affected by coronary artery disease (CAD) as a hypointense region surrounded by bright, normally perfused myocardium. The absence of any appreciable background vesicles within the cardiac chambers eliminates the problem with shadowing and facilitates making the diagnosis of CAD.

Example 27

This example demonstrates the targeted expression of a protein using a vesicle composition and methods within the scope of the present invention.

Three Sprague-Dawley rats, identified herein as rats (A), (B) and (C), were anesthetized with Ketamine acepromazine. pSVβ-gal, a plasmid containing the β-galactosidase gene with the SV40 promoter and enhancer genes, was combined with the cationic lipid compound prepared in Example 2. The plasmid and cationic lipid compound mixture was incubated for 15 minutes at room temperature. cGMP and the resulting incubated material was then added to a blend of DPPC, DPPA and DPPE-PEG5000 at a respective mole % ratio of 82:10:8 in normal saline:glycerol:propylene glycol (8:1:1). Vesicles were prepared by shaking the resulting mixture on a WIG-L-BUG™ for one minute at 3200 rpm. The resulting vesicle composition was injected into rats (A), (B) and (C). The dosages were as follows.

| Rat | Dose pSVβgal (μg) | Dose Cationic lipid (μg) |
|---|---|---|
| (A) | 5 | 30 |
| (B) | 5 | 30 |
| (C) | 25 | 150 |

During injection of the vesicle composition, Rats (B) and (C) were exposed to ultrasound energy from a therapeutic ultrasound machine (1.0 Mhz, Rich-Mar model 25, Rich-Mar Corporation, Inola, Okla.). The ultrasound was directed towards the inside of the left hind leg during the injection and for one minute post flush. Rat (A) did not receive any ultrasound treatment. After 48 hours, the rats were euthanized by asphyxiation with $CO_2$. The left and right leg muscle and skin were removed from each rat. The hearts, livers and kidneys were also removed. The excised tissues were fixed for 72 hours in 2% formalin. After fixing, the presence of β-galactosidase activity was assayed by soaking the tissue in a solution containing X-gal, potassium ferrocyanide and potassium ferricyanide. The tissues were stained, inspected and photographed. Expression was seen broadly dispersed throughout the leg tissues, particularly in the endothelial cells, muscle and skin, in rat (A). Inspection of the excised tissues from rat (13) showed expression in similar cell types but only at the site of ultrasound application. Rat (C) showed a point expression in the target leg and dispersed expression in the leg not targeted.

Example 28

This example is directed to the preparation of various lipid compositions.

DPPC, DPPA and DPPE-PEG5000 were blended at a respective mole ratio of 82:10:8. This lipid mixture is referred to herein as Composition (A). A portion of Composition (A) was mixed with the cationic lipid compound prepared in Example 2 at a 10:1 (w/w) ratio in distilled deionized water. This latter mixture is referred to herein as Composition (B). Compositions (A) and (13) were introduced into 1 ml serum vials. The vials were evacuated with a Sargent Welch vacuum pump (Skokie, Ill.) and the headspaces were replaced with perfluoropropane gas (Flura Chemical Corp, Newport, Tenn.). The vials were agitated with a Crescent Dental WIG-L-BUG™ 311OB (Lyons, Ill.) mechanical shaker. After shaking, heparin (Elkin Sinns Inc., Cherry Hill, N.J.) was added to a portion of the vials at an approximate molar ratio of lipid to heparin of 5:1. The mixture of heparin and Composition (A) are referred to herein as Composition (C). The mixture of heparin and Composition (B) are referred to herein as Composition (D).

Recombinant human basic fibroblast growth factor (BFGF) (Sigma, St. Louis, Mo.) was then added to Compositions (A), (B), (C) and (D), which are respectively referred to herein as Compositions (E), (F), (G) and (H). The BFGF was added to the compositions which contained heparin (Compositions (C) and (D)) at a molar ratio of 5:1 (BFGF:heparin). At least three samples from each of Composition (A) to (H) were sized using an Accusizer 770 Particle Sizing Systems, Santa Barbara, Calif.). Sizing showed no difference in the sizes of vesicles in Compositions (A) to (G). However, the vesicles in Composition (H), which contained cationic lipid, heparin and BFGF, had a smaller mean size.

Compositions (E) to (H) were then analyzed using a native polyacrylamide gel (protein gel PAGE mix, Boehringer Mannheim, Indianapolis, Ind.) to identify binding properties of heparin and BFGF. The gel was run on a Hoefer SE400 slab gel apparatus (Hoefer Scientific, San Francisco, Calif.). The gel was run at a constant current using an electrophoresis power supply (MBP300), IBI, Rochester, N.Y.). The gel was then stained using a rapid Coomassie blue (Eastman Kodak, Rochester, N.Y.) staining method and analyzed visually. Gel electrophoresis confirmed that in Composition (H), the presence of the cationic lipid enhances binding of heparin as well as the BFGF. It is contemplated that the heparin, which is anionic, binds to the cationic lipid, and that the BFGF, which is cationic, binds to the heparin. BFGF in compositions which contain no heparin and cationic lipid migrates during electrophoresis.

Example 29

Example 16 will be repeated, except that vascular endothelial growth factor (VEGF) the will be employed instead of anti-CEA antigen.

Example 30

DPPC, DPPA and DPPE -PEG5000 will be combined in a mole percent ratio of 82:10:8 in saline:propylene glycol:glycerol (8:1:1, w/w/w). The total concentration of lipids in the solution will be 1 mg/mL. Recombinant human growth hormone will be added to this mixture at a concentration of 10% by weight, relative to the total weight of lipids. An aliquot (1.5 mL) of this mixture will be placed in a 3 mL volume glass vial and the headspace of the vial will be exchanged with perfluoropropane gas. The vial will be sealed and shaken, resulting in gas filled vesicles which bind human growth hormone and which will be useful for targeting endothelial cells. The mean diameter of the vesicles will be about 3 μm.

Example 31

Distearoylphosphatidylglycerol (DSPG) and DPPE-PEG 5000 will be combined in sterile water at a molar ratio of 92:8. The concentration of lipid will be about 1 mg/mL. Chitosan will be derivatized with 10 mole percent by weight of basic fibroblast growth factor (bFGF) using amide bonds to attach the amine groups of the chitosan to carboxyl moieties of the bFGF. The derivatized chitosan will be added to the lipid suspension in an amount to provide a substantially equivalent concentration of cationic groups in the chitosan and anionic groups in the DSPG. An aliquot of this mixture (1.5 mL) will be placed into a 3 mL vial and the headspace will be replaced with perfluorobutane. The vial will be sealed and shaken on an ESPE Capmix (Seefeld, Germany) to provide gas-filled vesicles useful for targeting endothelial cells.

Example 32

A pegylated lipid will be prepared from DSPE and α,ω-bis(carboxymethyl)-PEG2000 (Shearwater Polymers, Huntsville, Ala.) to provide $MeO_2C$-PEG-DSPE. This lipid will be purified by column chromatography (silica gel) to provide the free acid ($HO_2C$-PEG-DSPE), after which VEGF will be linked to the free carboxyl group. DPPC, DSPA, DSPE-PEG and DSPE-PEG-VEGF will be combined, at a molar ratio of 82:10:6:2, in saline:glycerol::propylene glycol (8:1:1, w/w/w), at a total lipid concentration of 1.5 mg/ml. An aliquot of this mixture (1.5 mL) will be placed into a sterile 3 mL vial and the headspace of the vial will be replaced with perfluoropentane gas at 30° C. and the vial will be sealed. The vial will be shaken at 30° C. for about 90 seconds at 3,200 rpm on an ESPE Capmix (Seefeld, Germany) resulting in perfluoropentane gas filled targeted vesicles.

Example 33

DSPC, cholesterol and DPPA will be combined, at a mole percent ratio of 65:27:8, in a solution of saline:propylene glycol:glycerol (8:1:1 w/w/w). The total lipid concentration will be 5 mg/mL. An aliquot of this mixture (1.5 mL) will be placed in a sterile vial and the headspace will be replaced with perfluorobutane gas. The vial will be sealed and shaken for about 5 minutes on an ESPE Capmix (Seefeld, Germany) to provide a vesicle composition within the scope of the present invention. A Watanabi rabbit which had been fed a high cholesterol diet, will be administered i.v. a dose of 0.10 mL/Kg of the vesicle composition. Ultrasound imaging will be performed about 25 minutes after administration and will show that the vesicles accumulated in regions of endothelial cells affected by atherosclerotic plaque. This will illustrate that the vesicle compositions of the present invention are useful in detecting atherosclerotic regions of endothelial cells.

Example 34

Example 33 will be repeated except that among the lipids used will be cholesterolamine linked covalently via an amide linkage to DPPE-PEG-carboxylate. The lipid mixture will then comprise DPPC, DPPE-PEG5000, DPPE-PEG-cholesterolamine and DPPA which will be combined at a mole percent ratio of 82:7:1:10.

Example 35

Example 33 will be repeated except that the lipid concentration will be increased to about 5 mg/mL and the suspending medium will comprise a solution of normal saline, trehalose (10 mg/mL) and pluronic F-68 (10 mg/mL). This suspension of lipids will be microemulsified using a Microfluidizer (Microfluidics, Newton, Mass.) at 16,000 psi for a total of ten passes. The resulting vesicle composition will be lyophilized and the headspace of the lyophilization chamber will be restored gradually to ambient pressure over a period of 72 hours by slowly instilling perfluorobutane gas. The resulting gas-filled lyophilized vesicles will be stored as a dry powder until use.

Example 36

Example 35 will be repeated except that the lipid concentration will be increased to about 25 mg/mL, and the suspending medium will comprise a solution of normal saline, sorbitol (20 mg/mL) and pluronic F-68 (20 mg/mL). The lipid suspension will be cooled to 4° C. and to this mixture will be added perfluoropentane to provide a perfluoropentane concentration of 8 µL per mL of solution. This mixture will be passed through a microfluidizer maintaining the temperature at 4° C. for 20 passes at 16,000 psi. This will provide a vesicle composition of perfluoropentane-filled vesicles. This composition will be injected i.v. into a patient and will form gas filled vesicles in vivo useful for targeting endothelial cells. Gas-filled vesicles can also be obtained prior to i.v. injection by warming the vesicle composition to above about 30° C. and shaking, for example, on an ESPE Capmix (Seefeld, Germany) or other shaker or amalgamator device, or by withdrawing the plunger of a syringe which is filled with the composition of perfluoropentane-filled vesicles so as to decrease the pressure and convert the perfluoropentane liquid into perfluoropentane gas.

Example 37

12-Hydroxydodecanoic acid will be esterified with methacryloyl chloride and the ester will be converted to the anhydride to yield 12-(methacryloyloxy)dodecanoic anhydride. L-alpha-Glycerophosphocholine derived from egg lecithin will be acylated with the 12-methacryloyloxydodecanoic anhydride to yield bis[12-(methacryloyl)oxydodecanoyl]-L-alpha-phosphatidylcholine (1). Enzymatic hydrolysis of (1) with phospholipase $A_2$, derived from crude rattle snake venom (*Crotalus adamanteus*), will be followed by acylation with palmitoyl anhydride to yield 1-[2-(methacryloyloxy) dodecanoyl]-2-palmitoyl-L-alpha-phosphatidylcholine (2).

The above (2) will be combined with normal saline at a lipid concentration of 3 mg/mL. To this mixture will be added DSPE-PEG-VEGF at a concentration of 0.30 mg/ml. An aliquot of the mixture (1.5 mL) will be placed in a sterile 3 mL vial. The headspace of the vial will be evacuated and replaced with perfluoropropane gas and the vial will be sealed and wrapped with light impermeable foil. The vial will be shaken for about 3 minutes on an ESPE Capmix (Seefeld, Germany) to provide gas-filled vesicles. The foil will be removed and the vesicle composition will be irradiated with light (254 nm) to provide polymerized gas-filled vesicles bearing VEGF for targeting endothelial cells.

Example 38

Example 37 will be repeated, except that lipid (2) will be combined with DSPE-PEG (see Example 8). VEGF will be admixed with this lipid mixture prior to shaking on the ESPE Capmix (Seefeld, Germany) rather than being covalently attached to the DSPE-PEG. After photopolymerization, the VEGF will be embedded directly into the polymeric lipid membranes which coat the vesicles.

Example 39

This example is directed broadly to the preparation of albumin vesicles which are internally crosslinked and which comprise surfaces that are modified by the attachment of polyoxy($C_{1-4}$)alkylene chains as described in Published International Application WO 95/00126, the disclosures of which are hereby incorporated by reference, in their entirety. The termini of the alkylene chain modifiers will contain a reactive group, unlike the termini of the alkylene chains in WO 95/00126, which are ether groups. The reactive groups will be included for binding an endothelial targeting ligand.

Example 39A

An aqueous solution of 5% human bovine serum albumin (5 mL) will be introduced into an ultrasonic reaction vessel at a speed of 500 mL/min. The mixture will be sonicated using a Sonifier B-30 (Branson, FRG) for about 15 minutes at an energy flux of 100 Watt/cm$^2$. The temperature will be maintained at 22° C. by refrigeration of the reaction vessel. If desired, a bioactive agent, such as a drug, may be included in this mixture. Crosslinking will be initiated by adding to the albumin solution a solution of $CH_2Cl_2$ (0.2 mL) saturated with glutaraldehyde. The resulting solution will be stirred for about 1 hour. After washing with methanol, followed by acetone and finally with n-hexane, the crosslinked albumin vesicles will be obtained as a brown powder which will be dried under vacuum for about 24 hours. The size of the resulting vesicles will be determined by a Nicomps laser light particle scattering system at approximately 200 nm.

Example 39B

Albumin vesicles having a larger diameter than the vesicles prepared in Example 39A will be prepared by replacing the high intensity emulsifying process with a 4 bladed impeller and using higher concentrations of albumin, for example, from about 10 to about 25%. Crosslinking will be carried out as described above in Example 39A.

Example 39C

This example is directed to the preparation of gas-filled albumin vesicles.

Albumin vesicles will be prepared by placing 5 mL of 5% albumin in a sterile vial and filling the headspace of the vial with perfluorobutane gas. The vials will be shaken for about 5 minutes at 3,300 rpm on an ESPE Capmix (Seefeld, Germany). Crosslinking will be carried out as described above in Example 39A.

Example 39D

This example is directed to the preparation of gas-filled albumin vesicles.

Albumin vesicles will be prepared by sonicating a vial containing a 5% solution of human serum albumin and a headspace of perfluoropropane gas. This sonication will involve immersing minimally the sonicator horn tip into the liquid interface for about 5 minutes at medium power setting (Heat Systems Probe, Farmingdale, N.Y.). The albumin vesicles will be crosslinked as described above in Example 39A.

Example 39E

This example is directed to coupling heterobifunctional PEG to the albumin vesicles prepared above.

The ω carboxy group of α-amino, ω-carboxy-PEG5000 (Shearwater Polymers) will be protected with a suitable ester functionality, for example, a benzyl ester. The amino group of the PEG will be bonded covalently to the albumin vesicles to provide a 10:1 weight ratio of albumin to PEG by activating the appropriate amino acid moieties on the protein, such as, for example, the aspartic acid or glutamic acid moiety, with 1,1-carbonyldiimidazole. After covalent bonding of the PEG to the albumin via an amide linkage, the benzyl ester group will be removed. aFGF will be attached to the free carboxyl group by activating the carboxylate end of the PEG with 1,1-carbonyldiimidazole. This provides the endothelial targeting ligand bound to the albumin vesicles via the PEG linkers.

Alternatively, coupling may be accomplished by activating the appropriate amino acids of aFGF, for example, aspartic acid or glutamic acid, with carbonyldiimidazole, followed by the addition of carboxyl group protected α-amino, ω-carboxy-PEG. The protected carboxyl group will be deprotected, and the unprotected carboxyl group will be activated with carbonyldiimidazole. The activated aFGF-PEG will be combined and reacted with the albumin vesicles.

Gas will be instilled into the vesicles by careful dehydration of the vesicles under vacuum and gradual restoration to ambient pressure using a gas, such as perfluorobutane. One or more surfactants, for example, pluronic F-68, may be added prior to the dehydration and gas instillation step.

Example 40

This example is directed to the preparation of gas filled clathrates.

The ω carboxy group in a-hydroxy, ω-carboxy-PEG2000 will be protected with a suitable ester functionality, for example, a benzyl ester. The protected compound will be reacted with one equivalent of $POCl_3$ in $Et_3N$ and $CHCl_3$ at 0–5° C. to convert the hydroxy group to the phosphorous chloride ester. This compound will then be reacted with excess $NaHCO_3$ to produce the corresponding sodium phosphate ($PEG-PO_4Na_2$). This salt will be acidified with HCl, pH 3.0, to provide the corresponding acid ($PEG-PO_4H_2$). This product will be dialyzed against purified water using a membrane having a molecular weight cutoff of about 100.

After dialyzing, the above phosphoric acid product (2 g) will be combined with disodium dihydrogen pyrophosphate ($Na_2H_2P_2O_7$) (8 g) in water (100 mL). This solution will be introduced into a Buchi spray drying apparatus and spray dried. The resulting particles will be baked at 120° C. under vacuum for about 1 hour to provide hollow PEG-coated pyrophosphate vesicles. These vesicles will be resuspended in an aqueous medium and the benzyl protecting group will be removed. The deprotected carboxyl group of the PEG will be activated with 1,1-carbonyldiimidazole and the resulting compound will be coupled to a monoclonal antibody for ELAM for targeting endothelial cells. To an aqueous medium containing the targeted vesicles will be added DDPC and pluronic F-68 to provide a concentration of 1 mg/mL and 5 mg/mL, respectively. The aqueous medium containing the vesicles will be heated to about 45° C., agitated gently by hand and dried under vacuum using a rotary evaporator while maintaining this temperature. The resulting dried material will be introduced into a suitable container and lyophilized. Perfluorobutane gas will be instilled gradually in the headspace of the container over a period of about 48 hours until ambient pressure is achieved. The resulting gas filled pyrophosphate clathrates will be stored as a lyophilized powder until use.

Example 41

A 0.25M $Ca^{+2}$ solution will be prepared by dissolving $CaCl_2.H_2O$ (3.68 g) in distilled water (100 mL). The pH of this solution will be adjusted to pH 11 using 0.1M NaOH. A 0.74M solution of potassium dihydrogenphosphate ($KH_2PO_4$) will be prepared by dissolving 0.75 g of the salt in distilled water (10 mL). To this solution will be added 1.75 g of bifunctional PEG, α-phenylcarboxy ester, ω-phosphoryl-PEG5,000. The pH will be adjusted again with 0.1M NaOH to pH 11. The potassium dihydrogenphosphate/PEG phosphate solution will be added dropwise to a vigorously stirred solution of $CaCl_2$. The resulting precipitate will be sized by single particle optical sizing and by optical microscopy. The diameter of the particles will be in the range of about 1 to 2 μm. The particles will be filtered and resuspended in normal saline and the phenyl group will be removed from the carboxy group. The carboxy group will be activated with 1,1-carbonyldiimidazole and this will be reacted with a monoclonal antibody specific for ELAM. The monoclonal antibody may be prepared by conventional techniques according to the methods of Kohler and Milstein, *Nature* 1975, 256:495, the disclosures of which are incorporated herein by reference, in their entirety. The particles will be suspended in a solution of pluronic F-68 (20 mg/mL) and this suspension will be introduced into a suitable container and lyophilized. The headspace of the container will be equilibrated gradually to ambient pressure with perfluoropropane gas to provide the hydroxyapatite gas clathrates.

Example 42

In vivo experiments in rats were conducted which demonstrate the high effectiveness of the cationic lipid compounds of Example 3 to deliver genetic material intracellularly. The experiments demonstrate also the effectiveness of using ultrasound energy for targeting specific tissue in vivo with vesicle compositions containing genetic material. Plasmid pSV β-gal (Promega, Madison, Wis.), which contains the β-galactosidase gene, and the cationic lipid compound prepared in Example 3 were combined by mixing. The resulting mixture was injected into each of three Sprague Dawley rats (rats (A), (B) and (C)) via the tail vein. Rat (A) was not subjected to ultrasound. Ultrasonic energy was applied to the inside of the hind leg during injection for each of rats (B) and (C). After 48 hours, the rats were euthanized and the tissues were removed. The tissues were fixed for 72 hours in 2% formalin, sliced thin and placed in an X-gal solution. After 16 hours at 37° C., the tissues were inspected. The tissue from rat (A) exhibited a blue color which is indicative of general transfection. The tissue from rats (B) and (C) exhibited blue color only at the site where ultrasound energy was applied. This indicates that localization of gene expression can be achieved with the compounds and methods of the present invention.

Example 43

Fresh human blood was applied to gauze strips (Tillotson Health Care, Bedford, N.H.) and allowed to clot. Tygon tubing was cast into a 1% agarose (Boehringer Mannheim Biochemical, Indianapolis, Ind.) standoff pad. The strips bearing the blood clots were inserted into the Tygon tubing. Inline mixing elements (Cole-Parmer, Chicago, Ill.) were also inserted into the tubing to create a turbulent flow. Phosphate buffered saline (Boehringer Mannheim Biochemical) was pumped across the gauze strip using a MasterFlex peristaltic pump (Cole-Parmer). Ultrasound imaging was carried out using an Acoustic Imaging 5200 ultrasound machine with a 7.5 MHz peripheral vascular transducer (Phoenix, Ariz.). The transducer was fixed to a ring stand and imaging was carried out from underneath the standoff pad. After the unbound clot was washed from the strip, 1 mL each of a targeted vesicle composition which targets GPIIbIIIa and the vesicle composition from Example 6 (non-targeted) was injected into the PBS stream at a flow rate of approximately 2 mL/min. The vesicles were allowed to bind at this speed for 2 minutes and then the flow rate was turned up to 6 mL/min to remove unbound vesicles. After washing at 6 mL/min, the targeted vesicles were bound to the gauze strip, while the non-targeted vesicles were washed away. Ultrasound imaging revealed increased echogenicity in the clot with vesicles targeted to GPIIbIIIa.

Videodensitometric analysis was performed offline using a Macintosh 660 AV computer (Apple Computing, Cupertino, Calif.). The entire area of the clot was selected and the videodensitometry units were measured. The images were captured and analyzed using Image 1.55 National Institutes of Health, Washington, D.C.). This analysis involved collecting and superimposing the pre-contrast baseline image with the post-contrast image, and subtracting the pre-contrast image from the post-contrast image. This collection, superimposition, and subtraction were also conducted before and after washing to remove unbound vesicles. The videodensitrometric analysis was conducted using both continuous and intermittent ultrasound. The data obtained in this analysis is set forth in the following table, wherein higher numbers represent improved contrast.

TABLE 4

Videodensitometric Analysis of Targeted Vesicles-Ultrasound Backscatter Quantitation

| | Targeted Vesicles (before wash) | Non-Targeted Vesicles (before wash) | Targeted Vesicles (after wash) | Non-Targeted Vesicles (after wash) |
|---|---|---|---|---|
| CONTINUOUS IMAGING | | | | |
| | 28.46 | 17.64 | 46.01 | 16.5 |
| | 18.44 | 13.36 | 39.48 | 14.44 |
| | 14.44 | 7.62 | 17.22 | 7.58 |
| | 40.94 | 16.97 | 32.85 | 12.95 |
| | 22.86 | 6.81 | 19.52 | 8.08 |
| Mean | 25.57 | 13.9 | 33.89 | 12.87 |
| StDev | 11.82 | 4.59 | 12.34 | 3.81 |
| INTERMITTENT IMAGING | | | | |
| | 16.6 | 12.06 | 17.83 | 12.14 |
| | 15.47 | 16.55 | 20.35 | 13.7 |
| | 19.32 | 16.13 | 21.79 | 16.35 |
| | 20.12 | — | 22.41 | 8.68 |
| | 17.29 | 13.7 | 24.15 | 13.41 |
| Mean | 17.88 | 14.91 | 20.6 | 12.72 |
| StDev | 2.2 | 2.48 | 2.04 | 3.2 |

Inspection of the above table reveals increased backscatter from the targeted vesicles as compared to the non-targeted vesicles. T-tests were conducted which demonstrated a significant increase in videodensity signals for the targeted vesicles as compared to the non-targeted vesicles in both continuous and intermittent imaging $p<0.01$.

Example 44

This example is directed to the preparation of DPGS-NH-PEG-NH-maleimide, which has the following formula.

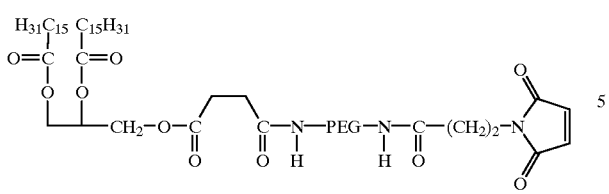

A. Preparation of dipalmitoyl glycerol succinate-polyethyleneglycol-amine (DPGS-NH-PEG-NH$_2$).

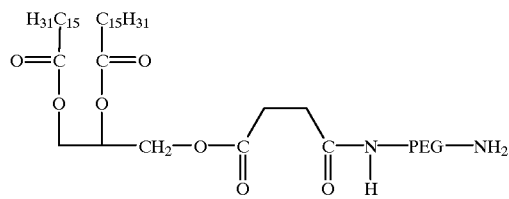

Into a round bottom flask (100 mL) was added a solution of DPGS (98 mg, 0.147 mmole, 1 eq.) in CH$_2$Cl$_2$. Into a separate round bottom flask (100 mL) was added a solution of H$_2$N-PEG-NH$_2$ (PEG-diamine) (50 mg, 0.147 mmole, 1 eq.) in CH$_2$Cl$_2$. To the PEG-diamine solution was added immediately a solution of DCC (31 mg, 0.15 mmole, 1.02 eq.) in CHCl$_3$ (5 mL). The resulting mixture of DCC and PEG-diamine was added dropwise to the DPGS at about 0 to about 5° C. The resulting reaction mixture was equilibrated with stirring to room temperature. After stirring for 24 hours, distilled-deionized water (50 mL) was added to the reaction mixture and the resulting white precipitate (dicyclohexylurea) was removed by filtration. The lower organic layer was isolated using a 250 mL separatory funnel and dried (Na$_2$SO$_4$). The dried organic solution was filtered and CH$_3$CN (80 mL) was added to the filtrate. The remaining white precipitate was removed by filtration and the filtrate was concentrated in vacuo to yield 0.44 g of DPGS-NH-PEG-NH$_2$ as a solid product.

IR: 1700 cm$^{-1}$.

TLC: R$_f$ 0.65.

B. Preparation of DPGS-PEG-NH-PEG-NH-maleimide.

Into a round bottom flask (100 mL) was added a solution of DPGS-NH-PEG-NH$_2$ from Step A (0.44 g, 0.13 mmole, 1 eq.) in CH$_2$Cl$_2$ (10 mL). To this solution was added a solution of triethylamine (13 mg, 0.13 mmole, 1 eq.) in CH$_2$Cl$_2$. To this mixture was added dropwise a solution of 34.6 mg N-maleoyl-β-alanine N-hydroxysuccinimide ester (34.6 mg) in CH$_2$Cl$_2$ (10 mL). After stirring overnight at room temperature, deionized-distilled water (30 mL) was added to the reaction mixture and stirring was continued an additional 3 hours. The lower organic layer was isolated using a separatory funnel and dried (NaSO$_4$). The organic layer was filtered and the filtrate was concentrated in vacuo to afford 360 mg of the title compound as a wax-like white solid.

IR: 1740 cm$^{-1}$, 1670 cm$^{-1}$, 1100 cm$^{-1}$.

TLC: Rf 0.75.

Example 45

This example is directed to the preparation of 1,2-dipalmitoyl-sn-glycerol-3-phosphoethanolamine-N-carbonylethylenecarbonyl-imino-polyethyleneglycolethylaminocarbonylethylenemaleimide (DPPE-NH-PEG-NH-maleimide), which has the following formula.

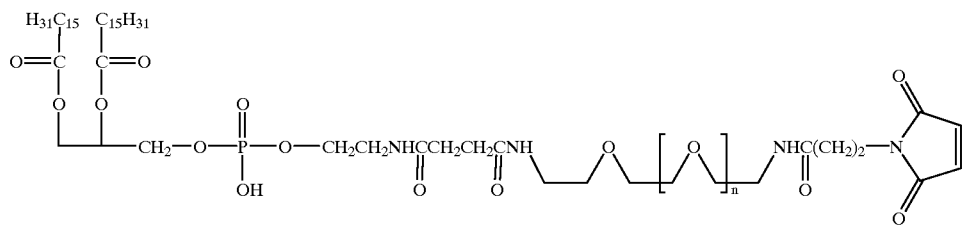

A. Preparation of 1,2-dipamitoyl-sn-glycerol-3-phosphoethanolamine-N-carbonylethylenecarbonylimi-nopolyethyleneglycolethylamine (DPPE-NH-PEG-NH$_2$).

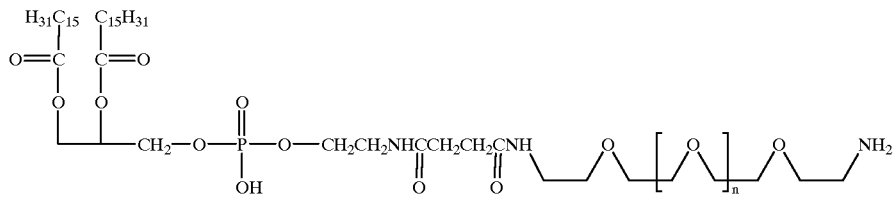

To a cooled (0 to 5° C.) solution of DPPE succinate (79 mg) and ω,ω'-diaminopolyethyleneglycol (340 mg) in CH$_2$Cl$_2$ (20 mL) was added a solution of DCC (22 mg) in CH$_2$Cl$_2$ (10 mL). The reaction mixture was stirred for 4 hours at 0 to 5° C. and then stirred overnight at room temperature. Water (10 mL) was added, and the reaction mixture was stirred for an additional hour. The lower organic layer was isolated and concentrated in vacuo using a rotary evaporator. The residue was redissolved in CH$_3$CN and the precipitate was removed by filtration. Concentration of the organic solution in vacuo yielded 390 mg of DPPE-NH-PEG-NH-maleimide as a white solid.

B. Preparation of DPPE-NH-PEG-NH-maleimide.

To a cooled (0 to 5° C.) solution of DPPE-NH-PEG-NH$_2$ from Step A (210 mg) and triethylamine (20 mg) in CH$_2$Cl$_2$ (20 mL) was added a solution of maleimidopropionic acid N-hydroxysuccinimide ester (26 mg) in CH$_2$Cl$_2$ (10 mL). The resulting mixture was stirred for 1 hour at 0 to 5° C., and then stirred overnight at room temperature. Water (10 mL) was added and the resulting mixture was acidified with added and the resulting mixture will be incubated for 16 hours at 4° C. The resulting products will be analyzed on a polyacrylamide electrophoresis gel to determine whether the Fab' and/or F(ab')$_2$ fragments became bound to the lipid. This can be determined by observing changes in molecular weight. Targeted vesicles will then be prepared using 1 wt % of the Fab' and/or F(ab')$_2$ bound lipids.

Example 47

This example is directed to the preparation of DPGS-NH-PEG-NH-PDP, which has the following formula.

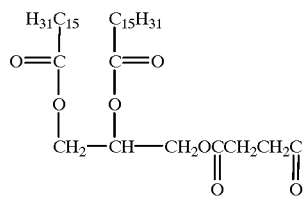
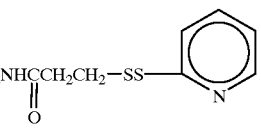

dilute HCl, with stirring, to a pH of 3. The organic layer was isolated, washed with water (10 mL) and dried (NaSO$_4$). Concentration to dryness in vacuo using a rotary evaporator provided 210 mg of the title compound (DPPE-NU-PEG-NH-maleimide) as a white solid.

Example 46

Fab' or F(ab')$_2$ fragments were bound to gas-filled vesicles via a lipid-PEG-maleimide lipid. The Fab' or F(ab')$_2$ fragments were prepared from anti-skeletal myosin (Sigma Chemical, St. Louis, Mo.) using Fab' and/or F(ab') kits from Pierce (Rockford, Ill.).

Fab' fragments were prepared by digesting the antibody with papain. This cleaves both Fab' fragments from the Fc region of the antibody. The Fc fragments were then bound to a Protein A column and the Fab' fragments were collected. The Fab' fragments were then lyophilized (Labconco Lyph-Lock 12, Kansas City, Mo.) and prepared for binding to the lipid-PEG-maleimide lipid.

Dipalmitoyl glycerol succinate-polyethyleneglycol-amine (DPGS-NH-PEG-NH$_2$) was prepared utilizing the procedure in Example 44, step A. DPGS-NH-PEG-NH$_2$ (440 mg, 0.13 mmol) and triethylamine (13 mg, 0.13 mmol) were dissolved in CH$_2$Cl$_2$ (10 mL). To this solution was added a solution of 3-(2-pyridyldithio)propionic acid N-hydroxysuccinimide ester (PDP) (31 mg) in CH$_2$Cl$_2$ (10 mL). After stirring overnight at room temperature, deionized water (30 mL) was added to the reaction mixture and stirring was continued for an additional 3 hours. The lower organic layer was isolated using a separatory funnel and dried (Na$_2$SO$_4$). The organic layer was filtered and the filtrate was concentrated in vacuo to afford 360 mg of the title compound (DPGS-NH-PEG-NH-PDP) as a wax-like white solid.

Example 48

This example is directed to the synthesis of DPPE-NH-PEG-NH-PDP, which has the following formula.

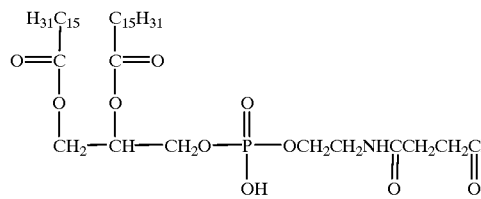
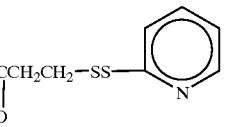

F(ab')$_2$ fragments were prepared in a similar manner as for the Fab' fragments. However, the enzyme pepsin was used instead of papain. Pepsin cleaves farther in the Fc region, and the two Fab' fragments remain connected. The F(ab')$_2$ fragments were then lyophilized.

The various fragments will be resuspended at a concentration of 1 mg/mL in coupling buffer (150 mM NaCl, 10 mM MOPS, 0.1 mM EDTA, 50 μm DTPA, pH 6.5) (all materials obtained from Sigma Chemical, St. Louis, Mo.). The lipid-PEG-maleimide lipid (0.2 to 10 mM) will then be 1,2 Dipamitoyl-sn-glycerol-3-phosphoethanolamine-N-carbonylethylene-carbonyliminopolyethylene glycol ethylamine (DPPE-NH-PEG-NH$_2$) was prepared utilizing the procedure described in Example 45, Step A. This material (210 mg) and triethylamine (20 mg) were combined in CH$_2$Cl$_2$ (20 mL). This solution was added to a solution of 3-(2-pyridyldithio)propionic acid N-hydroxysuccinimide ester (PDP) (31 mg) in CH$_2$Cl$_2$ (10 mL). The resulting mixture was stirred for 1 hour at 0 to 5° C., and then stirred overnight at room temperature. Distilled water (10 mL) was added and the resulting mixture was acidified with dilute HCl, with stirring, to pH of 3. The organic layer was isolated, washed with water (10 mL) and dried ($Na_2SO_4$). The organic layer was filtered and concentrated to dryness in vacuo using a rotary evaporator to provide 210 mg of the title compound (DPPE-NH-PEG-NH-PDP) as a white solid.

Example 49

This example is directed to the preparation of a lipid-hydrophilic polymer-protein conjugate within the scope of the present invention, which has the following formula.

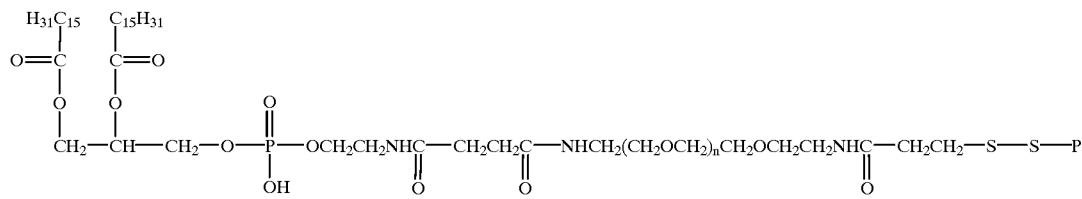

where "P" is -Protein A

The compound from Example 48 will be linked with Protein A by reacting a sulfur atom of the —S—S— disulfide bond in DPPE-NH-PEG-NH-PDP a sulfhydryl group of a protein. The resulting compound may be utilized in forming protein-bearing vesicles, such as protein-bearing liposomes.

Example 50

This example is directed to the preparation of a lipid-hydrophilic polymer-protein conjugate within the scope of the present invention, which has the following formula.

The compound from Example 47 (DPGS-NH-PEG-NH-PDP) will be coupled with maleimide-labeled Protein A to afford the above compound.

Example 51

This example is directed to the preparation of DPGS-NH-PEG-glucose, which has the following formula.

A. Preparation of $NH_2$-PEG-Glucose.

2,3,4,6-tetra-O-Benzyl-α-D-glucopyranosyl bromide (0.6 g) was prepared according to the procedure of C. A. A. van Broeckel and J. H. van Boom, *Tetrahedron*, 41, 4545 (1985). Drying of the mixture was initiated by the use of activated molecular sieves in DMF mixed with ω-trifluoroacetylaminopolyethyleneglycol (3.5 g), the latter being prepared from ω-aminopolyethyleneglycol and triacetic acid anhydride, and diisopropylethylamine (DIEA) (1.2 mL). The resulting solution was stirred for 4 days under nitrogen. The solution was diluted with $CHCl_3$ (150 mL) and washed with 10% $NaHCO_3$ (50 mL) and water. The organic layer was concentrated in vacuo, and the resulting residue was treated with sodium carbonate methanol-$H_2O$ solution at room temperature for 2 days. The solvent was removed in vacuo and the residue was extracted twice with $CHCl_3$ (100 mL). The combined chloroform extracts were were concentrated in vacuo, and the resulting residue was dissolved in methanol and hydrogenated over 10% palladium on charcoal (0.45 g) at 4 atmospheres of pressure and room temperature. The catalyst was filtered off and the filtrate was concentrated in vacuo to provide $NH_2$-PEG-Glucose (3 g) as a white solid. The product was purified on a silica gel column and eluted with an isocratic eluent of chloroform-methanol-water.

B. Preparation of DPGS-NH-PEG-Glucose.

NH$_2$-PEG-Glucose from Step A (1 g), triethylamine (0.5 g) and a solution of acetonitrile and water (50:50) were combined and added to a cooled (0–5° C.) solution of DPGS-succinimide from Example 13A (0.15 g) in acetonitrile (10 mL). The resulting mixture was stirred at room temperature for two days and the acetonitrile was evaporated. The resulting residue was diluted with water to 50 mL, dialyzed through a 500 MWCO membrane, and lyophilized to yield the title compound (DPGS-NH-PEG-Glucose) as a white solid.

Example 52

This example is directed to the preparation of DPGS-NH-PEG-NH-Mannose, which has the following formula.

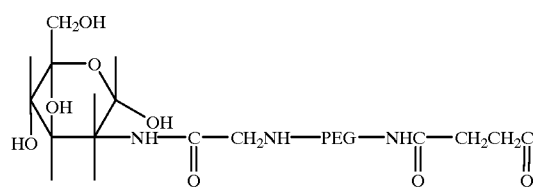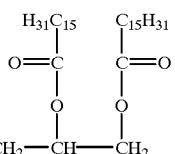

A. Preparation of α-bromo-acetylamino-D-mannose.

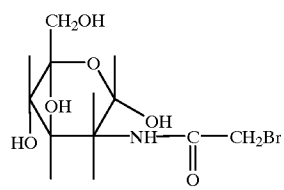

D-Mannosamine hydrochloride (2.1 g), triethylamine (3 g) and DMF (50 mL) were combined and added to a cooled (0–5° C.) solution of α-bromoacetyl bromide (2 g) in CH$_2$Cl$_2$ with stirring. The resulting mixture was stirred at room temperature for 8 hours, and then poured into ice water (50 mL). This aqueous mixture was stirred for 1 hour and then concentrated in vacuo to dryness. The resulting residue was recrystallized from a mixture of water and ethanol to afford α-bromo-acetylamino-D-mannose as a white solid (2.1 g).

B. Preparation of DPGS-NH-PEG-NH-Mannose.

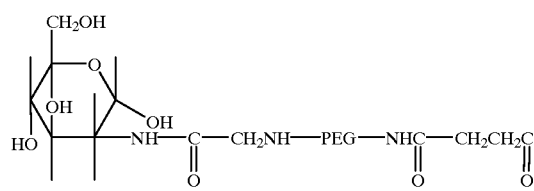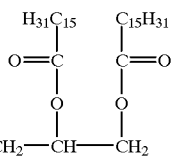

α-Bromoacetylamino-D-mannose from Step A (0.3 g), DPGS-NH-PEG-NH$_2$ from Example 44A (4 g), sodium carbonate (0.2 g) and KI (20 mg) were combined in a mixture of water and ethanol (1:1). The resulting mixture was heated to 40° C. for 8 hours. The ethanol was evaporated on a rotary evaporator, and the aqueous residue was dialyzed through a 500 MWCO membrane and lyophilized to yield 4 g of the title compound (DPGS-NH-PEG-NH-Mannose) as a white solid.

The following examples are directed to the preparation of targeted vesicles.

Example 53

Albumin vesicles (or albumin coated gas bubbles) were suspended in a buffer solution with a pH greater than 8. To this suspension was added 3-(2-pyridyl)dithiopropionic acid N-hydroxy-succinimide ester (SPDP) in CH$_3$CN at 0 to 5° C. The resulting mixture was incubated for 2 days at room temperature and dialyzed on a membrane of 500 MWCO to provide pyridyldithiopropionoyl bearing albumin vesicles. Maleimidophenylbutyrate conjugated antibody (MPB-AB) was then incubated with the surface modified albumin vesicles to obtain antibody linked to albumin vesicles.

Example 54

Polyglutamic acid vesicles (or polyglutamic acid coated-gas bubbles) were suspended in water. To this suspension was added ethyl-N,N-dimethylaminopropylcarbodiimide hydrochloride (EDC) in water at 0 to 5° C. The resulting mixture was gently stirred for 4 hours and then a peptide solution (in a buffer of pH of 8 to 9.5) was added. This mixture was incubated for 2 days at room temperature and dialyzed on a membrane of 500 MWCO to afford peptide conjugated polyglutamic acid vesicles.

Example 55

Example 53 was repeated, except that vesicles formulated from a copolymer of methyl cyanomethacrylate (2-cyano-2-propenoic acid, methyl ester) and ω-amino-tetraethyleneglycolyl methacrylate were substituted for the albumin vesicles.

Example 56

This example is directed to the preparation of a lipid-polymer-peptide conjugate and targeted vesicles therefrom.

Into a round bottom flask was introduced 1 equivalent of α-amino, ω-carboxy PEG-4000 having a tert-butyloxycarbonyl (t-Boc) protecting group. This was activated by the addition of carbonyldiimidazole (CDI) (1 eq.) and hydroxybenzotriazole (1 eq.) In N-methylpyrrolidone. To this solution was added the peptide Lys-Gln-Ala-Gly-Asp-Val deprotected on the amino terminus. The resulting solution was stirred and periodically checked for free amino groups by analysis with methylene blue or ninhydrin. When there was no further evidence of the free amino terminus, deprotection of the entire mixture was carried out via the addition of trifluoroacetic acid in methylene chloride. Free amine from the PEG was then isolated by standard methods. Into a separate flask was introduced a solution of DPPE (1 eq) in DMF and carbonyldiimidazole (1 eq). Stirring was continued for one hour over molecular sieves (4 angstroms). To this mixture was then added the PEG-peptide ligand mixture followed by continued stirring. The mixture was then dried in vacuo and added to a DEAE Sepharose size exclusion column, thereby isolating the DPPE-PEG-peptide conjugate. Gas filled vesicles were then prepared from the DPPE-PEG-peptide utilizing standard methodology.

Example 57

This example is directed to the preparation of DPGS-PEG-cyclic peptide, which has the following formula.

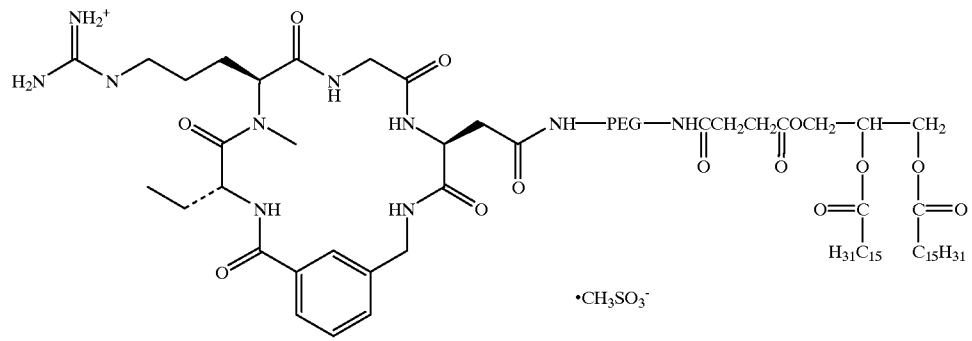

Cyclic[D-2-aminobutyryl-N-2-methyl-L-arginyl-glycyl-L-aspartyl-3-(aminomehtylbenzoic acid)] was prepared using standard peptide synthetic methodology. To a solution of 66 mg of this cyclic peptide in in water (20 mL) was added ethyl-N,N-dimethylaminopropylcarbodiimide hydrochloride (EDC) in water (10 mL) at 0 to 5° C. The resulting mixture was stirred for 4 hours at 0 to 5° C., followed by 8 hours at room temperature. To this solution was added DPGS-NH-PEG-NH$_2$ from Example 44A (400 mg) in CH$_3$CN (10 mL) at 0 to 5° C. After stirring overnight at room temperature, the reaction mixture was concentrated in vacuo and the aqueous residue was dialyzed through a 1000 MWCO membrane. Lyophilizing provided the above compound (410 mg) as a white solid.

Example 58

This example is directed to the preparation of vesicles targeted with a cyclic peptide.

To a solution of cyclic[D-2-aminobutyryl-N-2-methyl-L-arginyl-glycyl-L-asparty-3-(aminomehtylbenzoic acid)] (66 mg) in in water (20 mL) was added ethyl-N,N-dimethylaminopropylcarbodiimide hydrochloride (EDC) in water (10 mL) at 0 to 5° C. The resulting mixture was stirred for 4 hours at 0 to 5° C., followed by 8 hours at room temperature. The reaction mixture was then added to a suspension of albumin vesicles at 0 to 5° C. The resulting mixture was incubated for two days at room temperature, filtered and dialyzed using a membrane having a MWCO of 1000 to provide albumin vesicles targeted with a porphyrin targeting ligand.

Example 59

Example 58 was repeated, except that vesicles formulated from a copolymer of methyl cyanomethacrylate (2-cyano-2-propenoic acid, methyl ester) and ω-amino-tetraethyleneglycolyl methacryate were substituted for the albumin vesicles.

Example 60

Patients identified with atrial fibrillation (AF) were evaluated for the presence of left atrial thrombus by administering to the patients perfluorobutane gas filled lipid vesicles containing a peptide targeting ligand which targets the GPIIbIIIa receptor, and scanning the patient with echocardiography. The patients screened for episodes of AF by standard electrocardiography were found to have peripheral venous access established with a slow infusion of 0.9% sterile saline utilizing an 18–20 gauge angiocath. Cardiac ultrasound was performed with clinically available equipment. Images of the heart were first obtained transthoracically with fundamental harmonic imaging and Power Doppler.

Perfluorobutane gas filled GPIIbIIIa targeted lipid vesicles were infused to provide a total dose of 0.03 mL/kg body weight. Using aseptic techniques, the proscribed volume of the aforementioned gas filled targeted vesicles, based on a density of 1.0 mg/mL and the patient weight, were drawn from the vials and transferred to a 50 mL bag containing 0.9% saline. After the dilution of the gas filled targeted vesicles, the bag and peripheral infusion equipment were attached to an IMED or IVAC infusion pump to allow a constant administration rate. The infusion began at 4 mL/min and after approximately 5 minutes was decreased to 2 mL/min. The infusion was continued until the bag was empty.

Images of the cardiac chambers were obtained and recorded on SVHS tape. The clinically relevant imaging modes and views were determined at the time of the study. Imaging was interrupted at 15 minutes post initiation of infusion. At the conclusion of infusion, a single set of images was obtained with the mode, view and technique that best demonstrated the left atrium and/or appendage. The images were then processed offline to optimize the enhancement of the left atrium and/or appendage.

If the left atrium and/or appendage were not sufficiently imaged across the chest wall, the patient was administered transesophageal echocardiography in the manner described above.

Example 61

Patients identified with chest pain, either on-going or in the past, will be evaluated for the presence of myocardial perfusion deficits with perfluoropropane gas-filled vesicles.

The patients selected for this diagnostic procedure will have a peripheral venous access established with a slow infusion of 0.9% sterile saline utilizing an 18–21 gauge angiocath. Cardiac ultrasound will be performed with clinically available equipment. Images of the heart will be first obtained with fundamental, harmonic, Power Doppler, and/or any other clinically relevant imaging mode.

The gas filled vesicles will be infused to a total dose of 30 μL/kg body weight. The necessary number of 1.5 mL vials will be prepared in advance. Using aseptic technique, the desired volume of gas filled vesicles will be drawn from the vials and transferred to a bag containing 100 mL of sterile saline. After dilution of the gas filled vesicles, the bag and peripheral infusion equipment will be attached to an IMED or IVAC infusion pump to provide a constant administration rate. The infusion begins at a rate of 4 mL/min which is decreased to 1–2 mL/min after approximately 30 seconds. The final rate of infusion will be established by imaging the heart in the parasternal short axis view, utilizing harmonic imaging and triggering imaging acquisition at end systole (i.e., end of T-wave on ECG) at every eighth cardiac cycle. This technique enables titration of the infusion so that there is no attenuation in the posterior aspect of the cardiac chamber.

Harmonic, triggered, continuous gray scale images of the heart will be obtained and recorded on SVHS tape or optical disc. The clinically relevant views will be determined at the time of the study. The technique for obtaining the triggered images will be as follows: (a) the first trigger on the ultrasound equipment will be set at the end of the T-wave of the patient's ECG: and (b) the second trigger will be set 40 milliseconds after the first trigger. Employing this technique, a first single image will be obtained at end systole using the first trigger and a second single image will be obtained 40 milliseconds later using the second trigger. Three to five image pairs will be obtained at every 1, 4 and 8 cardiac cycles in the clinically relevant views. At the conclusion of image acquisition, the infusion of the gas filled vesicles will be discontinued.

The images on the SVHS tape or optical disc will then be processed (either on- or off-line) to provide enhanced demonstration of myocardial perfusion. This processing involves subtracting the second single image (obtained 40 milliseconds after the first single image) from the first single image in each pair of images obtained, and the resulting image will be displayed in gray scale or color format. Additional processing will include adding 3 to 5 processed frames from each of the sampling sequences and displaying them in gray scale or color format.

The disclosures of each patent, patent application and publication cited or described in this document are hereby incorporated herein by reference, in their entirety.

Various modification of the invention, in addition to those described herein, will be apparent to those skilled in the art from the foregoing description. Such modifications are also intended to fall within the scope of the appended claims.

What is claimed is:

1. A method for providing an image of an internal region of a patient comprising (a) administering to the patient a contrast agent which comprises, in an aqueous carrier, a lipid, protein or polymer, and a gas, and (b) scanning the patient using ultrasound imaging to obtain a visible image of the region, wherein said scanning step comprises:
   (i) applying a first quantity of ultrasound energy to the patient to provide a first image;
   (ii) applying within about 100 milliseconds thereafter a second quantity of ultrasound energy to the patient to provide a second image; and
   (iii) processing said first and second images,
wherein said processing step (iii) comprises subtracting said second image from said first image.

2. A method according to claim 1 wherein said contrast agent comprises a lipid.

3. A method according to claim 2 wherein said lipid comprises a phospholipid.

4. A method according to claim 3 wherein said phospholipid is selected from the group consisting of phosphatidylcholine, phosphatidylethanolamine and phosphatidic acid.

5. A method according to claim 4 wherein said phosphatidylcholine is selected from the group consisting of dioleoylphosphatidylcholine, dimyristoylphosphatidylcholine, dipalmitoylphosphatidylcholine and distearoylphosphatidylcholine.

6. A method according to claim 5 wherein said phosphatidylcholine comprises dipalmitoylphosphatidylcholine.

7. A method according to claim 6 wherein said phosphatidylethanolamine is selected from the group consisting of dipalmitoylphosphatidylethanolamine, dioleoylphosphatidylethanolamine, N-succinyldioleoylphosphatidylethanolamine and 1-hexadecyl-2-palmitoylglycerophosphoethanolamine.

8. A method according to claim 7 wherein said phosphatidylethanolamine comprises dipalmitoylphosphatidylethanolamine.

9. A method according to claim 4 wherein said phosphatidic acid comprises dipalmitoylphosphatidic acid.

10. A method according to claim 2 wherein said lipid further comprises a polymer.

11. A method according to claim 10 wherein said polymer comprises a hydrophilic polymer.

12. A method according to claim 11 wherein said polymer comprises polyethylene glycol.

13. A method according to claim 1 wherein said contrast agent comprises a protein.

14. A method according to claim 13 wherein said protein comprises albumin.

15. A method according to claim 1 wherein said contrast agent comprises a polymer.

16. A method according to claim 15 wherein said polymer comprises synthetic polymers or copolymers which are prepared from monomers selected from the group consisting of acrylic acid, methacrylic acid, ethyleneimine, crotonic acid, acrylamide, ethyl acrylate, methyl methacrylate, 2-hydroxyethyl methacrylate, lactic acid, glycolic acid, ε-caprolactone, acrolein, cyanoacrylate, bisphenol A, epichlorhydrin, hydroxyalkylacrylates, siloxane, dimethylsiloxane, ethylene oxide, propylene oxide, ethylene glycol, hydroxyalkylmethacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-aminobenzylstyrene, sodium styrene sulfonate, sodium 2-sulfoxyethyl-methacrylate, vinyl pyridine, aminoethyl methacrylates and 2-methacryloyloxytrimethyl-ammonium chloride.

17. A method according to claim 15 wherein said polymer comprises synthetic polymers or copolymers selected from the group consisting of polyacrylic acid, polyethyleneimine, polymethacrylic acid, polymethylmethacrylate, polysiloxane, polydimethylsiloxane, polylactic acid, poly(ε-caprolactone), epoxy resin, poly(ethylene oxide), poly (propylene oxide), poly(ethylene glycol), polyamide, polyvinylidene-polyacrylonitrile, polyvinylidene-polyacrylonitrile-polymethylmethacrylate and polystyrene-polyacrylonitrile.

18. A method according to claim 17 wherein said polymer comprises polyvinylidene-polyacrylonitrile copolymer.

19. A method according to claim 1 wherein said gas comprises a fluorinated gas.

20. A method according to claim 19 wherein said fluorinated gas is selected from the group consisting of a perfluorocarbon, sulfur hexafluoride and heptafluoropropane.

21. A method according to claim 20 wherein said fluorinated gas comprises a perfluorocarbon.

22. A method according to claim 21 wherein said perfluorocarbon gas is selected from the group consisting of perfluoromethane, perfluoroethane, perfluoropropane, perfluorobutane and perfluorocyclobutane.

23. A method according to claim 1 wherein said gas is derived, at least in part, from a gaseous precursor.

24. A method according to claim 23 wherein said gaseous precursor has a boiling point of greater than about 37° C.

25. A method according to claim 23 wherein said gaseous precursor comprises a fluorinated compound.

26. A method according to claim 25 wherein said fluorinated compound comprises a perfluorocarbon.

27. A method according to claim 26 wherein said perfluorocarbon is selected from the group consisting of perfluoropentane and perfluorohexane.

28. A method according to claim 1 wherein said contrast agent comprises vesicles.

29. A method according to claim 28 wherein said vesicles are selected from the group consisting of micelles and liposomes.

30. A method according to claim 2 wherein said lipid is selected from the group consisting of unilamellar lipids, oligolamellar lipids and multilamellar lipids.

31. A method according to claim 30 wherein said lipids comprise unilamellar lipids.

32. A method according to claim 31 wherein said lipid comprises one monolayer.

33. A method according to claim 32 wherein said lipid is a phospholipid and said gas is sulfur hexafluoride.

34. A method according to claim 32 wherein said lipid is a phospholipid and said gas is perfluoropropane.

35. A method according to claim 32 wherein said lipid is a phospholipid and said gas is perfluorobutane.

36. A method according to claim 32 wherein said gas is derived, at least in part, from a gaseous precursor.

37. A method according to claim 36 wherein said lipid is a phospholipid and said gas or gaseous precursor is perfluoropentane.

38. A method according to claim 31 wherein said lipid comprises one bilayer.

39. A method according to claim 38 wherein said lipid is a phospholipid and said gas is sulfur hexafluoride.

40. A method according to claim 38 wherein said lipid is a phospholipid and said gas is perfluoropropane.

41. A method according to claim 38 wherein said lipid is a phospholipid and said gas is perfluorobutane.

42. A method according to claim 38 wherein said gas is derived, at least in part, from a gaseous precursor.

43. A method according to claim 42 wherein said lipid is a phospholipid and said gaseous precursor is perfluoropentane.

44. A method according to claim 30 wherein said lipids are selected from the group consisting of oligolamellar lipids and multilamellar lipids.

45. A method according to claim 44 wherein said lipids comprise one monolayer.

46. A method according to claim 45 wherein said lipid is a phospholipid and said gas is sulfur hexafluoride.

47. A method according to claim 45 wherein said lipid is a phospholipid and said gas is perfluoropropane.

48. A method according to claim 45 wherein said lipid is a phospholipid and said gas is perfluorobutane.

49. A method according to claim 45 wherein said gas is derived, at least in part, from a gaseous precursor.

50. A method according to claim 49 wherein said lipid is a phospholipid and said gaseous precursor is perfluoropentane.

51. A method according to claim 44 wherein said lipids comprise one bilayer.

52. A method according to claim 51 wherein said lipid is a phospholipid and said gas is sulfur hexafluoride.

53. A method according to claim 51 wherein said lipid is a phospholipid and said gas is perfluoropropane.

54. A method according to claim 51 wherein said lipid is a phospholipid and said gas is perfluorobutane.

55. A method according to claim 51 wherein said gas is derived, at least in part, from a gaseous precursor.

56. A method according to claim 55 wherein said lipid is a phospholipid and said gaseous precursor is perfluoropentane.

57. A method according to claim 2 wherein said lipid is a polymerized lipid.

58. A method according to claim 2 wherein said contrast agent further comprises polyethyleneglycol.

59. A method according to claim 28 wherein said vesicles comprise lipid vesicles.

60. A method according to claim 59 wherein said vesicles are selected from the group consisting of unilamellar vesicles, oligolamellar vesicles and multilamellar vesicles.

61. A method according to claim 60 wherein said vesicles comprise unilamellar vesicles.

62. A method according to claim 61 wherein said vesicles comprise one monolayer.

63. A method according to claim 62 wherein said lipid is a phospholipid and said gas is sulfur hexafluoride.

64. A method according to claim 62 wherein said lipid is a phospholipid and said gas is perfluoropropane.

65. A method according to claim 63 wherein said lipid is a phospholipid and said gas is perfluorobutane.

66. A method according to claim 62 wherein said gas is derived, at least in part, from a gaseous precursor.

67. A method according to claim 66 wherein said lipid is a phospholipid and said gas or gaseous precursor is perfluoropentane.

68. A method according to claim 62 wherein said lipid is a polymerized lipid.

69. A method according to claim 61 wherein said vesicles comprise a bilayer.

70. A method according to claim 69 wherein said lipid is a phospholipid and said gas is sulfur hexafluoride.

71. A method according to claim 69 wherein said lipid is a phospholipid and said gas is perfluoropropane.

72. A method according to claim 69 wherein said lipid is a phospholipid and said gas is perfluorobutane.

73. A method according to claim 69 wherein said gas is derived, at least in part, from a gaseous precursor.

74. A method according to claim 73 wherein said lipid is a phospholipid and said gaseous precursor is perfluoropentane.

75. A method according to claim 69 wherein said lipid comprises a polymerized lipid.

76. A method according to claim 60 wherein said vesicles are selected from the group consisting of oligolamellar vesicles and multilamellar vesicles.

77. A method according to claim 76 wherein said vesicles comprise one monolayer.

78. A method according to claim 77 wherein said lipid is a phospholipid and said gas is sulfur hexafluoride.

79. A method according to claim 77 wherein said lipid is a phospholipid and said gas is perfluoropropane.

80. A method according to claim 77 wherein said lipid is a phospholipid and said gas is perfluorobutane.

81. A method according to claim 77 wherein said gas is derived, at least in part, from a gaseous precursor.

82. A method according to claim 81 wherein said lipid is a phospholipid and said gaseous precursor is perfluoropentane.

83. A method according to claim 77 wherein said lipid is a polymerized lipid.

84. A method according to claim 76 wherein said vesicles comprise a bilayer.

85. A method according to claim 84 wherein said lipid is a phospholipid and said gas is sulfur hexafluoride.

86. A method according to claim 84 wherein said lipid is a phospholipid and said gas is perfluoropropane.

87. A method according to claim 84 wherein said lipid is a phospholipid and said gas is perfluorobutane.

88. A method according to claim 84 wherein said gas is derived, at least in part, from a gaseous precursor.

89. A method according to claim 88 wherein said lipid is a phospholipid and said gas or gaseous precursor is perfluoropentane.

90. A method according to claim 13 wherein said gas comprises a perfluorocarbon.

91. A method according to claim 90 wherein said perfluorocarbon is selected from the group consisting of perfluoromethane, perfluoroethane, perfluoropropane, perfluorobutane, perfluorocyclobutane, perfluoropentane, perfluorohexane, perfluoroheptane, perfluorooctane and perfluorononane.

92. A method according to claim 91 wherein said perfluorocarbon is perfluoropropane.

93. A method according to claim 13 wherein said protein is crosslinked.

94. A method according to claim 91 wherein said protein is crosslinked.

95. A method according to claim 1 wherein said region comprises the myocardial region.

96. A method according to claim 95 wherein said region comprises the left atrium.

97. A method according to claim 1 wherein said contrast agent is administered to the patient at a rate which substantially eliminates diagnostic artifacts in the image.

98. A method according to claim 1 wherein each of said first and second quantities of ultrasound energy comprises a pulse of ultrasound energy.

99. A method according to claim 98 wherein said first and second images are obtained during the same cardiac cycle.

100. A method according to claim 99 wherein said first pulse of ultrasound energy is applied at end systole or end diastole.

101. A method according to claim 100 wherein said first pulse of ultrasound energy is applied at end systole.

102. A method according to claim 100 wherein said first pulse of ultrasound energy is applied at end diastole.

103. A method according to claim 99 wherein said second pulse of ultrasound energy is applied from about 5 to less than about 100 milliseconds.

104. A method according to claim 103 wherein said second pulse of ultrasound energy is applied from about 10 to about 80 milliseconds after said application of said first pulse of ultrasound energy.

105. A method according to claim 104 wherein said second pulse of ultrasound energy is applied from about 20 to about 60 milliseconds after said application of said first pulse of ultrasound energy.

106. A method according to claim 105 wherein said second pulse of ultrasound energy is applied from about 30 to about 40 milliseconds after said application of said first pulse of ultrasound energy.

107. A method according to claim 106 wherein said second pulse of ultrasound energy is applied about 40 milliseconds after said application of said first pulse of ultrasound energy.

108. A method according to claim 99 wherein said first quantity of energy is applied at a time which corresponds to about the end of the T-wave in the patient's ECG.

109. A method according to claim 99 wherein said first quantity of energy is applied at a time which corresponds to about the end of the R-wave in the patient's ECG.

110. A method according to claim 1 wherein said processed images are displayed in gray scale or color format.

111. A method according to claim 1 which comprises administering said contrast agent to the patient at a rate of constant infusion.

112. A method according to claim 111 comprising administering said contrast agent using a constant infusion device.

113. A method according to claim 1 wherein said region comprises the myocardial region.

114. A method according to claim 113 wherein said region comprises the left atrium.

115. A method for diagnosing the presence of diseased tissue in a patient comprising (a) administering to the patient a contrast agent which comprises, in an aqueous carrier, a lipid, protein or polymer, and a gas, and (b) scanning the patient using ultrasound imaging to obtain a visible image of any diseased tissue in the patient, wherein said scanning step comprises:

(i) applying a first quantity of ultrasound energy to the patient to provide a first image;

(ii) applying within about 100 milliseconds thereafter a second quantity of ultrasound energy to the patient to provide a second image; and (iii) processing said first and second images, wherein said processing step (iii) comprises subtracting said second image from said first image.

* * * * *

UNITED STATES PATENT AND TRADEMARK OFFICE
CERTIFICATE OF CORRECTION

PATENT NO. : 6,231,834 B1
DATED : May 15, 2001
INVENTOR(S) : Evan C. Unger, Thomas A. Fritz and Edward W. Gertz It is certified that error appears in the above-identified patent and that said Letters Patent is hereby corrected as shown below:

Title page,
Item [56], References Cited, U.S. PATENT DOCUMENTS
"4,663,161", please delete "Mannimo" and insert -- Mannino -- therefor.
FOREIGN PATENT DOCUMENTS
"93/00933", please insert -- WO -- before "93/00933".
"WO 9/06477", please delete "WO 9/06477" and insert -- WO 94/06477 -- therefor.
"WO 84/02909", please delete "WO 84/02909" and insert -- WO 94/02909 -- therefor.
OTHER PUBLICATIONS
"Fukuda et al.," reference please delete "Diotadecyldimenthylammonium" and
insert -- Dioctadecyldimethylammonium -- therefor.
"Shiina et al.," reference please delete "Hyperthermiably" and insert -- Hyperthermia by -- therefor.
"Ter-Pogossian," reference please delete "Tomography, Kee, et al., n,"; please delete "Body eds.," and insert -- Body Tomography, Lee et al., eds., -- therefor.
"Aronberg," reference please delete "Kee" and insert -- Lee -- therefor.
"Keller et al.," reference please delete "Microcirulation" and insert -- Microcirculation -- therefor.
""Properties and Applications of the 'Freon' Fluorocarbons"," reference please delete "pp. 1-10" and insert -- pp. 1-11--therefor.
"Villanueva et al.," reference please delete "Patters" and insert -- Patterns -- therefor.
"Kohler, G. et al.," reference please delete "celles" and insert -- cell -- therefor.

Column 4,
Line 7, please delete "thombi" and insert -- thrombi -- therefor.

Column 7,
Line 33, please delete "clatlirate" and insert -- clathrate -- therefor.

Column 17,
Line 47, please delete "dipahnitoylphosphati-" and insert -- dipalmitoylphosphati- -- therefor.
Line 48, please delete "distearoylphosphatidylefhano-" and insert -- distearoylphosphatidylethano- -- therefor.
Line 54, please delete "dipahmitoylphosphatidic" and insert -- dipalmitoylphosphatidic -- therefor.

Column 18,
Line 26, please delete "palritate" and insert -- palmitate -- therefor.
Line 30, please delete "dipahmitate" and insert -- dipalmitate -- therefor.

Column 22,
Line 12, please delete "At".
Line 21, please delete "erytbrulose" and insert -- erythrulose -- therefor.

UNITED STATES PATENT AND TRADEMARK OFFICE
CERTIFICATE OF CORRECTION

PATENT NO.    : 6,231,834 B1
DATED         : May 15, 2001
INVENTOR(S)   : Evan C. Unger, Thomas A. Fritz and Edward W. Gertz It is certified that error appears in the above-identified patent and that said Letters Patent is hereby corrected as shown below:

Column 30,
Line 54, please delete "galatocarolose" and insert -- galactocarolose -- therefor.

Column 32,
Line 29, please delete "tie" and insert -- the -- therefor.

Column 34,
Line 32, please delete "form" and insert -- from -- therefor.

Column 40,
Line 47, please delete "a-amino" and insert -- α-amino -- therefor.

Column 43,
Line 51, please delete "–SOP$_2$–" and insert -- –SO$_2$– -- therefor.
Line 54, please delete "–R$_5$–X$_4$–C(–X$_5$)–" and insert -- –R$_5$–X$_4$–C(=X$_5$)– -- therefor.

Column 44,
Line 6, please delete "about carbons" and insert -- about 10 carbons -- therefor.
Line 66, please delete "polethylene" and insert -- polyethylene -- therefor.

Column 48,
Line 21, please delete "inidate" and insert -- imidate -- therefor.

Column 49,
Line 29, please delete "polyhyhydroxypropyloxazolines" and insert
-- polyhydroxypropyloxazolines -- therefor.

Column 52,
Line 46, please delete "bydrophilic" and insert -- hydrophilic -- therefor.

Column 55,
Line 34, please delete "...ethylenediamnine-..." and insert -- ...ethylenediamine-... -- therefor.

Column 66,
Line 8, please delete "$V_{gs}=4/3\pi(r_{gas})^3$" and insert -- $V_{gas}=4/3\pi(r_{gas})^3$ -- therefor.

Column 70,
Line 51, please delete "perparation" and insert -- preparation -- therefor.

Column 71,
Line 23, please delete "foaiming" and insert -- foaming -- therefor.
Line 38, please delete "gluteradehyde" and insert -- gluteraldehyde -- therefor.

UNITED STATES PATENT AND TRADEMARK OFFICE
CERTIFICATE OF CORRECTION

PATENT NO. : 6,231,834 B1
DATED : May 15, 2001
INVENTOR(S) : Evan C. Unger, Thomas A. Fritz and Edward W. Gertz It is certified that error appears in the above-identified patent and that said Letters Patent is hereby corrected as shown below:

Column 74,
Line 6, please delete "Phannacopeial" and insert -- Pharmacopeial -- therefor.

Column 99,
Line 66, please delete "form" and insert -- from -- therefor.

Column 104,
Line 19, please delete "(dicycohexylurea)" and insert -- (dicyclohexylurea) -- therefor.

Column 114,
Line 18, please delete "a-hydroxy" and insert -- α-hydroxy -- therefor.

Column 116,
Line 28, please delete "videodensitrometric" and insert -- videodensitometric -- therefor.

Column 119,
Line 30, please delete " (DPPE-NU-PEG- " and insert -- (DPPE-NH-PEG- - therefor.

Column 122,
Line 32, please delete the second occurrence of "were".

Column 125,
Lines 37 and 54, please delete "(aminomehtylbenzoic" and insert -- (aminomethylbenzoic -- therefor.

Signed and Sealed this

Twenty-eighth Day of September, 2004

JON W. DUDAS
*Director of the United States Patent and Trademark Office*